(12) United States Patent
Ann et al.

(10) Patent No.: US 11,311,608 B2
(45) Date of Patent: Apr. 26, 2022

(54) METHODS FOR TREATING BREAST AND OTHER CANCERS BY TARGETING ARGININOSUCCINATE SYNTHETASE 1-DEFICIENCY

(71) Applicant: CITY OF HOPE, Duarte, CA (US)

(72) Inventors: David K. Ann, Arcadia, CA (US); Yun-Ru Chen, Duarte, CA (US); Fuming Qiu, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/089,227

(22) Filed: Apr. 1, 2016

(65) Prior Publication Data

US 2016/0206712 A1  Jul. 21, 2016

Related U.S. Application Data

(63) Continuation of application No. PCT/US2014/059196, filed on Oct. 3, 2014.

(60) Provisional application No. 61/887,304, filed on Oct. 4, 2013.

(51) Int. Cl.
| | | |
|---|---|---|
| *A61K 38/50* | (2006.01) | |
| *A61K 45/06* | (2006.01) | |
| *A61K 31/704* | (2006.01) | |
| *A61K 47/60* | (2017.01) | |

(52) U.S. Cl.
CPC ............ *A61K 38/50* (2013.01); *A61K 31/704* (2013.01); *A61K 45/06* (2013.01); *A61K 47/60* (2017.08); *C12Y 305/03006* (2013.01)

(58) Field of Classification Search
None
See application file for complete search history.

(56) References Cited

U.S. PATENT DOCUMENTS

| | | | |
|---|---|---|---|
| 7,323,167 B2 | 1/2008 | Clark | |
| 9,333,268 B2 * | 5/2016 | Bomalaski | ........... A61K 31/337 |

FOREIGN PATENT DOCUMENTS

WO       2013/151568 A1    10/2013

OTHER PUBLICATIONS

Klionsky, D. J., et al., "Guidelines for the use and interpretation of assays for monitoring autophagy," Autophagy 8 (4):445-544 (2012).
Kobayashi, E., et al., "Reduced Argininosuccinate synthetase is a predictive biomarker for the development of pulmonary metastasis in patients with osteosarcoma," Mol. Cancer Ther. 9(3):535-544 (2010).
Kvam, E., et al., "Nucleus-vacuole junctions and piecemeal microautophagy of the nucleus in S. cerevisiae," Autophagy 3(2):85-92 (2007).
Levine, B., et al., "Autophagy in the pathogenesis of disease," Cell 132(1 ):27-42 (2008).
Lin, T.C., et al., "Autophagy: Resetting glutamine-dependent metabolism and oxygen consumption," Autophagy 8 (10):1477-1493 (2012).
Lind, D. S., "Arginine and cancer," J. Nutr. 134:2837S-2841S (2004).
Locasale, J. W., et al., "Phosphoglycerate dehydrogenase diverts glycolytic flux and contributes to oncogenesis," Nat. Genet. 43(9):869-874 (2013).
Matsushita, M., et al., "Structure of Atg5.Atg16, a complex essential for autophagy," J. Biol. Chern. 282 (9):6763-6772 (2007).
Mitra, K., "Mitochondrial fission-fusion as an emerging key regulator of cell proliferation and differentiation," Bioessays 35:955-964 (2013).
Mizushima, N., et al., "Autophagy: Renovation of cells and tissues," Cell 147:728-741 (2011).
Morris, S. M., Jr., "Arginine: beyond protein," Am. J. Clin. Nutr. 83(suppl):508S-512S (2006).
Muller, H.J., et al., "Use of L-asparaginase in childhood ALL," Crit. Rev. Oncol. Hematol. 28:97-113 (1998).
Narendra, D., et al., "Parkin is recruited selectively to impaired mitochondria and promotes their autophagy," J. Cell Biol. 183(5):795-803 (2008).
Narendra, D. P., et al., "PINK1 is selectively stabilized on impaired mitochondria to activate parkin," PLoS Biol. 8(1):e10000298 (2010).
Ogawa-Goto, K., et al., "Microtubule network facilitates nuclear targeting of human cytomegalovirus capsid," J. Virol. 77(15):8541-8547 (2003).
Park, Y.E., et al., "Autophagic degradation of nuclear componenets in mammalian cells," Autophagy 5(6):795-804 (2009).
Perkins, G., et al., "New insights into mitochondrial structure during cell death," Exp. Neurol. 218(2):183-192 (2009).
Perou, C. M., et al., "Molecular portraits of human breast tumours," Nature 406:747-752 (2000).
Possemato, R., et al., "Functional genomics reveals serine synthesis is essential in PHGDH-amplified breast cancer," Nature 476(7360):346-350 (2012).
Pyo, J.O., et al., "Essential roles of Atg5 and FADD in autophagic cell death," J. Biol. Chem. 280(21):20722-20729 (2005).
Qiu, F., et al., "Arginine starvation impairs mitochondrial respiratory function in ASS1-deficient breast cancer cells," Sci. Signal. 7(319):ra31 (2015).

(Continued)

*Primary Examiner* — Nelson B Moseley, II
(74) *Attorney, Agent, or Firm* — Perkins Coie LLP; Lara J. Dueppen; Yang Tang

(57) ABSTRACT

Autophagy is the principal catabolic response to nutrient starvation. However, excessive autophagy can be cytotoxic or cytostatic, and contribute to cell death, but its mechanism of induction remains elusive. Here, it was demonstrated that prolonged arginine starvation by ADI-PEG20 induced an autophagy-dependent death of argininosuccinate synthetase 1 (ASS1)-deficient breast cancer cells. Consequently, arginine depleting agents such as ADI-PEG20 may be used in methods for killing one or more argininosuccinate synthetase 1 (ASS1)-deficient breast cancer cells. Further, abundance of ASS1 was either low or absent in more than 60% of 149 random breast cancer biosamples, which could be exploited as candidates for arginine starvation therapy.

7 Claims, 76 Drawing Sheets

Specification includes a Sequence Listing.

(56) References Cited

OTHER PUBLICATIONS

Rardin, M. J., et al., "Label-free quantitative proteomics of the lysine acetylome in mitochondria identifies substrates of SIRT3 in metabolic pathways," PNAS 110(16):6601-6606 (2013).
Rello-Varona, S., et al., "Autophagic removal of micronuclei," Cell Cycle 11(1): 170-176 (2012).
Roberts, P., et al., "Piecemeal microautophagy of nucleus in saccharomyces cerevisiae," Mol. Biol. Cell 14:129-141 (2003).
Roth, M., et al., "Sorting out functions of sirtuins in cancer," Oncogene 33(13):1609-1620 (2014).
Shacka, J. J., et al., "Autophagy, bafilomycin and cell death: The "A-B-Cs" of plecomacrolide-induced neuroprotection," Autophagy 2(3):228-230 (2006).
Shchepina, L. A., et al., "Oligomycin, inhibitor of the F0 part of H+-ATP-synthase, suppresses the TNF-induced apoptosis," Oncogene 21:8149-8157 (2002).
Shvets, E., et al., "Utilizing flow cytometry to monitor autophagy in living mammalian cells," Autophagy 4(5):621-628 (2008).
Sorlie, T., et al., "Gene expression patterns of breast carcinomas distinguish tumor subclasses with clinical implications," PNAS 98(19):10869-10874 (2001).
Syed, N., et al., "Epigenetic status of argininosuccinate synthetase and argininosuccinate lyase modulates autophagy and cell death in glioblastoma," Cell Death and Disease 4:e458 (2013).
Szlosarek, P. W., et al., "In vivo loss of expression of argininosuccinate synthetase in malignant pleural mesothelioma is a biomarker for susceptibility to arginine depletion," Clin. Cancer Res. 12(23):7126-7131 (2006).
Takaku, H., et al., "In vivo anti-tumor activity of arginine deiminase purified from mycoplasma arginini," Int. J. Cancer 51:244-249 (1992).
Tanida, I., et al., "LC3 conjugation system in mammalian autophagy," Int. J. Biochem. Cell Biol. 36:2503-2518 (2004).
Tanida, I., et al., "LC3 and Autophagy," Methods Mol. Biol. 445:77-88 (2008).
Tolkovsky, A. M., "Mitophagy," Biochimica et Biophysica Acta 1793:1508-1515 (2009).
Trachootham, D., et al., "Targeting cancer cells by ROS-mediated mechanisms: A radical therapeutic approach?" Nat. Rev. Drug Disc. 8:579-591 (2009).
Tsai, W.B., et al., "Resistance to arginine deiminase treatment in melanoma cells is associated with induced argininosuccinate synthetase expression involving c-Myc/HIF-1α/Sp4," Mol. Cancer Ther. 8(12):3223-3233 (2009).
Van De Vijver, M. J., et al., "A gene-expression signature as a predictor of survival in breast cancer," New Engl. J. Med. 347(25):1999-2009 (2002).
Vander Heiden, M. G., et al., "Understanding the Warburg effect: The metabolic requirements of cell proliferation," Science 324(5930):1029-1033 (2009).
Vargas, J. D., et al., "Transient nuclear envelope rupturing during interphase in human cancer cells," Nucleus 3 (1):88-100 (2012).
Vincow, E. S., et al., "The PINK1-Parkin pathway promotes both mitophagy and selective respiratory chain turnover in vivo," PNAS 110(16):6400-6405 (2013).
Wang, X., et al., "Overexpression of HMGA2 promotes metastasis and impacts survival of colorectal cancers," Clin. Cancer Res. 17(8):2570-2580 (2011).
Warburg, O., et al., "The metabolism of tumors in the body," The Journal of General Physiology 8:519-530 (1927).
Weinhouse, S., et al., "On respiratory impairment in cancer cells," Science Translational Medicine 124 (3215):267-272 (1956).
Westermann, B., "Mitochondrial fusion and fission in cell life and death," Nat. Rev. Mol. Cell Biol. 11:872-884 (2010).
Wetzler, M., et al., "Effective asparagine depletion with pegylated asparaginase results in improved outcomes in adult acute lymphoblastic leukemia: Cancer and leukemia group B study 9511," Blood 109:4164-4167 (2007).

Wheatley, D.N., et al., "Arginine deprivation, growth inhibition and tumour cell death: 3. Deficient utilisation of citrulline by malignant cells," Br. J. Cancer 89:573-576 (2003).
Wise, D. R., et al., "Glutamine addiction: A new therapeutic target in cancer," Trends Biochem. Sci. 35(8):427-433 (2010).
Wu, F.L. L., et al., "RNA interference of argininosuccinate synthetase restores sensitivity to recombinant arginine deiminase (rADI) in resistant cancer cells," J. Biomed. Sci. 18:25 (2011).
Wu, G., et al., "Arginine metabolism: Nitric oxide and beyond," Biochem. J. 336:1-17 (1998).
Ackrell, B. A.C., "Progress in understanding structure-function relationships in respiratory chain complex II," FEBS Letters 466:1-5 (2000).
Ahn, B.H., et al., "A role for the mitochondiral deacetylase Sirt3 in regulating energy homeostasis," PNAS 105 (38):14447-14452 (2008).
American Cancer Society, Cancer Facts & Figures 2013, Atlanta:American Cancer Society (2013).
Ascierto, P. A., et al., "Pegylated arginine deiminase treatment of patients with metastatic melanoma: Results from phase I and II studies," J. Clin. Oncol. 23(30):7660-7668 (2005).
Beloussow, K., et al., "Recombinant arginine deiminase as a potential anti-angiogenic agent," Cancer Letters 183:155-162 (2002).
Bianchi, C., et al., "Structural and functional organization of Complex I in the mitochondrial respiratory chain," BioFactors 18:3-9 (2003).
Bianchi, C., et al., "The mitochondrial respiratory chain is partially organized in a supercomplex assembly," J. Biol. Chem. 279(35):36562-36569 (2004).
Birrell, J. A., et al., "Investigation of NADH binding, hydride transfer, and NAD+ dissociation during NADH oxidation by mitochondrial Complex I using modified nicotinamide nucleotides," Biochemistry 52:4048-4055 (2013).
Boren, J., et al., "Apoptosis-induced mitochondrial dysfunction causes cytoplasmic lipid droplet formation," Cell Death and Differentiation 19:1561-1570 (2012).
Bowles, T. L., et al., "Pancreatic cancer cell lines deficient in argininosuccinate synthetase are sensitive to arginine deprivation by arginine deiminase," Int. J. Cancer 123(8):1950-1955 (2008).
Brennan, J. P., et al., "Mitochondrial uncoupling, with low concentalion FCCP, induces ROS-dependent cardioprotection independent of KATP channel activation," Cardiovascular Research 72:313-321 (2006).
Bryant, H. E., et al., "Specific killing of BRCA2-deficient tumours with inhibitors of poly(ADP-ribose) polymerase," Nature 434:913-917 (2005).
Cadenas, E., et al., "Enhancement of hydrogen peroxide formation by protophores and ionophores in antimycin-supplemented mitochondria," Biochem. J. 188:31-37 (1980).
Cassidy-Stone, A., et al., "Chemical inhibition of the mitochondrial division dynamin reveals its role in Bax/Bak-dependent mitochondrial outer membrane permeabilization," Dev. Cell 14(2):193-204 (2008).
Cecchini, G., et al., "Function and structure of complex II of the respiratory chain," Annu. Rev. Biochem. 72:77-109 (2003).
Chan, D. C., "Mitochondria: Dynamic organelles in disease, aging, and development," Cell 125:1241-1252 (2006).
Chang, H. Y., et al., "Robustness, scalability, and integration of a wound-response gene expression signature in predicting breast cancer survival," PNAS 102(10):3738-3743 (2005).
Cheng, P. N.M., et al., "Pegylated recombinant human arginase (rhArg-peg5,000mw) inhibits the in vitro and in vivo proliferation of human hepatocellular carcinoma through arginine depletion," Cancer Res. 67(1):309-317 (2007).
Chou, T.C., et al., "Quantitative analysis of dose-effect relationships: the combined effects of multiple drugs or enzyme inhibitors," Advances in Enzyme Regulation 22:27-55 (1984).
Chou, T.C., "Theoretical basis, experimental design, and computerized simulation of synergism and antagonism in drug combination studies," Pharmacol. Rev. 58(3):621-681 (2006).
Dang, C. V., "Relinking the Warburg effect with Myc micromanaging glutamine metabolism," Cancer Res. 70 (3):859-862 (2010).
Deberardinis, R. J., et al., "Cellular metabolism and disease: what do metabolic outliers teach us?" Cell 148 (6):1132-1144 (2012).

(56) References Cited

OTHER PUBLICATIONS

Delage, B., et al., "Promoter methylation of argininosuccinate synthetase-1 sensitises lymphomas to arginine deiminase treatment, autophagy and caspase-dependent apoptosis," Cell Death and Disease 3:e342 (2012).
Denko, N. C., "Hypoxia, HIF1 and glucose metabolism in the solid tumour," Nat. Rev. Cancer 8:705-713 (2008).
Ding, W.X., et al., "Parkin and mitofusins reciprocally regulate mitophagy and mitochondrial spheroid formation," J. Biol. Chem. 287(50):42379-42388 (2012).
Ensor, C. M., et al., "Pegylated arginine deiminase (ADI-SS PEG20,000 mw) inhibits human melanomas and hepatocellular carcinomas in vitro and in vivo," Cancer Res. 62:5443-5450 (2002).
Farmer, H., et al., "Targeting the DNA repair defect in BRCA mutant cells as a therapeutic strategy," Nature 434:917-921 (2005).
Feun, L., et al., "Arginine deprivation as a targeted therapy for cancer," Curr. Pharm. Des. 14(11):1049-1057 (2008).
Forman, H. J., et al., "Role of superoxide radical in mitochondrial dehydrogenase reactions," Biochem. Biophys. Res. Commun. 60(3):1044-1050 (1974).
Frezza, C., et al., "Mitochondria in cancer: Not just innocent bystanders," Seminars in Cancer Biology 19:4-11 (2009).
Fujiwara, Y., et al., "Discovery of a novel type of autophagy targeting RNA," Autophagy 9(3):403-409 (2013).
Fujiwara, Y., et al., "Direct uptake and degradation of DNA by lysosomes," Autophagy 9(8):1167-1171 (2013).
Gimenez-Xavier, P., et al., "Effects of dopamine on LC3-II activation as a marker of autophagy in a neuroblastoma cell model," NeuroToxicology 30:658-665 (2009).
Glazer, E. S., et al., "Phase II study of pegylated arginine deiminase for nonresectable and metastatic hepatocellular carcinoma," J. Clin. Oncol. 28(13):2220-2226 (2010).
Gong, H., et al., "Arginine deiminase inhibits proliferation of human leukemia cells more potently than asparaginase by inducing cell cycle arrest and apoptosis," Leukemia 14:826-829 (2000).
Hatch, E. M., et al., "Catastrophic nuclear envelope collapse in cancer cell micronuclei," Cell 154(1):47-60 (2013).
Hirayama, A., et al., "Quantitative metabolome profiling of colon and stomach cancer microenvironment by capillary electrophoresis time-of-flight mass spectrometry," Cancer Res. 69(11):4918-4925 (2009).
Hsueh, E. C., et al., "Deprivation of arginine by recombinant human arginase in prostate cancer cells," J. Hematol. Oncol. 5:17 (2012).
Huang, C.C., et al., "Arginine deprivation as a new treatment strategy for head and neck cancer," Oral Oncol. 48:1227-1235 (2012).
Huang, H.Y., et al., "ASS1 as a novel tumor suppressor gene in myxofibrosarcomas: Aberrant loss via epigenetic DNA methylation confers aggressive phenotypes, negative prognostic impact, and therapeutic relevance," Cancer Res. 19(11):2861-2872 (2013).
Husson, A., et al., "Argininosuccinate synthetase from the urea cycle to the citrulline-NO cycle," Eur. J. Biochem. 270:1887-1899 (2003).
Izzo, F., et al., "Pegylated arginine deiminase treatment of patients with unresectable hepatocellular carcinoma: Results from phase I/II studies," J. Clin. Oncol. 22(10):1815-1822 (2004).
Jemal, A., et al., "Global cancer statistics," CA Cancer J. Clin. 61:69-90 (2011).
Kalyanaraman, B., et al., "Measuring reactive oxygen and nitrogen species with fluorescent probes: challenge and limitations," Free Radic. Biol. Med. 52(1):1-6 (2012).
Kami, K., et al., "Metabolomic profiling of lung and prostate tumor tissues by capillary electrophoresis time-of-flight mass spectrometry," Metabolomics 9:444-453 (2013).
Kang, R., et al., "The Beclin 1 network regulates autophagy and apoptosis," Cell Death and Differentiation 18:571-580 (2011).
Kelly, M.P., et al., "Arginine deiminase PEG20 inhibits growth of small cell lung cancers lacking expression of argininosuccinate synthetase," Br. J. Cancer 106:324-332 (2012).
Kim, J.W., et al., "Cancer's molecular sweet tooth and the Warburg effect," Cancer Res. 66(18):8927-8930 (2006).
Kim, R. H., et al., "ADI, autophagy and apoptosis: Metabolic stress as a therapeutic option for prostate cancer," Autophagy 5(4):567-568 (2009).
Kim, R. H., et al., "Arginine deiminase as a novel therapy for prostate cancer induces autophagy and caspase-independent apoptosis," Cancer Res. 69(2):700-708 (2009).
Ascierto, P. A., et al., "Pegylated Arginine Deiminase Treatment of Patients with Metastatic Melanoma: Results from Phase I and II Studies," J. Clin. Oncol. 23:7660-7668 (2005).
Dillon, B. J., et al., "Incidence and Distribution of Argininosuccinate Synthetase Deficiency in Human Cancers. A Method for Identifying Cancers Sensitive to Arginine Deprivation," Cancer 100:826-833 (2004).
European Patent Office, Extended Search Report and Opinion dated Feb. 22, 2017 for European Application No. 14850304.8.
Kolaric, K., et al., "Phase-II Clinical Trial of 4'-Epi-Doxorubicin in Metastatic Solid Tumors," J. Cancer Res. Clin. Oncol. 106:148-152 (1983).
Polaris Group, "Ph 1 ADI-PEG 20 Plus Doxorubicin; Patients With HER2 Negative Metastatic Breast Cancer," NCT01948843, accessed at www.clinicaltrials.gov.
You, M., et al., "Abstiact 61: Enhancing Arginine Deprivation Therapy in Melanoma by Combining with Cisplatin," Cancer Res. Cell. Mol. Biol. 70(8 Suppl):Abstract nr61 (2010).
Kang, T.S., et al., "A randomised phase II study of pegylated arginine deiminase (ADI-PEG 20) in Asian advanced hepatocellular carcinoma patients," Br. J. Cancer 103:954-960 (2010).
Yoon, C.Y., et al., "Renal cell carcinoma does not express argininosuccinate synthetase and is highly sensitive to arginine deprivation via arginine deiminase," Int. J. Cancer 120:897-905 (2006).
Youle, R. J., et al., "Mitochondrial fission, fusion, and stress," Science 337(6098):1062-1065 (2012).
Youle, R. J., et al., "Mechanisms of mitophagy," Nat. Rev. Mol. Cell Biol. 12(1):9-14 (2011).
Yue, Z., et al., "Beclin 1, an autophagy gene essential for early embryonic development, is a haploinsufficient tumor suppressor," PNAS 100(25):15077-15082 (2003).

* cited by examiner

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
gaggatgcct gaattctaca                                               20

<210> SEQ ID NO 2
<211> LENGTH: 18
<212> TYPE: DNA
<213> ORGANISM: Artificial Sequence
<220> FEATURE:
<223> OTHER INFORMATION: reverse primer

<400> SEQUENCE: 2
gttggtcacc ttcacagg                                                 18

<210> SEQ ID NO 3
<211> LENGTH: 20
<212> TYPE: DNA
<213> ORGANISM: Artificial Sequence
<220> FEATURE:
<223> OTHER INFORMATION: forward primer

<400> SEQUENCE: 3
cgagcagaag gaaagtaatg                                               20

<210> SEQ ID NO 4
<211> LENGTH: 19
<212> TYPE: DNA
<213> ORGANISM: Artificial Sequence
<220> FEATURE:
<223> OTHER INFORMATION: reverse primer

<400> SEQUENCE: 4
```
agcaggataa cagatgagt                                                19

<210> SEQ ID NO 5
<211> LENGTH: 21
<212> TYPE: DNA
<213> ORGANISM: Artificial Sequence
<220> FEATURE:
<223> OTHER INFORMATION: forward primer

<400> SEQUENCE: 5
agttcaatgg tggtggtcat a                                             21

<210> SEQ ID NO 6
<211> LENGTH: 21
<212> TYPE: DNA
<213> ORGANISM: Artificial Sequence
<220> FEATURE:
<223> OTHER INFORMATION: reverse primer

<400> SEQUENCE: 6
caatccccag cagtggaata a                                             21

<210> SEQ ID NO 7
<211> LENGTH: 20
<212> TYPE: DNA
<213> ORGANISM: Artificial Sequence
<220> FEATURE:
<223> OTHER INFORMATION: forward primer

<400> SEQUENCE: 7
acgctggcga ggacgacctg                                               20

<210> SEQ ID NO 8
<211> LENGTH: 22
<212> TYPE: DNA
<213> ORGANISM: Artificial Sequence
<220> FEATURE:
<223> OTHER INFORMATION: reverse primer

<400> SEQUENCE: 8
gcttcttgcg ctctgagtgc tc                                            22

<210> SEQ ID NO 9
<211> LENGTH: 22
<212> TYPE: DNA
<213> ORGANISM: Artificial Sequence
<220> FEATURE:
<223> OTHER INFORMATION: forward primer

<400> SEQUENCE: 9
tagacacgct ggaacaggtt gc                                            22

<210> SEQ ID NO 10
<211> LENGTH: 22
<212> TYPE: DNA
<213> ORGANISM: Artificial Sequence
<220> FEATURE:
<223> OTHER INFORMATION: reverse primer

<400> SEQUENCE: 10
ctcctcgtac agcttcacag tc                                            22

<210> SEQ ID NO 11
<211> LENGTH: 23
<212> TYPE: DNA
<213> ORGANISM: Artificial Sequence

```
<220> FEATURE:
<223> OTHER INFORMATION: forward primer

<400> SEQUENCE: 11
ctgcggaact tattctccca gac                                           23

<210> SEQ ID NO 12
<211> LENGTH: 22
<212> TYPE: DNA
<213> ORGANISM: Artificial Sequence
<220> FEATURE:
<223> OTHER INFORMATION: reverse primer

<400> SEQUENCE: 12
ccaccaaaca gatgactctg cg                                            22

<210> SEQ ID NO 13
<211> LENGTH: 22
<212> TYPE: DNA
<213> ORGANISM: Artificial Sequence
<220> FEATURE:
<223> OTHER INFORMATION: forward primer

<400> SEQUENCE: 13
ccctggaaac tacaagccca ac                                            22

<210> SEQ ID NO 14
<211> LENGTH: 22
<212> TYPE: DNA
<213> ORGANISM: Artificial Sequence
<220> FEATURE:
<223> OTHER INFORMATION: reverse primer

<400> SEQUENCE: 14
gcagaggcaa aggttccatg ag                                            22

<210> SEQ ID NO 15
<211> LENGTH: 22
<212> TYPE: DNA
<213> ORGANISM: Artificial Sequence
<220> FEATURE:
<223> OTHER INFORMATION: forward primer

<400> SEQUENCE: 15
gtggatgctt tgcacaccaa gg                                            22

<210> SEQ ID NO 16
<211> LENGTH: 22
<212> TYPE: DNA
<213> ORGANISM: Artificial Sequence
<220> FEATURE:
<223> OTHER INFORMATION: reverse primer

<400> SEQUENCE: 16
ggttcaggac ttggaaacgc tc                                            22

<210> SEQ ID NO 17
<211> LENGTH: 23
<212> TYPE: DNA
<213> ORGANISM: Artificial Sequence
<220> FEATURE:
<223> OTHER INFORMATION: forward primer

<400> SEQUENCE: 17
gtccacacga aaccagattt gcc                                           23
```

```
<210> SEQ ID NO 18
<211> LENGTH: 22
<212> TYPE: DNA
<213> ORGANISM: Artificial Sequence
<220> FEATURE:
<223> OTHER INFORMATION: reverse primer

<400> SEQUENCE: 18
tcctctgaag gtcggaacac ca                                              22

<210> SEQ ID NO 19
<211> LENGTH: 22
<212> TYPE: DNA
<213> ORGANISM: Artificial Sequence
<220> FEATURE:
<223> OTHER INFORMATION: forward primer

<400> SEQUENCE: 19
tggcagtctt ccagtgtggt gt                                              22

<210> SEQ ID NO 20
<211> LENGTH: 22
<212> TYPE: DNA
<213> ORGANISM: Artificial Sequence
<220> FEATURE:
<223> OTHER INFORMATION: reverse primer

<400> SEQUENCE: 20
cgctctcaaa ggtggtgtcg aa                                              22

<210> SEQ ID NO 21
<211> LENGTH: 22
<212> TYPE: DNA
<213> ORGANISM: Artificial Sequence
<220> FEATURE:
<223> OTHER INFORMATION: forward primer

<400> SEQUENCE: 21
tggagtgtgg acactgcttc ag                                              22

<210> SEQ ID NO 22
<211> LENGTH: 22
<212> TYPE: DNA
<213> ORGANISM: Artificial Sequence
<220> FEATURE:
<223> OTHER INFORMATION: reverse primer

<400> SEQUENCE: 22
ccgtcacagt tctgagacac ca                                              22

<210> SEQ ID NO 23
<211> LENGTH: 21
<212> TYPE: DNA
<213> ORGANISM: Artificial Sequence
<220> FEATURE:
<223> OTHER INFORMATION: forward primer

<400> SEQUENCE: 23
ccccttcatt gacctcaact a                                               21

<210> SEQ ID NO 24
<211> LENGTH: 20
<212> TYPE: DNA
<213> ORGANISM: Artificial Sequence
<220> FEATURE:
<223> OTHER INFORMATION: reverse primer
```

```
<400> SEQUENCE: 24
ctcctggaag atggtgatgg                                                    20

<210> SEQ ID NO 25
<211> LENGTH: 21
<212> TYPE: DNA
<213> ORGANISM: Artificial Sequence
<220> FEATURE:
<223> OTHER INFORMATION: forward primer

<400> SEQUENCE: 25
cgtctgccct atcaactttc g                                                  21

<210> SEQ ID NO 26
<211> LENGTH: 22
<212> TYPE: DNA
<213> ORGANISM: Artificial Sequence
<220> FEATURE:
<223> OTHER INFORMATION: reverse primer

<400> SEQUENCE: 26
ggatgtggta gccgtttctc ag                                                 22
```

METHODS FOR TREATING BREAST AND OTHER CANCERS BY TARGETING ARGININOSUCCINATE SYNTHETASE 1-DEFICIENCY

PRIORITY CLAIM

This application is a continuation of International Application No. PCT/US14/59196, filed Oct. 3, 2014, which claims priority to U.S. Provisional Patent Application No. 61/887,304, filed Oct. 4, 2013, the subject matter of which is hereby incorporated by reference as if fully set forth herein.

STATEMENT OF GOVERNMENT INTEREST

This invention was made with Government support under Grant Numbers R01DE10742 and R01DE14183, awarded by the National Institutes of Health. The Government has certain rights in the invention.

BACKGROUND

Breast cancer is one of the most common cancers that kill women (Jemal et al. 2011). Gene expression analyses of breast cancer have identified five intrinsic molecular "subtypes" (normal-like, luminal A, luminal B, basal and HER2 positive), each of which has unique clinical and histological phenotypes (Parous et al. 2000; Sorlie, et al. 2001). Currently, breast cancers are subtyped so that different treatments can be tailored for maximizing therapeutic benefit. However, it is still estimated that 39,620 women and 410 men will die of breast cancer in the United States in 2013 (Society 2013). Therefore, it is necessary to identify new therapeutic targets, especially for treatment-refractory tumors.

Altered cellular metabolism has emerged as a common phenotype of cancers and other complex diseases (DeBerardinis & Thompson 2012). Cancer cells adapt their metabolic pathways to meet the high-energy demands required for their accelerated growth and proliferation and the associated metabolic stresses. Metabolomic studies have revealed that the steady-state abundance of many amino acids in stomach, colon, lung and prostate cancers are higher than in the corresponding normal tissue, suggesting the tumors have increased biosynthetic needs for amino acids (Hirayama et al. 2009; Kami et al. 2013). For example, some tumor cells are addicted to glutamine because it supports anabolic processes and fuels proliferation (Wise & Thompson 2010; Vander Heiden et al. 2009). The serine and glycine biosynthetic pathways have also been suggested to play critical roles in oncogenesis (Locasale et al. 2011; Possemato et al. 2011). However, little is known about the metabolic requirements for cell growth and proliferation of breast cancer (BC). Thus, it would be desirable to determine and exploit distinct metabolic requirements of BCs in hopes of identifying impaired metabolic pathways that can be targeted for BC treatment.

SUMMARY

In one embodiment, methods for killing one or more argininosuccinate synthetase 1 (ASS1)-deficient cancer cells (e.g., one or more breast cancer cells) are provided. Such methods may include a step of contacting the one or more ASS1-deficient cancer cells (e.g., breast cancer cells) with an effective amount of an arginine-depleting agent.

In another embodiment, methods for treating an arginine-auxotrophic cancer (e.g., arginine-auxotrophic breast cancer) in a subject are provided. Such methods may include a step of administering a therapeutically effective amount of a pharmaceutical composition to the subject. In some aspects, the pharmaceutical composition includes an arginine-depleting agent and a carrier.

In another embodiment, methods for optimizing treatment of breast cancer in a subject are provided. In some embodiments, these methods may include steps of detecting an expression level of ASS1 in a breast tumor tissue sample from the subject, identifying the subject as a responsive subject when the expression level of ASS1 is at or below a low level of ASS1 and administering a therapeutically effective amount of a pharmaceutical composition to the responsive subject. In some aspects, the pharmaceutical composition includes an arginine-depleting agent and a carrier.

BRIEF DESCRIPTION OF THE DRAWINGS

FIG. 1A shows different breast cancer cell lines and immortalized MCF-10A cells are with distinct ASS1 abundance. ASS1 mRNA abundance was analyzed by quantitative RT-PCR (qRT-PCR; upper panel) and ASS1 protein abundance was assessed by Western blotting (lower panel). GAPDH message or GAPDH protein abundance was used to normalize qRT-PCR results or to assure equal loading; N=3. FIG. 1B shows an inverse correlation between ASS1 protein abundance and cytotoxic effects of ADI-PEG20 on four breast cancer cell lines; N=4. FIG. 1C shows that the anchorage-independent growth of MDA-MB-231 cells is affected by ADI-PEG20 (left). Quantified bar graph is shown in the right. N=6. FIG. 1D shows that overexpression of ASS1 increases the $IC_{50}$ of ADI-PEG20 in MDA-MB-231 cells from 0.2 µg/ml to 0.3 µg/ml; N=3. FIG. 1E shows that knockdown of ASS1 abundance decreases $IC_{50}$ of ADI-PEG20 in T47D cells (from over 0.4 µg/ml to 0.075 µg/ml); N=3. FIG. 1F shows that knockdown of ASS1 abundance sensitizes MCF-7 cells to ADI-PEG20 in colony formation assays (left panel). Bar graph is shown in the right panel; N=6. FIGS. 1C and 1F are representative images show total colony area or a selected area of colony growth (enlarged; insets) on day 28. Viability and qRT-PCR data are shown as mean±SD; *: $p<0.05$.

FIG. 2A shows that MDA-MB-231 cell proliferation is sensitive to ADI-PEG20-treatment in time course growth assays. The respective cell index at 0 hour treatment is designated as 1; N=5 sets of cells. FIGS. 2B and 2C show that ASS1-overexpressing MDA-MB-231/ASS1 (FIG. 2B) and ASS1-knockdown T47D (T47D/sh-ASS1) cells (FIG. 2C) were established by lentiviral transduction. The abundance of ASS1 mRNA and ASS1 protein were confirmed by qRT-PCR and Western blot analyses, respectively. FIGS. 2D and 2E show that knockdown of ASS1 sensitizes T47D cells to ADI-PEG20-treatment analyzed by time course growth assays (FIG. 2D) and anchorage-independent colony formation (FIG. 2E). The relative cell proliferation in FIG. 2D is plotted against the tracing from respective cells at 0 hour treatment; N=5 sets of cells. Representative images in FIG. 2E show overall view of total colony area or a selected area of colony growth (enlarged; insets) on day 28. The number of colonies from three independent experiments were calculated and plotted as a bar graph (right); N=3 independent experiments performed in duplicate; *:p<0.05. FIG. 2F shows that qRT-PCR and Western blots of ASS1 mRNA and ASS1 protein abundancies in MCF-7 cells showing a 90% decrease in mRNA abundance, but only 50% decrease in protein abundance. The relative ASS1 mRNA abundance is calculated as described in FIG. 1A. qRT-PCR data were collected from three independent experiments and shown as mean±SD; N=3 sets of cells.

(FIG. 3A) ADI-PEG20 treatment or arginine starvation moderately increases apoptotic cell percentage in MDA-MB-231 cells. Knockdown of ATG5 in MDA-MB-231 cells does not significantly affect response to ADI-PEG20 or arginine starvation. Histograms are presented as mean±SD; N=3. FIG. 3B shows representative images of GFP-LC3 puncta formation (indicated by arrows) using fluorescence microscopy; N=5. Bar: 50 μm. FIG. 3C shows that ADI-PEG20 induces LC3 lipidation, which is reversed by bafilomycin A1, a vacuolar type V-ATPase inhibitor. One representative Western is shown; N=3. The relative level of LC3-II, after normalization with actin, is shown in italic with the normalized densitometric tracing value at 0 hour as 1. FIG. 3D shows that ADI-PEG20 induces autophagic flux. MDA-MB-231 cells over-expressing GFP-LC3 were treated with ADI-PEG20 for indicated time periods and analyzed by flow cytometry (left panel). Data are shown as the mean±SD (right panel): N=3*: p<0.05. FIGS. 3E and 3F show a knockdown of ATG5 (FIG. 3E) or BECLIN 1 (FIG. 3F) abundance reduces ADI-PEG20-induced cytotoxicity. N=3; *: p<0.05.

FIG. 4A shows that ADI-PEG20 treatment (middle panels) or arginine starvation (right panels) moderately increases apoptotic cell percentage in MDA-MB-231 cells. Knockdown of ATG5 in MDA-MB-231 cells does not significantly affect annexin V/PI profiling in response to ADI-PEG20-treatment or arginine-starvation (lower panels). Representative images are shown; N=5 sets of cells. FIG. 4B shows the reduced abundance of autophagy proteins, ATG5 and BECLIN 1, in their respective knockdown cells, verified by Western analyses. FIGS. 4C and 4D show that autophagy is employed for growth inhibition by ADI-PEG20 (FIG. 4C) and arginine-deprivation (FIG. 4D). Representative phase contrast images of arginine-starved MDA-MB-231 cells show marked morphological changes that are not seen ATG5-knockdown MDA-MB-231 cells (MDA-MB-231/sh-ATG5 cells). Bar: 200 mm and 50 mm (zoomed). N=3 sets of cells. FIG. 4E shows that chloroquine (an autophagy inhibitor), but not rapamycin (an autophagy inducer), affects ADI-PEG20-induced cell death. The relative cell viability showing in percentage is determined by ACP assay and uses the value from 0 μg/ml treatment as the reference. Results are shown as the mean±SD; N=5 sets of cells; *: p<0.05.

FIG. 5A shows that Autophagy-dependent ATP concentration decreases over time in ADI-PEG20-treated MDA-MB-231 cells; N=3; *: p<0.05. FIG. 5B shows that a combination of ADI-PEG20 and autophagy ATG5 gene context regulates the basal and maximal mitochondrial respiration. The tracing revealed ATG5 knockdown partially rescued the maximal respiration stimulated by FCCP in MDA-MB-231 cells treated with ADI-PEG20; N=3. FIG. 5C shows that extracellular arginine reverses the reduced cell proliferation induced by ADI-PEG20 in a dose-dependent manner; N=5; *: p<0.05. FIG. 5D shows that ADI-PEG20 treatments reversibly suppress the abundance of mRNAs encoding mitochondrial respiratory chain proteins (left panel). A list of top candidates includes messages encoding proteins of complex I (shown in blue) and complex II (shown in orange). Other messages shown in black are (UQCRFS1, complex III), (COX5A, complex IV) and (ATP5G1 and ATP5J2, complex V). Arginine supplementation rescued ASS1 message and protein abundance in ADI-PEG20-treated MDA-MB-231 cells (right panel), serving as the control to verify the effectiveness of arginine supplementation. ATP5L (complex V) messages increased in response to ADI-PEG20, then decreased in response to the addition of arginine. FIG. 5E shows that succinate rescues the cytotoxic effect of ADI-PEG20. Data are shown as the mean±SD; N=3; *: p<0.05. FIG. 5F shows that knockdown of ASS1 suppresses basal and uncoupled mitochondrial OCR in T47D cells; N=3.

In FIG. 6A, OCR was normalized using cell numbers and is shown as the mean±SD; N=3 sets of cells. FIG. 6B shows that glutamine supplementation does not rescue the cytotoxic effect induced by ADI-PEG20. Cell viability was determined using the value from cells treated with vehicle (ADI-PEG20 (0 μg/ml) and glutamine (4 mM) set as 1. Results are shown as the mean±SD; N=3 sets of cells. FIG. 6C shows that supplementation of arginine rescues OCR in ADI-PEG20-treated cells. OCR was normalized using cell numbers and is shown as the mean±SD; N=3 sets of cells. FIG. 6D illustrates that succinate reverses the ADI-PEG20-induced growth inhibition. MDA-MB-231 and corresponding ATG5-knockdown cells were treated with the indicated combinations of ADI-PEG20 and succinate. Cell viability was determined by ACP assay using the value from cells treated with vehicle (ADI-PEG20 (0 μg/ml) and succinate (0 mM)) set as 1. Results are shown as the mean±SD; N=3 sets of cells.

FIGS. 7A-C show that ADI-PEG20 increases ROS. Respective DCFDH oxidation (FIG. 7A), MitoSox Red oxidation (FIG. 7B) and mitochondria membrane potential (MMP) (FIG. 7C) were determined by flow cytometry after staining with DCFDA, MitoSOX Red and DiOC6, respectively. Data are shown as the mean±SD; N=3; *: p<0.05. (FIG. 7D) Representative Western blot shows that autophagy promotes ADI-PEG20-induced decrease of the mitochondrial protein Cyclophilin D, TOM20, COX IV and SIRT3 abundance in MDA-MB-231 cells; N>3. Equal amounts of whole cell lysates were analyzed by Western blot for the indicated mitochondrial proteins. FIG. 7E shows that SIRT3 abundance governs ADI-PEG20 sensitivity. SIRT3 abundance was modified using lenti-viral system for both overexpression (+SIRT3) or knockdown (sh-SIRT3). Data are shown as the mean±SD; N=3; *: p<0.05. In FIGS. 7F and 47G, both SIRT3 and ASS1 are involved in regulating ROS production in ADI-PEG20-treated breast cancer cells. DCFDH oxidation was determined by flow cytometry after staining with DCFDA in MDA-MB-231, SIRT3-overexpressing MDA-MB-231 cells (FIG. 7F), and T47D and ASS1-underexpressing T47D cells (FIG. 7G). The positively stained population in vehicle-treated parental cells is designated as 1 to calculate relative oxidized DCF level. Data shown as mean±SD; N=5; *: p<0.05.

In FIG. 9A, mitochondrial fission was more noticeable after ADI-PEG20 treatment in MDA-MB-231 cells. Representative MitoTracker images (N=4 sets of cells) with zoomed (right) are shown. In FIG. 9B, ADI-PEG20 increases lipid droplet accumulation. Representative transition electron microscopy (TEM) micrographs from 10 images are shown. Boxed areas in upper panels are zoom images from below. Vehicle-treated MDA-MB-231 cells had normal mitochondria and intact cristae (left panels). A representative image shows a mitochondrion was wrapped with a double-membraned structure, as indicated by an arrow (lower right panel). An increase in the numbers of lipid droplets is also noticed. N: nucleus; M: mitochondria; LD: lipid droplet. Bar: 1 μm (upper panels) and 200 nm (lower panels); N=3 sets of cells.

FIG. 10A shows that GFP-LC3 puncta colocalize with MitoTracker. The number of GFP-LC3 puncta was highest in cells treated with ADI-PEG20 for 12 hours, and then they decreased after 24 hours treatment. Part of GFP-LC3 and MitoTracker signals are co-localized after ADI-PEG20 treatment. Zoom images are shown in the upper right corner (Merge). N=3; Bar: 5 μm. FIG. 10B shows representative confocal images of MDA-MB-231 cells treated with a combination of ADI-PEG20 and Mdivi1 for 24 hours and stained with an anti-TOM20 antibody (upper panel); N=3. Mitochondria lengths were measured and scored as: fragmented (<2 μm; arrowheads), intermediate (2 μm~3 μm; arrows) and filamentous (>3 μm, block arrows). The percentage of cells with indicated dominant mitochondrial morphologies was determined by dividing by the total number of counted cells as indicated (lower panel); Bar: 20 μm. Zoom images are shown in the insets (upper left); Bar: 10 μm. FIG. 10C shows representative TEM micrographs with damaged and swollen mitochondria upon treatment with ADI-PEG20 for 24 hour (indicated by arrows). Bar: 1 μm (upper panels) and 0.5 μm (lower panels). FIG. 10D shows representative images of Oil Red O staining after treatment with ADI-PEG20 for indicated time periods; N=4. The percentage of cells with the oil droplets were counted and determined as a percentage of the total number of examined cells. Bar: 10 μm; *: p<0.05.

FIG. 11A shows representative ASS1 immunohistochemical staining of 149 breast cancer biospecimens. Normal breast epithelium (left panels), breast cancer tumors with low ASS1 abundance (middle panel; score: 0 and 1) and breast cancer tumors with high ASS1 abundance (right panels; score: 2 and 3). Bar: 100 μm. FIG. 11B shows the results of a Kaplan-Meier analysis indicates that reduced ASS1 abundance in breast tumors is significantly associated with poor overall survival. FIG. 11C shows the Kaplan-Meier analysis shows low ASS1 abundance in breast tumors impacts disease-free survival. The sample number was reduced from 149 to 148 because a patient died before metastasis occurred. FIG. 11D shows representative images of tumors harvested from either vehicle- or ADI-PEG20-treated mice xenografted with MDA-MB-231 or corresponding ATG5-underexpressing cells. Magnification: 50×; bar: 1000 μm. FIG. 11E is a scatter plot of tumor weight measured at the end point of experiment. One dot represents one mouse with total of five mice per group, and "-" represents the average (145.4±28.4, 176.6±42.2, 92.4±28 and 185.8±18.9 mg, respectively; N=5; *: p<0.05). Statistical analysis showed a significant difference between with vehicle- or ADI-PEG20-treated MDA-MB-231 group and between ADI-PEG20-treated MDA-MB-231 and ATG5-knockdown MDA-MB-231 group. FIG. 11F shows a synergistic effect of ADI-PEG20 combined with doxorubicin. The combination index (CI) was 0.886 at ED50, 0.7 at ED75 and 0.566 at ED90, illustrating the synergistic effect (CI<0.9: synergism; 0.9<CI<1.1: additive; CI>1.1: antagonism); N=3. FIG. 11G is a proposed model depicting ADI-PEG20-induced cytotoxic killing. The location of the ADI-PEG20-induced alterations within mitochondrial and cell death pathways are indicated by the numbers inside blue crosses: respiration chain (1), membrane permeability (2), oxidative stress (3) and activation of excessive autophagy (4).

FIG. 12A shows the results of a Multivariate Cox analysis, indicating a reduced hazard ratio (HR) of ASS1-H in overall survival of breast cancer patients. FIG. 12B is a multivariate analysis that was used to adjust the HR for disease-free survival of patients with high ASS1-abundance breast tumors. A Kaplan-Meier analysis determined the survival of subgroups of patients with high or low ASS1 abundance breast tumors that were ER negative (FIG. 12C), PR negative (FIG. 12D), Ki-67 positive (FIG. 12E), HER2 negative (FIG. 12F) and HER2 positive (FIG. 12G). Multivariate Cox analysis was applied to further determine the relative disease-specific death risk (HR) in the above subgroups. The ASS1 HRs were based on high abundance versus low abundance. #: note that no HR is shown for patients who had breast cancers with high ASS1 abundance in the ER negative and HER2 positive subgroups because there were no breast cancer-associated deaths in those subgroups during the follow-up period. FIG. 12H shows that breast cancer specimens from patients with longer than five years of overall survival or disease-free survival have higher ASS1 mRNA abundance. Analyses were performed using microarray-determined ASS1 mRNA abundance and stratified with associated clinical data extracted from published NK1295 breast cancer data (57, 58) using shared software at ITTACA (http://bioinfo-out.curie.fr/ittaca). For Overall Survival, >5 years: n=231 and <5 years: n=61; for Disease-free Survival, >5 years: n=196 and <5 years: n=99; *: p<0.05.

FIG. 14A shows CWR22Rv1 cells that were treated with ADI-PEG20 and stained with propidium iodide (PI). The percentage of hypodiploid cells began to rise at 48-h, and significantly increased after 72-h. FIG. 14B is Western blotting showing the lack of Caspase 7, Caspase 8 and Caspase 9 activation in cells treated with ADI-PEG20. FIG. 14C is DAPI staining which reveals nuclear DNA before leakage at 24-h (early time points) and after leakage at 96-h and 120-h (late time points) post-treatment. FIG. 14D shows the same samples of FIG. 14C that were stained with another fluorescent DNA dye, DRAQ5. Cells were stained with plasma membrane marker, E-Cadherin, to reveal its boundary. Cells were treated with UV or Taxol (1 nM) to demonstrate the appearance of apoptotic body and mitotic catastrophe, respectively. Rapamycin (2 uM) treatment did not produce the same effect. FIG. 14E shows a prolonged incubation with arginine-depleted medium that also induced the same phenotype. FIG. 14F shows a Bar graph illustrating the positive increment of leaked DNA particles in population of cells showing the phenotype.

In FIG. 15A, E-cadherin staining in ADI-PEG20-treated cells (120 h) with DNA leakage phenotype reveals the complete cellular outline. White arrow indicates the leaked DNA localized within an intact cell (Upper Right). Additional Z-section images also show that both autophagosomes (GFP-LC3) and lysosomes (LysoTracker) colocalized with leaked DNA particle (white arrows) throughout all sections (Lower). In FIG. 15B, a similar phenotype could also be found in other prostate cancer cell line (PC3), pancreas cancer cell lines (Mia and L3.3), and a urinary bladder cancer cell line (UMUC3) with prolonged ADI-PEG20 treatment. Both Mia and UMUC3 cells are known to undergo caspase-dependent cell death with ADI-PEG20 treatment. Both cell lines were treated with 0.3 µg/mL ADI-PEG20 for 0, 24, 48, 72, and 96 h, and the DNA-leakage phenotype (yellow arrowhead) began to appear around 72 h.

FIG. 16A is a set of representative time-lapse images showing ADI-PEG20-treatment induces autophagy and facilitates the fusion of autophagosome (green) and lysosome (red, LysoTracker) into autophagolysosome (yellow). Outline: white. Estimated nucleus location: yellow line. FIG. 16B shows that prolonged ADI-PEG20-treatment induces abnormally-sized autophagosomes (green), which colocalize with lysosome (red) and leaked DNA (blue). FIG. 16C shows that ADI-PEG20-treatment induces autophagic flux with distinct kinetics. Mean GFP-LC3 intensity in each group was plotted as a bar graph. Data were collected from three independent experiments and are shown as mean±S.D.; *; p<0.05.

In FIG. 17A, the marked size difference, compared with normal autophagosome (thin white arrow at small bright green dots compared with thick white arrow), is indicated by a thick white arrow. Merged images showing leaked DNA particles (DAPI) colocalized with giant-sized autophagosomes (GFP-LC3) and lysosomes (LAMP1). In FIG. 17B, CWR22Rv1 cells were treated with 0.3 µg/mL ADI-PEG20 for 0, 24, 48, and 72 h. The abundance of LC3 and p62 were determined by Western blot analysis. There are no LC3 lipidation and p62 degradation but accumulation of LC3-I in CWR22Rv1 cells, suggesting the induction of an atypical autophagy by ADI-PEG20 treatment. CWR22Rv1 cells were treated with 0.3 µg/mL ADI-PEG20 for 0, 24, 48, and 72 h with or without BafA1 or the addition of 3-MA for 6 h before cell harvesting. The abundance of LC3 and p62 was determined by Western blot analysis.

FIG. 18A is an immunofluorescence analysis showing that histone H3, acetylated H2B and Ku70 were found associated with exo-nucleus DNA cluster. FIG. 18B is an immunofluorescence analysis of NUP98 (white), GFP-LC3 (green), lysosome (red) and DAPI (blue) showing that uniform NUP98 signals were both around and outside of nucleus, and colocalized with lysosome signal (white arrowheads). FIG. 18C is a TEM demonstrating that autophagosome could potentially fuse with the nuclear membrane (white arrow). FIG. 18D shows that autophagosomes were found in the close proximity of nucleus (red arrowhead, with higher magnification shown in inset). Nucleus membrane also showed partial breakages (Red line, ~150 nm). A typical nuclear pore complex has a thin layer of electron dense disc with an opening about 120 nm; however, it may appear smaller under Cryo-EM (35) (yellow arrowheads, 47 nm~53 nm). M: mitochondria; N: nucleus. FIG. 18E is a set of representative immunofluorescence images showing reduced lamin signals at site of excessive autophagy. FIG. 18F shows that abnormal nucleus membrane morphology was found in treated cells at later time points. Expansion of intramembrous space was observed between inner membrane and outer membrane (white arrows). One Representative cyro-EM image is shown in FIG. 18C, FIG. 18D and FIG. 18F. For FIGS. 18A-F, N=3.

FIG. 19C shows that colocalization of double-strand-break binding protein Ku70 with leaked DNA (white arrows) could be found in ADI-PEG20-treated cells at later time points.

FIG. 20A shows that ADI-PEG20-treatment suppresses basal oxygen consumption rate (OCR) and reserve capacity. The tracing revealed the basal OCR decreased in a time-dependent manner with the incubation of ADI-PEG20. FIGS. 20B-D show that ADI-PEG20 impairs mitochondrial membrane potential (MMP) and elevates reactive oxygen species (ROS). Respective MMP (FIG. 20B) CellROX oxidation (FIG. 20C), and MitoSox Red oxidation (FIG. 20D) were determined by flow cytometry after staining with DiOC6, DCFDA and MitoSOX Red. Data are collected from three independent experiments and shown as mean±S.D. *; p<0.05. FIG. 20E show an increase of 8-OHdG after ADI-PEG20-treatment. Data were collected from three independent experiments with mean± S.D.; *: p<0.05. FIG. 20F shows the ROS scavenger, NAC, attenuated DNA leakage phenotype (right panel, n>300), and formation of giant autophagosomes (left panel).

21A shows control, shATG5 and shBECLIN1-stably transfected CWR22Rv1 cells overexpressing GFP-LC3 (green) that were treated with ADI-PEG20 for 96-h, followed by staining with anti-γH2AX antibody (Red) and DAPI (blue). FIG. 21B shows approximately 120-150 cells that were analyzed for DNA leakage, γH2AX staining and autophagosome formation. Western blot of ATG5-ATG12 and BECLIN1 demonstrates the expression of these proteins in modified cells.

In FIG. 22A, CWR22Rv1/shATG5 and shBECLIN1 cells were treated with ADI-PEG20 (0.3 μg/mL) for 0, 24, 48, 72, and 96 h. The abundance of LC3 and p62 was determined by Western blot analysis. There was a little LC3-I accumulation in shATG5 and shBECLIN1 cells, which might be due to the incomplete knockdown. In FIG. 22B, CWR22Rv1 cells were treated with ADI+Bafilomycin A1 (100 nM) for 24, 28, 72, 96, and 120 h and stained with DAPI to reveal the nucleus. Nuclear morphology was evaluated under fluorescence microscope with DAPI. In FIG. 22C, the percentage of cells with chromatophagy was counted under fluorescence microscope. Addition of Bafilomycin A1 with ADI treatment can reduce occurrence of chromatophagy.

DETAILED DESCRIPTION

Figure 1A:
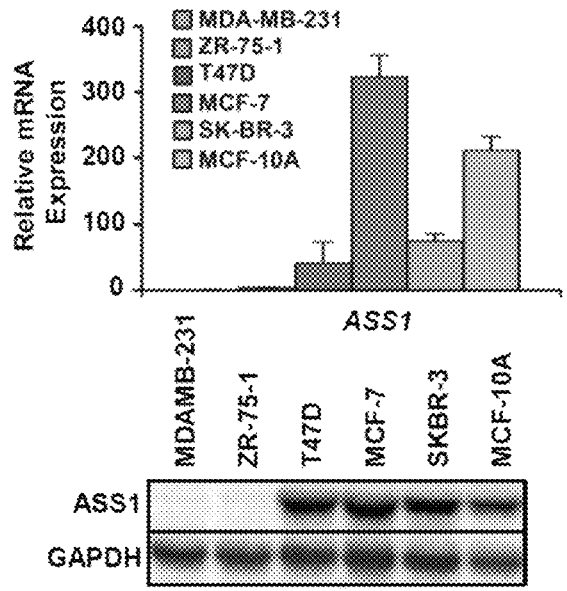
FIGS. 1A-F Illustrate that arginine starvation inhibits cell proliferation of ASS1-deficient breast cancer cells according to one embodiment.

Methods for treating an arginine auxotrophic cancer cells, and methods for determining a prognosis or progression of an arginine auxotrophic cancer are provided herein. Among the metabolic adaptations that occur in cancer cells is the increased use of the amino acid arginine to fuel anabolic processes. Arginine is a non-essential amino acid in humans, but it plays an important role in multiple metabolic pathways, including protein synthesis, and the production of nitric oxide, polyamines, urea, creatine, nucleotides, proline, glutamate, and agmatine (Wu & Morris 1998; Morris 2006). Arginine levels in cells are partly maintained by de novo synthesis from citrulline, which is converted to arginine by argininosuccinate synthetase 1 (ASS1) and argininosuccinate lyase (ASL). Accumulating evidence suggests that the endogenous production of arginine is not sufficient to meet the needs of rapidly proliferating tumor cells (Huller & Boos 1998; Husson et al. 2003; Wheatley & Campbell 2003; Ensor et al. 2002; Huang et al. 2012; Feun et al. 2008; Lind 2004). Thus, arginine may be considered a semi-essential amino acid under stress conditions, and "arginine auxotrophs" are cells that have lost the ability to synthesize arginine and are dependent on external arginine sources. Paradoxically, although there is an increased demand for arginine by tumor cells, many human tumor cells, including melanoma, lymphoma, glioma and prostate cancer, lose ASS1 abundance and become arginine auxotrophs (http://www.proteinatlas.org/ENSG00000130707). The biological mechanisms underlying this paradox are not completely understood and it may be that arginine auxotrophs have a previously overlooked metabolic liability that could be exploited to treat many cancers, including breast cancers. Thus, the analyses described herein not only improve understanding of the biology of ASS1 deficiencies in cancer development and recurrence, but may also lead to the development of therapies that target arginine-auxotrophic breast cancers.

In some embodiments, a method for killing argininosuccinate synthetase 1 (ASS1)-deficient cancer cells is provided. Such a method may be used to kill any cancer cells that are determined to be ASS1-deficient. In some embodiments, the methods are used to kill ASS1-deficient breast cancer cells. A "cancer cell," including specific cancer cells such as breast cancer cells, prostate cancer cells, melanoma cancer cells, or any other cancer cells specific to a particular tissue, may include any type of tumor cells, circulating tumor cells or a population of tumor cells that form a primary or metastatic solid tumor. Further, a tissue-specific cancer cell, such as a breast cancer cell may refer to any cell originating from a primary breast cancer, including any circulating or metastatic cells originating or derived from a primary breast cancer. For example, a breast cancer tumor may metastasize to the lungs or the brain, the cells of which may be referred to as breast cancer cells.

In some embodiments, a method for killing ASS1-deficient cancer cells may include, among other things, a step of contacting one or more ASS1-deficient breast cancer cells with an effective amount of an arginine-depleting agent. Arginine-depleting agents that may be used in accordance with the embodiments described herein may include any suitable isolated or recombinant molecule (e.g., enzyme, protein, antibody, peptide, ligand) or modified isolated or recombinant molecule (e.g., pegylation, molecule fragments) that acts to deplete arginine levels locally or systemically. The molecule may accomplish arginine depletion by any mechanism, including an enzymatic inhibition of arginine synthesis, stimulation of arginine breakdown, or by binding one or more target proteins responsible for arginine metabolism. In certain embodiments, the arginine depleting agent may be arginase I, arginase II, a recombinant arginase I or II, a pegylated arginase I or II, arginine deiminase (ADI), a recombinant ADI (rADI), a pegylated ADI, or a recombinant pegylated ADI. In one embodiment, the arginine depleting agent is a recombinant pegylated ADI known as ADI-PEG20.

Arginine deiminase (ADI) is a microbial enzyme originally isolated from *mycoplasma* that metabolizes arginine to citrulline and is 300-fold more effective than arginase at depleting arginine from the environment (Takaku et al. 1992; Beloussow et al. 2002; Kim et al. 2009a). Recombinant ADI has been used as a therapy to deprive arginine-auxotrophic tumors of external arginine, thereby inhibiting their growth. Sensitive tumors are usually ASS1-deficient, and therefore incapable of synthesizing endogenous arginine (Ensor et al. 2002; Szlosarek et al. 2006; Yoon et al. 2007; Cheng et al. 2007; Bowles et al. 2008; Kim et al. 2009b). Conversely, overexpressing ASS1 in ASS1-deficient melanoma cells confers resistance to ADI (Ensor et al. 2002; Tsai et al. 2009). Recombinant ADI-based therapies have been used in several clinical trials to treat advanced arginine-auxotrophic melanoma and hepatocellular carcinoma, and have had acceptable response rates and minimal side effects (Ascierto et al. 2005; Izzo et al. 2004; Glazer et al. 2010; Yang et al. 2010). However, besides arginine depletion, the mechanism by which ADI mediates its effect is unknown. Recombinant pegylated ADI (ADI-PEG20) is a form of ADI with increased safety and efficacy profiles. As described in the Examples below, a nutrient starvation approach, including arginine depletion (e.g., arginine depletion using ADI or ADI-PEG20), will induce autophagy in many cancer cells (Levine & Kroemer 2008; Mizushima & Komatsu 2011); though, the biological significance and consequence of autophagy induction in this context is not yet understood.

Autophagy can induce either survival or death in the same cell type in response to different stress conditions. For example, $H_2O_2$ induces autophagy for survival, whereas etoposide induces caspase-independent, autophagic cell death in Bax$^{-/-}$ Bak$^{-/-}$ MEFs (Narendra et al. 2008). Autophagy can also promote the survival of established tumors under stress conditions and in response to chemotherapy (reviewed in (Narendra et al. 2010) and references therein). However, some conflicting evidence suggests that autophagy and/or mitophagy can promote cell death (Ding et al. 2012; Vincow et al. 2013; Rardin et al. 2013; Ahn et al. 2008; Huang et al. 2013; Kobayashi et al. 2010; Warburg 1956). The Examples below demonstrate that, in response to arginine depletion by ADI-PEG20, cellular autophagy is induced. This is evidenced by the detection of the autophagic marker LC3-II, autophagosomes and autophagic flux in ADI-PEG20-treated cells. However, in several types of cancer cells other than BC, autophagy has been shown to be an early protective response against ADI-PEG20-induced arginine deprivation in several types of cancer cells other than BC.

In addition, autophagy and apoptosis may corroborate to kill cells in certain therapeutic contexts (Narendra et al. 2010; Trachootham et al. 2009). Mitophagy may selectively remove damaged mitochondria that cannot be repaired by fusion, or when fusion would harm other mitochondria (Farmer et al. 2005. The balance between autophagy and the extent of the mitochondrial damage may decide the fate of the ADI-PEG20-treated cells. If damaged mitochondria are limited to a fraction of mitochondria within the capacity of mitophagic removal, autophagy may play a pro-survival role. In contrast, if the number of damaged mitochondria is overwhelming, excessive mitophagy may be lethal or a death stimulus. Conceivably, if autophagy plays a protective role in ADI-PEG20-treated BC cells, inhibiting autophagy by knocking down components of autophagy machinery could increase the sensitivity of the cells to ADI-PEG20. However, the results described in the Examples below demonstrated that the knockdown of ATG5 or BECLIN 1 increased the resistance of MDA-MB-231 cells to ADI-PEG20 in vitro and in vivo, without affecting apoptosis. Therefore, it was determined that depletion of arginine by ADI-PEG20 induced excessive, lethal autophagy in these BC cells.

The arginine-depleting agent causes a reduction arginine levels in the environment surrounding and adjacent to the ASS1-deficient breast cancer cells, thereby killing the cells by starving the cells of arginine. As described further in the Example below, molecular determinants of sensitivity and resistance to arginine starvation therapy were identified. These determinants may be used to guide patient selection or the choice of agents to be given in combination. It was found that arginine starvation killed ASS1-deficient breast cancer cells by impairing mitochondrial energy production and increasing reactive oxygen species (ROS), which compromised mitochondrial integrity. The presence of damaged mitochondria triggered mitophagy and resulted in cell death. Further, ASS1-deficient breast cancer cell lines and mouse xenografts were susceptible to ADI-PEG20 only if they were autophagy competent. In addition, more than 60% of a random sample of 149 breast cancers had low abundance of ASS1 or no detectable ASS1, irrespective of the breast cancer molecular subtype. Thus, the mechanisms underlying the sensitivity of arginine auxotrophic breast cancer cells to arginine starvation were defined, and then the role of autophagy in this process was analyzed.

According to some embodiments, the one or more cancer cells (e.g., breast cancer cells) targeted by the arginine-depleting agent are part of solid tumor. As described in the Examples below, contact or treatment of a solid tumor using an arginine depleting agent (e.g., ADI-PEG20) causes the tumor to regress or shrink.

In another embodiment, a method of treating an arginine-auxotrophic cancer in a subject is provided. In certain embodiments, the method is for treating an arginine-auxotrophic breast cancer in a subject. A subject may be diagnosed as having an arginine-auxotrophic cancer—such as an arginine-auxotrophic breast cancer—by analyzing the level of expression of ASS1 in a tumor tissue sample from the subject (e.g., tissue from a biopsy or surgically resected sample). Any suitable method for detecting or determining the level of ASS1 expression may be used, including quantitative or qualitative methods known in the art such as immunostaining (e.g., immunohistochemistry, immunocytochemistry), hybridization methods, fluorescent staining, PCR, real time PCR, or RT-PCR. A tumor tissue may be determined to have a high ASS1 expression level where the sample is determined to have strong diffuse staining, or contains a significant number of transcripts. A tumor tissue sample is determined to have a low ASS1 expression level where the sample is determined to have weak cytoplasmic staining or no staining; or contains a relatively small number or a negligible number of transcripts. When a tumor tissue sample is determined to have a low ASS1 level, i.e., the tumor is determined to be ASS1-deficient, the tumor may be considered an arginine-auxotrophic tumor or an arginine-auxotrophic cancer.

In some embodiments, methods of treating arginine-auxotrophic cancer may include administering a therapeutically effective amount of an arginine depleting agent to a subject having the arginine auxotrophic cancer. As described above, arginine-depleting agents that may be used in accordance with the embodiments described herein may include any suitable isolated or recombinant molecule (e.g., enzyme, protein, antibody, peptide, ligand) or modified isolated or recombinant molecule (e.g., pegylation, molecule fragments) that acts to deplete arginine levels locally or systemically. The molecule may accomplish arginine depletion by any mechanism, including an enzymatic inhibition of arginine synthesis, stimulation of arginine breakdown, or by binding one or more target proteins responsible for arginine metabolism. In certain embodiments, the arginine depleting agent may be arginase I, arginase II, a recombinant arginase I or II, a pegylated arginase I or II, arginine deiminase (ADI), a recombinant ADI (rADI), a pegylated ADI, or a recombinant pegylated ADI. In one embodiment, the arginine depleting agent is a recombinant pegylated ADI known as ADI-PEG20.

The arginine depleting agent that may be used in accordance with the methods described herein may be administered by any suitable route of administration, alone or as part of a pharmaceutical composition. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

The term "effective amount" as used herein refers to an amount of an arginine depleting agent that produces a desired effect. For example, a population of cells may be contacted with an effective amount of an arginine depleting agent to study its effect in vitro (e.g., cell culture) or to produce a desired therapeutic effect ex vivo or in vitro. An effective amount of an arginine depleting agent may be used to produce a therapeutic effect in a subject, such as preventing or treating a target condition, alleviating symptoms associated with the condition, or producing a desired physiological effect. In such a case, the effective amount of an arginine depleting agent is a "therapeutically effective amount," "therapeutically effective concentration" or "therapeutically effective dose." The precise effective amount or therapeutically effective amount is an amount of the arginine depleting agent that will yield the most effective results in terms of efficacy of treatment in a given subject or population of cells. This amount will vary depending upon a variety of factors, including but not limited to the characteristics of the arginine depleting agent (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the arginine depleting agent is administered alone or in combination with a compound, drug, therapy or other therapeutic method or modality. One skilled in the clinical and pharmacological arts will be able to determine an effective amount or therapeutically effective amount through routine experimentation, namely by monitoring a cell's or subject's response to administration of an arginine depleting agent and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, Pa., 2005, which is hereby incorporated by reference as if fully set forth herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition.

In other embodiments, a method for optimizing treatment of an arginine-auxotrophic cancer is provided. In certain embodiments, the method is for optimizing treatment of an arginine-auxotrophic breast cancer in a subject. In some aspects, such a method may include a step of detecting an expression level of ASS1 in a breast tumor tissue sample from a subject. This expression level may be used to determine a subject's responsiveness to an arginine depleting agent like those described herein.

Detecting the expression level of ASS1 may be accomplished by analyzing the level of expression of ASS1 in a tumor tissue sample from the subject (e.g., tissue from a biopsy or surgically resected sample). Any suitable method for detecting or determining the level of ASS1 expression may be used, including quantitative or qualitative methods known in the art such as immunostaining (e.g., immunohistochemistry, immunocytochemistry), hybridization methods, fluorescent staining, PCR, real time PCR, or RT-PCR. A tumor tissue may be determined to have a high ASS1 expression level where the sample is determined to have strong diffuse staining, or contains a significant number of transcripts. A tumor tissue sample is determined to have a low ASS1 expression level where the sample is determined to have weak cytoplasmic staining or no staining; or contains a relatively small number or a negligible number of transcripts. According to one embodiment of the methods for optimizing treatment of an arginine-auxotrophic cancer described above, a subject may be identified as a responsive subject when the expression level of ASS1 is a low ASS1 expression level.

According to some embodiments of the method for optimizing treatment of an arginine-auxotrophic cancer, a therapeutically effective amount of an arginine-depleting agent, alone or as part of a pharmaceutical composition may be administered to a responsive subject. As described above, arginine-depleting agents that may be used in accordance with the embodiments described herein may include any suitable isolated or recombinant molecule (e.g., enzyme, protein, antibody, peptide, ligand) or modified isolated or recombinant molecule (e.g., pegylation, molecule fragments) that acts to deplete arginine levels locally or systemically. The molecule may accomplish arginine depletion by any mechanism, including an enzymatic inhibition of arginine synthesis, stimulation of arginine breakdown, or by binding one or more target proteins responsible for arginine metabolism. In certain embodiments, the arginine depleting agent may be arginase I, arginase II, a recombinant arginase I or II, a pegylated arginase I or II, arginine deiminase (ADI), a recombinant ADI (rADI), a pegylated ADI, or a recombinant pegylated ADI. In one embodiment, the arginine depleting agent is a recombinant pegylated ADI known as ADI-PEG20.

In some embodiments, an arginine depleting agent as described above may be administered in combination with one or more additional anti-cancer therapeutics (or "therapeutic agents"). "In combination" or "in combination with," as used herein, means in the course of treating the same disease in the same subject using two or more agents, drugs, treatment regimens, treatment modalities or a combination thereof, in any order. This includes simultaneous administration, as well as in a temporally spaced order of up to several days apart. Such combination treatment may also include more than a single administration of any one or more of the agents, drugs, treatment regimens or treatment modalities. Further, the administration of the two or more agents, drugs, treatment regimens, treatment modalities or a combination thereof may be by the same or different routes of administration.

Examples of additional anti-cancer therapeutics that may be administered in combination with an arginine depleting agent include, but are not limited to, chemotherapeutics (e.g., alkylating agents, antimetabolites, anti-tumor antibiotics, topoisomerase inhibitors, including anthracycline topoisomerase inhibitors, mitotic inhibitors); autophagy-modulating agents (e.g., rapamycin and chloroquine); hormones (e.g., corticosteroids); targeted therapeutics (e.g., selective estrogen receptor modulators (SERMs)); toxins; immune adjuvants, immunomodulators, and other immunotherapeutics (e.g., therapeutic antibodies and fragments thereof, recombinant cytokines and immunostimulatory molecules—synthetic or from whole microbes or microbial components); enzymes (e.g., enzymes to cleave prodrugs to a cytotoxic agent at the site of the tumor); nucleases; antisense oligonucleotides; nucleic acid molecules (e.g., mRNA molecules, cDNA molecules or RNAi molecules such as siRNA or shRNA); chelators; boron compounds; radioisotopes, photoactive agents and dyes. Examples of anthracycline topoisomerase inhibitors that may be administered in combination with an arginine depleting agent include, but are not limited to, doxorubicin, epirubicin, daunorubicin, and idarubicin. For example, in one embodiment, the arginine depleting agent may be administered in combination with doxorubicin. In certain embodiments, the arginine depleting agent may be administered in combination with a doxorubicin analog. Examples of the doxorubicin analogs that may be administered in combination with an arginine depleting agent include, but are not limited to, N-(5,5-Diacetoxypent-1-yl)doxorubicin (1 b), 4'-epidoxorubicin (epi-Dx), 4'-deoxy-doxorubicin (deoxy-Dx), 4'-O'methyldoxorubicin (O-Me-Dx), and N-(trifluoroacetyl) doxorubicin (FDOX). The therapeutic agent may also include a metal, metal alloy, intermetallic or core-shell nanoparticle bound to a chelator that acts as a radiosensitizer to render the targeted cells more sensitive to radiation therapy as compared to healthy cells.

As described in the Examples below, reduced or low expression of ASS1 is associated with poor survival, independent of a breast cancer molecular subtype. In contrast, it was shown that high levels of ASS1 is associated with a lower risk of breast cancer specific mortality. It was also shown that a low ASS1 expression is associated with advanced tumor stages. ASS1 engages a rate-limiting step in de novo arginine biosynthesis to maintain arginine serum levels. The results described below indicate that ASS1 expression is an independent prognostic indicator of BC survival. Altering ASS1 expression in isogenic BC cell lines, followed by performing clonogenic assays in vitro, confirmed ASS1's role in inhibiting anchorage-independent cell growth. In separate studies, reduced ASS1 expression was found to be an informative prognostic factor for lymphatic dissemination of esophageal cancer (Bryant et al. 2005). In addition, a gene microarray was used to compare the gene profile of osteosarcoma with and without pulmonary metastasis and found reduced ASS1 expression correlated with the occurrence of pulmonary metastasis and poor prognosis (Wang et al. 2011). Consistent with the results described, ASS1 has also been suggested as a novel tumor suppressor gene in myxofibrosarcomas and is highly correlated to disease-free survival and metastasis-free survival through epigenetic DNA methylation control (Wu et al. 2001). Thus ASS1 may have a tumor suppressor function during tumorigenesis of the cancers examined. The studies described in the Examples below indicate that arginine deprivation by ADI-PEG20-treatment damaged mitochondria and impaired mitochondrial bioenergetics. ASS1-deficient tumor cells could experience transient arginine deprivation due to insufficient angiogenesis during tumorigenesis. The ROS are produced during transient arginine deprivation and might cause genome instability, thereby facilitating tumorigenesis. Alternatively, the molecular mechanism underlying this anti-tumorigenic activity could be associated with ASS1's non-enzymatic function.

In some embodiments, ASS1 expression level may therefore be used to predict risk of cancer-specific mortality; advanced tumor progression; or overall or disease-free survival rate in a subject having cancer (e.g., breast cancer). In some embodiments, the subject may have an increased likelihood of overall or disease-free survival based upon a low level of ASS1 as determined by the methods described herein. In other embodiments, it may be determined that a subject is likely to have an advanced stage tumor based upon a low level of ASS1 expression as determined by the methods described herein. In further embodiments, it may be determined that a subject has a lower risk of cancer-specific mortality based upon a high level of ASS1 expression as determined by the methods described herein.

The following examples are intended to illustrate various embodiments of the invention. As such, the specific embodiments discussed are not to be construed as limitations on the scope of the invention. For example, although many of the examples are directed to breast cancer, one skilled in the art would understand that any arginine-auxotrophic cancer may be applicable to the methods described herein. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Arginine Starvation Impairs Mitochondrial Respiratory Function in ASS1-Deficient Breast Cancer Cells Materials and Methods Patients, Follow-Up and Tissue Array.

Patients included in this study were those diagnosed with breast cancer and treated by surgical resection. The history of each patient case was analyzed by haematoxylin and eosin (H&E)-stained slides by a breast pathologist using clinicopathological parameters. The clinicopathological parameters that were evaluated included patient age at the time of diagnosis, tumor node metastasis (TNM) stage, date of last follow-up and overall patient survival. Exclusion criteria were breast cancer samples from patients without a pathologic diagnosis, patients with multiple cancers, or patients who had lost contact after surgery. A total of 149 patients with breast cancer met the inclusion criteria. All participants were periodically followed-up and surgery relapse and death data were collected. Overall survival (OS) rate was calculated from the date of surgery to date of death by breast cancer-associated illness. Disease-free survival (DFS) rate was calculated from date of surgery to date of local recurrence or metastasis. If no death or relapse occurred, the OS and DFS rates were calculated from date of surgery to the end of the study. All of the formalin-fixed, paraffin-embedded (FFPE) breast cancer tissue samples that were collected were reassembled into multiple tissue arrays. Analysis indicated that ASS1 immunohistological signals did not correlate with storage time (likelihood, p=0.246), indicating the storage time would not affect the immunohistochemical outcome.

Immunohistochemistry (IHC).

Figure 6A:
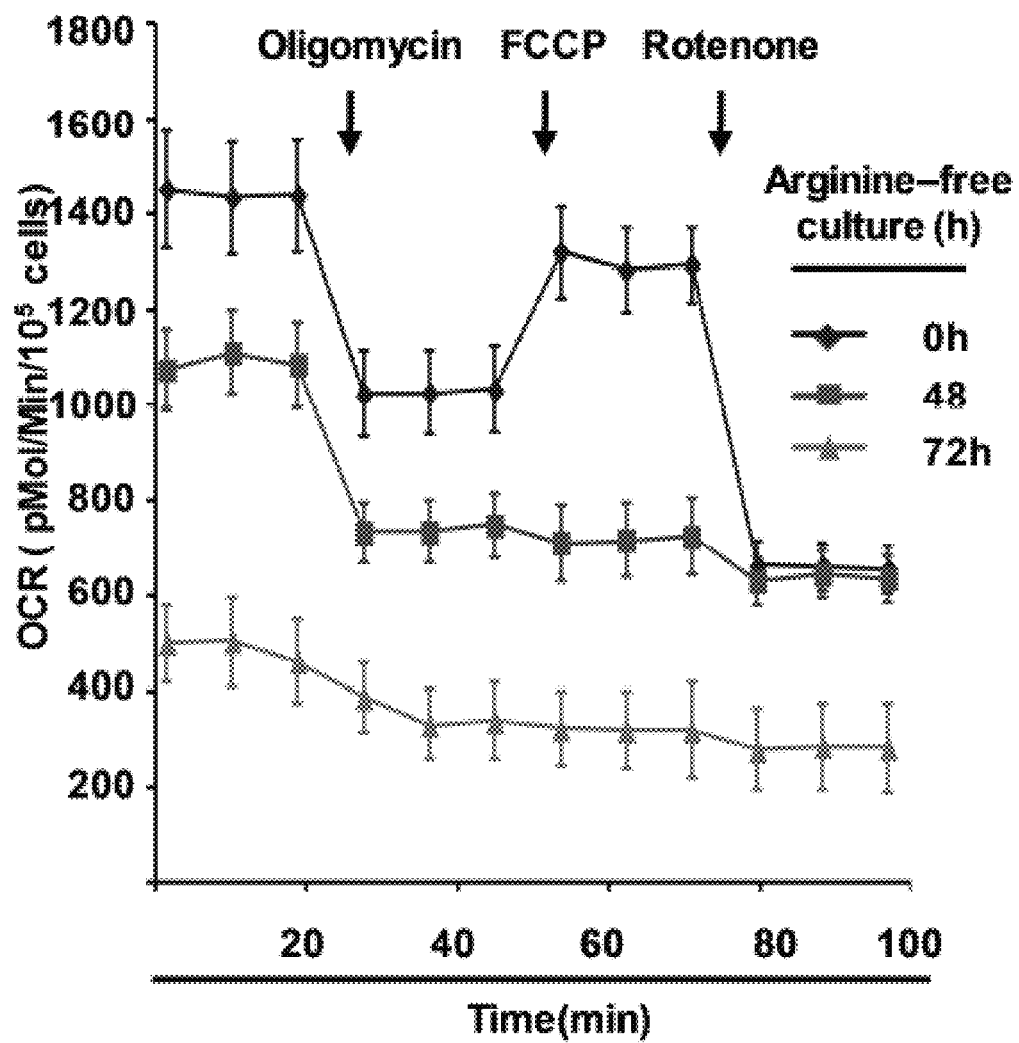
FIGS. 6A-D illustrate that arginine depletion suppresses the basal oxygen consumption rate and reserve capacity according to one embodiment.

ASS1 protein levels in the 149 breast cancer samples were assessed by IHC using an anti-ASS1 antibody (1:75 dilution) as previously described (Wu et al. 2011). The IHC conditions for ASS1 abundance determination were pre-optimized on checkerboards with multiple tissue samples. Briefly, after de-paraffinization, endogenous peroxidase activity was blocked by pre-treatment with 3% $H_2O_2$. The slides were incubated with normal goat serum for 20 minutes at room temperature (RT) to block non-specific signal, then incubated with the primary antibody for 20 minutes at RT. The array slides were then incubated with polymer horseradish peroxidase-labeled secondary antibodies for 30 minutes at RT, then 3,3-Diaminobenzidine (DAB)-treated (0.05 g DAB and 100 ml 30% $H_2O_2$ in 100 ml PBS) for 5 and 10 minutes, respectively. Each slide was counterstained with DAKO's haematoxylin. For each IHC staining, the negative and positive checkerboards were applied as a quality control. The specificity of anti-ASS1 antibody was validated by Western blotting. ASS1 staining was predominantly cytoplasmic, and ASS1 abundance was assessed using a visual grading system on the basis of the intensity of staining signals observed using a light microscope. Each sample was independently scored by two investigators, including one breast pathologist, using a double-blind design to avoid scoring bias. Discrepancies were re-evaluated by joint review between the two readers. ASS1-high was defined as strong diffusive staining and ASS1-low was defined as weak diffusive staining or no staining (see FIG. 6A).

Cell Lines, Media and Chemicals.

HEK293T/FT, MDA-MB-231, ATG5-, BECLIN 1- or SIRT3-knockdown MDA-MB-231, ASS1, SIRT3 or GFP-LC3 stably-transfected MDA-MB-231, MCF-7, ASS1-knockdown MCF7, ZR-75-1 and MCF-10A cells were cultured in Dulbecco's modified Eagle's medium (DMEM) (Cellgro, 10-013-CV) containing fetal bovine serum (10%; Gibco, 26140), penicillin (100 U/ml) and streptomycin (100 μg/ml) (Gibco, 15240) at 37° C. and 5% $CO_2$ in a humidified incubator. T47D and ASS1-knockdown T47D cells were cultured in RPMI 1640 medium under similar conditions. Recombinant ADI-PEG20 was a gift of Polaris Pharmaceuticals Inc. (San Diego, Calif.). Bafilomycin A1 (B1793), chloroquine diphosphate salt (C6628), rapamycin (R8781), succinic acid (S9512), L-arginine (A8094) and MG132 (M7449) were from Sigma. L-glutamine solution was from Gibco (25030).

Antibodies.

Anti-MAP1LC3-I/II antibody (M115-3) was from Medical & Biological Laboratories, anti-SIRT3 antibody (C73E3) was from Cell signaling, anti-Tom20 antibody (sc-17764) and anti-GAPDH antibody (sc-25778) were from Santa Cruz, anti-Cyclophilin D antibody (ab110324) and anti-COX IV antibody (ab110261) were from Abcam and anti-actin antibody (MAB1501R) was from Millipore. Anti-human ASS1 antibody and the lenti-sh-ASS1 construct were a gift. (68).

Virus Production and Transduction.

Target gene DNA in a lentiviral backbone (pLKO.puro or pSin) (21 μg), pΔ8.7 (14 μg) and pVSV-G (7 μg) were transfected using Lipofectamine™ 2000 (Life Technologies, 11668-019), into HEK293T/FT cells that had been seeded in a T-175 flask and had reached 60% confluence on the day of transfection. On the second day after transfection, cells were treated with sodium butyrate (10 mM) to stimulate virus production. Media containing viruses were harvested on the fifth day and filtered through a 0.45 μm filter. For viral transduction, cells were treated with media containing viruses overnight in the presence of polybrene (8.3 μg/ml) and this was followed by selecting the cells using puromycin (1 μg/ml) or G418 (200 μg/ml), or analyzing them by fluorescence-activated cell sorting (FACS).

RNA Extraction, qRT-PCR and cDNA Microarray Analyses.

Total RNA was isolated from cells using RNeasy® mini Kit (QIAGEN, 74104) following the manufacturer's instructions. The RNA concentration and purity were determined by spectrophotometry (Nanodrop Technologies Inc., LLC, Wilmington, Del.). One μg of total RNA was used as the template for synthesizing cDNA using the iScript™ cDNA Synthesis Kit (Bio-Rad, 170-8893). Real-time Q-PCR was performed using the Single Color Real-Time PCR Detection System (Bio-Rad). Equal amounts of mRNA from respective MDA-MB-231 cells subjected to a combination of ADI-PEG20 (0.3 μg/ml) and arginine (420 μg/ml) were analyzed. The relative abundance of ASS1 mRNA in each sample was compared to that of untreated MDA-MB-231 cells, which is designated as 1. For cDNA microarray analyses, the Illumina TotalPrep RNA Amplification Kit (Ambion) was used to transcribe 500 ng RNA by following the manufacture's protocol. HumanHT-12 Expression BeadChips (Illumina) used the Direct Hybridization Assay and were scanned on the BeadArray Reader to quantify signal and background intensity for each feature. The selected array data were validated by Real-time PCR. All primer pair sequences are listed below:

| Name | Forward Primer | Reverse Primer |
| --- | --- | --- |
| ASS1 | 5'-GAGGATGCCTGAATTCTACA-3' (SEQ ID NO: 1) | 5'-GTTGGTCACCTTCACAGG-3' (SEQ ID NO: 2) |
| SOD1 | 5'-CGAGCAGAAGGAAAGTAATG-3' (SEQ ID NO: 3) | 5'-AGCAGGATAACAGATGAGT-3' (SEQ ID NO: 4) |
| SOD2 | 5'-AGTTCAATGGTGGTGGTCATA-3' (SEQ ID NO: 5) | 5'-CAATCCCCAGCAGTGGAATAA-3' (SEQ ID NO: 6) |
| SOD3 | 5'-ACGCTGGCGAGGACGACCTG-3' (SEQ ID NO: 7) | 5'-GCTTCTTGCGCTCTGAGTGCTC-3' (SEQ ID NO: 8) |
| SIRT1 | 5'-TAGACACGCTGGAACAGGTTGC-3' (SEQ ID NO: 9) | 5'-CTCCTCGTACAGCTTCACAGTC-3' (SEQ ID NO: 10) |
| SIRT2 | 5'-CTGCGGAACTTATTCTCCCAGAC-3' (SEQ ID NO: 11) | 5'-CCACCAAACAGATGACTCTGCG-3' (SEQ ID NO: 12) |
| SIRT3 | 5'-CCCTGGAAACTACAAGCCCAAC-3' (SEQ ID NO: 13) | 5'-GCAGAGGCAAAGGTTCCATGAG-3' (SEQ ID NO: 14) |
| SIRT4 | 5'-GTGGATGCTTTGCACACCAAGG-3' (SEQ ID NO: 15) | 5'-GGTTCAGGACTTGGAAACGCTC-3' (SEQ ID NO: 16) |
| SIRT5 | 5'-GTCCACACGAAACCAGATTTGCC-3' (SEQ ID NO: 17) | 5'-TCCTCTGAAGGTCGGAACACCA-3' (SEQ ID NO: 18) |

-continued

| Name | Forward Primer | Reverse Primer |
|---|---|---|
| SIRT6 | 5'-TGGCAGTCTTCCAGTGTGGTGT-3' (SEQ ID NO: 19) | 5'-CGCTCTCAAAGGTGGTGTCGAA-3' (SEQ ID NO: 20) |
| SIRT7 | 5'-TGGAGTGTGGACACTGCTTCAG-3' (SEQ ID NO: 21) | 5'-CCGTCACAGTTCTGAGACACCA-3' (SEQ ID NO: 22) |
| GAPDH | 5'-CCCCTTCATTGACCTCAACTA-3' (SEQ ID NO: 23) | 5'-CTCCTGGAAGATGGTGATGG-3' (SEQ ID NO: 24) |
| 18S | 5'-CGTCTGCCCTATCAACTTTCG-3' (SEQ ID NO: 25) | 5'-GGATGTGGTAGCCGTTTCTCAG-3' (SEQ ID NO: 26) |

Cytotoxicity and Apoptosis Assays.

Four methods were used to measure cytotoxicity: 1) DIMSCAN assay, 2,500 to 5,000 cells were seeded onto 96-well plates. At the end of the indicated time periods for which they were treated with ADI-PEG20, cells were incubated with fluorescein diacetate (FDA; 40 µg/ml), which is selectively accumulated in viable cells. A semiautomatic, fluorescence-based, digital image microscopy system was used to measure the viability, 2) real-time cell growth was monitored by using a 16×E-plates RTCA DP Analyzer (ACEA, Bioscience, San Diego, Calif.), 3) acid phosphatase (ACP) assays were used to avoid the effect of mitochondria dysfunction. Between 2,500 and 5,000 cells were seeded onto 96-well plates. At the end of the indicated time periods for which they were treated with ADI-PEG20, cells were washed twice with PBS then incubated at 37° C. for 30 minutes with 100 µL of pNPP solution (pNPP (5 mM) in a buffer containing sodium acetate (0.1 M) and Triton X-100 (0.1% (v/v), pH 5.5). The reaction was terminated by adding NaOH (1 N, 10 µl), and the absorbance was measured at 410 nm using a microplate reader, and 4) trypan blue exclusion was used to count viable cells under a light microscope. Relative cell viability of ADI-PEG20-treated cells was calculated relative to the respective viability of the corresponding matched, vehicle-treated cells, which is designated as 1. Data were collected from three independent experiments and are shown as the mean±SD. The interaction between drug combinations was analyzed using the Calcusyn software program (Biosoft, Cambridge, UK) to determine if the combination was antagonistic, additive or synergistic. This program is based on the Chou-Talalay method to calculate a combination index (CI), and CI values below 0.9 indicate synergistic effect. The CIs were determined from cell viability DIMSCAN or ACP assays as the fraction of cells killed by individual drugs, or combination of drugs, by comparing to vehicle-treated cells. For the apoptosis assay, cells were treated with ADI-PEG20 (0.3 µg/ml) or subjected to arginine starvation for the indicated time periods. After trypsinization, cells were washed twice with cold PBS and collected by centrifugation at 1000 rpm. Cells were then resuspended in 1× Binding Buffer at a concentration of 1×10⁶ cells/ml and 100 µl of the suspension (1×10⁵ cells) was transferred to a polystyrene round-bottom tube. Cells were then stained with FITC-conjugated annexin V (4 µl) and propidium iodide (PI) (50 µg/ml, 5 µl). The mixture was gently vortexed and incubated for 15 minutes at RT and 1× Binding Buffer (400 µl) was added to each tube before analyzing by flow cytometry.

Soft Agar Colony Assays.

Between 0.5 and 3×10⁴ cells were mixed in 0.35% agarose/complete media and plated on a 0.7% agarose/complete media bottom layer in each well of a 6-well plate. The culture media contained vehicle or different concentrations of ADI-PEG20 and was changed every 2 to 3 days during the 4-week to 6-week cell growth period. Colonies were stained with methylthiazolyldiphenyl-tetrazolium bromide (MTT; 0.2 mg/ml; Sigma M5655) and were counted using colony counting software (VersaDoc Imaging System from Bio-Rad) or counted manually. Each experiment was performed at least twice in triplicate wells.

Whole Cell Extracts and Immunoblotting.

Cells treated with ADI-PEG20 were harvested at the end of incubation period and lysed on ice for 30 minutes in RIPA buffer (Cell Signaling, #9806) containing complete protease inhibitor cocktail (Roche, 11836145001) and PhosSTOP (Roche, 04906837001). The protein concentrations of whole cell extracts were determined using a Bio-Rad Protein Assay Kit (Bio-Rad, 500-0001). Approximately 20-40 µg of protein was mixed with an equal volume of 2×SDS loading buffer, boiled for 5 minutes, then separated by Tris-glycine SDS-PAGE and transferred to PVDF membranes. The membranes were blocked with 5% nonfat milk in PBST (PBS containing 0.05% Tween 20) and incubated with primary antibodies at 4° C. overnight. The membranes were then washed with three times with PBST for 10 minutes, 3 times, and incubated with HRP (horseradish peroxidase)-labeled secondary antibodies for 2 hours at RT. Immunoblots were visualized using VersaDoc 5000 imaging system (Bio-Rad). The intensity was determined using Quantity One (Bio-Rad) and compared to 0 hour treatment after normalizing with actin. Three independent experiments were performed and a representative image is shown.

ATP Assay.

The ENLITEN® ATP Assay System (Promega, FF2000) was used according to manufacturer's instructions. At the indicated time points, cells were harvested by scraping and resuspending in PBS (500 µl). The cell suspension was divided into unequal aliquots and 400 µl of cell suspension was mixed with 5% trichloroacetic acid (TCA, 100 µl). The remaining cells (100 µl) were used for cell number calculation. Tris-acetate buffer (900 µl, pH 7.75) was then added to neutralize the TCA and to dilute the TCA to a final concentration of 0.1%. The extracts were further diluted 100-fold with dilution buffer (0.1% TCA, 0.08×PBS and 0.9× Tris-Acetate). Diluted sample (40 µl) was added to an equal volume of rL/L Reagent (Promega, FF2000) that contained D-luciferin and recombinant luciferase, then luminescence was measured using a TD-30e luminometer (Turner). The ATP standard (Promega, FF2000) was serially diluted to generate a regression curve for calculating ATP levels in individual samples. The relative ATP level per cell was determined and normalized to that of vehicle-treated cells, which is designated as 1. Three independent experiments were performed and results are presented as the mean±SD.

Oxygen Consumption Rate (OCR).

Cellular mitochondrial function was measured using the Seahorse Bioscience XF24 Extracellular Flux Analyzer. The mitochondrial function was assayed by sequential injections of oligomycin, FCCP (Carbonyl cyanide p-trifluoromethoxy phenylhydrazone) and rotenone to define basal OCR, ATP-linked OCR, proton leak, maximal respiratory capacity, reserve respiratory capacity and non-mitochondrial oxygen consumption, all according to manufacturer's instructions. Oligomycin A inhibits ATP synthase by blocking proton channel and significantly reduce electron flow through the electron transport chain, which is necessary for oxidative phosphorylation of ADP to ATP. FCCP is a protonophore (H+ ionophore) and uncoupler of oxidative phosphorylation in mitochondria, which is capable of depolarizing plasma and mitochondrial membranes. Rotenone, an inhibitor of mitochondrial electron transport at NADH:ubiquinone oxidoreductase, inhibits the transfer of electrons from iron-sulfur centers in complex I to ubiquinone and interferes with NADH. Herein, basal OCR is used to represent the function of mitochondria. Briefly, $2\times10^4$ cells were seeded onto 24-well plates and incubated overnight prior to the sequentially adding pre-optimized concentrations of oligomycin, FCCP and rotenone in that order. After washing the cells with 1 ml seahorse buffer [DMEM medium without phenol red containing glucose (4.5 g/l; Sigma, G7021), sodium pyruvate (1 mM; Gibco, 11360070) and glutamine (4 mM; Gibco, 25030081)], 600 µl seahorse buffer plus 60 µl each of oligomycin (50 µg/ml; Sigma, 75351), FCCP (10 µM; Sigma, C2920) and rotenone (10 µM; Sigma, R8875), was automatically injected. At the end of recording period, cells were collected and the individual cell numbers were determined using a trypan blue exclusion assay. OCR values were calculated after normalizing with the cell number and plotted as the mean±SD.

Fluorescence-Based Methods to Measure DCFDH Oxidation, MitoSOX Red Oxidation, Mitochondria Membrane Potential (MMP) and Autophagic Flux.

To measure DCFDH oxidation, cells were stained with DCFDA (10 µM; Sigma, D6883) for 30 minutes before flow cytometry analysis (Gallios, Beckman Coulter). In a second fluorescent dye oxidation measurement, cells were incubated with MitoSOX RED™ (Life Technologies, M36008; 5 mM) for 30 minutes in serum-free DMEM. In this report, increased oxidized DCF and MitoSOX red fluorescence are used as the measure or indicator of increased non-metabolic oxidation, which is consistent with oxidative stress, although the caveat that dye oxidation alone does not actually represent the increased production of ROS is acknowledged (Kalyanaraman et al. 2012). For mitochondrial membrane potential (MMP) analyses, cells were incubated in DMEM with DiOC6 (Sigma, 318426, 10 nM) for 30 minutes prior to analyses. For autophagic flux analyses, MDA-MB-231/GFP-LC3 cells were harvested after ADI-PEG20 treatment for different time periods, and immediately analyzed by flow cytometry. Data were collected from three independent experiments and are presented in a histogram. The flow cytometry analyses were performed using Flowjo software (Tree star).

Confocal and Transmission Electron Microscopy.

MDA-MB-231/GFP-LC3 cells were cultured in six-well plates with cover slips at a density of $1\times10^5$ cells/well, and then treated with ADI-PEG20 for 0, 12, and 24 hours, respectively. Cells were stained with MitoTracker Deep Red FM (Life Technologies, M22426; 300 nM) for 15 minutes in serum-free DMEM. After washing with PBS, the cover slips were mounted over a microscope slide in Prolong anti-fade reagent that contained DAPI (Life Technologies, P-36931), and examined using a Stallion Digital imaging station (Carl Zeiss microscopy, Gottingen, Germany). For mitochondria morphology characterization, MDA-MB-231 cells were cultured in six-well plates with cover slips at a density of $5\times10^5$ cells/well, and then treated with Mdivi1 (10 µM; Sigma, M0199), ADI-PEG20 or combination of both for 24 hours. Cells were stained with TOM20 for 1 hour at room temperature after fixation with 4% paraformaldehyde in PBS and permeabilized with 1% triton X-100. After washing, secondary antibody conjugate with Alexa-488 was added and incubated for 30 minutes at room temperature. Finally, slides were mounted using ProLong® Gold Antifade Reagent and imaged using confocal as described above. For transmission electron microscopy studies, cell pellets were fixed in glutaraldehyde (2% in 0.1 M Cacodylate buffer $(Na(CH_3)_2AsO_2.3H_2O)$, pH 7.2) at 4° C., overnight. The cell pellets were then washed three times with 0.1 M Cacodylate buffer (pH 7.2), post-fixed with $OsO_4$ (1% in 0.1 M Cacodylate buffer) for 30 minutes, and then washed three times again with Cacodylate buffer (0.1 M). The samples were dehydrated using a series of 60%, 70%, 80% and 95% ethanol, then 100% absolute ethanol (twice) and propylene oxide (twice), and were then placed in propylene oxide/Eponate (1:1) overnight at RT. The vials were sealed for the overnight incubation, and then opened the next day for 2-3 hours to allow the propylene oxide to evaporate. Finally, the samples were infused with 100% Eponate and polymerized at −64° C. for 48 hours. Ultra-thin sections (~70 nm thick) were prepared using a Leica Ultracut UCT ultramicrotome with a diamond knife, picked up on 200 mesh copper EM grids. Grids were stained with uranyl acetate (2%) for 10 minutes, followed by Reynold's lead citrate staining for 1 minute. The samples were viewed using a FEI Tecnai 12 transmission electron microscope equipped with a Gatan Ultrascan 2K CCD camera. Three independent experiments were performed and a representative image is shown.

Oil Red O Staining.

MDA-MB-231 cells were cultured in six-well plates with cover slips at a density of $5\times10^5$ cells/well, and then treated ADI-PEG20 for 0, 24 and 48 hours, respectively. Cells were fixed using 4% paraformaldehyde in PBS for 30 minutes. Each well was gently rinsed twice with 1 ml of deionized water. 1.5 ml of 60% isopropanol was added to each well for 5 minutes. Isopropanol was then removed and replaced with 1.5 ml of Oil Red O working solution (2 mg/ml in 60% isopropanol; Sigma, O0625) for 10 minutes at room temperature. Each well was rinsed with tap water until the clear and counterstained with hematoxylin for 1 minute. Lastly, each well was rinsed with tap water and mounted with 70% glycerol.

Xenograft Studies.

For tumorigenesis, $5\times10^6$ MDA-MB-231 and ATG5-knockdown MDA-MB-231 cells (MDA-MB-231/sh-ATG5) (resuspended in 100 µl serum-free DMEM media) were injected subcutaneously into the right flank of six-week-old female NOD.Cg-Prkdc$^{scid}$Il2rg$^{tm1Wjl}$/SzJ (NSG) (NOD-SCID) mice. Mice were randomized at day-10 after tumor inoculation and received weekly either vehicle or 4 IU of ADI-PEG20 (0.2 ml) through tail vein injection (iv) for three weeks (N=5 per group). Tumor volume was measured weekly. Mice were killed on day−35, 4 days after last injection. Tumors were harvested for weight measurement and H&E staining. All animal experiments were approved by the institutional animal care and use committee at City of Hope.

Statistical Analysis.

The database was created using MS-Access and analyzed using Microsoft Excel, JMP 8.0 (SAS Institution) and GraphPad Prism 5.0 software. Group comparisons for normal distribution data were done by t-test (two samples) and Oneway ANOVA (multiple comparison). The nonparametric Wilcoxon test was used for continuous non-normal distribution data. For multiple comparisons, Tukey-Kramer HSD and Steel-Dwass methods were applied for following pairs' comparison in ANOVA and nonparametric Wilcoxon test, respectively. Each cell biology experiment was performed at least three times to obtain presented mean±SD and one representative image is shown. Categorical variables were compared using a chi square ($\chi^2$) analysis, Fisher's exact test or binomial test of proportions. Kaplan-Meier analysis and a COX hazard proportional model were used to analyze overall survival and disease-free-survival. Multivariate analysis and stratification were used to reduce the confounder's impact on the estimation of the Hazard Ratio (HR). Statistical significant was set as p<0.05, two-tailed.

Results

Figure 1B:
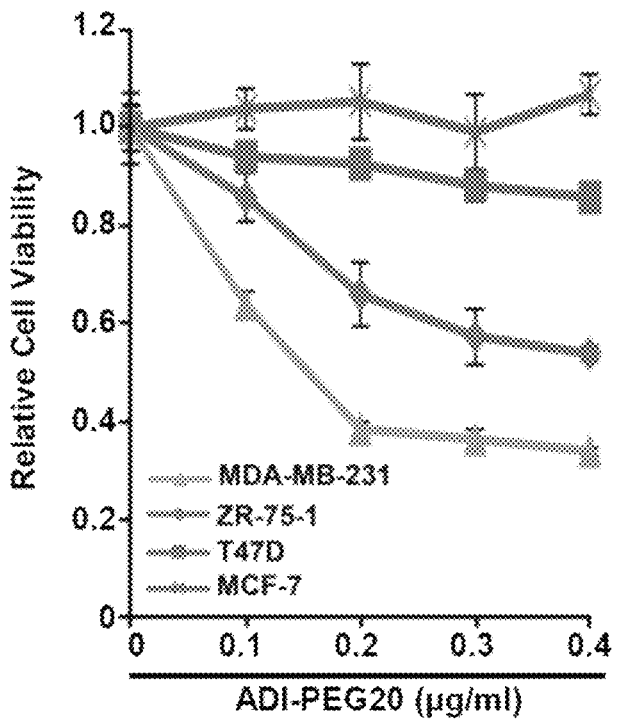
Figure 1C:
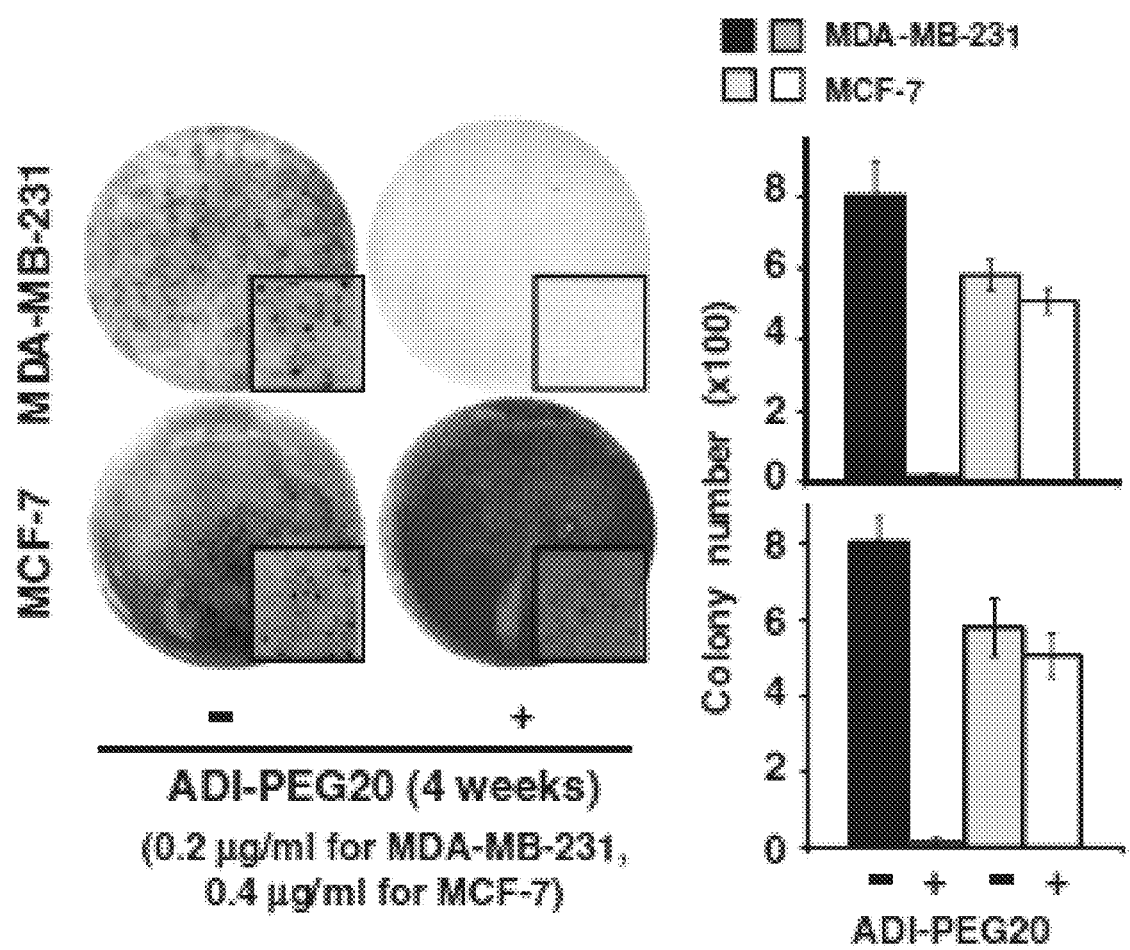
Figure 1D:
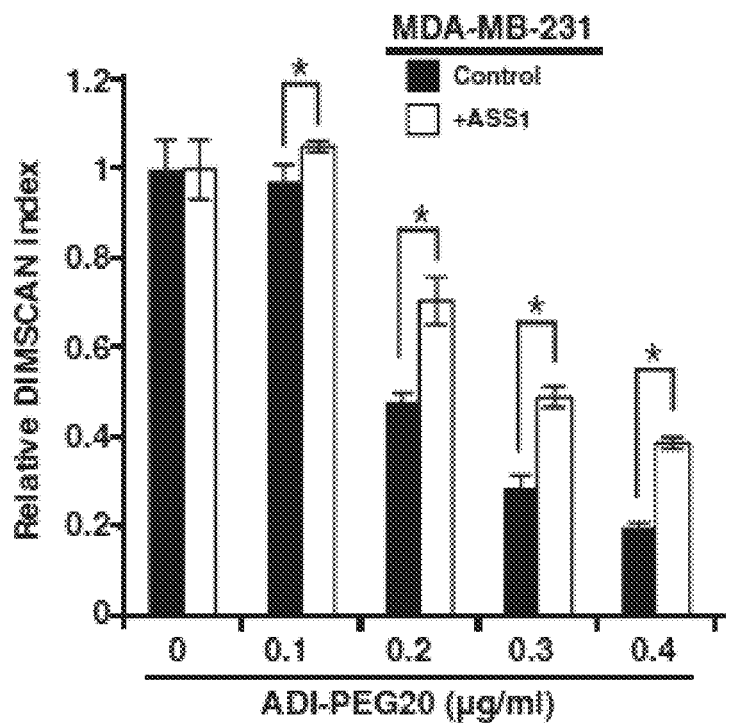
Figure 1E:
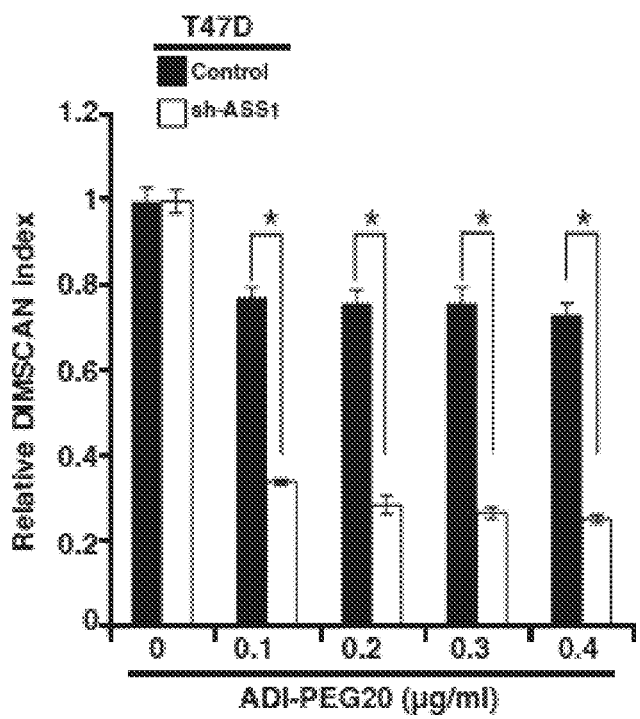
Figure 1F:
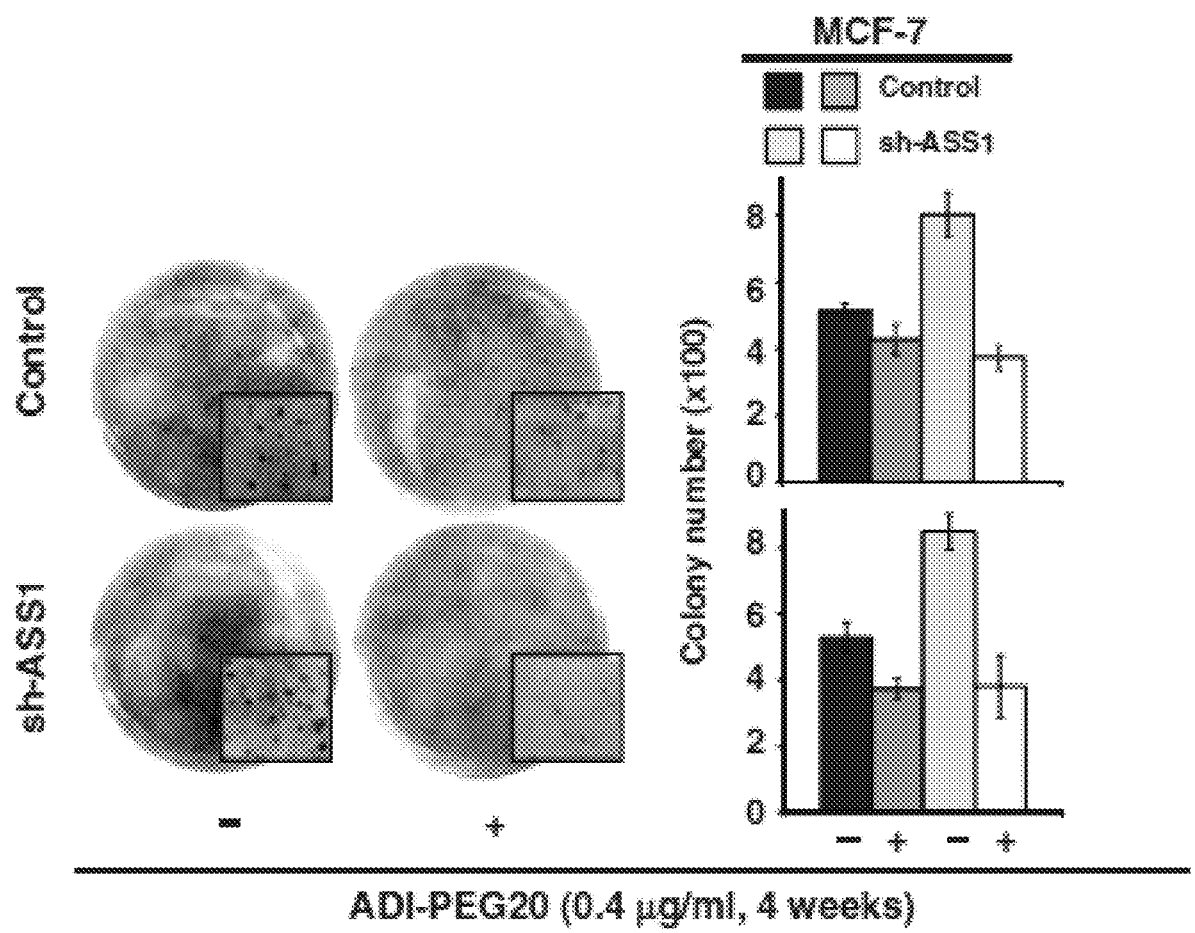
Figure 2A:
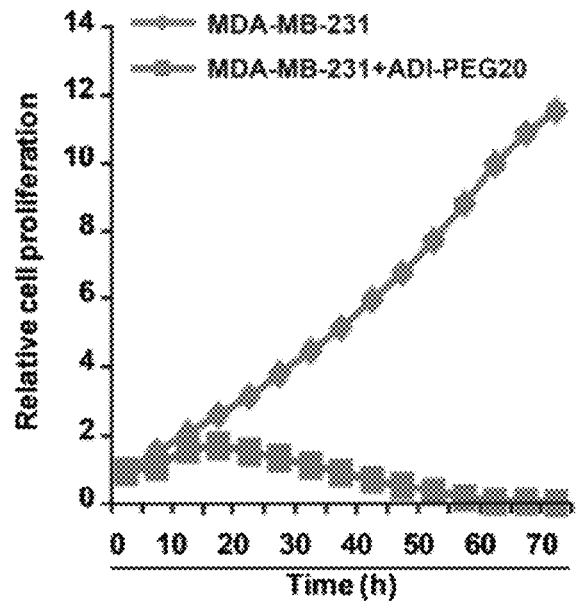
FIGS. 2A-F illustrate that a knockdown of ASS1 expression increases sensitivity to ADI-PEG20-treatment according to one embodiment.
Figure 2B:
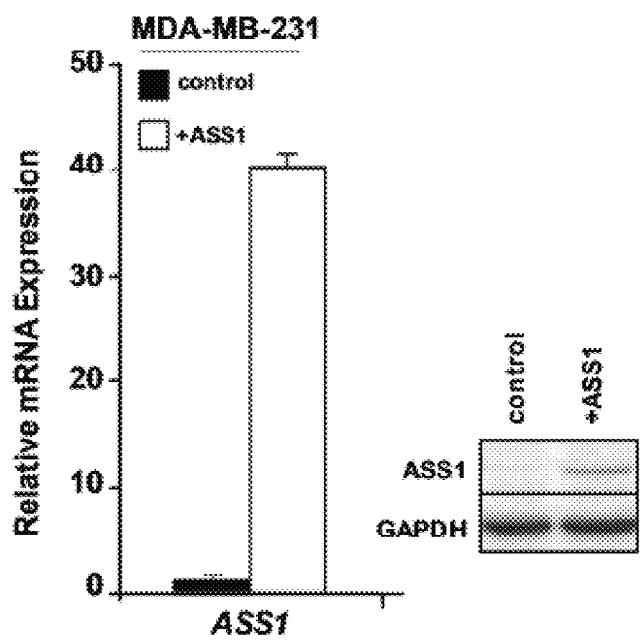
Figure 2C:
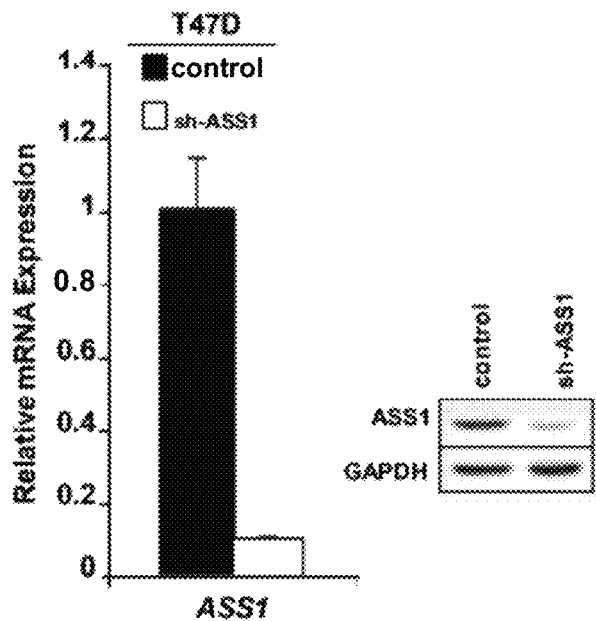
Figure 2D:
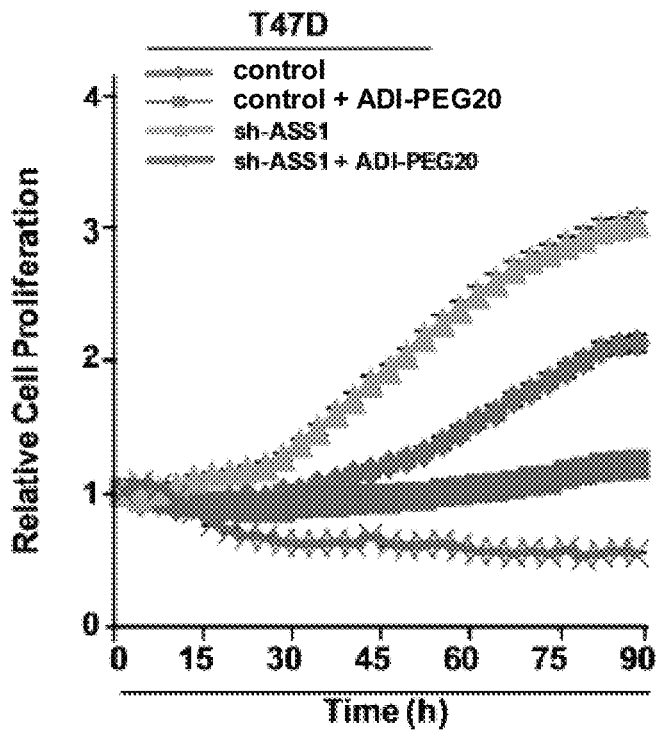

ADI-PEG20 Selectively Inhibits the Proliferation of ASS1-Deficient BC Cells. The relationship between ASS1 expression and proliferation of several BC cell lines was examined to determine whether reduced ASS1 abundance would increase the sensitivity of breast cancer cells to arginine starvation by treatment with recombinant ADI-PEG20. It was found that ASS1 mRNA and ASS1 protein abundance were relatively low in MDA-MB-231 and ZR-75-1 cells compared to MCF-7 and T47D cells (FIG. 1A). The relative sensitivity of these four breast cancer cells lines to ADI-PEG20-induced inhibition of proliferation was inversely correlated with the abundance of ASS1 (MDA-MB-231>ZR-75-1>T47D=MCF-7, FIG. 1B). The inhibition of proliferation in MDA-MB-231 cells was independently validated using time course growth assay (FIG. 2A) and by anchorage-independent colony formation assay (FIG. 1C). To confirm that the inhibition of proliferation by ADI-PEG20 was inversely related to ASS1 abundance, ASS1-overexpressing MDA-MB-231 (+ASS1; FIG. 2B) and ASS1-knockdown T47D cells (sh-ASS1; FIG. 2C) were established. As predicted, MDA-MB-231 cells overexpressing ASS1 were more resistant to ADI-PEG20 (FIG. 1D) and the knockdown of ASS1 sensitized T47D cells to ADI-PEG20 (FIG. 1E). Altogether, these results indicate that recombinant ADI-PEG20 effectively inhibits the proliferation of breast cancer cells with low ASS1 abundance, which cannot synthesize sufficient endogenous arginine for their metabolic needs. Unexpectedly, it was noticed although that knockdown of ASS1 promoted ADI-PEG20 sensitivity (FIG. 1E), decreased ASS1 abundance increased the proliferation (FIG. 2D) and the ability to form colonies (FIG. 2E) in T47D cells. Thus, ASS1 may have a tumor suppressor role in breast cancer cells. To test this possibility, ASS1 was knocked down in MCF-7 cells, which had the greatest ASS1 abundance of the five breast cancer cell lines (FIG. 1A) and exhibited resistance to ADI-PEG20 (FIGS. 1B, 1C). A 50% knockdown of ASS1 in MCF-7 cells (FIG. 2F) was sufficient to increase the anchorage-independent, colony forming ability of MCF-7 cells as well as their sensitivity to ADI-PEG20 when grown in soft agar (FIG. 1F). These data suggest that ASS1 may have a tumor suppressor function that prevents anchorage-independent breast cancer cell growth.

ADI-PEG20 Induces Autophagy-Dependent Cell Death.

Figure 3A:
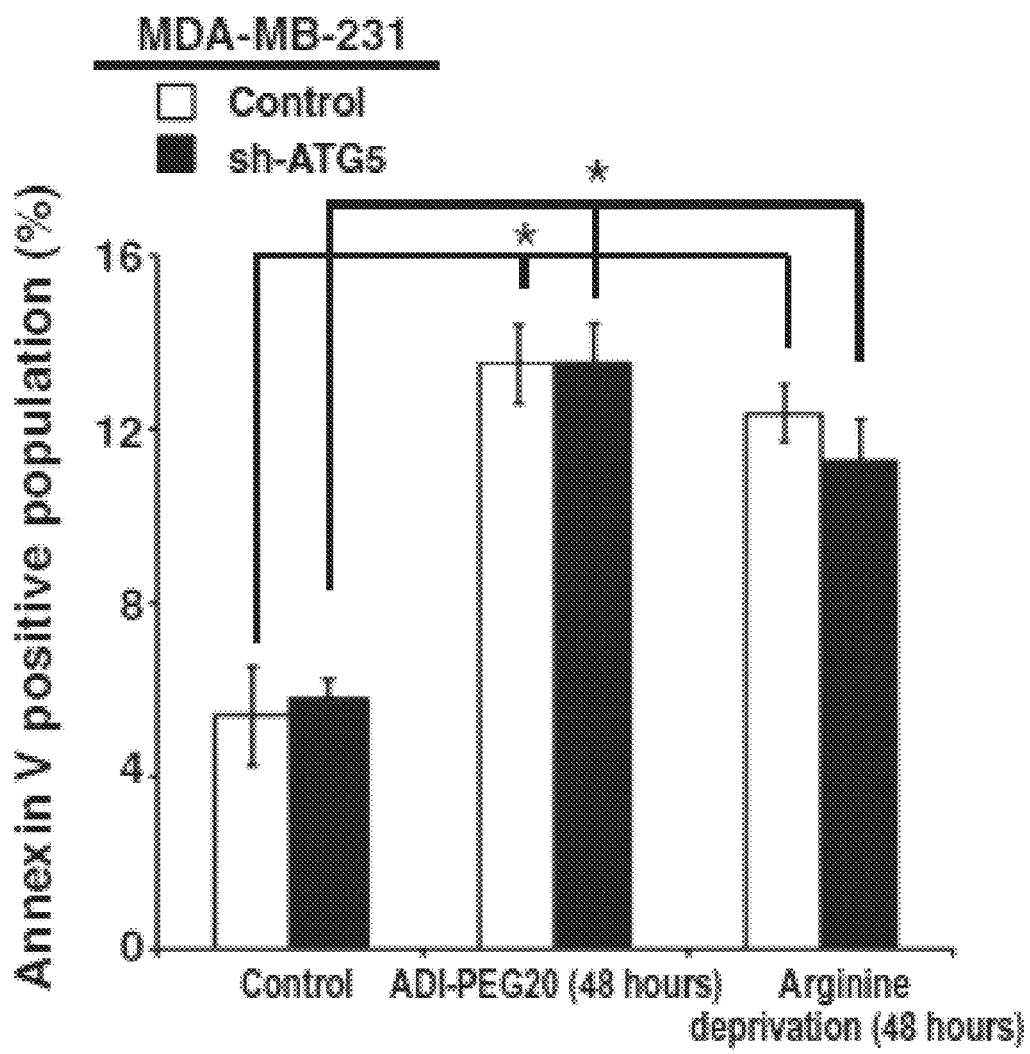
FIGS. 3A-F illustrate that ADI-PEG20 induces autophagy-dependent cell death according to one embodiment.
Figure 4A:
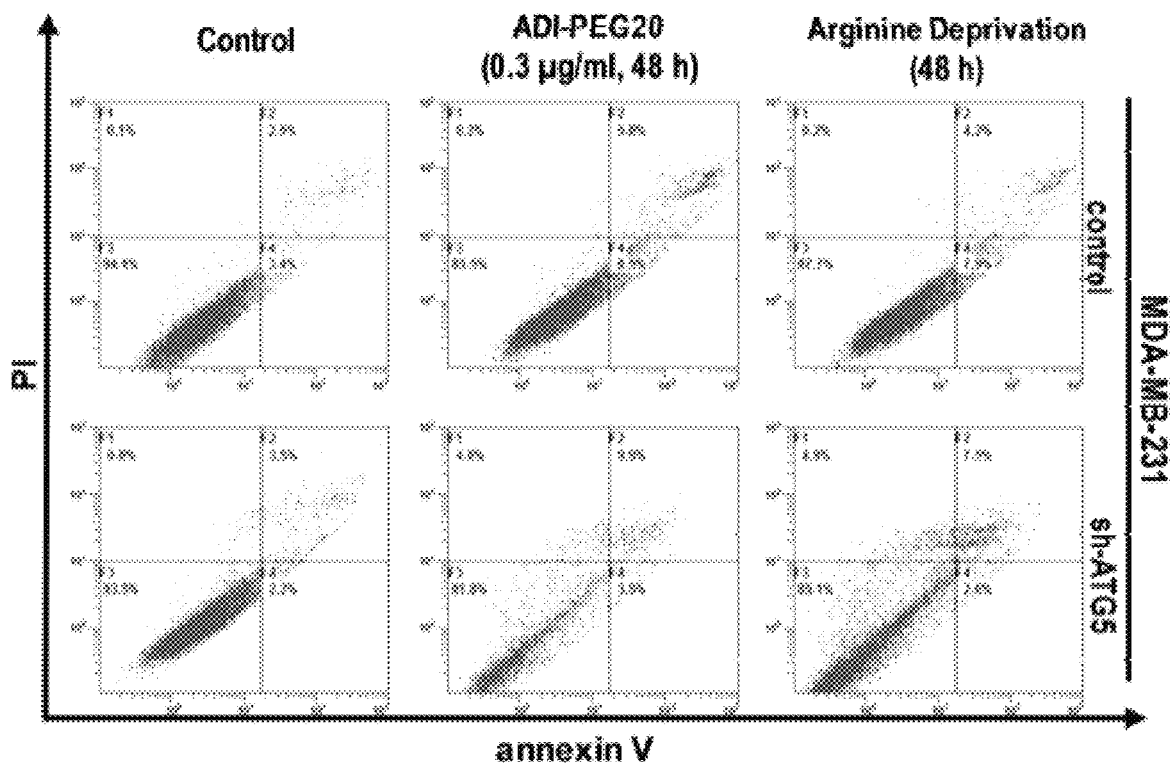
FIGS. 4A-E illustrate that autophagy is employed for arginine-starvation-induced cell death according to one embodiment.

Using MDA-MB-231 cells, the mechanism underlying the arginine deprivation-induced cell death of breast cancer cells with low ASS1 was abundance was investigated. First, it was determined if ADI-PEG20 induces apoptosis in MDA-MB-231 cells, as previously suggested by studies using other types of cancer cells (Kim et al. 2009b; Delage et al. 2012). Flow cytometry indicated that approximately 13% of MDA-MB-231 cells were annexin V positive after being treated with ADI-PEG20 (FIGS. 3A, 4A, upper middle panel) or starved of arginine (FIGS. 3A, 4A, upper right panel). However, based on the extent that ADI-PEG20 inhibited cell proliferation (FIG. 1B), the apoptotic cell population was smaller than expected. It seemed likely that another pathway was induced by ADI-PEG20 that inhibited cell proliferation.

Figure 3B:
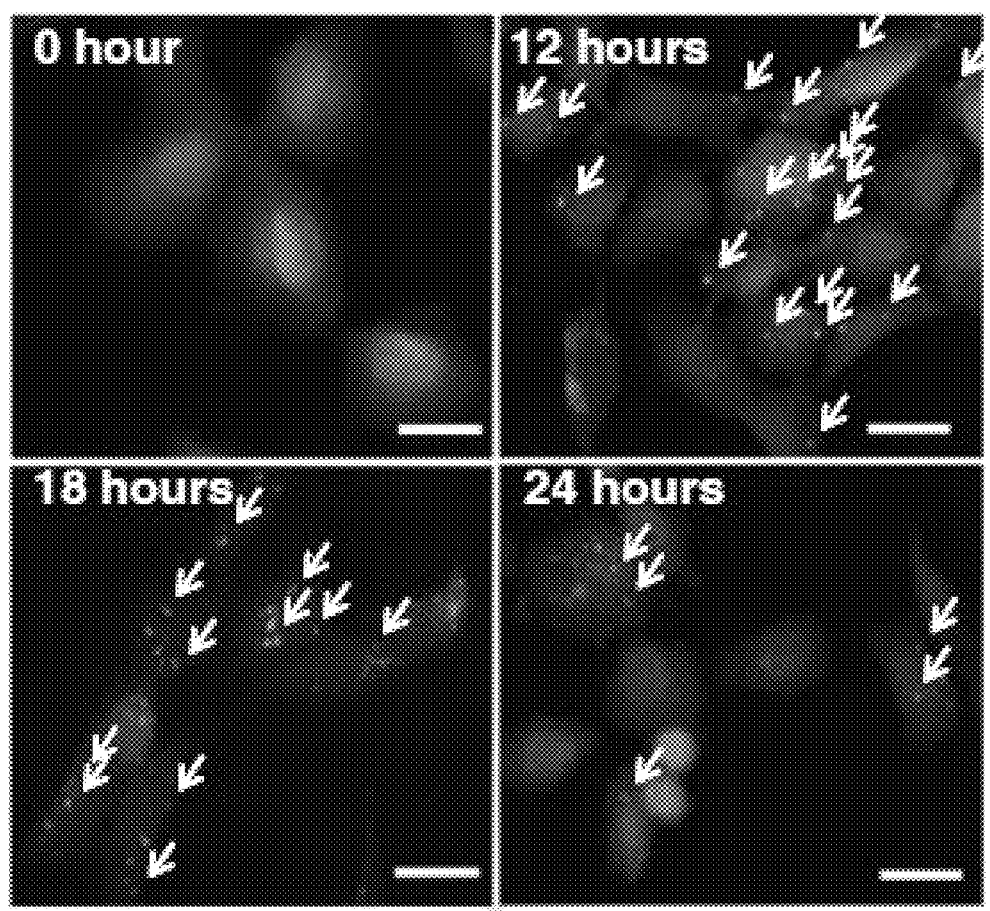
Figure 3C:
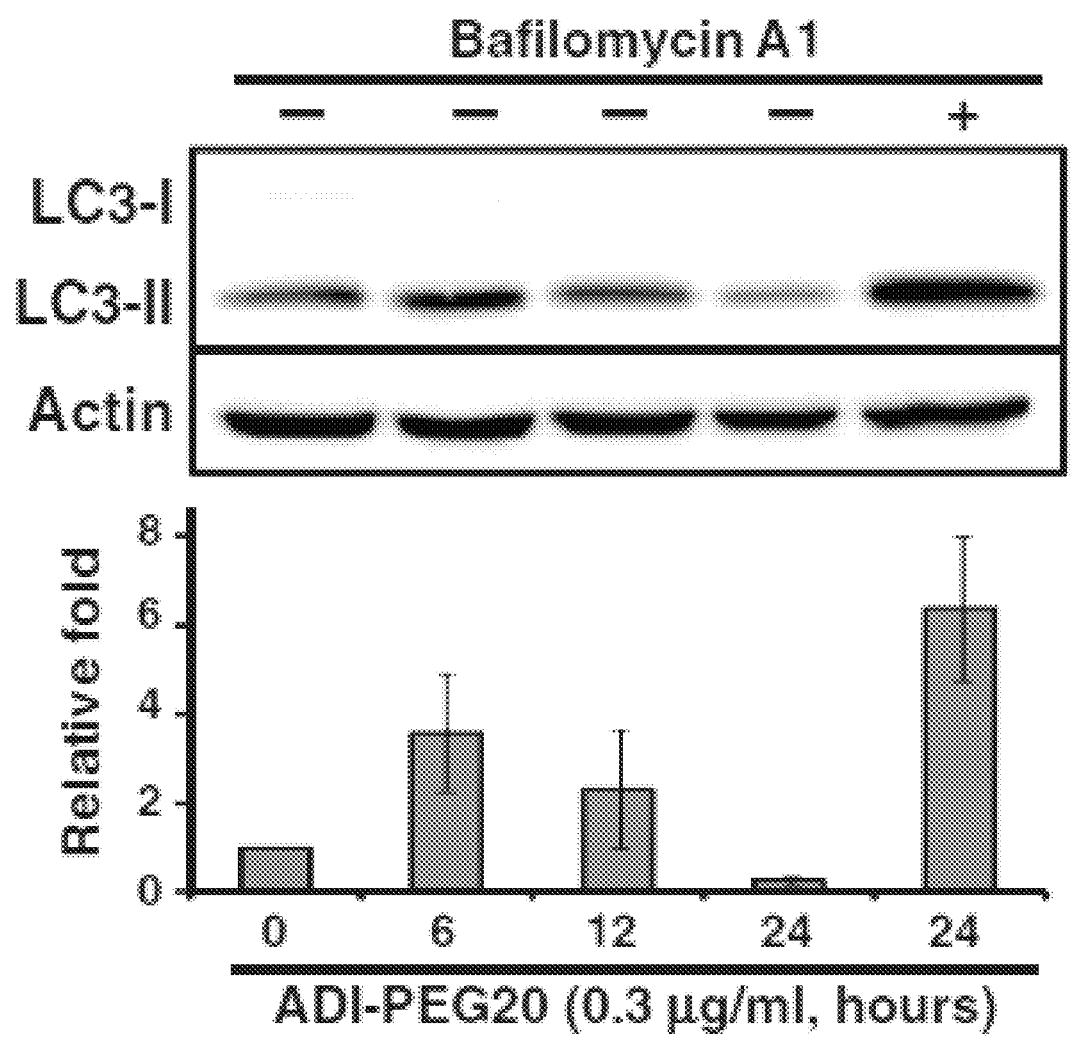
Figure 3D:
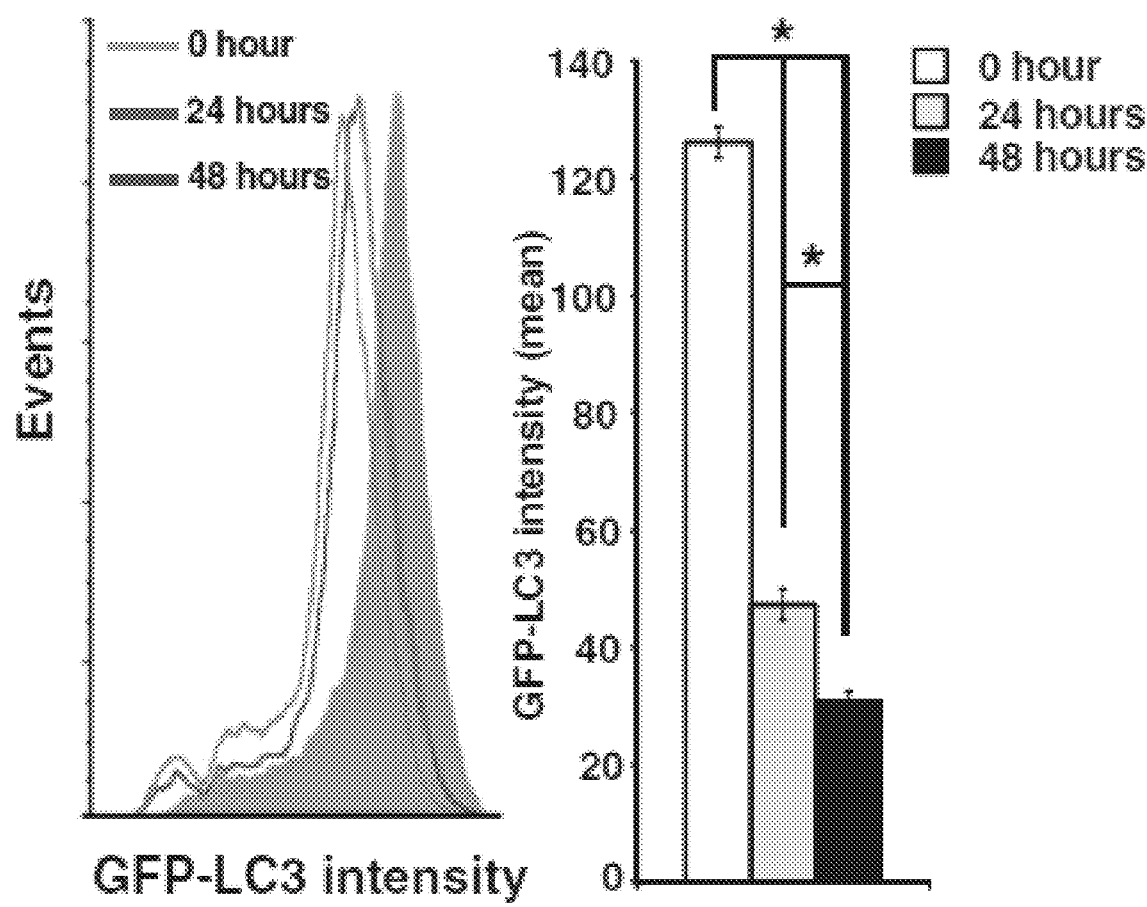

Arginine starvation has been reported to induce autophagy (Kim et al. 2009b; Shvets et al. 2008). First, it was determined whether ADI-PEG20 induced autophagy in MDA-MB-231 cells. During autophagy, a cytosolic form of microtubule-associated protein 1A/1B-light chain 3 (LC3-I) is conjugated by phosphatidylethanolamine to form LC3-II, which in turn recruited to autophagosomal membranes (Tanida et al. 2008; Klionsky et al. 2012; Tanida et al. 2004; Giminez-Zavier et al. 2009). Formation of GFP-LC3-positive puncta, a marker for autophagy (Klionsky et al. 2012), was monitored in GFP-LC3 stably-transfected MDA-MB-231 cells treated with ADI-PEG20. GFP-LC3 puncta were observed 12 hours after ADI-PEG20 treatment, but were decreased after 24 hours, indicating the appearance and disappearance of autophagosomes (FIG. 3B). Next, Western blotting was used to show that LC3 was lipidated (LC3-II) and that LC3-II abundance increased to approximately 2-fold at six hours following ADI-PEG20 treatment, and then decreased over time (FIG. 3C). Furthermore, bafilomycin A1, a vacuolar-type H+-ATPase inhibitor that prevents the maturation of autophagic vacuoles (Shacka et al. 2006), reversed the decrease in LC3-II that occurred 24 hours after ADI-PEG20 treatment, suggesting there was active autophagic flux (FIG. 3C). To confirm that ADI-PEG20 induced autophagic flux, a flow cytometry-based assay was used to show that GFP-LC3 intensity was significantly decreased at 24 and 48 hours after treating with ADI-PEG20 (FIG. 3D).

Figure 3E:
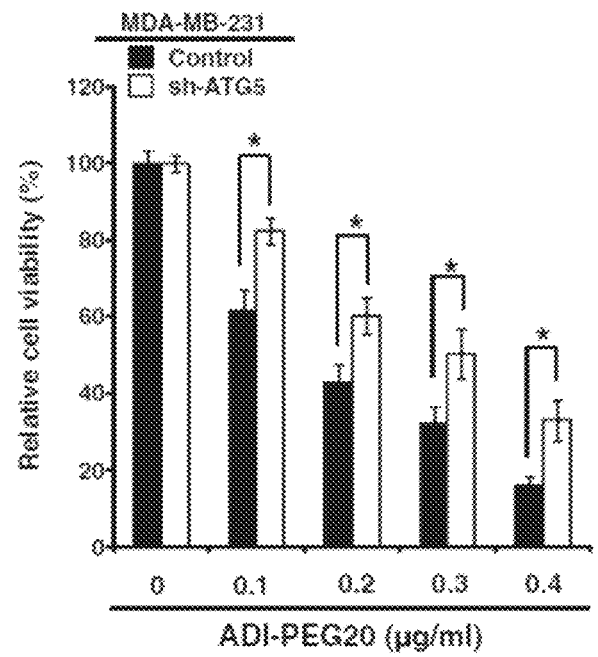
Figure 3F:
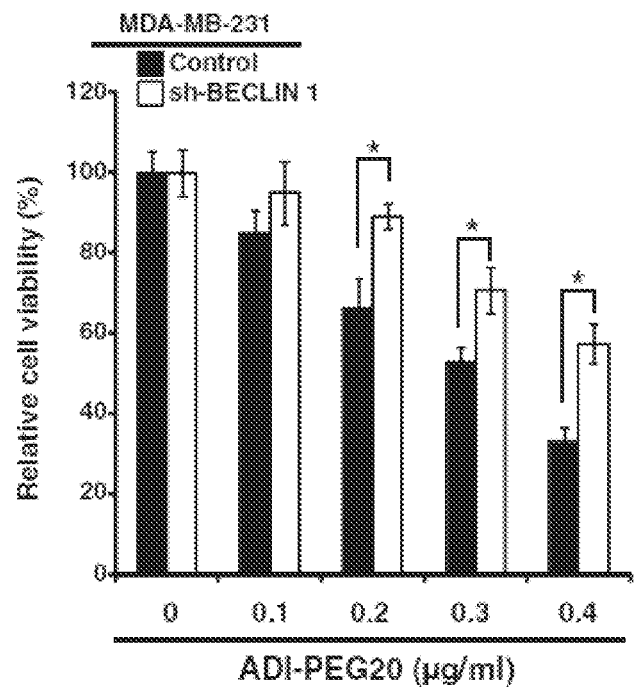
Figure 4B:
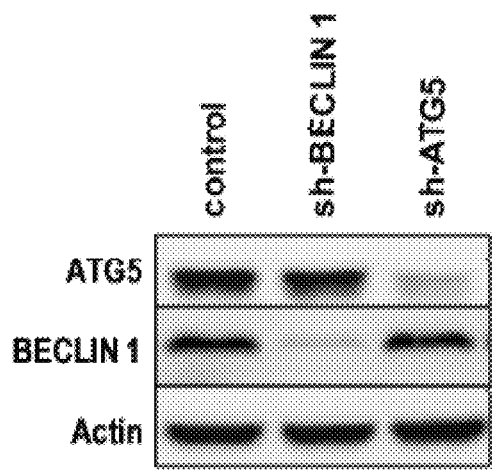
Figure 4C:
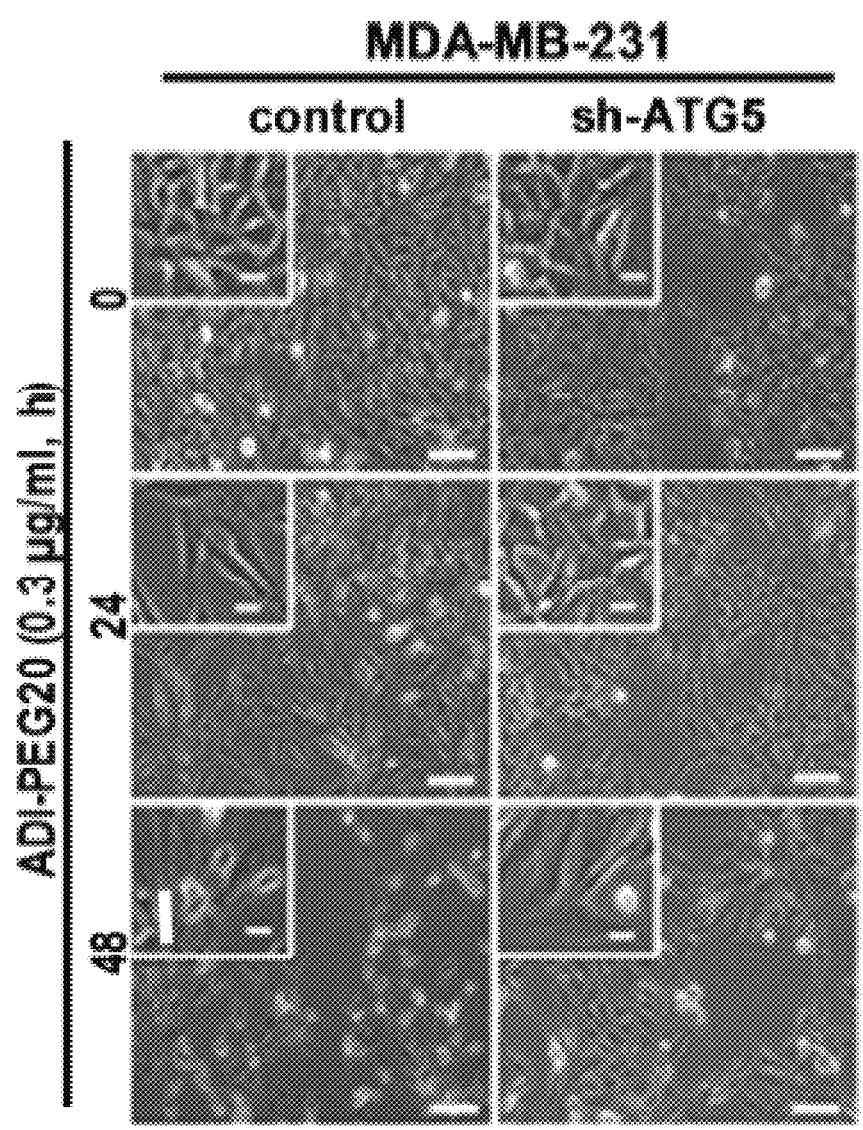
Figure 4D:
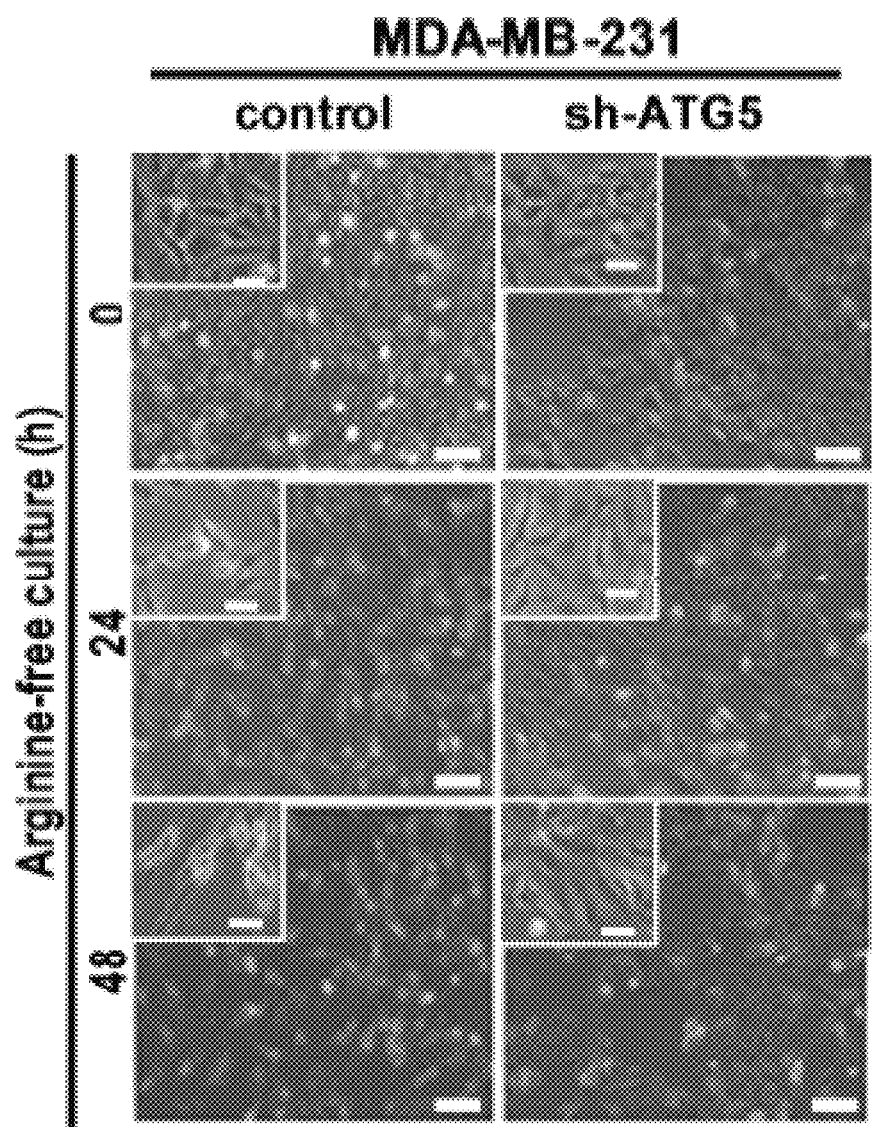
Figure 4E:
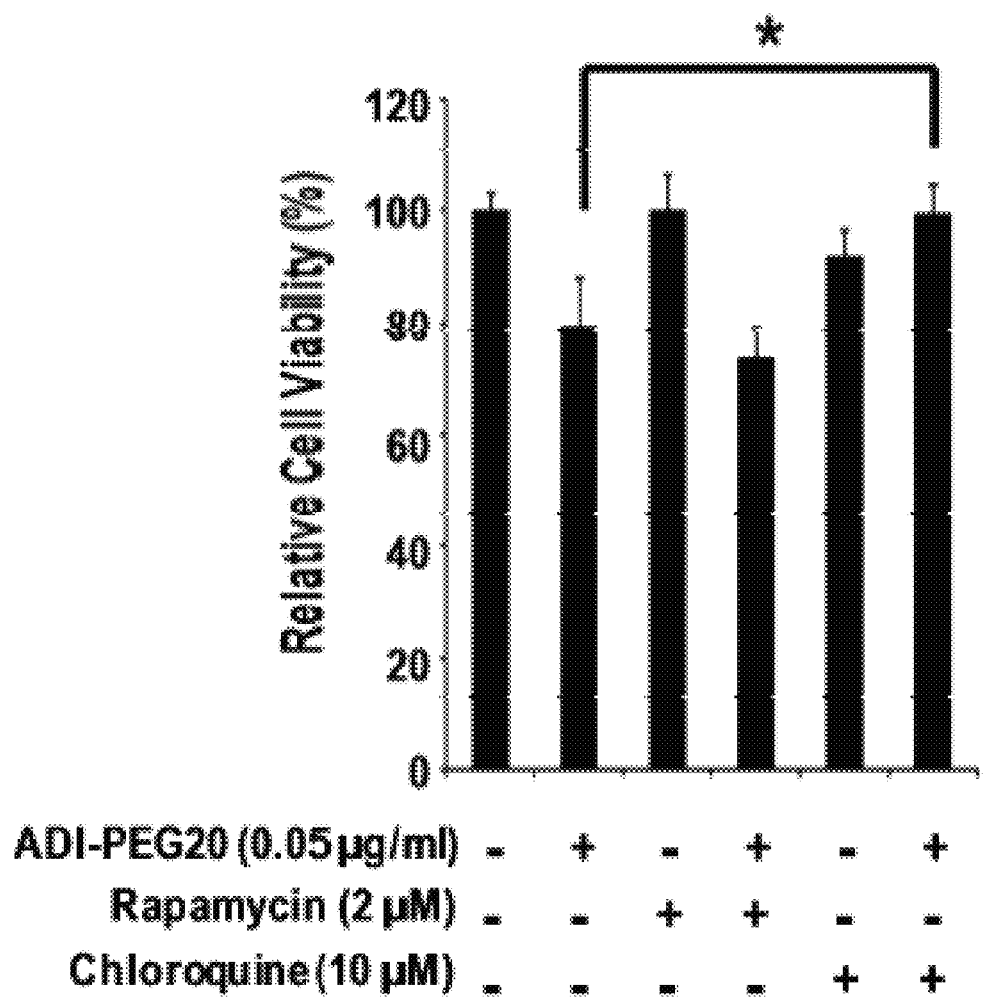

To determine the role of autophagy in inhibiting cell proliferation mediated by ADI-PEG20, shRNA was used to knock down the expression of ATG5 and BECLIN 1 (FIG. 4B), two important components of the autophagy machinery (Levine & Kroemer 2008; Mizushima & Komatsu 2011). Knockdown of ATG5 or BECLIN 1 caused MDA-MB-231 cells relatively resistant to ADI-PEG20 (FIGS. 3E, 3F). The size of the annexin V-positive population of MDA-MB-231 cells expressing shRNA against ATG5 cells was not significantly altered in response to ADI-PEG20 or arginine starvation (FIG. 4A, lower middle and right panels, summarized in FIG. 3A). In addition, phase contrast microscopy revealed that ADI-PEG20 or arginine starvation altered the overall morphology of MDA-MB-231, but not cells stably-transfected with ATG5 shRNA at 24 or 48 hours after treatment (FIGS. 4C, 4D). Lastly, while the combination of ADI-PEG20 with rapamycin (mTOR inhibitor), an autophagy inducer, did not increase ADI-PEG20-mediated cell killing, addition of chloroquine, an autophagic flux inhibitor, decreased ADI-PEG20-induced cell death (FIG. 4E). Therefore, autophagy is likely required for recombinant ADI-PEG20 to suppress MDA-MB-231 cell proliferation.

ADI-PEG20 Impairs Mitochondrial Bioenergetics.

Figure 5A:
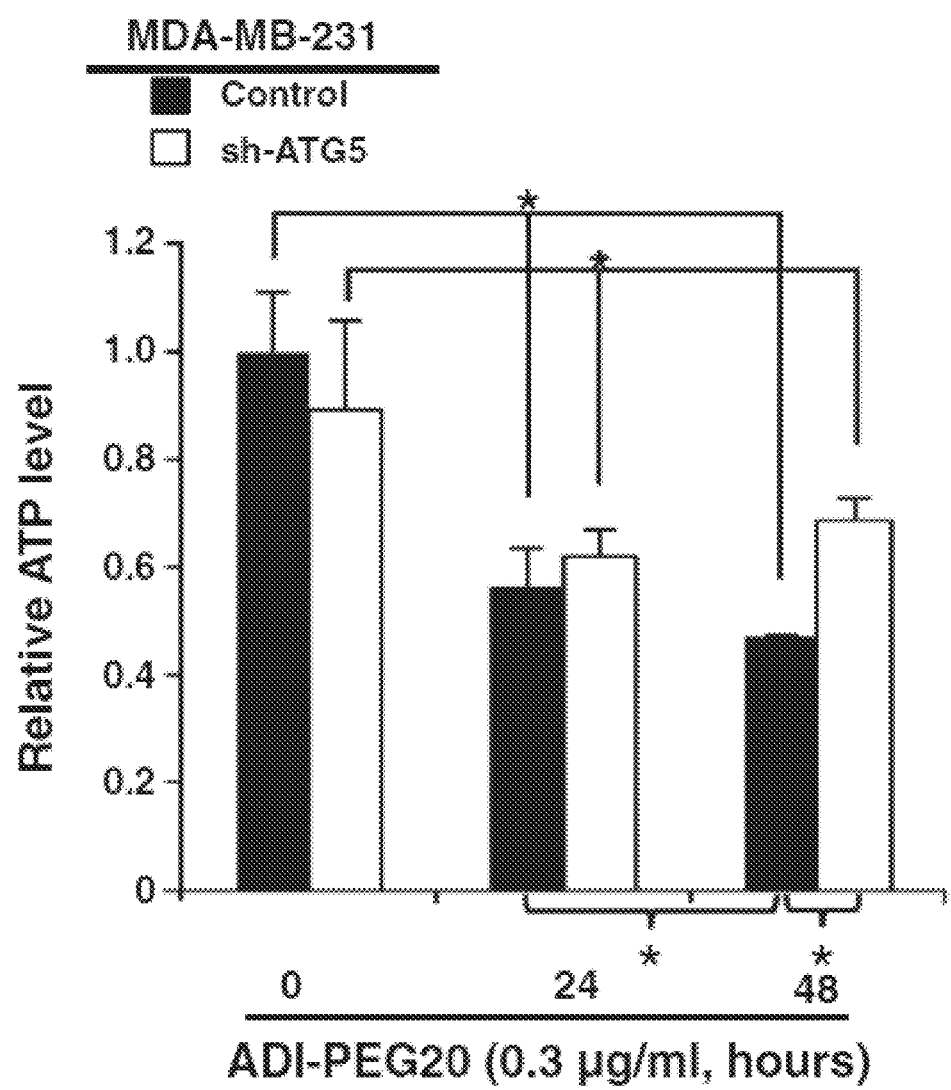
FIGS. 5A-F illustrate that ADI-PEG20 impairs mitochondrial function according to one embodiment.
Figure 5B:
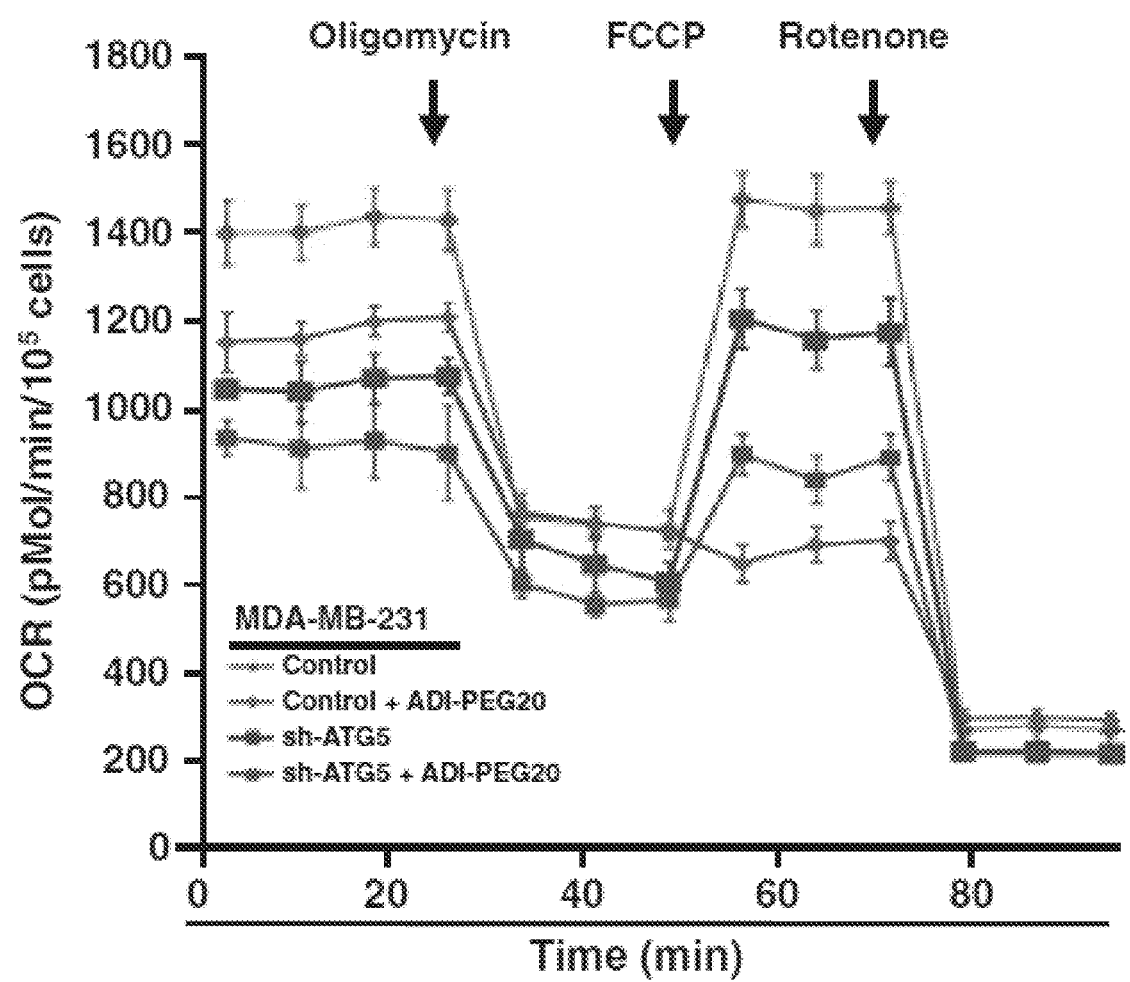

Autophagy is a catabolic process that delivers intracellular proteins or organelles sequestered in autophagosomes to lysosomes for recycling, thereby providing energy during metabolic stress (Levine & Kroemer 2008; Mizushima & Komatsu 2011). Glutamine depletion or autophagy-impairment decreases ATP production (Lin et al. 2012). Thus, the difference of ATP concentrations during the course of ADI-PEG20 treatment was analyzed in MDA-MB-231 cells stably-transfected with sh-control or sh-ATG5. ATP concentrations began to decrease 24 hours after ADI-PEG20 treatment and continued to decrease to less than 50% of vehicle-treated control cells at 48 hours after treatment (FIG. 5A). Knocking down ATG5 appeared to slow the reduction of ATP 48 hours after ADI-PEG20 treatment in MDA-MB-231 cells (FIG. 5A). Because mitochondria are the major subcellular organelles that produce ATP through oxidative phosphorylation, it was determined whether arginine starvation by ADI-PEG20 affected the oxygen consumption rate of living cells. Oxygen consumption was assayed in the presence of the mitochondrial inhibitor oligomycin or in the presence of the mitochondrial uncoupler FCCP (Carbonyl cyanide-4-(trifluoromethoxy)phenylhydrazone) to assess maximal oxidative capacity. First, it was shown that MDA-MB-231 cells were already at maximal respiratory capacity under basal conditions for ATP synthesis, because oxygen consumption rate did not increase in response to FCCP treatment (FIG. 5B). Knockdown of ATG5 markedly decreased mitochondria-dependent respiration in MDA-MB-231 cells (FIG. 5B), consistent with that in MEFs (Lin et al. 2012). In cells treated with ADI-PEG20, the oxygen consumption, used to make ATP was decreased and further inhibited by the ATP synthase blocker oligomycin. Moreover, the subsequent addition of FCCP failed to stimulate maximal respiration, and instead, caused it to fall below basal respiration, indicating that there is little or none of the uncoupled maximal respiration and reserve capacity (FIG. 5B). In contrast, FCCP, an uncoupler, partially stimulated rotenone-sensitive respiratory capacity in ADI-PEG20-treated cells with ATG5-knockdown. Likewise, oxygen consumption rate detected in MDA-MB-231 cells cultured under arginine-free condition showed comparable results with those treated with ADI-PEG20 (FIG. 6A), suggesting that the lack of arginine is mainly responsible for ADI-PEG20-caused mitochondrial dysfunction. Together, these results suggest the possibility that autophagy exacerbates the impaired mitochondrial functions by ADI-PEG20 or arginine starvation in MDA-MB-231 cells.

Figure 5C:
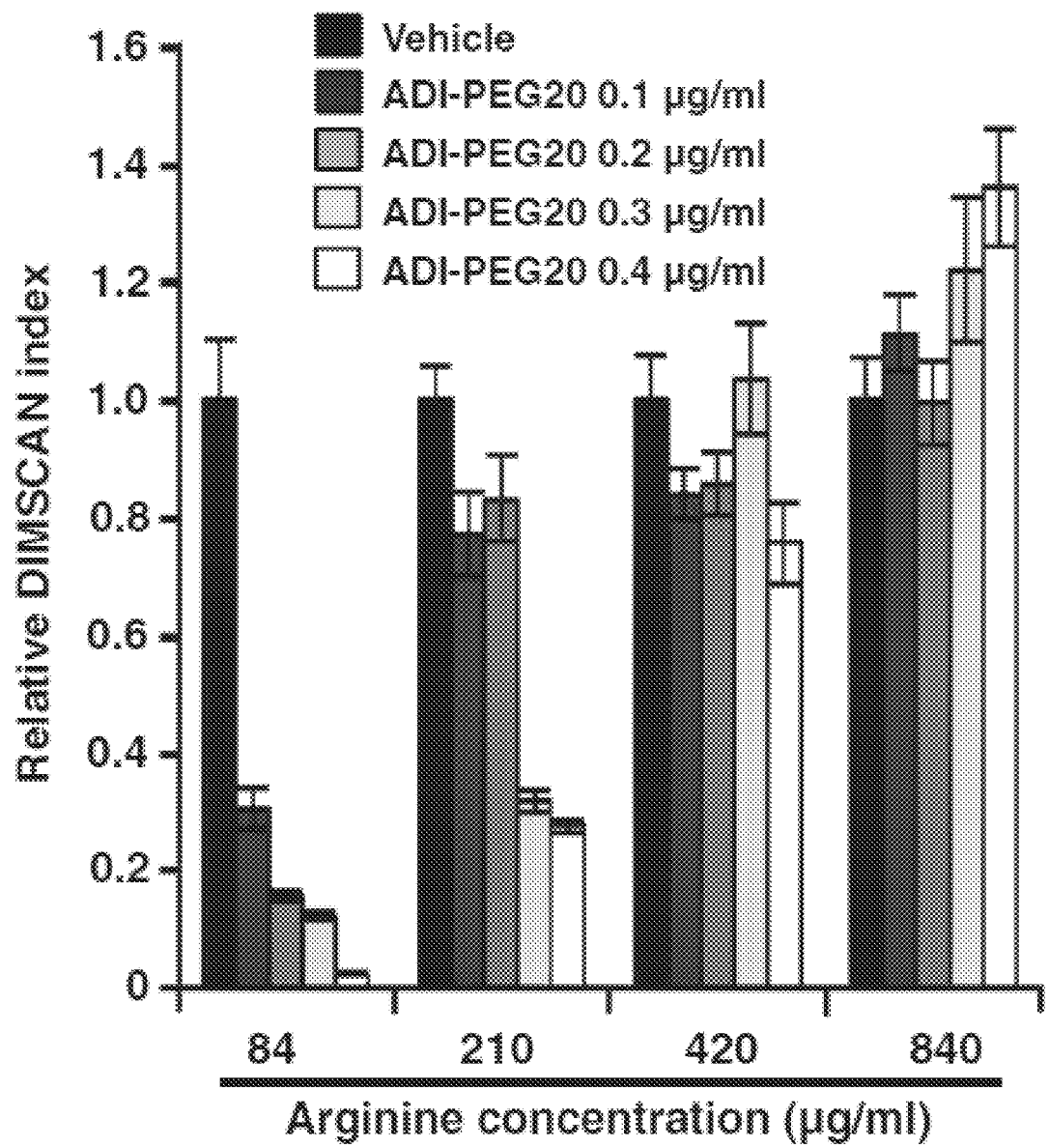
Figure 5D:
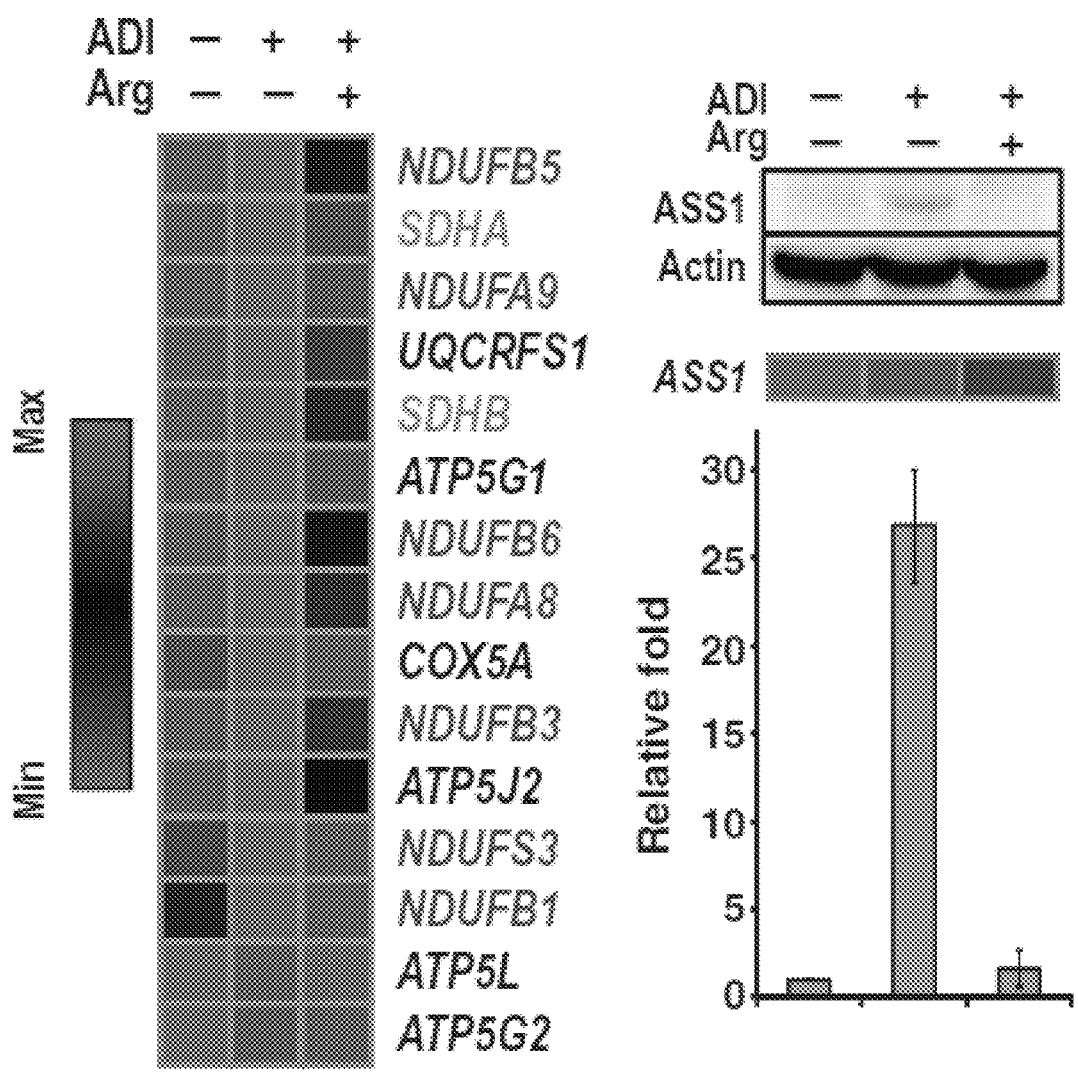
Figure 6B:
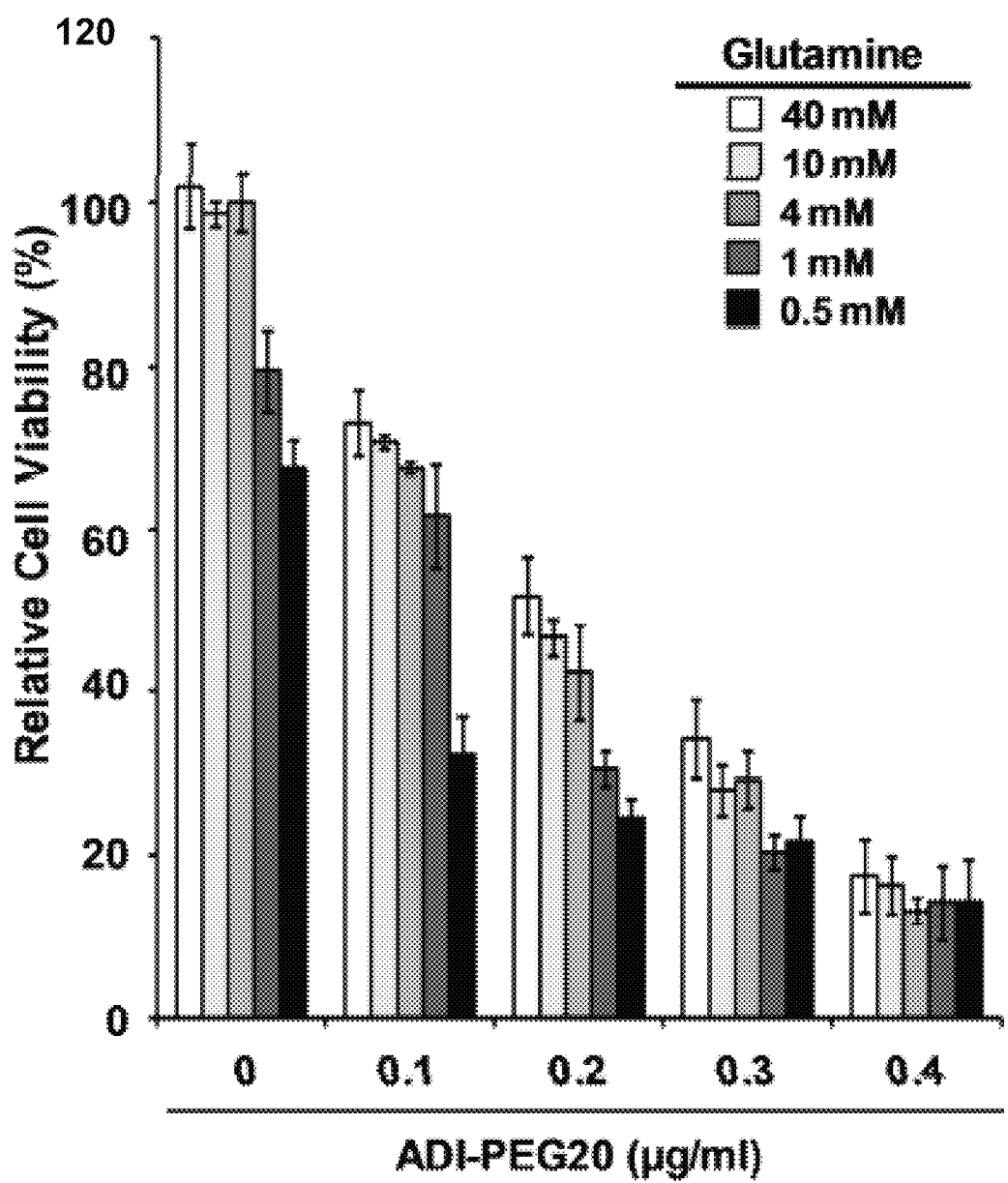
Figure 6C:
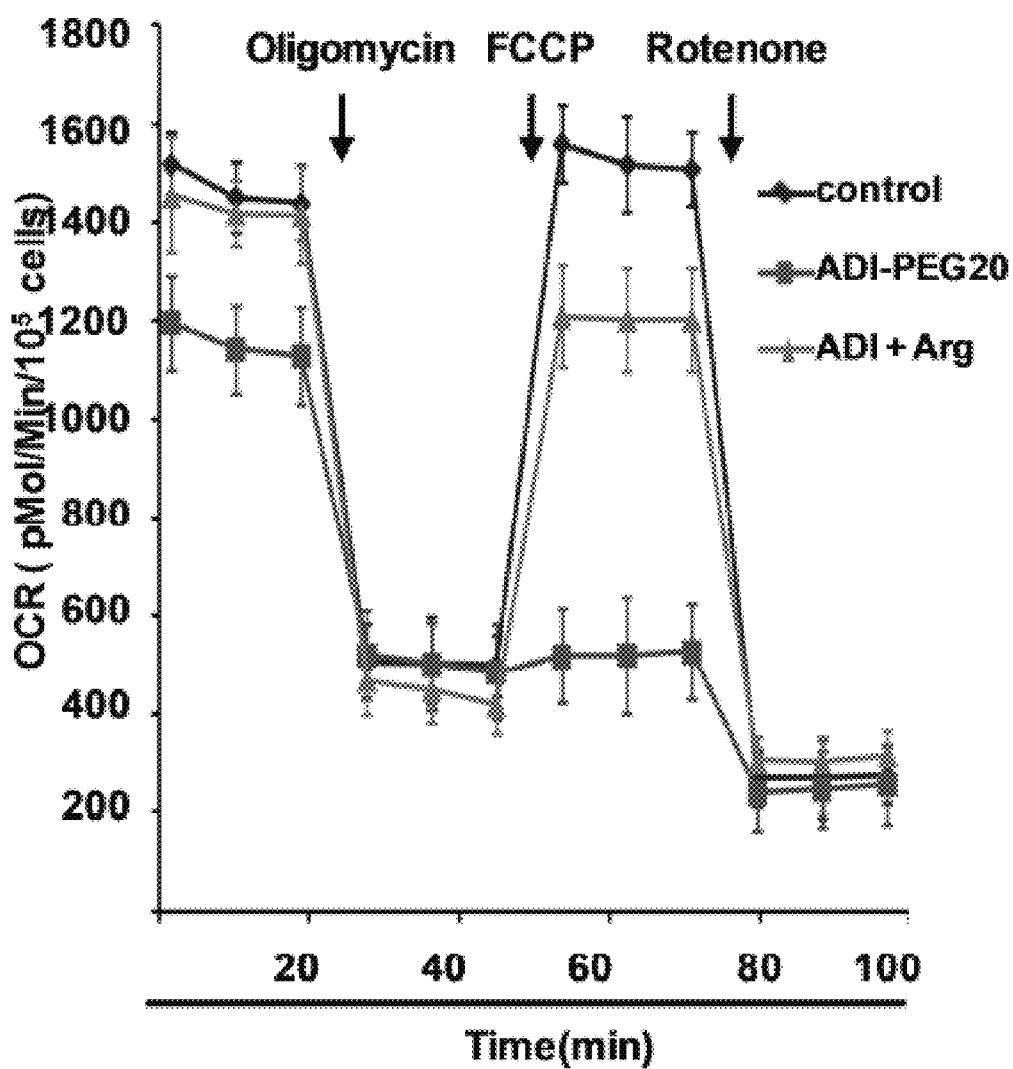

Increasing the extracellular concentration of arginine, but not that of glutamine, attenuated the reduction in cell proliferation induced by ADI-PEG20 (FIGS. 5C, 6B). Moreover, excess arginine also rescued oxygen consumption rate in ADI-PEG20-treated cells, thus confirming that arginine deprivation was the critical mechanism underlying the cytotoxic effects of ADI-PEG20, ruling out potential off-target effect by ADI-PEG20 (FIG. 6C). To investigate the metabolic defects caused by ADI-PEG20, the microarray message abundance profiles of untreated, ADI-PEG20-treated, or ADI-PEG20-treated and arginine-supplemented cells was analyzed on oligonucleotide microarray chips and validated the array data by qRT-PCR. The top candidates affected by ADI-PEG20 included NDUFB5, NDUFA9, NDUFB6, NDUFA8, NDUFB3, NDUFS3 and NDUFB1 for complex I; SDHA and SDHB from complex II; UQCRFS1 from complex III; COX5A from complex IV; ATP5G1, ATP5G2, ATP5J2 and ATP5L from complex V (FIG. 5D, left panel). The heatmap analysis also confirmed that the decreased transcript abundance in ADI-PEG20-treated cells was reversed by supplementation with extracellular arginine. Notably the ASS1 message and ASS1 protein abundance were induced by ADI-PEG20 and reversed by arginine supplementation (FIG. 5D, right panel).

Figure 5E:
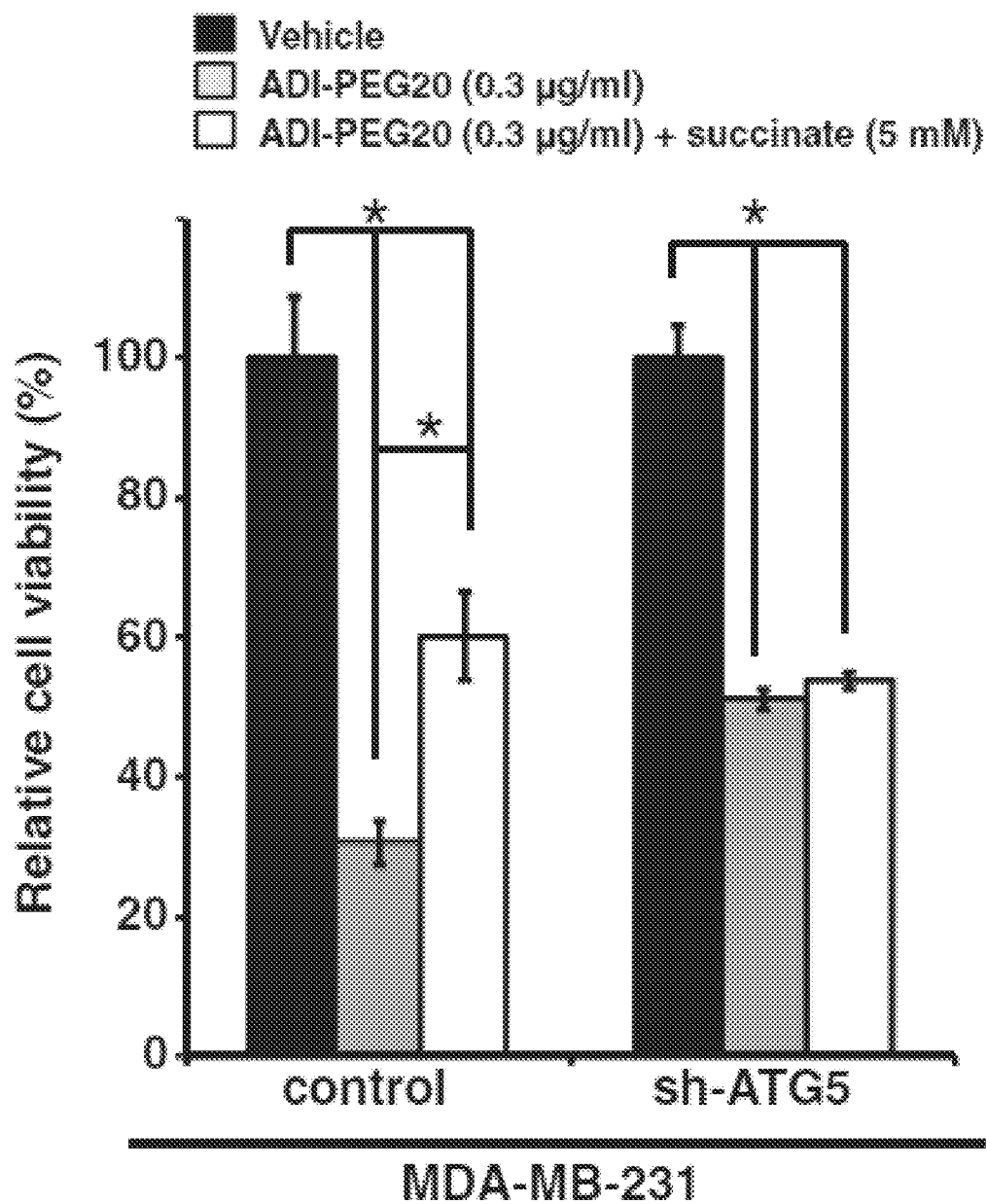
Figure 5F:
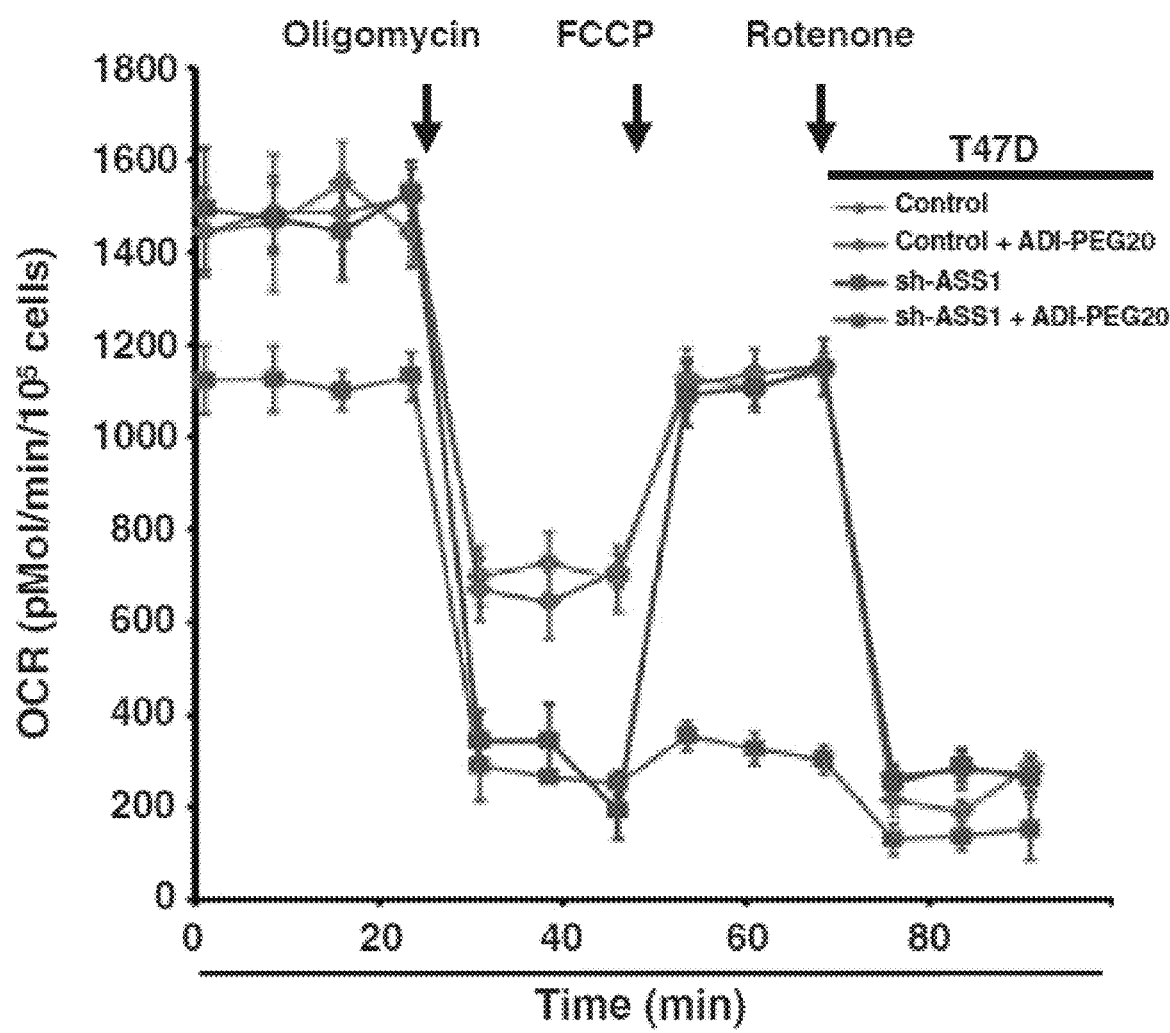
Figure 6D:
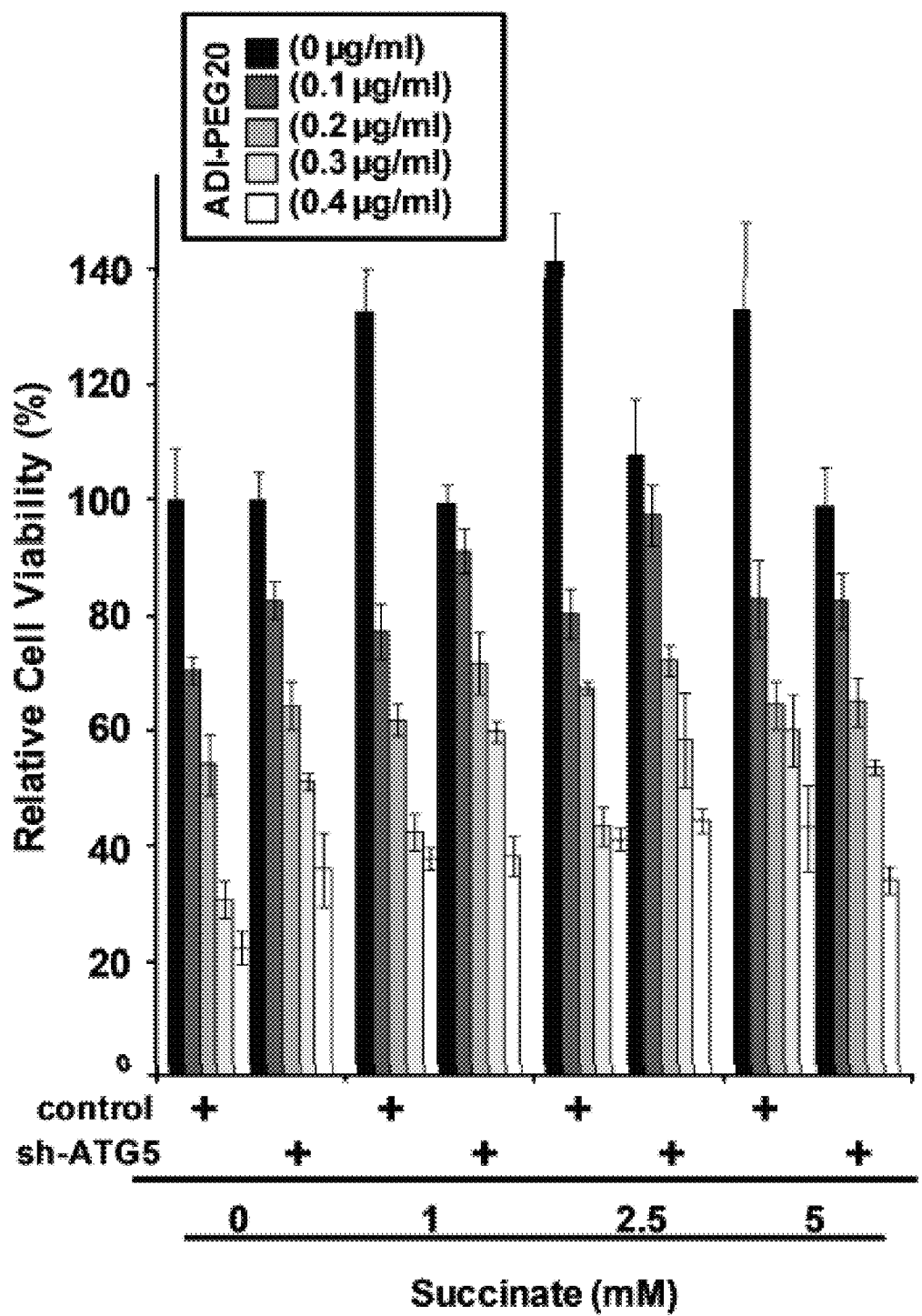

During mitochondrial electron transfer to the ATP synthase, both complexes I and II are involved in shuttling electrons to complex III (Birrell & Hirst 2013; Cecchini 2003; Ackrell 2000; Bianchi et al. 2004; Bianchi 2003). It was found that adding more succinate substrate for the complex II reaction rescued the reduced proliferation of ADI-PEG20-treated MDA-MB-231 cells in a concentration-dependent manner (FIG. 6D) from 70% to 40% (FIG. 5E). The rescue effect was not very noticeable in ATG5-knockdown MDA-MB-231 cells in the presence of succinate (FIGS. 5E, 6D). Lastly, to assess whether ASS1 status affects vulnerability of mitochondrial bioenergetics to ADI-PEG20, oxygen consumption rate was measured in both T47D and ASS1-knockdown T47D cells in the presence and absence of ADI-PEG20. Knockdown of ASS1 decreased both basal and uncoupled oxygen consumption rate in the context of ADI-PEG20 treatment (FIG. 5F). Together, these results suggest that the combination of loss of ASS1 and ADI-PEG20 treatment severely dampens mitochondrial respiratory function.

Figure 7A:
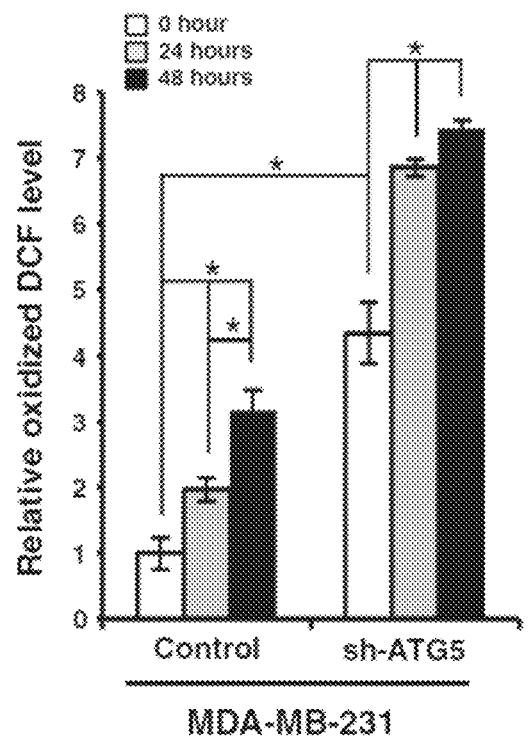
FIGS. 7A-G illustrate that ADI-PEG20 induces mitochondrial ROS according to one embodiment.
Figure 7B:
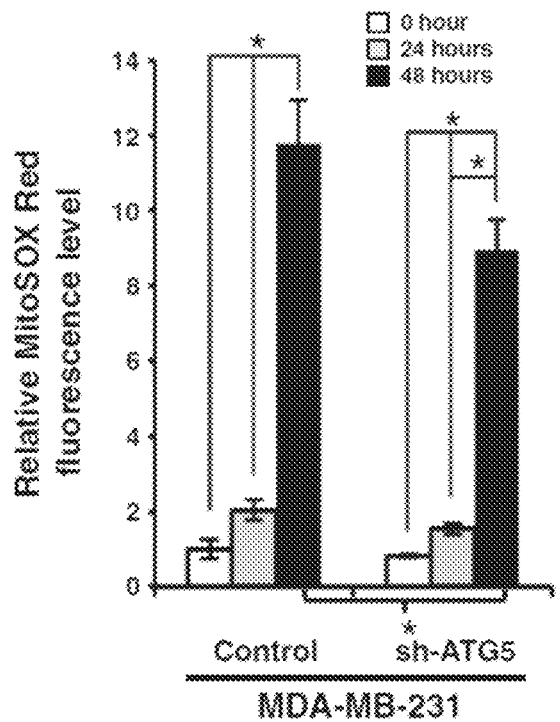
Figure 7C:
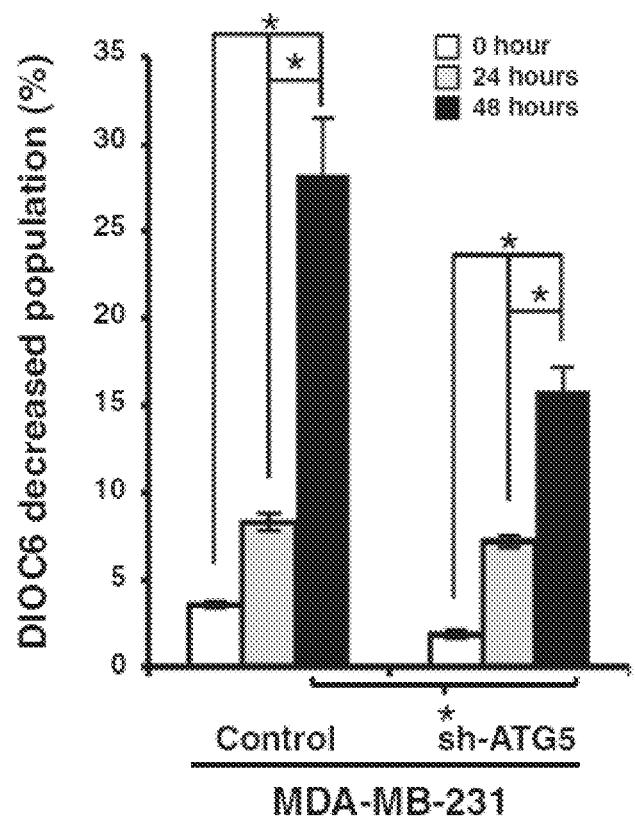

ADI-PEG20 increases ROS and decreases mitochondrial MMP in ASS1-deficient MDA-MB-231 cells. There is a complex relationship between oxidative phosphorylation, electron transport and the production of superoxide by mitochondria. Physiological uncoupling of ATP production from electron transport decreases superoxide production, whereas inhibiting the electron transport chain increases superoxide production (Forman & Kennedy 1974). Furthermore, simultaneously uncoupling and inhibiting electron transport increases superoxide production (Cadenas & Boveris 1980). The oxidation of DCFDH to DCF (Kalyanaraman et al. 2012) was used as the first approach (due to the limitations of fluorescent dyes to measure specific reactive species) to determine whether ADI-PEG20 increases the intracellular concentration of reactive oxygen species (ROS) that impair mitochondrial respiratory function. Although the relative DCF signal in MDA-MB-231 cells was lower than that in autophagy-impaired isogenic cells, ADI-PEG20 increased the relative signals of oxidized DCF in both MDA-MB-231 and MDA-MB-231/sh-ATG5 cells (FIG. 7A). The relative increase was greater in MDA-MB-231 cells (~3-fold) than in MDA-MB-231/sh-ATG5 cells (<2-fold) (FIG. 7A). MitoSox Red was used to further analyze the effect of ADI-PEG20 on non-metabolic oxidation in MDA-MB-231 and MDA-MB-231/sh-ATG5 cells. ADI-PEG20 increased MitoSox red fluorescence ~12-fold in MDA-MB-231 cells, an increase that was significantly higher than the ~9-fold increase in the MDA-MB-231/ATG5-knockdown cells (FIG. 7B). Consistently, mitochondrial membrane potential (MMP) was reduced by ADI-PEG20 to a greater extent in MDA-MB-231 cells compared to ATG5-knockdown MDA-MB-231 cells (FIG. 7C). Altogether, these observations suggest that autophagy competence exacerbated the mitochondrial damage induced by ADI-PEG20 in MDA-MB-231 cells (FIGS. 5B, 7A-7C), supporting the studies suggesting that ADI-PEG20-induced cell death is autophagy-dependent (FIGS. 3E, 3F).

Figure 7D:
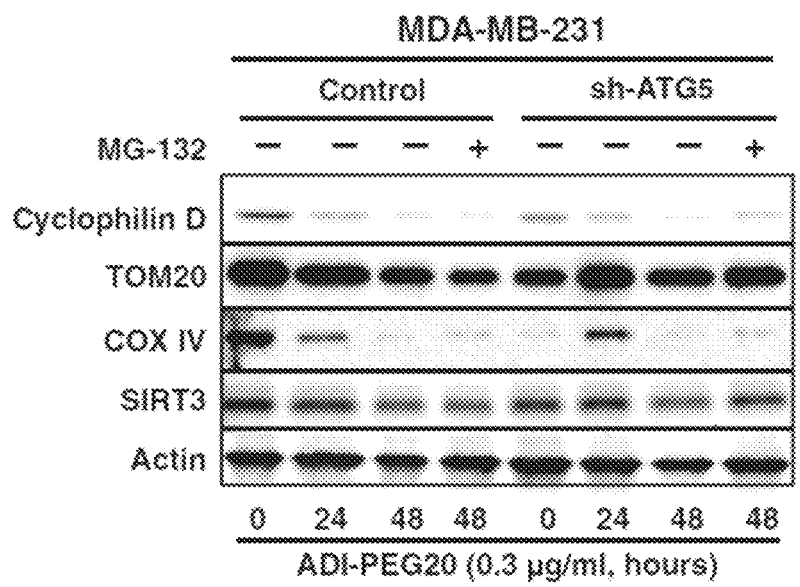
Figure 7E:
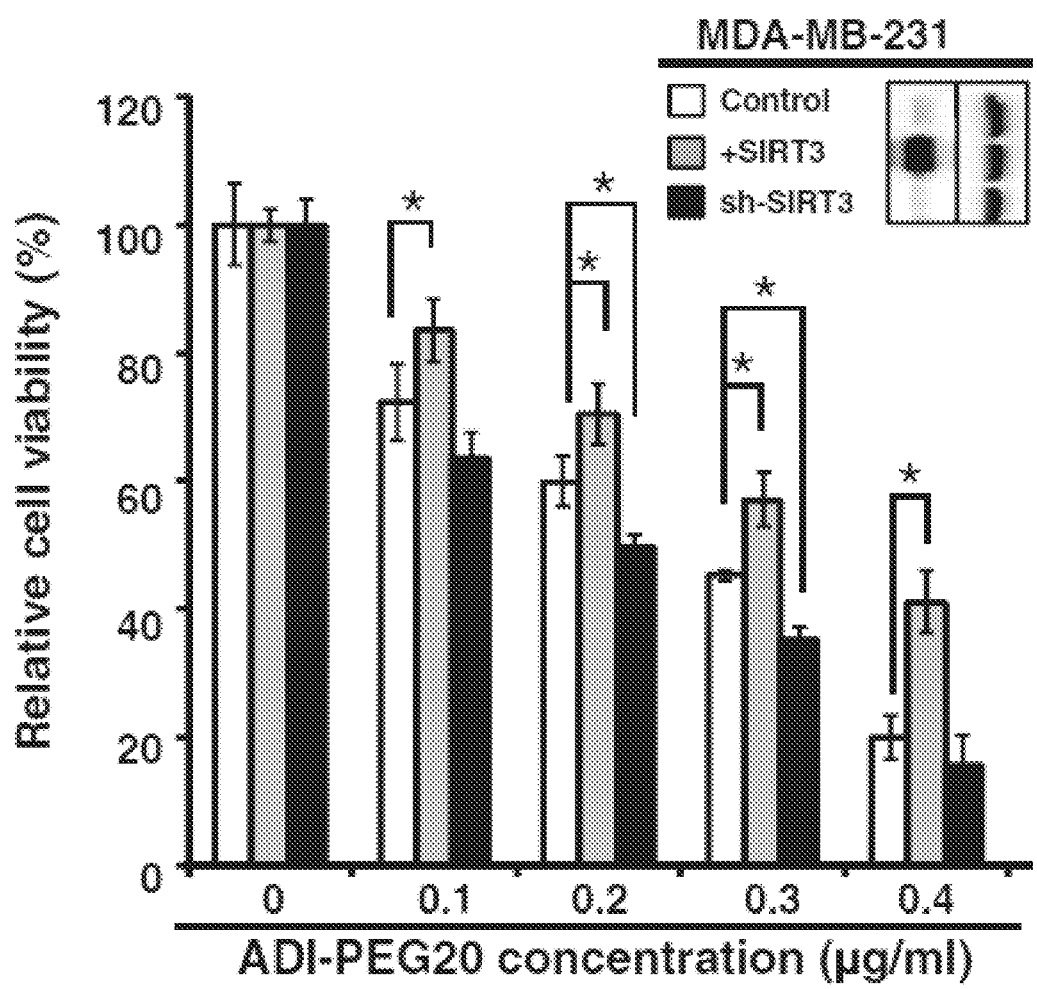
Figure 7F:
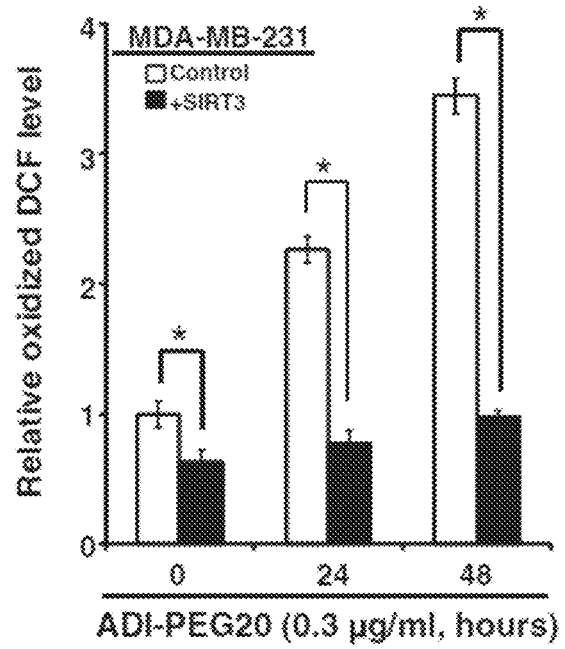
Figure 7G:
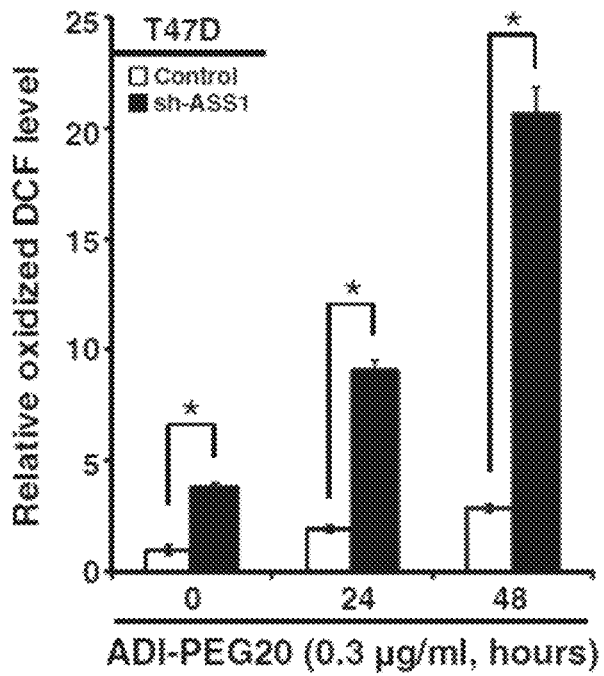
Figure 8A:
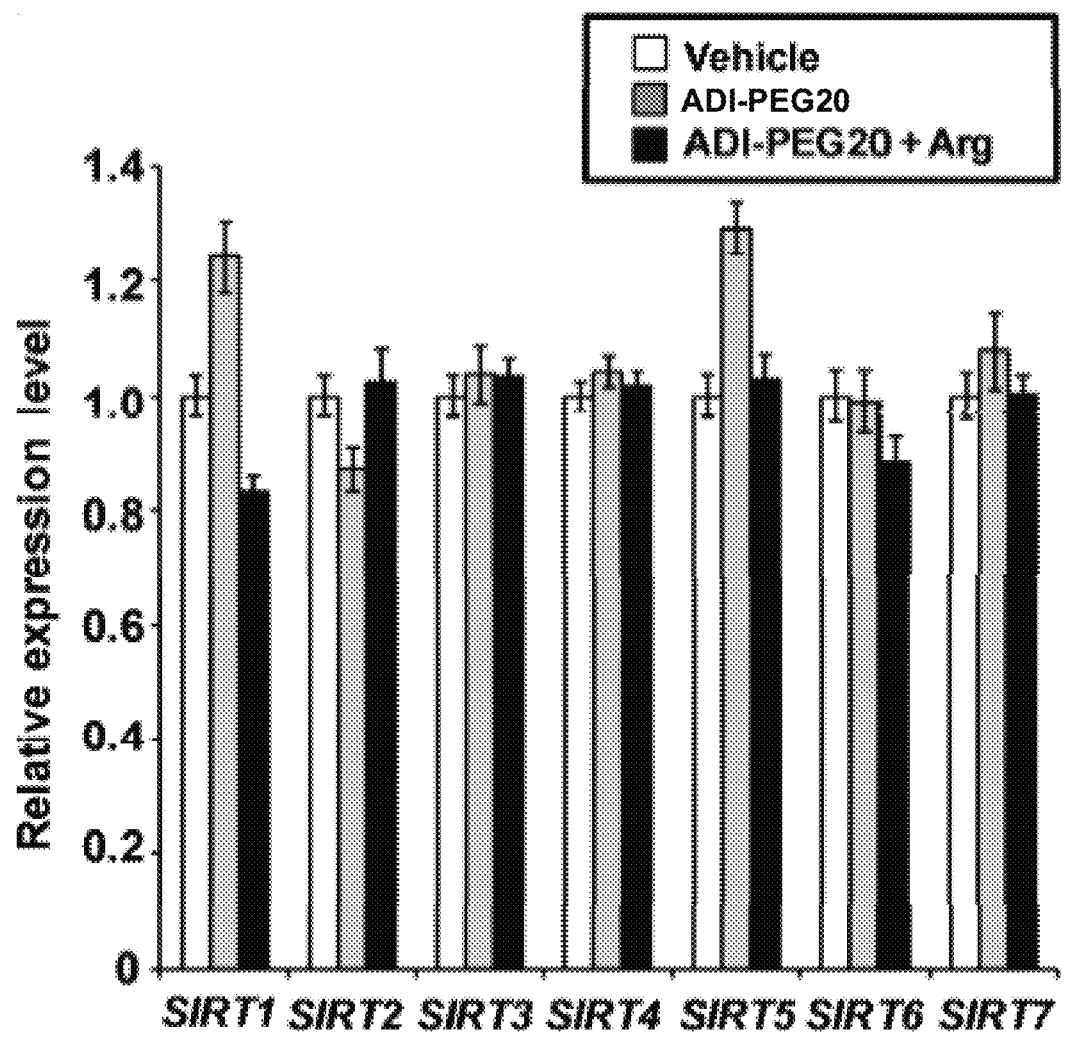
FIGS. 8A-F illustrate that ADI-PEG20 does not affect SOD and SIRT mRNA abundance, but decreases mitochondrial protein abundance, according to one embodiment. qRT-PCR analyses validate the relative steady-state abundance of SIRT (FIG. 8A) and SOD (FIG. 8B) mRNA extracted from array data. The relative abundance of SIRT3 and SOD2 mRNA show no differences in response to ADI-PEG20 with or without arginine supplementation rescue. Results are shown as the mean±SD; N=3 sets of cells. The bar graphs show the quantitative analysis of densitometric tracing for mitochondrial proteins Cyclophilin D (FIG. 8C), TOM20 (FIG. 8D), COXIV (FIG. 8E) and SIRT3 (FIG. 8F) shown in FIG. 4D after normalization with actin. Results are shown as mean±SD; N=3 sets of paired cells.
Figure 8B:
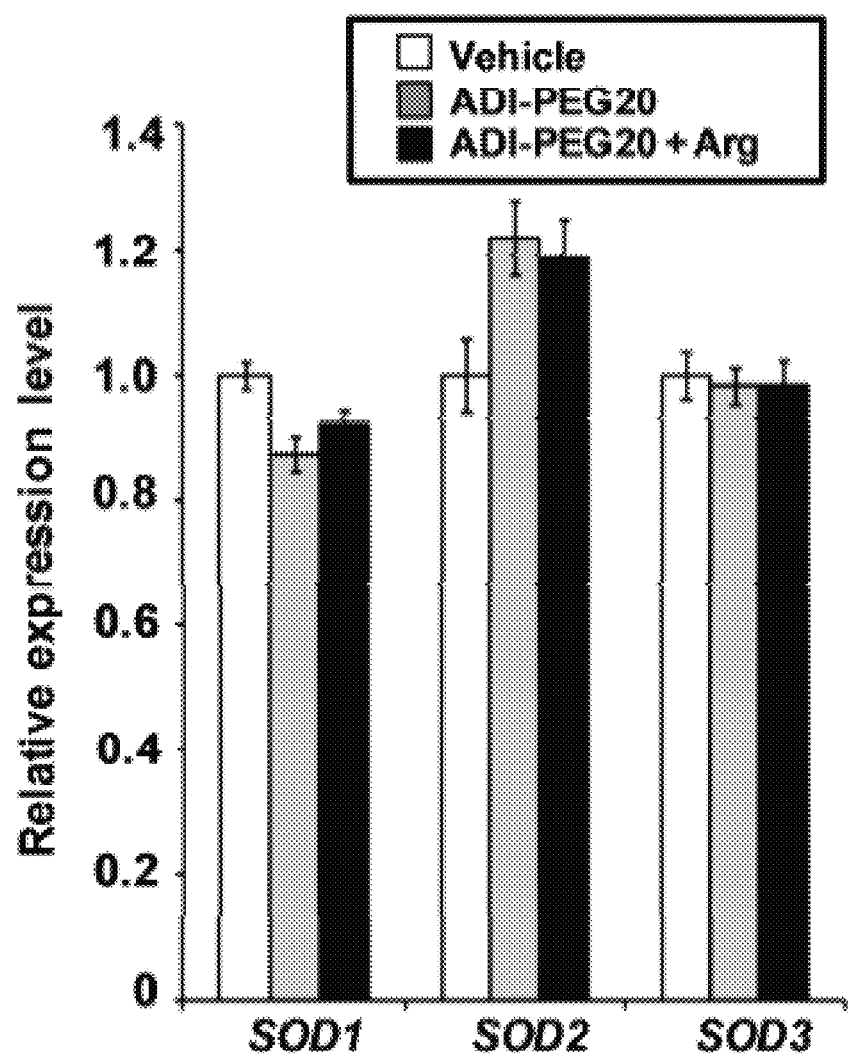
Figure 8C:
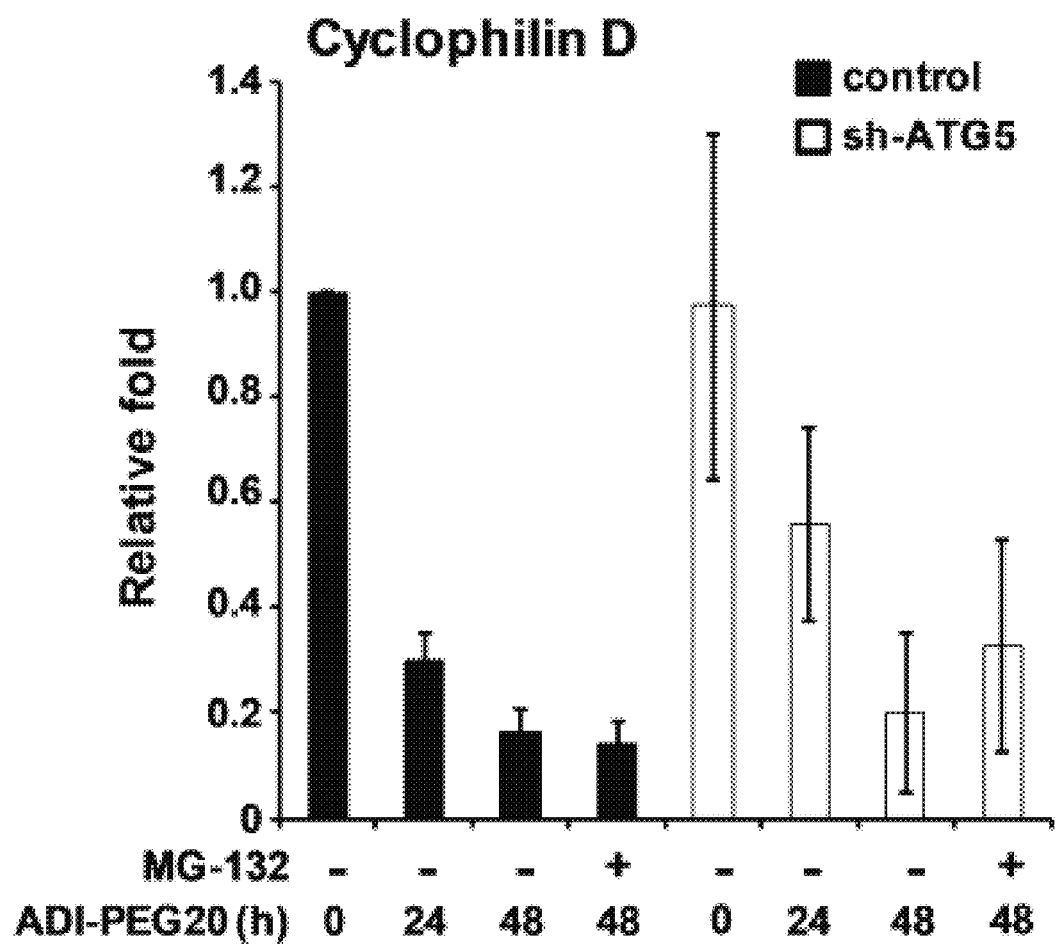
Figure 8D:
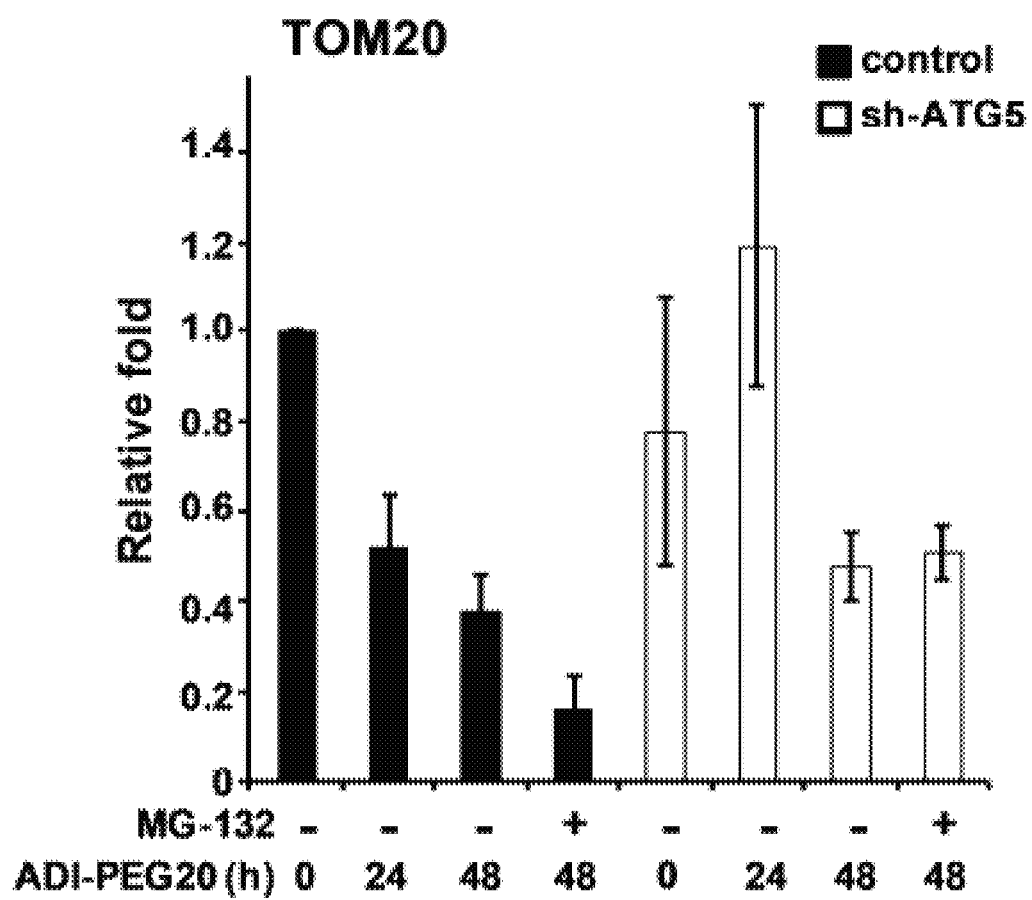
Figure 8E:
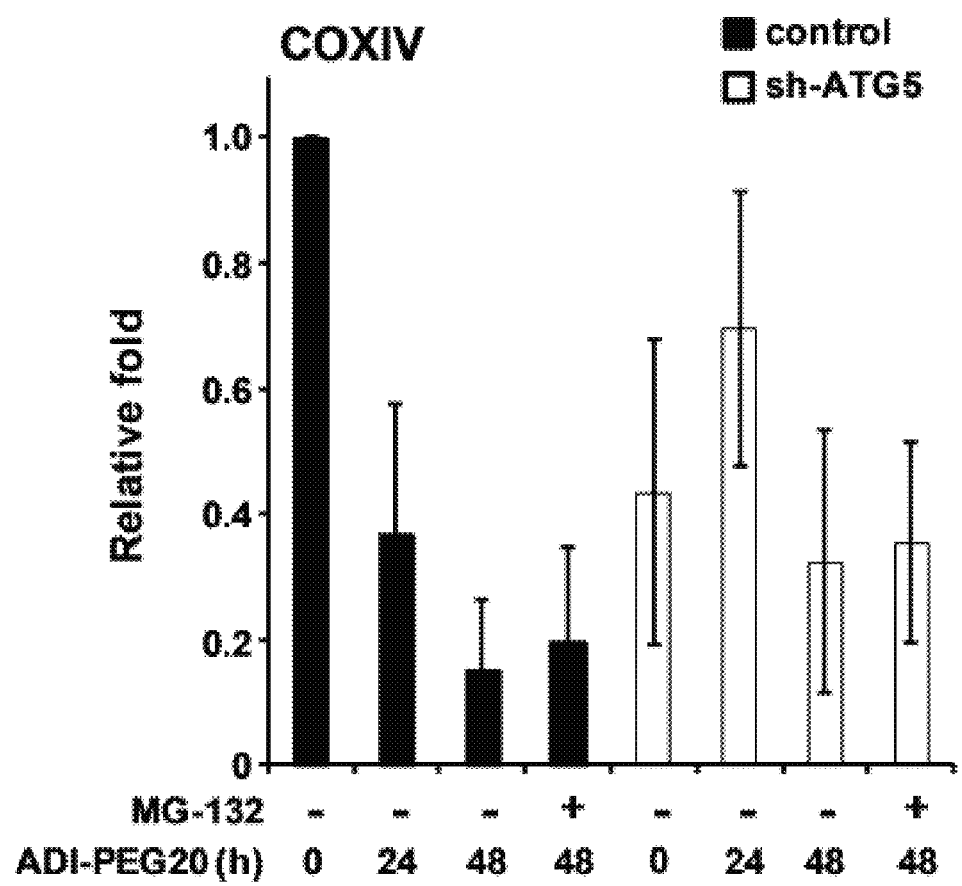
Figure 8F:
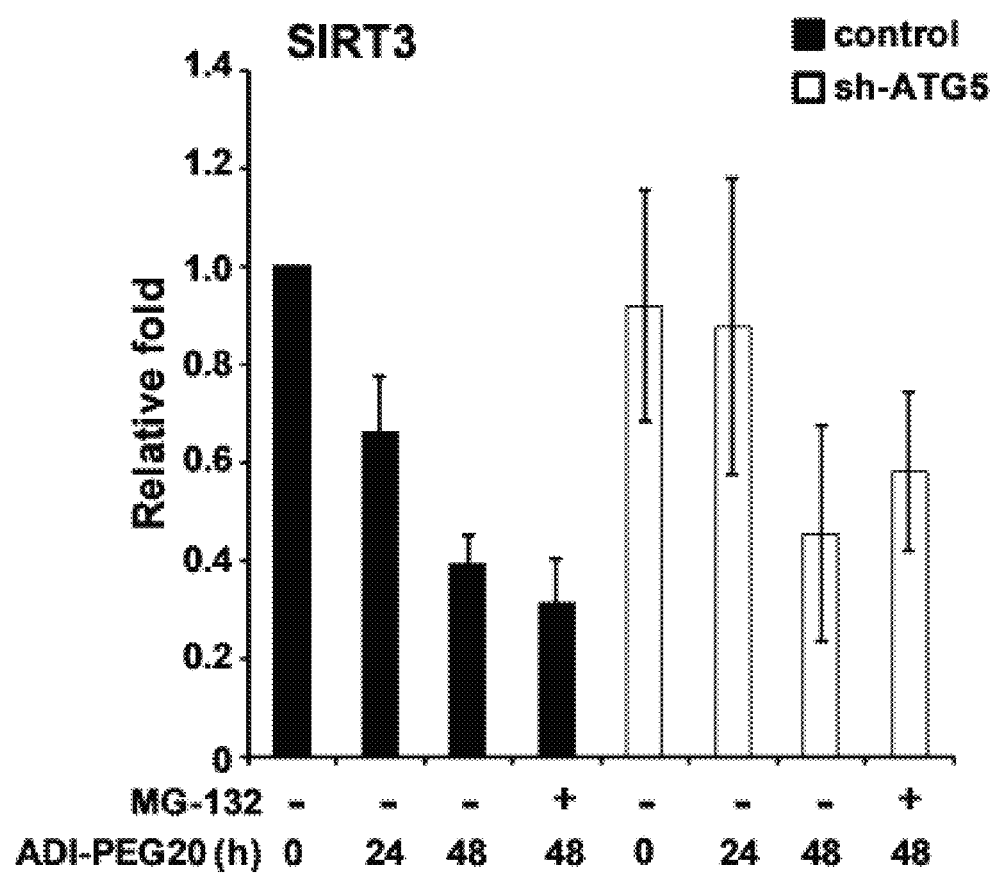

The ADI-PEG20-increased generation of ROS (FIGS. 7A, 7B) could result from a decrease of the abundance of SIRT or SOD members. However, the mRNA abundance of SIRT and SOD family members showed no change in ADI-PEG20-treated or arginine-supplemented, ADI- PEG20-treated MDA-MB-231 cells (FIGS. 8A, 8B). As such, Western blotting was used to assess whether there is a change in the abundance of mitochondrial proteins, including TOM20 (located in the mitochondrial outer membrane), COX IV (cytochrome c oxidase subunit IV; located in the mitochondrial inner membrane), Cyclophilin D (located in the mitochondrial matrix) and SIRT3 (NAD-dependent deacetylase sirtuin-3; located in the mitochondrial matrix) in MDA-MB-231 and MDA-MB-231/sh-ATG5 cells in response to ADI-PEG20 treatment. Decreased mitochondrial-specific SIRT3 protein abundance was observed, albeit modestly, which occurred earlier in MDA-MB-231 cells (24 hours) than in the ATG5-knockdown MDA-MB-231 cells (48 hours) (FIG. 7D). Furthermore, adding the proteasome inhibitor MG132 mainly altered SIRT3 abundance in the ATG5-knockdown MDA-MB-231 cells. A decrease of other mitochondria-specific proteins, including TOM20, Cyclophilin D and COX IV over time in response to ADI-PEG20 was also observed, supporting the involvement of mitochondrial dysfunction in response to ADI-PEG20. SIRT3 is located within mitochondria and is implicated in regulating metabolic processes through deacetylation of transcription factors or metabolic enzymes (Roth & Chen 2013). Together with bioenergetics data (FIGS. 5A and 5B), these results showed that ADI-PEG20 disrupted mitochondrial components in MDA-MB-231 cells. It was also demonstrated that modifying the abundance of SIRT3 (FIG. 7E, inset) affected the sensitivity of cells to ADI-PEG20. SIRT3 over-expressing (+SIRT3) cells were more resistant to ADI-PEG20, whereas the knockdown of SIRT3 (sh-SIRT3) increased the cytotoxicity (FIG. 7E). Consistently, overexpression of SIRT3 decreased the basal concentration of ROS and attenuated its increase upon ADI-PEG20 treatment in MDA-MDA-231 cells (FIG. 7F). Lastly, knockdown of ASS1 increased the basal concentration of ROS and sensitized T47D cells to ADI-PEG20-mediated ROS induction (FIG. 4G).

ADI-PEG20 Induces Mitophagy in ASS1-Deficient MDA-MB-231 Cells.

Figure 9A:
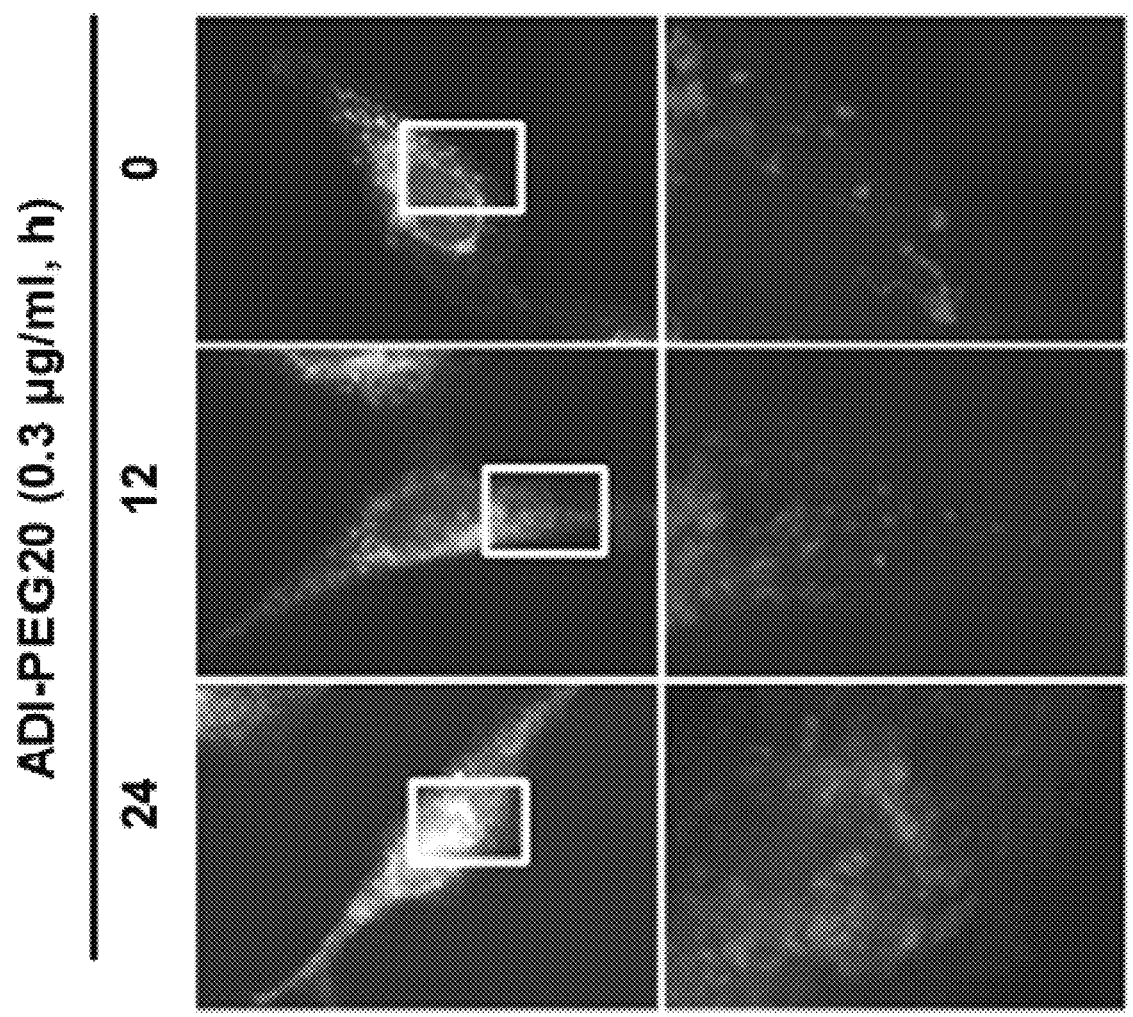
FIGS. 9A-B show that ADI-PEG20 induces mitochondrial fragmentation in MDA-MB-231 cells according to one embodiment.
Figure 9B:
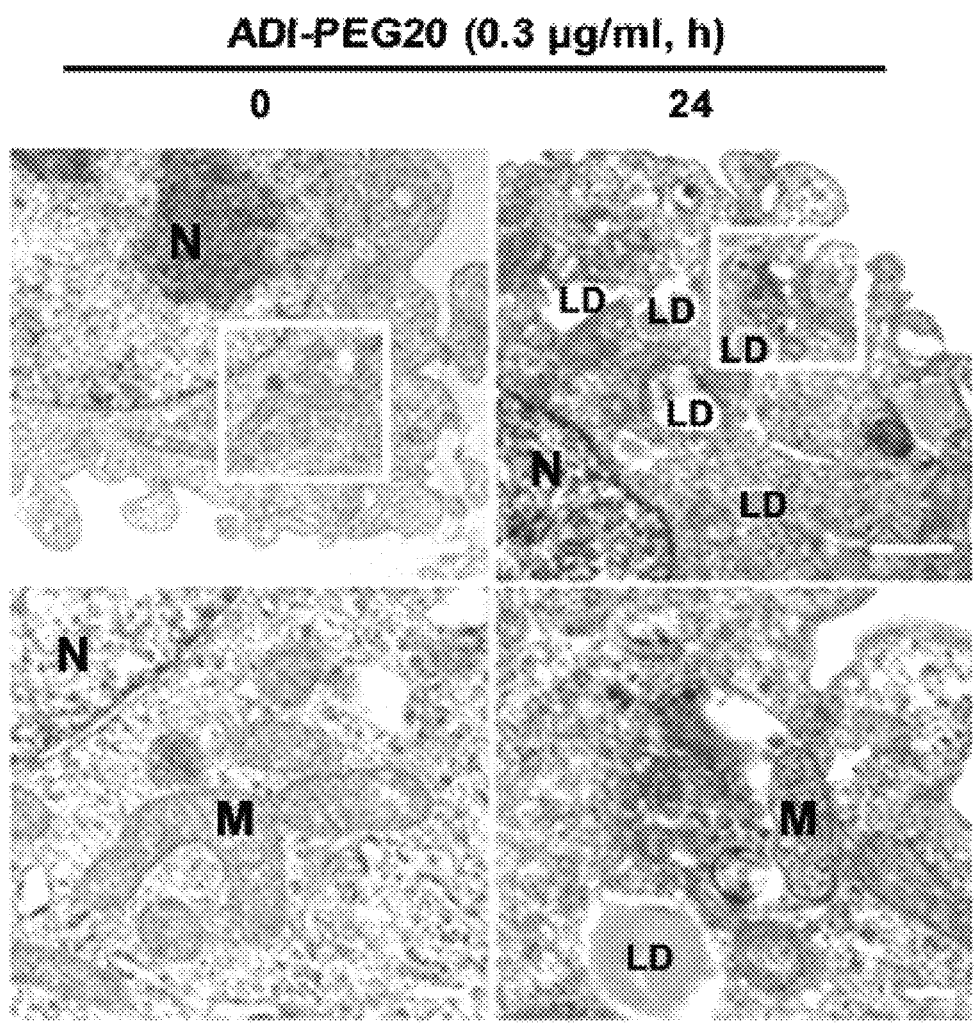
Figure 10A:
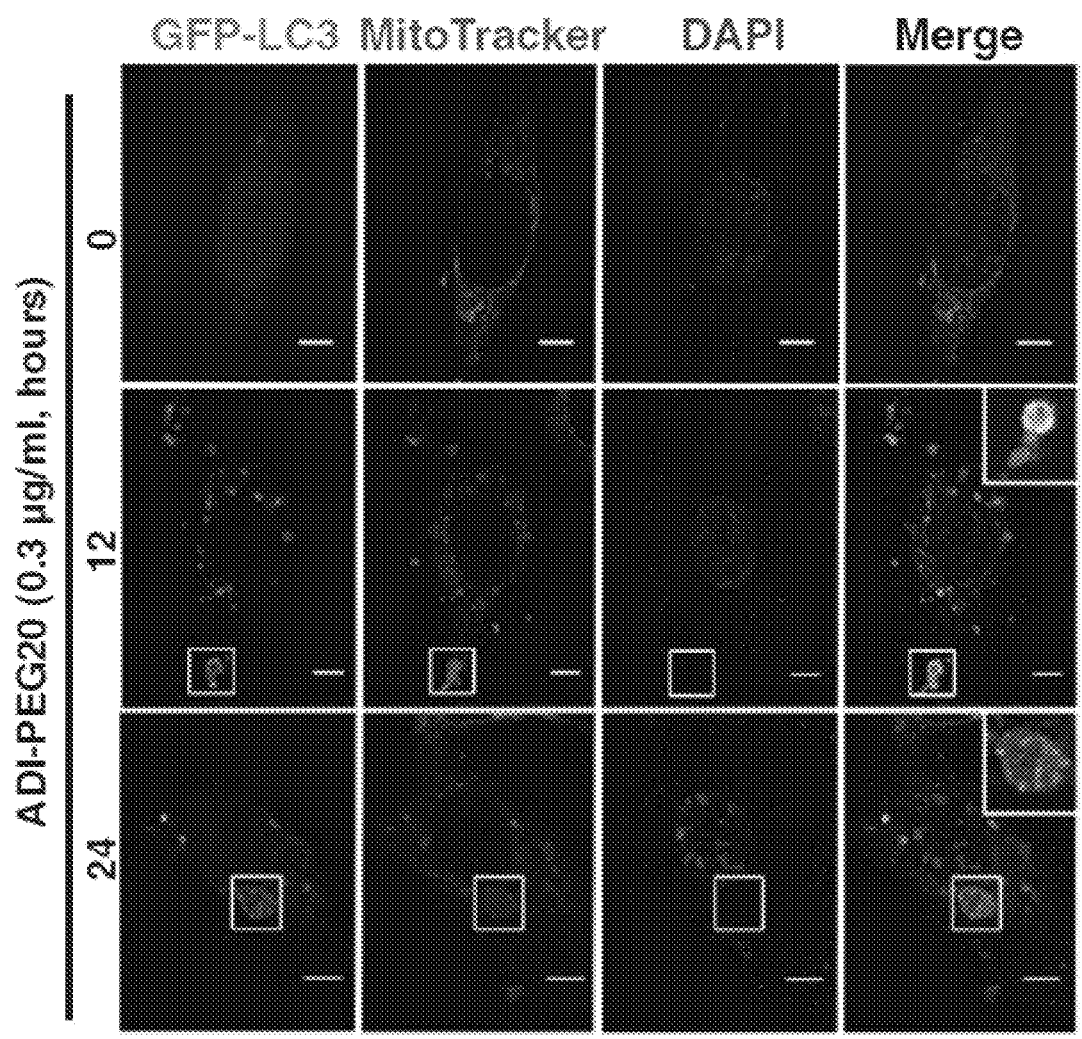
FIGS. 10A-D illustrate that ADI-PEG20 causes mitochondrial fragmentation according to one embodiment.
Figure 10B:
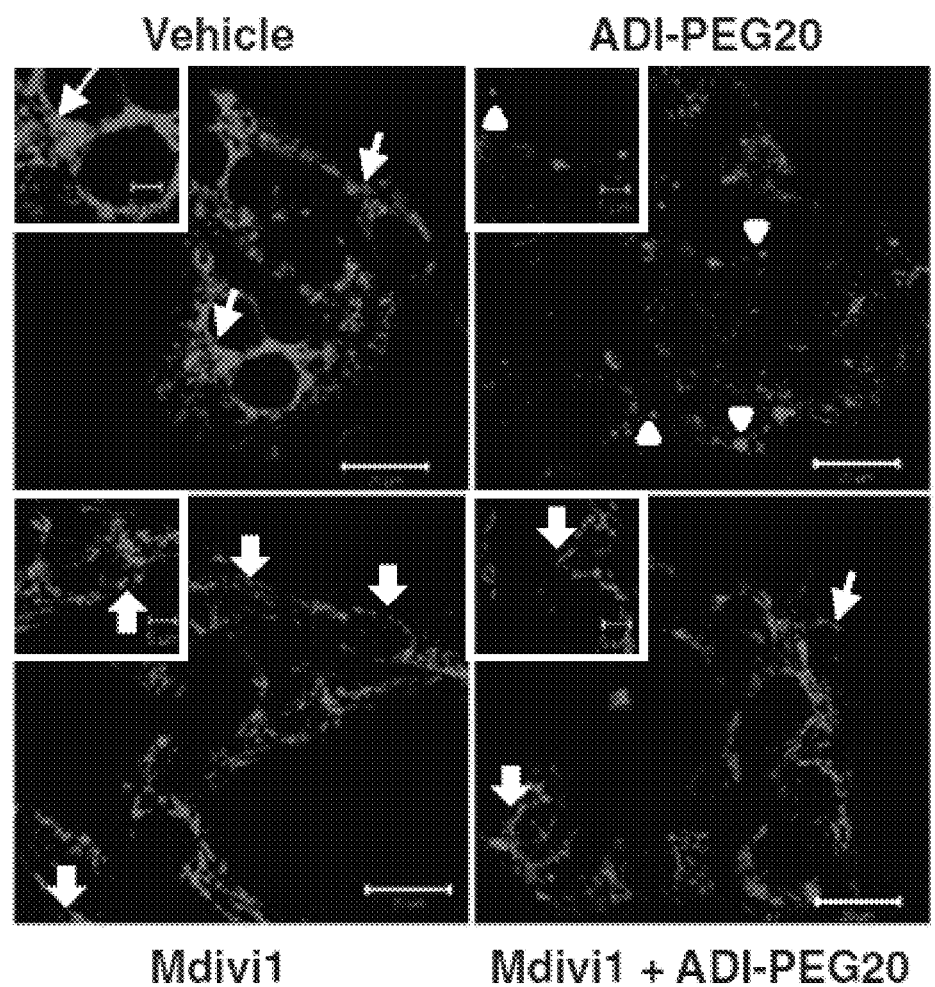
Figure 10C:
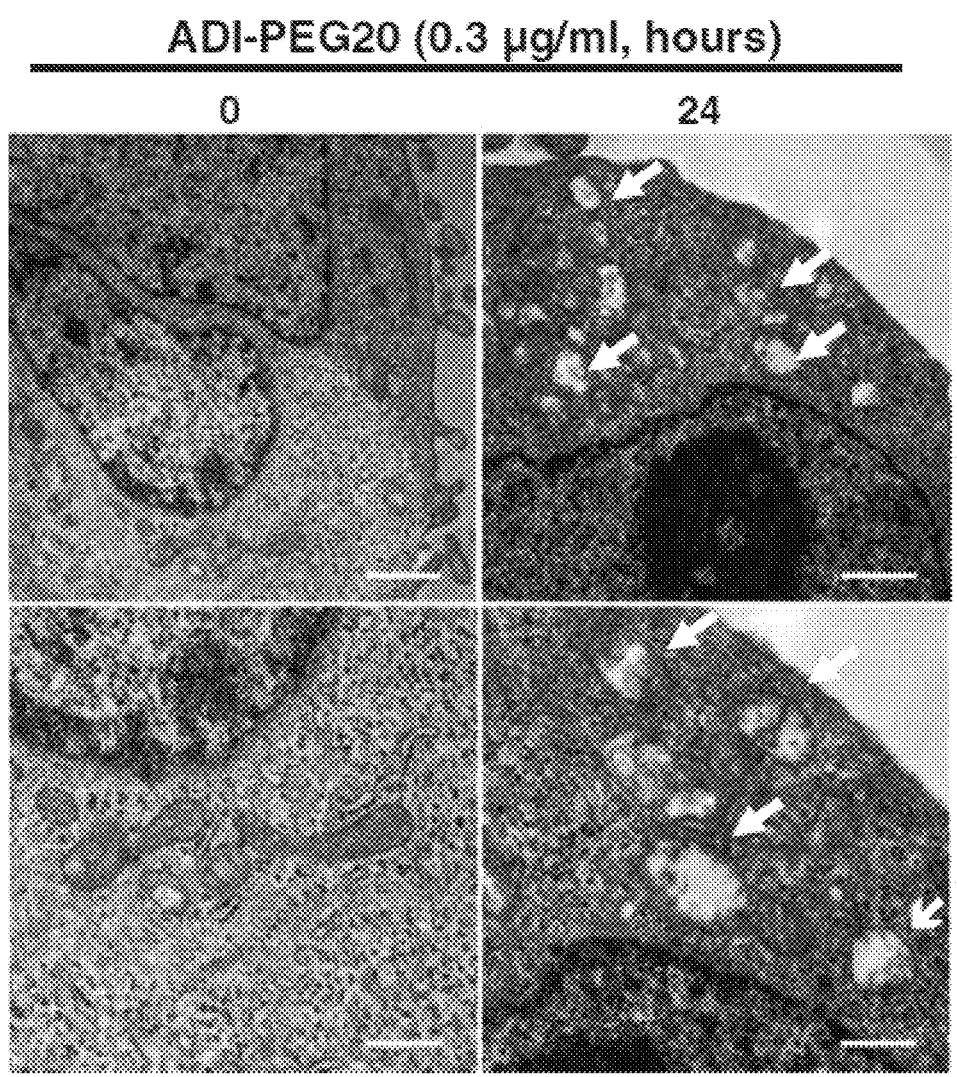
Figure 10D:
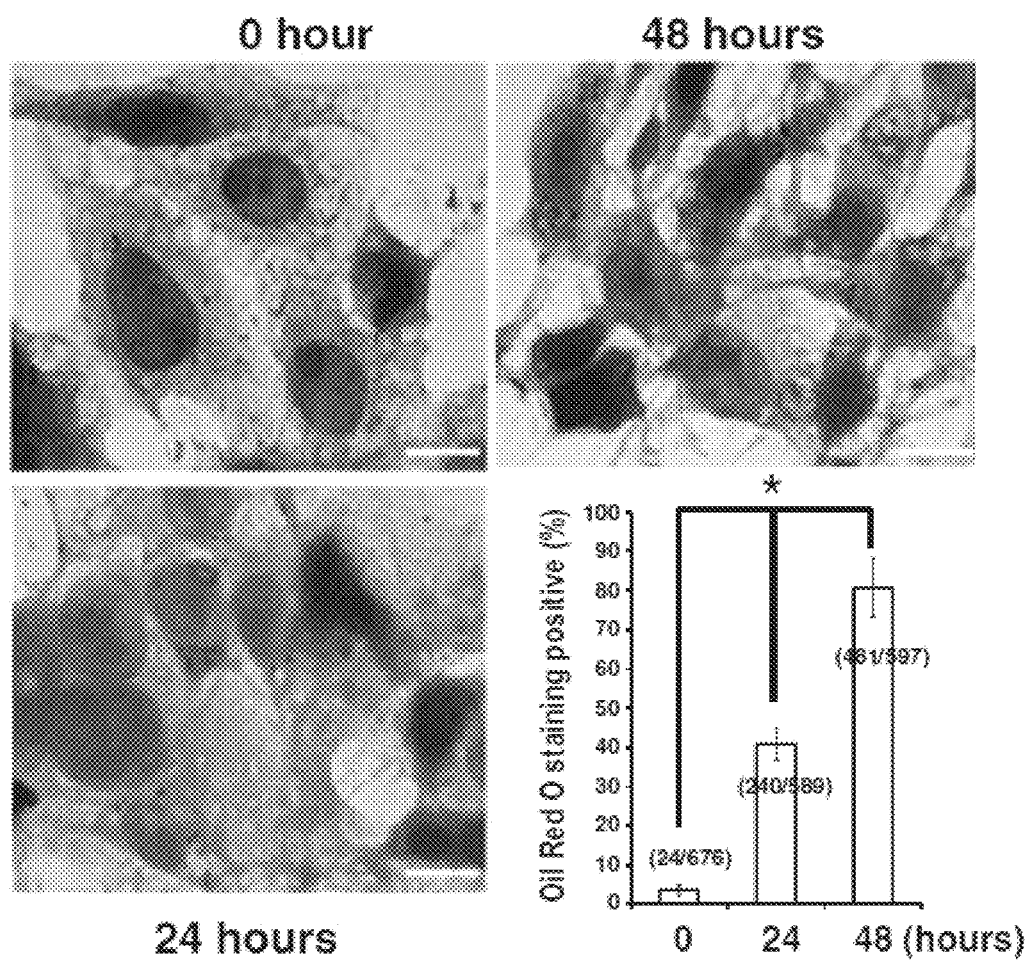

The observations that autophagy-competent MDA-MB-231 cells were more likely to be subjected to ADI-PEG20-induced loss of mitochondrial function, such as decreased ATP production and oxygen consumption (FIGS. 5A, 5B), suggesting an active role for autophagy in impairing mitochondrial function. MitoTracker staining was used to follow mitochondrial network over the course of ADI-PEG20. Mitochondrial morphology, determined by the balance of activity of fission and fusion (Mitra 2013), and mitochondrial syncytia were shown to be disrupted in a time-dependent manner, suggesting there was mitochondrial structural changes (FIG. 9A). Next, mitochondria in GFP-LC3 stably-transfected MDA-MB-231 cells were stained with MitoTracker Red. Confocal microscopy revealed that GFP-LC3 and MitoTracker co-localized at 12 and 24 hours after ADI-PEG20 treatment, suggesting that mitochondria were being engulfed by autophagosomes (FIG. 10A). Then, it was determined how treatment of MDA-MB-231 cells with ADI-PEG20 affects the mitochondrial network. As shown in FIG. 10B, more than 50% cells, prior to ADI-PEG20 treatment (1st left and 3rd panels), harbored vermiform mitochondria (FIG. 9B, lower left panel). Exposure to ADI-PEG20 led to nearly all of the cells acquiring a fragmented mitochondrial structure (FIG. 10B, 1st right and 3rd panels). Next, cells co-treated with ADI-PEG20 and Mdivi-1, an inhibitor for mitochondrial fission (Cassidy-Stone et al. 2008), showed a largely preserved filamentous mitochondrial morphology compared with cells treated with ADI-PEG20 alone (FIG. 10B, 2nd right and 3rd panels). Transmission electron microscopy (TEM) further revealed mitochondria that were engulfed in what were presumably autophagosomes in ADI-PEG20-treated MDA-MB-231 cells (FIG. 9B, lower right panel, indicated by an arrow). Moreover, TEM images also revealed swollen, fragmented mitochondria, which had lost their electron-dense staining (FIG. 10C, right panels). We propose that the observed swollen and decreased matrix density by TEM was caused by limited degradation and/or loss of the mitochondrial matrix and cristae, the site of the mitochondrial respiratory chain, as well as degradation or loss of numerous carrier proteins (Perkins et al. 2009). These data also insinuate a role of mitochondrial structural damage in ADI-PEG20-induced mitochondrial dysfunction. Notably, there was an increased lipid droplet number (FIG. 9B, right panels). Oil Red O staining confirmed that more than 70% MDA-MB-231 cells accumulated lipids at 48 hours after ADI-PEG20 treatment (FIG. 10D). This increase provided additional, supporting evidence for the presence of damaged mitochondria, because damaged mitochondria decrease the use of fat through β-oxidation, resulting in the accumulation of lipid droplets (Boren & Brindle 2012).

ASS1 Expression is a Prognostic Factor for Overall Breast Cancer Survival.

Figure 2E:
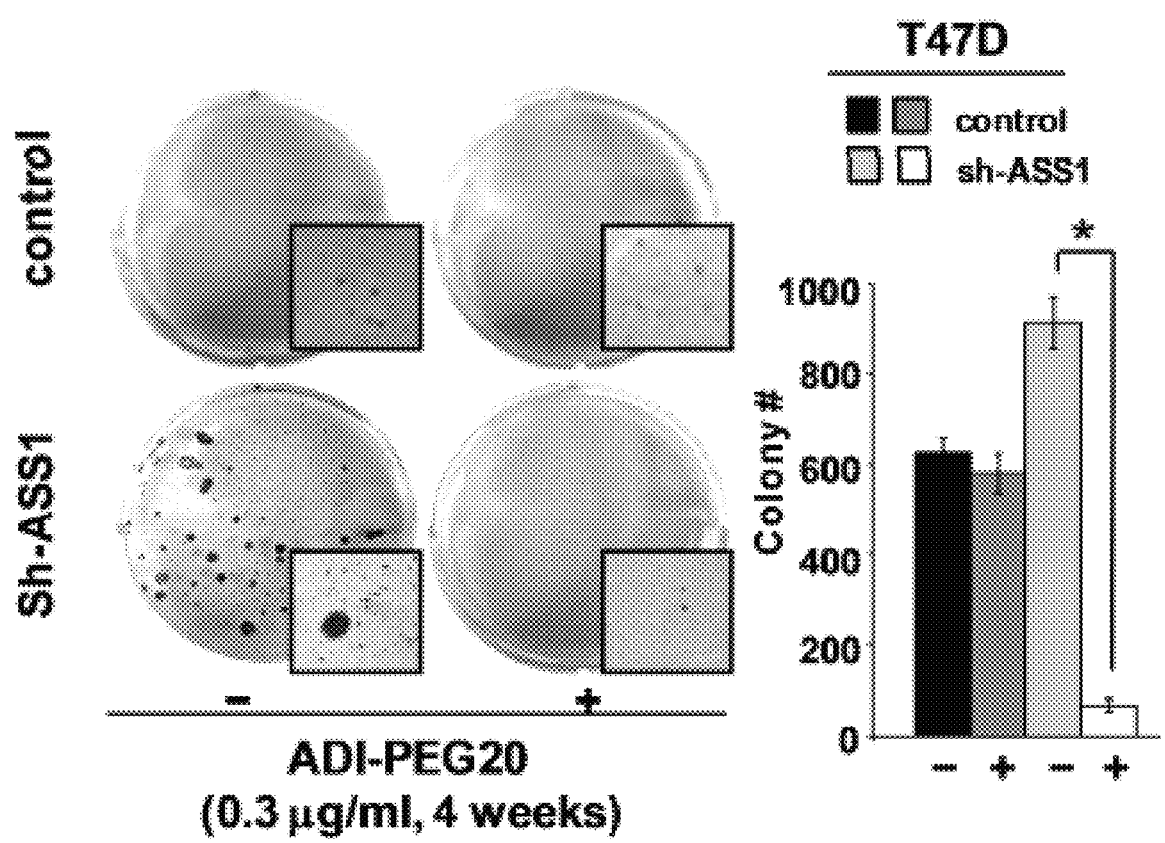
Figure 2F:
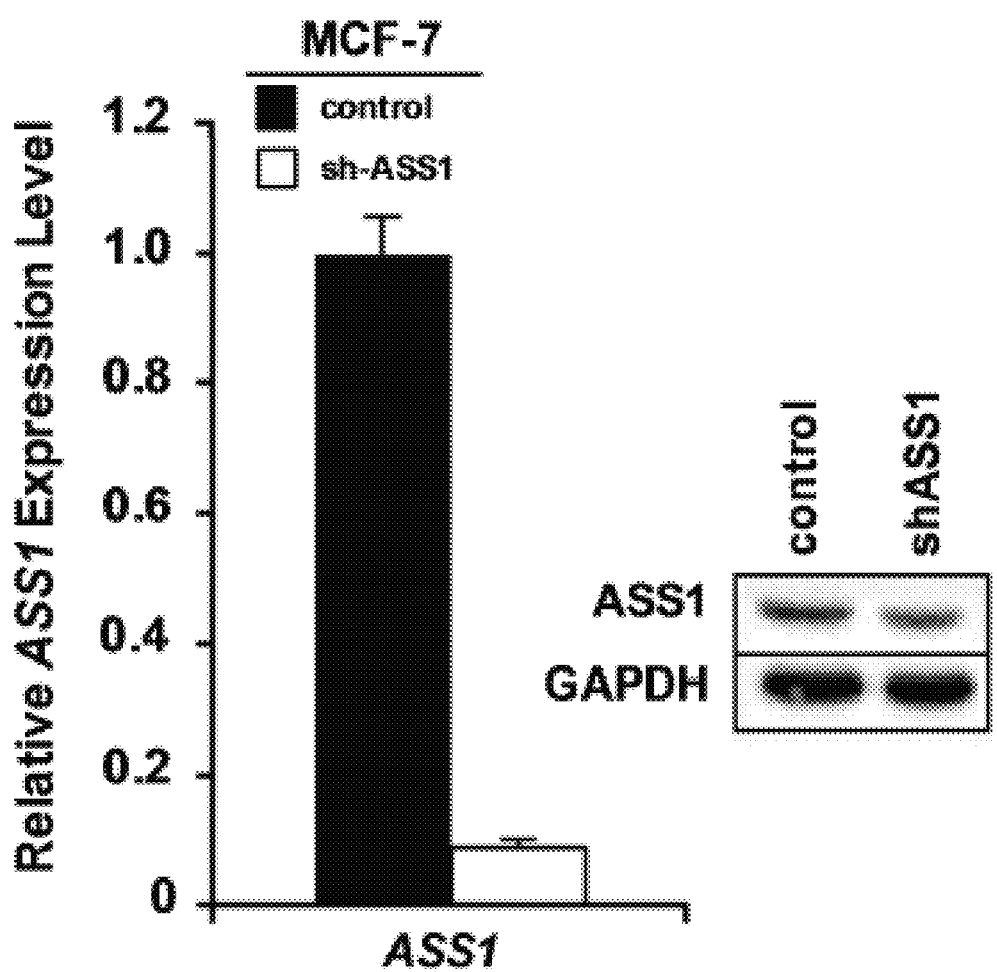
Figure 11A:
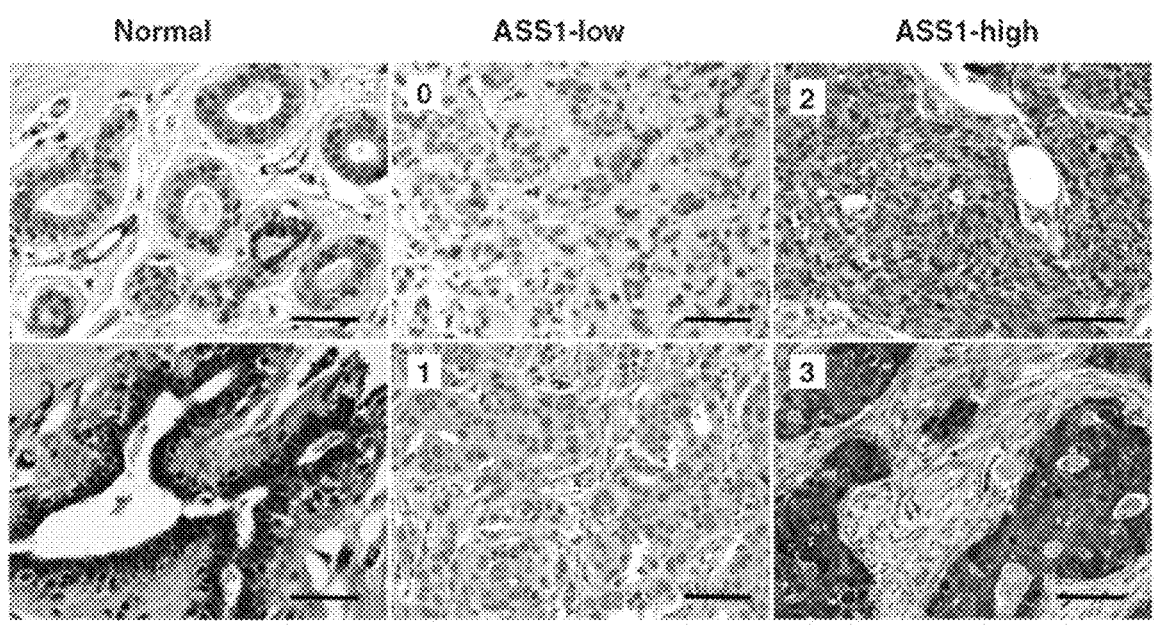
FIGS. 11A-G illustrate that low ASS1 abundance is prognostic of poor breast cancer survival and predisposes MDA-MB-231 cells to ADI-PEG20-mediated tumor shrinkage in an autophagy-dependent manner in vivo according to one embodiment.

It was observed that ASS1 abundance suppressed the ability of breast cancer cells to grow anchorage-independently (FIGS. 1F, 2E). To determine if altered ASS1 abundance affected overall survival of patients with breast cancer, the ASS1 abundance was examined in 149 breast cancer samples by IHC staining three independent multiple tissue arrays with an anti-ASS1 antibody. We found that normal mammary tissues were ASS1 positive (FIG. 11A, left panels). However, 95 (63.8%) of the 149 breast cancer samples were with low ASS1-low abundance which was defined as having little or no diffuse cytoplasmic ASS1 staining (FIG. 11A, middle panels). In contrast, the remaining 54 breast cancer samples (36.2%) were with high ASS1 abundance because they had strong diffuse staining in the cytoplasm (FIG. 11A, right panels). Our analyses of the clinical characteristics and pathology of the tumors revealed that reduced ASS1 abundance was significantly associated with advanced tumor stage and with progesterone receptor (PR)-positive and Ki-67-positive BCs (Table 1). However, there was no significant association with lymph node metastasis, or estrogen receptor (ER), HER2 or p53 status (Table 1). Lastly, the frequency of low ASS1 abundance was significantly different among all of the four different molecular breast cancer subtypes (Table 1).

TABLE 1

Clinicopathological characteristics and ASS1 distribution of eligible BCs

| | No. of cases | No. of ASS1-L[a] (%) | p-value |
|---|---|---|---|
| Age | | | |
| <40 | 12 | 9 (75.0) | |
| 40-49 | 53 | 34 (64.1) | |
| 50-59 | 43 | 26 (60.5) | |
| 60-69 | 23 | 15 (65.2) | |
| 70-79 | 14 | 10 (81.4) | |
| >80 | 4 | 3 (75.0) | 0.573 |

TABLE 1-continued

Clinicopathological characteristics and ASS1 distribution of eligible BCs

| | No. of cases | No. of ASS1-L[a] (%) | p-value |
|---|---|---|---|
| T stage[b] | | | |
| T0-T1 | 36 | 15 (41.7) | |
| T2-T4 | 108 | 76 (70.4) | 0.002* |
| N stage[b] | | | |
| N0 | 72 | 44 (61.1) | |
| N1-3 | 77 | 51 (66.2) | 0.516 |
| ER | | | |
| Negative | 52 | 30 (57.7) | |
| Positive | 73 | 47 (64.4) | 0.448 |
| PR | | | |
| Negative | 62 | 30 (48.4) | |
| Positive | 60 | 43 (71.7) | 0.009* |
| Ki-67 | | | |
| Negative | 48 | 36 (75.0) | |
| Positive | 78 | 51 (55.3) | 0.012* |
| Her2 | | | |
| Negative | 97 | 63 (64.9) | |
| Positive | 30 | 14 (46.7) | 0.07 |
| Molecular Subtype[c] | | | |
| Luminal A | 36 | 27 (75.0) | |
| Luminal B | 43 | 26 (60.5) | |
| TNBC | 22 | 12 (54.5) | |
| Her2 | 12 | 2 (16.7) | 0.005* |
| p53 | | | |
| Negative | 62 | 42 (67.7) | |
| Positive | 61 | 33 (54.1) | 0.12 |

[a]ASS-low denotes either no staining or weak cytoplasmic ASS1 staining.
[b]TNM stage is according to AJCC cancer staging manual (6th version).
[c]Molecular subtype is categorized according to ER, PR, HER2 and Ki-67 status. Luminal A subtype is defined as ER positive and/or PR positive, HER2 negative and Ki-67 negative; Luminal B subtype is defined as ER positive and/or PR positive, HER2 positive (or HER2 negative with high Ki-67); TNBC subtype is defined as ER negative, PR negative, HER2 negative; HER2 subtype is defined as ER negative, PR negative, HER2 positive.
*Statistical significance, p < 0.05.

Figure 11B:
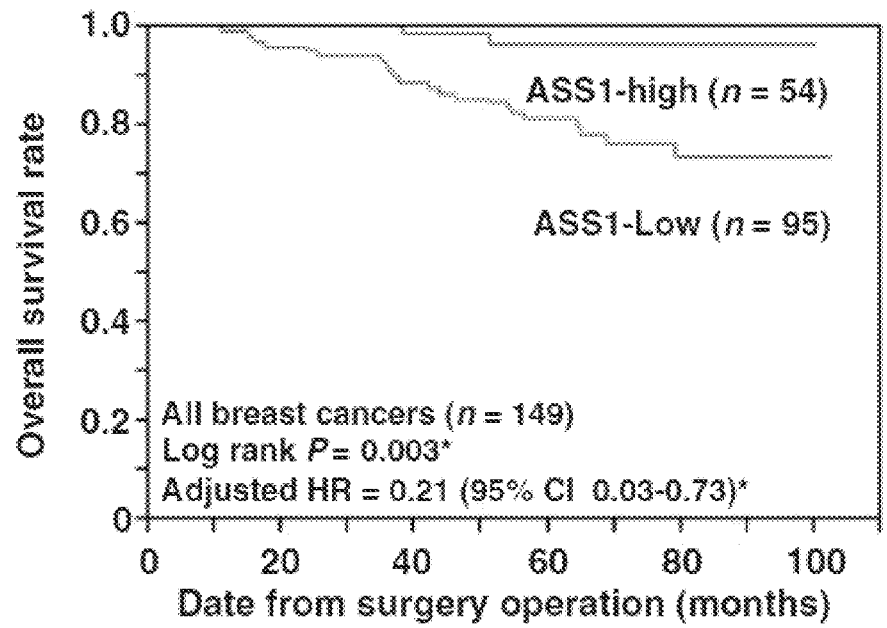
Figure 11C:
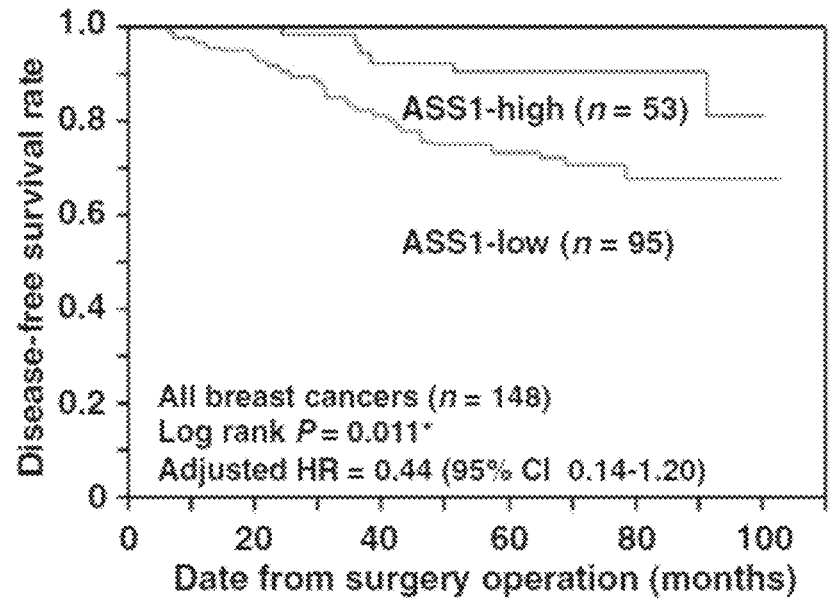
Figure 12A:
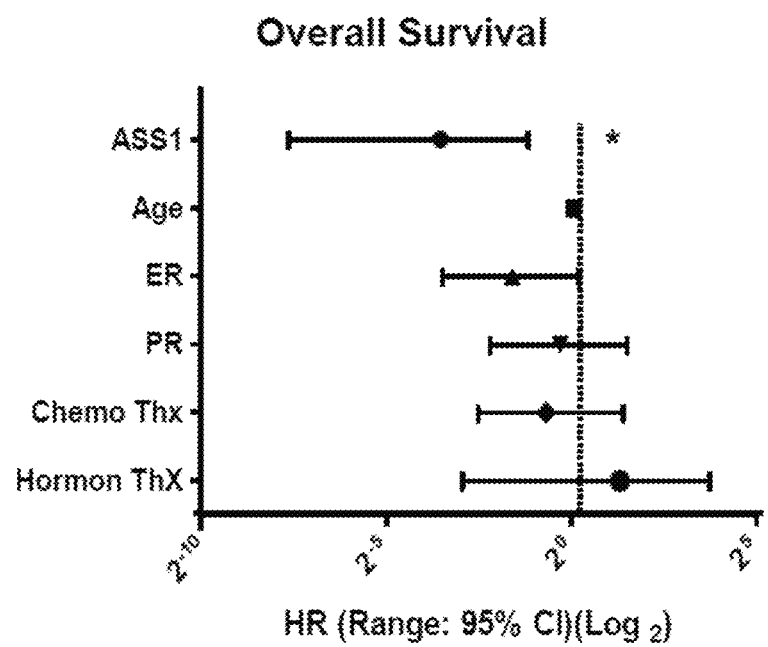
FIGS. 12A-H illustrate that ASS1 expression predicts overall survival according to one embodiment.
Figure 12B:
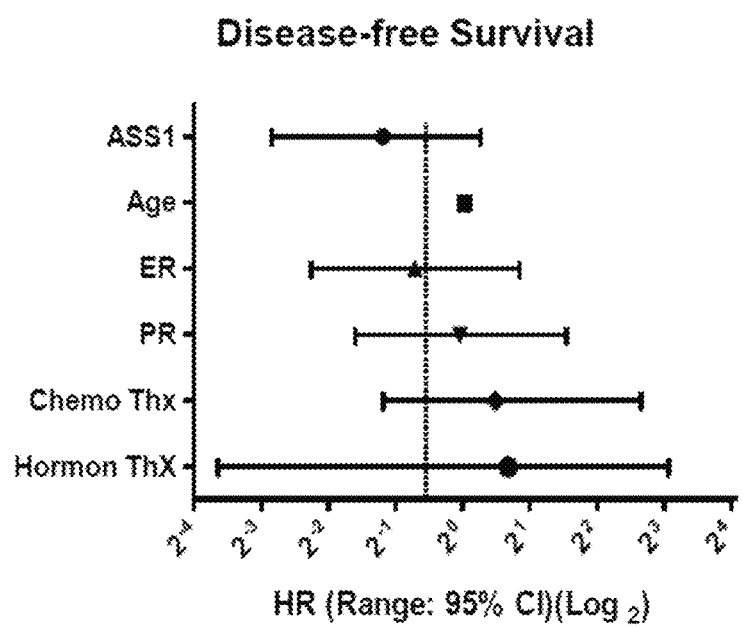
Figure 12C:
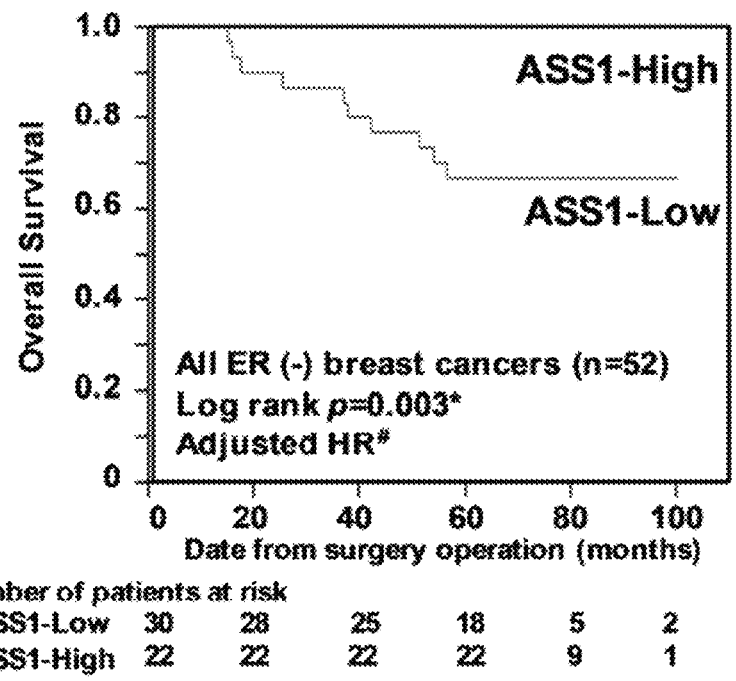
Figure 12D:
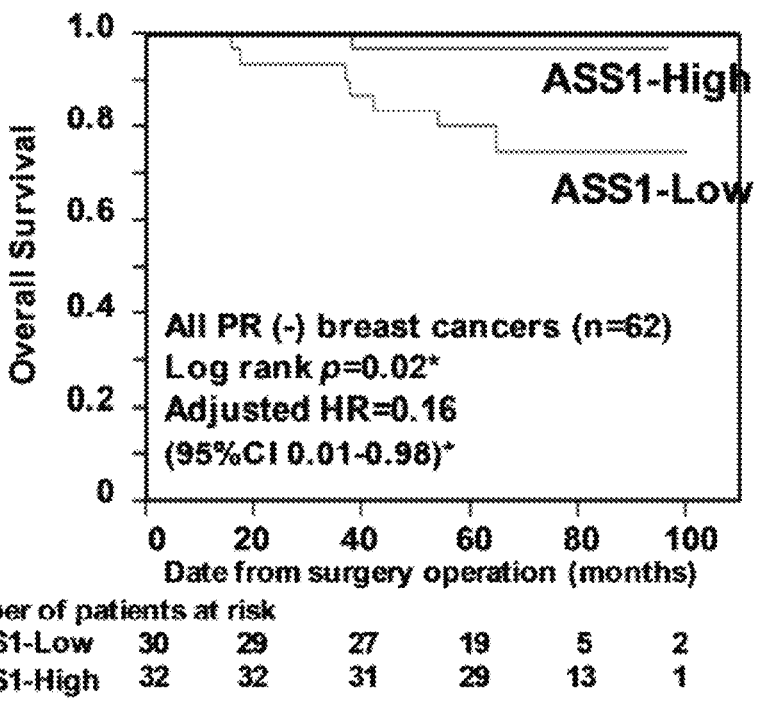
Figure 12E:
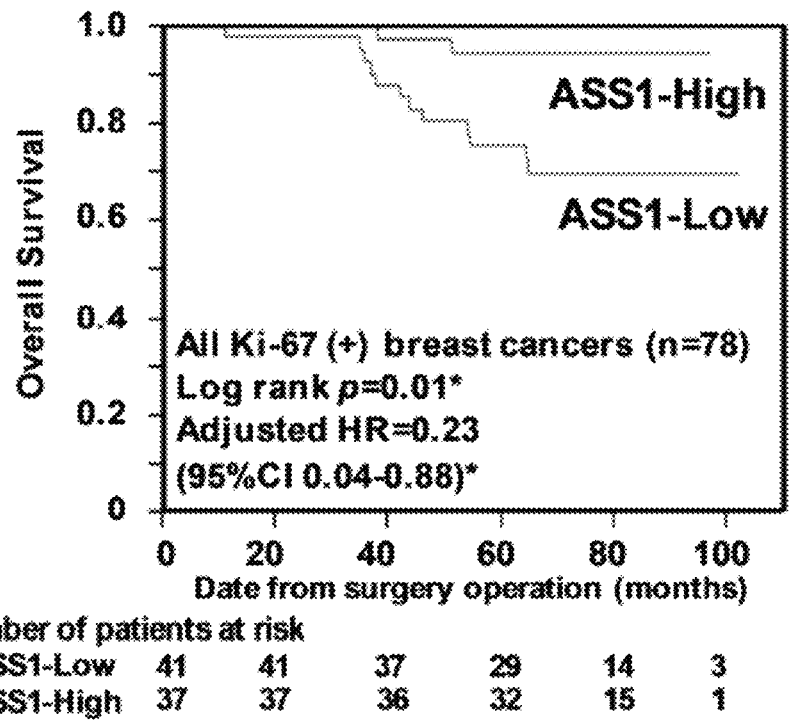
Figure 12F:
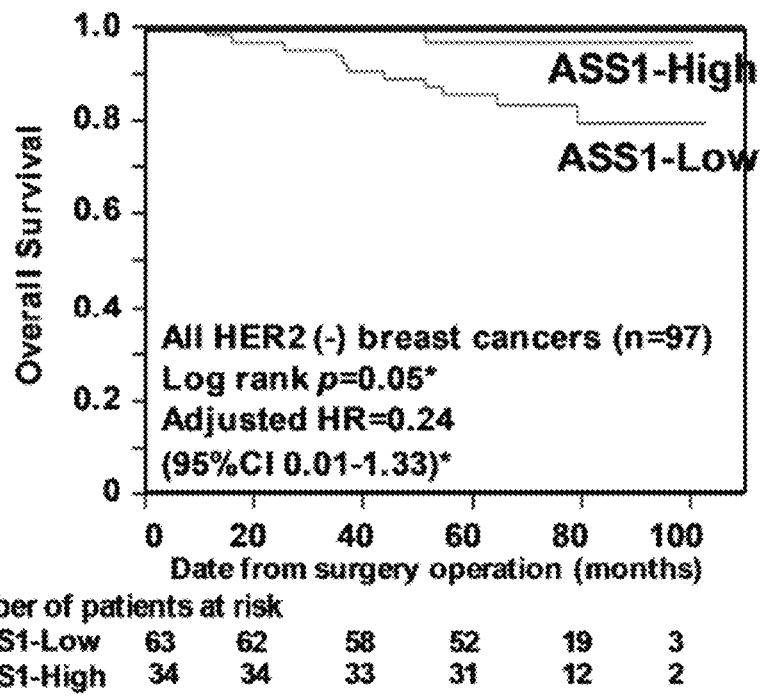
Figure 12G:
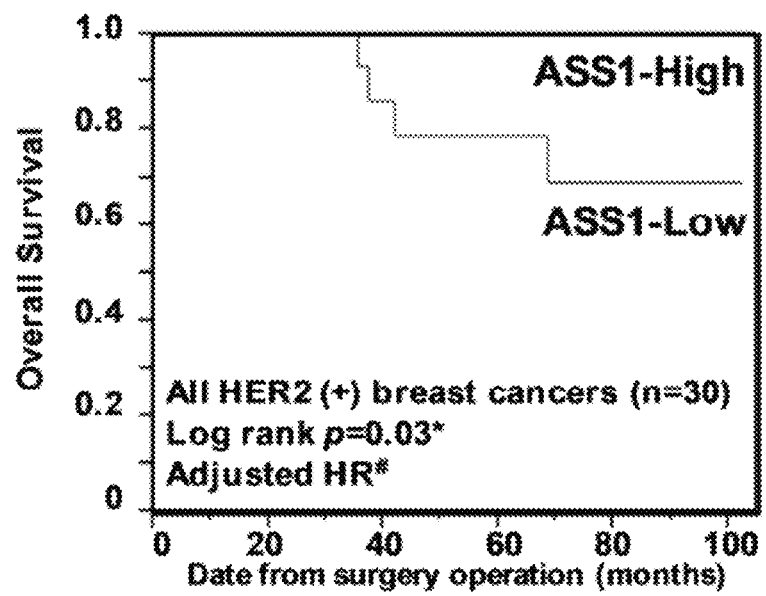
Figure 12H:
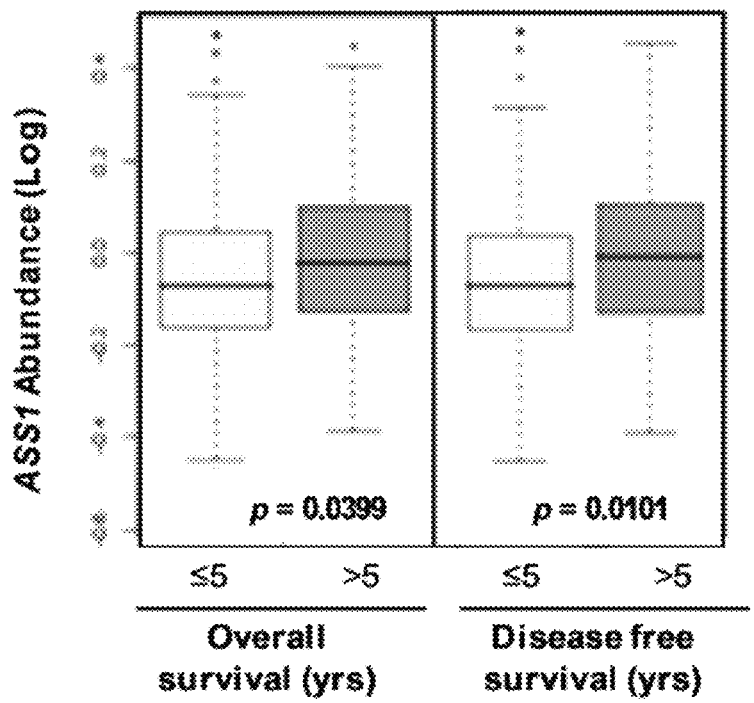

Kaplan-Meier analyses indicated that reduced ASS1 abundance was a critical prognostic indicator for both overall (FIG. 11B; Log rank p=0.003) and disease-free (FIG. 11C; Log rank p=0.011) survival for all 149 patients with breast cancer. Multivariate Cox analyses for overall survival rate indicated that patients with high ASS1 abundance had a lower relative risk of breast cancer specific mortality (Hazard ratio (HR)=0.21; 95% CI 0.03-0.73) (FIG. 12A). Multivariate analysis also showed that ASS1-high was associated with a lower relative risk of breast cancer relapse (HR=0.44; 95% CI 0.14-1.20) (FIG. 12B). Stratification analyses revealed that reduced ASS1 abundance was significantly associated with poor overall survival in the subgroups of patients with breast cancer who had ER-negative, PR-negative, and Ki-67-positive cancers (FIGS. 12C-12E). The HR of ASS1-high could not be calculated in ER-negative and HER2-positive breast cancer because no deaths were reported within these two subgroups during the follow-up period (FIGS. 12C, 12G). In comparison with ASS1-low, the adjusted HR of ASS1-high was 0.16 (95% CI 0.01-0.98) and 0.23 (95% CI 0.04-0.88) in subgroups of PR-negative and Ki-67-positive breast cancers, respectively (FIGS. 12D and 12E). Uni- and multivariate analyses indicated that reduced ASS1 abundance poorly impacted survival in both HER2-negative and HER2-positive subgroups (FIGS. 12F, 12G), indicating the loss of ASS1 abundance was associated with poor overall patient survival, independent of breast cancer molecular subgroup. Moreover, analyses using microarray message abundance data and associated clinical data extracted from a published study of 295 breast cancers revealed that ASS1 mRNA level from breast cancer samples of patients with more than five years overall or disease-free survival was significantly higher than that in patients with less than five years overall or disease-free survival (FIG. 12H; (van de Vijver et al. 2002; Chang et al. 2005)). Therefore, the abundance of ASS1 may be a useful biomarker for breast cancer prognosis and is consistent with the results of soft agarose assays, which indicated that low expressers of ASS1 were more able to grow anchorage independently (FIGS. 1F, 2E).

Autophagy is Required for ADI-PEG20 to Cause Shrinkage or Regression of Tumors In Vivo.

Figure 11D:
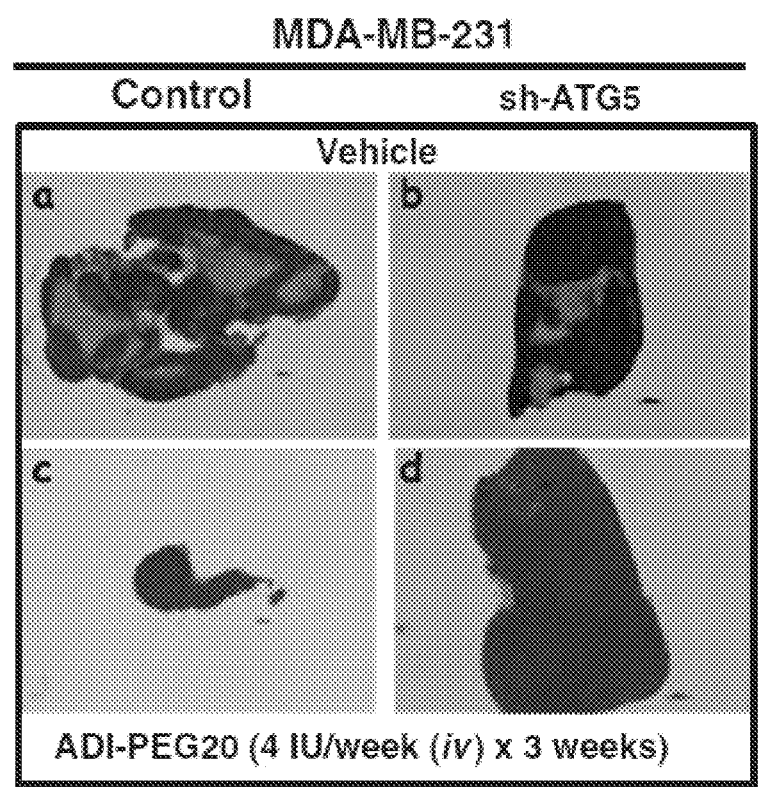
Figure 11E:
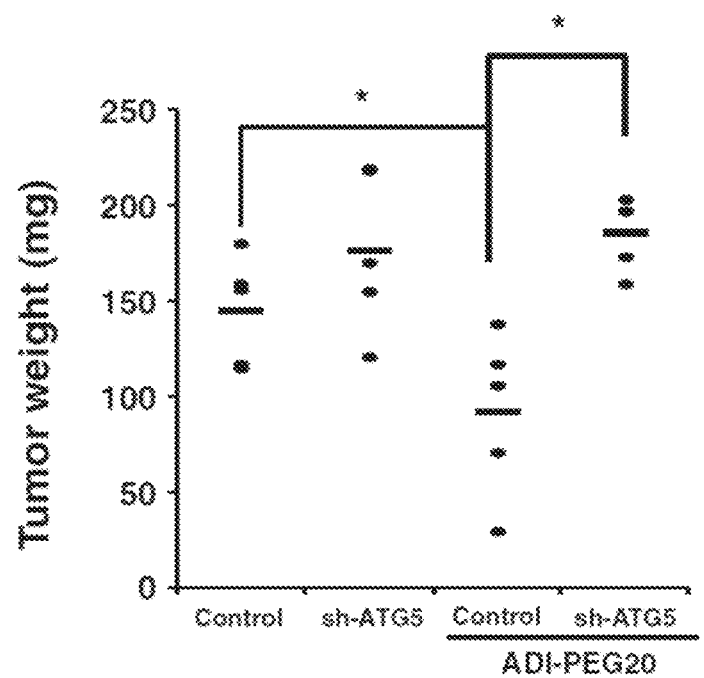

For proof of principle, the effects of autophagy-competence and treatment with ADI-PEG20 on tumors in vivo were determined. Female NOD.Cg-PrkdcscidIl2rgtm1Wjl/SzJ mice with xenografts formed from MDA-MB-231 or MDA-MB-231/shATG5 cells were injected intravenously with vehicle control or ADI-PEG20. The MDA-MB-231 tumors from ADI-PEG20-treated mice were smaller than tumors from control mice (FIG. 11D, panels a, c) at 19 days after beginning treatment. Although ATG5 deficiency did not impair MDA-MB-231 tumor growth (FIG. 11D, panels a, b), it markedly impaired shrinking of the tumors in response to ADI-PEG20. FIG. 11D, panels b, d). The average weight of ADI-PEG20-treated MDA-MB-231 tumors was significantly (50%) less than ADI-PEG20-treated MDA-MB-231/sh-ATG5 tumors (FIG. 11E). The data showing MDA-MB-231/sh-ATG5 cells were more resistant to ADI-PEG20 in vivo than MDA-MB-231 cells supports the conclusion that tumor shrinkage induced by ADI-PEG20 is autophagy-dependent.

Figure 11F:
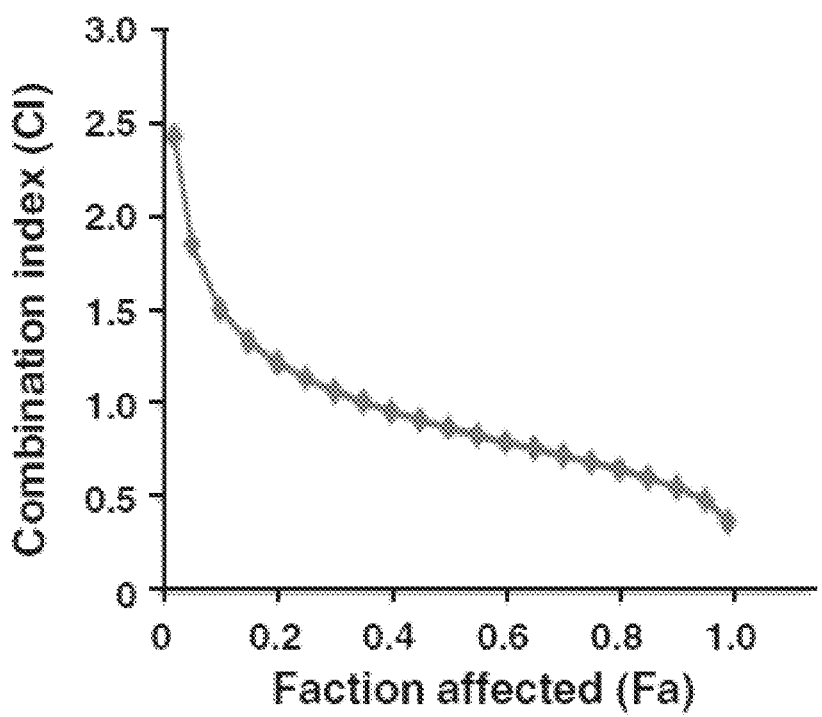
Figure 13A:
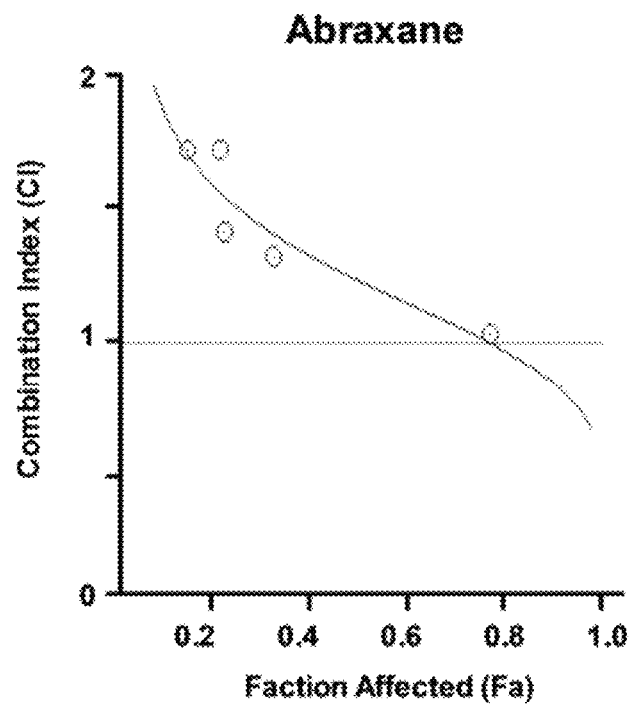
FIGS. 13A-B illustrate the lack of synergistic effect of ADI-PEG20 combined with Abraxane or carboplatin according to one embodiment. The combination index for ADI-PEG20 and Abraxane (FIG. 13A) or carboplatin (FIG. 13B) was calculated as described in FIG. 11F.
Figure 13B:
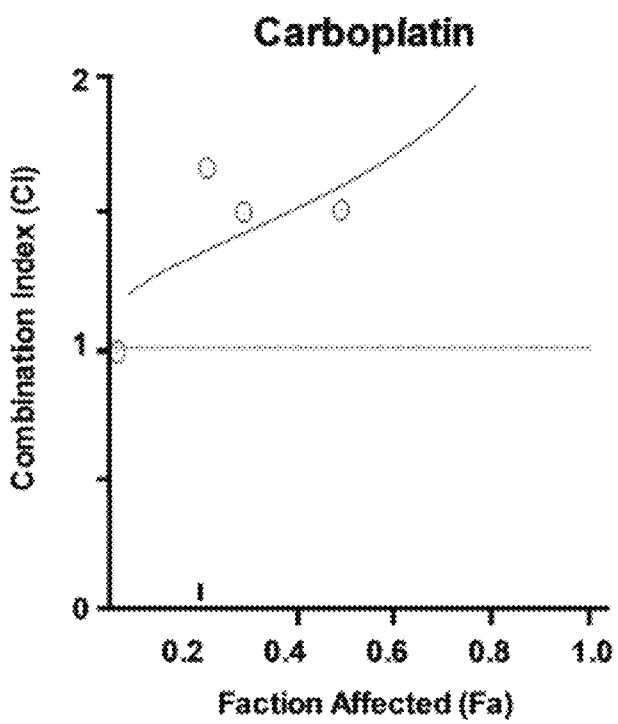

Further, it was examined if there was a synergistic effect between ADI-PEG20 and doxorubicin, cisplatin or taxol, which are conventionally used as therapeutic agents against breast cancer, in MDA-MB-231 cells. The combination index (CI) of ADI-PEG20 with doxorubicin was assessed as described by Chou and the computer software of Chou and Martin (Chou & Talalay 1984; Chou 2006; C. T. a M. N. 2005). CI<1, =1, and >1 indicate synergism, additive effect, and antagonism, respectively (Chou 2006; C. T. a M. N. 2005). The calculated CI suggested a synergistic effect between ADI-PEG20 and doxorubicin (FIG. 11F). However, synergy was not observed when ADI-PEG20 was combined with Abraxane or carboplatin (FIG. 13). In summary, ADI-PEG20, alone or combined with doxorubicin, may represent a promising therapeutic strategy for treating breast cancers that are arginine-auxotrophs.

Discussion

Figure 11G:
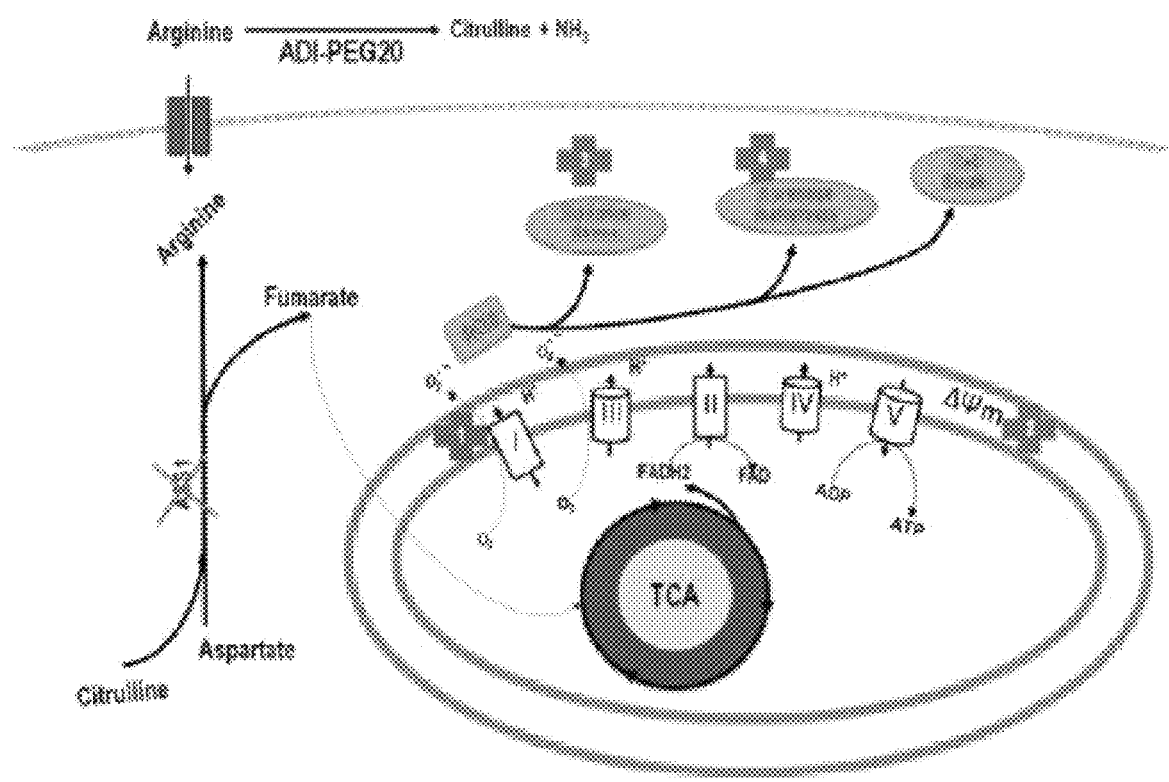

Understanding the metabolic differences between normal cells and tumor cells could provide the unique opportunity to design selective personalized therapy against breast cancer and other cancers. Considerable attention has been paid to glucose metabolism and glutamine addiction in tumor cells (DeBerardinis & Thompson 2012). However, the metabolism of cancer cells is complex, and involves various re-wiring of metabolic pathways that occurs during malignant transformation. In this regard, the studies described above illustrate a novel mechanism connecting the metabolic stress caused by arginine starvation to induce cell death of ASS1-deficient breast cancer cells (FIG. 11G). This is particularly interesting because the arginine deprivation affected mitochondrial bioenergetics and integrity by decreasing the stability of the mitochondrial inner membrane and matrix proteins, and impairing mitochondrial oxidative phosphorylation and ATP production that was accompanied by increased ROS production.

The molecular mechanisms underlying cell death induced by ADI-PEG20-mediated arginine starvation of ASS1-deficient cells are not yet fully understood. Nutritional starvation often leads to autophagosome induction and arginine deprivation is of no exception (Feun et al. 2008; Kim et al. 2009a; Shvets et al. 2008). Paradoxically, while previous studies suggested that autophagy protects cells from dying upon the initiation of starvation, the results presented in the studies above showed that prolonged autophagy induction by sustained ADI-PEG20 treatment or arginine starvation eventually leads to cell death. To decipher this paradox, the function and fate of mitochondria inside ADI-PEG20-treated MDA-MB-231 cells was examined because mitochondria play a central role in satisfying higher demands for energy and anabolic needs during stress. Stressed cells have developed mechanisms, known as mitochondrial quality control, to deal with dysfunctional mitochondria in order to maintain homeostasis. Fusion between damaged mitochondria and healthy mitochondria may serve as one mechanism, either to dilute the damaged and detrimental components or to regain functional counterparts (Westermann 2010; Chan 2006; Youle & van der Bliek 2012). Alternatively, sustained starvation is known to induce the degradation of mitochondria by an autophagy-mediated system, known as mitophagy (Youle & Narendra 2011). Specifically, when damaged mitochondria lose their membrane potential (FIG. 7C) and/or undergo fragmentation (FIG. 10B), they are likely engulfed by autophagosomes for lysosomal degradation (Youle & Narendra 2011; Tolkovsky 2009). These results suggest that the dysfunctional mitochondria, probably due to increased mitochondrial ROS production and the loss of MMP caused by disruptions in the respiratory chain (FIGS. 5, 7), resulted in cytotoxic autophagy in ADI-PEG20-treated MDA-MB-231 cells. This possibility is supported by studies in other systems that used mitochondrial respiratory chain uncouplers, which resulted in mitophagy (Narendra et al. 2008; Narendra et al. 2010; Ding et al. 2012).

It was found that ADI-PEG20 down-modulated the steady-state abundance of complex I/I transcripts (FIG. 5D). It is possible that a decreased capacity for mitochondrial biogenesis may play a key role in favoring ADI-PEG20-induced cell death, though, supplementing with succinate partially rescued the viability of arginine-starved cells (FIG. 5E). Most likely, arginine starvation of cells lacking ASS1 induces several types of damages to mitochondria that affect their homeostasis. Thus, ADI-PEG20 in the context of ASS1-deficiency creates a pathological "vicious cycle," wherein the impairment in the mitochondrial electron transport that leads to a loss of mitochondrial membrane potential is also responsible for an incomplete 02 reduction, resulting in an increment in ROS production that further amplifies the generation of ROS. Consequently, sustained and excessive autophagy exacerbates the arginine starvation-induced cytotoxic effect (FIG. 11G). The consequence of sustained autophagy is reinforced by reduced biogenesis of new mitochondria caused by decreased levels of complex I/II, which further inhibits oxidative phosphorylation and induces cell death. In support of this, it was shown that several fly respiratory complex I proteins were selectively routed for autophagosomal degradation (Vincow et al. 2013) suggesting that impairing or losing the mitochondrial electron transport chain could account for the lack of mitochondrial FCCP response in ADI-PEG20-treated cells (FIGS. 5B, 5F).

The observation that SIRT3 protein was reduced by prolonged ADI-PEG20 treatment (FIG. 7D) is of particular interest because SIRT3, which is located in the mitochondrial matrix, is a member of an evolutionary conserved family of NAD+-dependent deacetylases that functions as the primary regulator of mitochondrial lysine acetylation (Roth & Chen 2013). It was shown that an absence of SIRT3 in the livers of fasted mice led to selective hyperacetylation at 283 sites that represented 136 of the 483 acetylated mitochondrial proteins (Rardin et al. 2013). One of the largest fold changes in lysine acetylation was observed in ATP synthase, a key enzyme involved in oxidative phosphorylation. In addition, several SIRT3-regulated sites in complex I, II and IV have been reported. Lysine acetylation of mitochondrial proteins has been proposed to reduce complex I activity and decrease basal ATP level (Ahn et al. 2008). Besides oxidative phosphorylation, the SIRT3-regulated metabolic pathways in mitochondria also include fatty acid oxidation, the TCA cycle, and branched chain amino acid catabolism (Rardin et al. 2013). Conceivably, the observed decrease of the SIRT3 steady-state abundance, albeit modest (FIG. 7D), could exacerbate the overall metabolic stress upon prolonged ADI-PEG20 treatment. This is supported by the fact that over-expressing SIRT3 can rescue the viability of cells treated with ADI-PEG20 (FIG. 7E) by suppressing ROS levels (FIG. 7F).

ASS1 engages in a rate-limiting step in de novo arginine biosynthesis to maintain arginine serum levels. Our analyses indicate that ASS1 abundance is an independent prognostic indicator of the survival of patients with breast cancer (FIGS. 11B, 11C). Consistently, by altering ASS1 abundance in breast cancer cell lines and then performing anchorage-independent assays in vitro (FIGS. 1F, 2E), the potential role of ASS1 in inhibiting cells from growing anchorage-independently was confirmed. Malignant transformation can be caused by or lead to metabolic changes, because tumor cells tend to increase their glycolytic activity without a matching increase of oxidative phosphorylation and dependence on oxygen (the Warburg effect) (Warburg 1956; Warburg et al. 1927). Key to this metabolic re-wiring is the decrease of mitochondrial respiration (Frezza & Gottlieb 2009) that allows the cancer cells to grow in hypoxic conditions usually found in the interior of the tumor mass (Denko 2008). However, the molecular mechanisms that could suppress oxidative phosphorylation during tumorigenesis are still unclear. Based on the findings from the Examples above, the down-modulating ASS1 abundance leads to decreased oxidative phosphorylation (i.e., decreased maximal respiratory capacity), potentially promoting neoplastic transformation. Indeed, it was found that ASS1 behaves like a tumor suppressor because 1) ASS1 abundance suppressed the anchorage-independent proliferation of breast cancer cells in vitro, and 2) ASS1 deficiency or low ASS1 abundance is associated with a poor prognosis for patients with breast cancers. Further, down-modulating ASS1 may create a pro-oxidant state (FIG. 7G) that favors tumorigenesis, because even a moderate increase in ROS production can promote cell proliferation and tumorigenesis (Trachootham et al. 2009). However, reduced ASS1 abundance also makes the breast cancer cells vulnerable to ADI-PEG20, which effectively kills them by starving them of arginine. This is reminiscent of the synthetic lethal interaction between BRCA1/2 deficiency and PARP1 inhibitors (Farmer et al. 2005; Bryant et al. 2005).

In summary, we focused on how to take advantage of the mitochondrial dysfunction that is induced by sustained treatment of ADI-PEG20 in ASS1-deficient breast cancers to kill the cells. It was shown that reduced ASS1 abundance results in the arginine dependency of mitochondria, causing subsequent cell death. This provides important implications for the development of tumor therapies, because conventional thoughts suggest that activating autophagy may contribute to the survival, rendering and recurrence of refractory tumors that are resistant to conventional chemotherapy. The observed synergistic effect between doxorubicin and ADI-PEG20 supports the possibility of exploiting arginine starvation as a therapeutic strategy by targeting a specific metabolic liability due to ASS1 deficiency in breast cancer cells. The number of breast cancers and other human malignancies that have substantial subtypes that lack ASS1 abundance provides opportunities to validate our findings of a previously unrecognized "mitochondria-targeting mechanism" in human patients with ASS1-deficient breast cancers and other types of ASS1-deficient cancers.

Example 2

Arginine-Deprivation Therapy Induces Chromatin Autophagy and Mitochondria Dysfunction in Prostate Cancer Cells As discussed in the example below, autophagy is the principal catabolic pro-survival pathway during nutritional starvation. However, excessive autophagy could be cytotoxic, contributing to cell death, but its mechanism remains elusive. Arginine starvation has emerged as a potential therapy for several types of cancers, due to their tumor-selective deficiency of the arginine metabolome. Here, it was demonstrated that arginine depletion by arginine deiminase induces a cytotoxic autophagy in argininosuccinate synthetase (ASS1) deficient prostate cancer cells. Advanced microscopic analyses of arginine-deprived dying cells revealed a novel phenotype with giant-autophagosome formation, nucleus membrane rupture, and histone-associated-DNA leakage encaptured by autophagosomes, which shall be referred to herein as chromatin-autophagy or chromatophagy. In addition, nuclear inner membrane (lamin A/C) underwent localized rearrangement and outer membrane (NUP98) partially fused with autophagosome membrane. Further analysis showed that prolonged arginine depletion impaired mitochondrial OXPHOS function and depolarized mitochondrial membrane potential. Thus, ROS production significantly increased in both cytosolic and mitochondrial fractions, presumably leading to DNA damage accumulation. Addition of ROS scavenger, N-Acetyl-Cysteine (NAC), or knockdown of ATG5 or BECLIN1, attenuated chromatophagy phenotype. These data uncover an atypical autophagy-related death pathway and suggest that mitochondrial damage is central to linking arginine starvation and chromatophagy in two distinct cellular compartments.

Introduction

Nutritional starvation therapy is under intensive investigation, as it provides potentially a lower toxicity with higher specificity than conventional cancer therapy. Autophagy often triggered by starvation, represents an energy-saving, pro-survival cellular function; however, dysregulated autophagy could also lead to cell death, a process distinct from the classical caspase-dependent apoptosis. This study shows how arginine starvation specifically kills tumor cells by a novel mechanism involving mitochondria dysfunction, ROS generation, DNA leakage and chromatin autophagy, where leaked DNA is captured by giant autophagosome. These results not only provide insights into the fundamental process of metabolic stress-based cancer therapy, but also uncover a new cell-death mechanism.

There is considerable evidence that tumor and normal cells differ in their metabolic requirements. The most prominent examples are the addiction of tumor cells to glucose (i.e., Warburg effect) and to glutamine (Kim & Dang 2006; Vander Heiden et al. 2009; Dang 2010). Therapeutics based on selective targeting of these metabolic pathways are under intensive investigations. Starvation therapy generally posts an advantage of having lower toxicity than the conventional radiation and chemotherapy. In addition to glutamine, the differential requirement of other amino acids by tumor cells also exist and has been exploited in developing amino-acid depletion therapy. The choices however are limited, as only eleven amino acids are considered semi-essential or non-essential. Nevertheless, recent studies showed that starvation of arginine, asparagine, cysteine, leucine and glutamine seems to provide preferential killing of tumor cells (Fuen et al, 2008; Huang et al, 2012; Huang et al. 2012; Muller & Boos 1998; Possemato et al. 2011; Wheatley & Campbell 2003; Wise & Thompson 2010). Among them, arginine and asparagine depletion probably are the most advanced in amino-acid starvation therapies and have reached clinical trials (Ascierto et al. 2005; Wetzler et al. 2007).

Argininosuccinate synthetase (ASS1), a rate-limiting enzyme for intracellular arginine synthesis was found to have reduced expression in many cancer types including prostate cancer (Feun et al. 2008; Huang et al. 2012; Gong et al. 2000; Ensor et al. 2002; Bowles et al. 2008; Kobayashi et al. 2010; Hsueh et al. 2012; Kelly et al. 2012; Kim et al. 2009b). As a result, prostate cancer cells become "auxotroph" for and addicted to external arginine. Indeed, it has been shown that depletion of arginine effectively induces cell death of castration-resistant prostate cancer cells, but not normal prostate epithelial cells in vitro and in vivo (Kim et al. 2009b; Kim et al. 2009a). This was made possible by the availability of pegylated arginine deiminase (ADI-PEG20) a recombinant *mycoplasma* protein (Polaris, Calif.), which converts arginine to citrulline and effectively removes extracellular arginine. Previous worldwide clinical trials of ADI-PEG20 showed it is well tolerated, and the FDA has recently approved it for Phase III clinical trials in hepatocellular carcinoma (Ascierto et al. 2005; Lin et al. 2012).

ADI-PEG20-treatment of prostate cancer cells was accompanied by profound autophagy and caspase-independent cell death (Kim et al. 2009b; Kim et al. 2009a). In the experiments described below, it was further demonstrated that prolonged ADI-PEG20-treatment leads to DNA leakage and that this leaked DNA, together with histones and other chromatin-associated proteins were captured by LC3-containing autophagosomes. This process may be referred to herein as "chromatophagy". This nuclear leakage phenomenon was associated with compromised mitochondrial OXPHOS and increased ROS, and accumulated DNA damage. These studies revealed a new cellular death mechanism associated with therapeutic arginine deprivation.

Materials and Methods

Reagents.

Recombinant arginine deiminase (ADI), formulated with linear 20,000-molecular-weight polyethylene glycol molecules (ADI-PEG20), was generously provided by Polaris Pharmaceuticals, Inc.

Antibodies.

Antibodies used in this study were as follows: mouse monoclonal anti-caspase 7 (10-1-62; BD Pharmingen), mouse monoclonal anti-caspase 8 (3-1-9; BD Pharmingen), mouse monoclonal anti-caspase 9 (2-22; BD Pharmingen), rabbit monoclonal E-cadherin (24E10; Cell Signaling Technology), rabbit polyclonal anti-Ku70 (Abcam), mouse monoclonal anti-lamin A/C (JoL3; Abcam), mouse monoclonal anti-LAMP1 (H4A3; Developmental Studies Hybridoma Bank), rabbit monoclonal NUP98 (C39A3; Cell Signaling Technology), rabbit polyclonal anti-gamma-H2A.X (phospho S139; Abcam), rabbit monoclonal anti-ATG5 (D5G3; Cell Signaling Technology), rabbit monoclonal anti-Histone H3 (D1H2; Cell Signaling Technology), and rabbit polyclonal anti-acetyl-Histone H2B (Cell Signaling Technology).

Cell Culture and Treatment.

Prostate cancer cell lines CWR22Rv1, CWR22Rv1 GFP-LC3 (stably transfected), and PC3 were cultured in RMPI 1640 supplemented with 10% (vol/vol) FBS and 1% (vol/vol) penicillin/streptomycin. Pancreas cancer cell lines Mia and L3.3 were culture in DMEM supplemented with 10% (vol/vol) FBS and 1% (vol/vol) penicillin/streptomycin. All cells were maintained at 37° C. in a 5% (vol/vol) CO2, 95% (vol/vol) air incubator. For autophagy induction, CWR22Rv1, CWR22Rv1 GFP-LC3, PC3, Mia, and L3.3 cells were seeded in six-well plates or glass-bottom dishes (P35GC-1.5; MatTek) and treated with ADI-PEG20 (0.3 µg/mL) for 24, 48, 72, 96, or 120 h the following day. For autophagy inhibition, CWR22Rv1 and CWR22Rv1 GFP-LC3 were treated with 3-methyladenine (3-MA, 1 mM; Sigma), ADI-PEG20 (0.3 µg/mL), or both for 24, 48, 72, 96, or 120 h the following day. All cell samples were collected at each time point and analyzed by immunofluorescence microscopy (see below). For antioxidant treatment, ADI-PEG20-treated CWR22Rv1 cells were incubated with or without N-acetyl cysteine (NAC, 10 µM, Sigma) for 96 h at 37° C.

Arginine Deprivation.

Arginine-depleted RPMI-1640 medium was prepared by adding back 0.05 g/L L-leucine (L8912; Sigma) and 0.04 g/L lysine (L5501; Sigma) into RMPI-1640 medium without L-arginine, L-leucine, lysine and Phenol Red (R1780; Sigma), and was supplemented with 10% (vol/vol) FBS and 1% (vol/vol) penicillin/streptomycin. Arginine-depleted RPMI was sterilized by vacuum filtration system with a 47-mm membrane (Nalgene). Cells were initially cultured in regular RMPI-1640 until proper cell density was reached. Regular media was aspirated and cells were washed briefly with PBS and continued to incubate in arginine-depleted RPMI for 24, 48, 72, 96, or 120 h at 37° C. Samples were collected at each time point and later analyzed by immunofluorescence microscopy (see below).

Microscope Image Acquisition and Image Analysis.

For autophagy image acquisition, cells were imaged with wide-field DeltaVision deconvolution microscope (Applied Precision Inc.), equipped with 60×/1.42 NA oil immersion objective lens. Both microscope and camera were controlled by SoftWorX application suite software. Stacks of optical section images, with image size of 512×512 pixels, were collected for all fluorochromes.

For live-cell autophagy imaging, cells were seeded onto a 35-mm glass-bottom dish (1.5, poly-lysine coated; MatTek) or microfluidic plate (CellASIC) and visualized under a DeltaVision deconvolution microscope, which was also equipped with both environmental chamber and ONIX microfluidic perfusion system (CellASIC) to main constant temperature at 37° C., humidity, and 5% (vol/vol) CO2 concentration. For fixed-cell autophagy imaging, cells were seeded on coverslip (1.5 or 170-µm thickness) and fixed in 4% (vol/vol) paraformaldehyde/1×PBS (PFA) for 10 min at room temperature. After rinsing with washing buffer [Hepes buffered saline and 1% (vol/vol) BSA] three times, cells were permeabilized in permeabilization buffer [Hepes buffered saline, 1% (vol/vol) BSA, 2.5% (vol/vol) casein, and 0.05% (vol/vol) saponin (Sigma)] for 10 min at room temperature. Blocking buffer [Hepes buffered saline, 1% (vol/vol) BSA, and 2.5% (vol/vol) casein] was added for 1 h at room temperature. Primary antibodies used were described above, and appropriate secondary antibodies (Alexa Fluor 488, 555, 647; Invitrogen) were used after primary antibody incubation at 4° C. overnight. All coverslips were mounted over a microscope slide in Prolong Gold anti-fade reagent (Life Technologies).

For γH2AX and 8-hydroxy-2'-deoxyguanosine (8-OHdG) immunofluorescence microscopy and image analysis, cells were seeded on coverslip and fixed in PFA for 30 min at room temperature. After washing with PBS three times, blocking solution [0.1% (vol/vol) Triton X-100 and 5% (vol/vol) BSA in PBS] was added for 1 h at room temperature or 4° C. overnight. The slides are incubated with an anti-γH2AX antibody (A300-081; Bethyl) or 8-OHdG (sc-66036; Santa Cruz) at 4° C. overnight and appropriate secondary antibodies (Alexa Fluor 568; Invitrogen) were used after primary antibody incubation. After washing with PBS, the coverslips were mounted over a microscope slide in Prolong anti-fade reagent that contained DAPI (P-36931; Life Technologies) and examined using a Stallion Digital imaging station (Carl Zeiss Microscopy).

Nucleus was visualized with DAPI or DRAQ5 (BioStatus) staining with manufacturer's protocol. Lysosomes were labeled with anti-LAMP1 (DSHB) for fixed-cells, or by LysoTracker Red (Invitrogen) for live-cells following manufacturer's protocol. Stacks of fluorescence images were deconvolved by using SoftWorX software (Applied Precision Inc.), and later analyzed with VoloCITY software (Perkin Elmer). All cell samples were scored for the presence of DNA leakage, and more than one leaked DNA or captured DNA by autophagosomes per cell reflects ADI-induced DNA damage.

Transmission Electron Microscopy.

The ADI-PEG20-treated CWR22Rv1 cells were collected and loaded into flat specimen holders for high pressure freezing in an electron microscopy PACT HPF station (Leica Microsystems, Vienna). The samples were freeze substituted in acetone containing 0.2% glutaraldehyde and 0.1% uranyl acetone at −90° C. for 72-h and then warmed up gradually to −20° C. (AFS; Leica Microsystems) to complete substitution. After dehydration in ethanol of increasing concentration, followed by a series of Lowicryl-Ethanol mixtures and then infiltrated with pure Lowicryl resin for 16-h. Finally, the resin polymerization was performed at −50° C. under UV light. The sample block was then trimmed and sectioned with a Leica Ultracut microtome. Sections of 100 nm-120 nm thick were collected on copper grids for imaging under a JEOL 1230 electron microscope. The electron micrographs were recorded on a F214CCD camera (TVIPS Gauting).

Hypodiploid Cell (DNA Content<2n) Analyses Using Propidium Iodide. ADI-PEG20-treated cells, including the supernatant, were harvested and washed with PBS. Resuspended cells (in 300 µL PBS) were added with 700 µL of absolute cold ethanol dropwise with vortexing and fixed at −20° C. overnight. The cells were pelleted with centrifugation at 1,000×g at 4° C. for 5 min. Supernatant was decanted carefully and washed twice in PBS at room temperature. Resuspended the cells (in 495 μL PBS) were added with 5 μL of RNase A (1 mg/mL) and incubated at 37° C. for 30 min to avoid the interference of RNA. Finally, 500 μL of PBS containing 10 μg/mL propidium iodide was added to make the finally concentration 5 μg/mL, and cells were stained for 15 min in darkness. The samples are subjected to flow-cytometric analysis for their DNA content histogram and the hypodiploid cell populations were scored (Gallios; Beckman Coulter).

Fluorescence-Based Methods to Measure CelROX Oxidation, MitoSOX Red Oxidation, Mitochondria Membrane Potential, and Autophagic Flux.

Cells were stained with CellROX Deep Red (C10422, 5 μM; Molecular Probes) for 30 min before flow cytometry analyses (Gallios; Beckman Coulter). In a second fluorescent dye oxidation measurement, cells were incubated with MitoSOX Red (M36008, 5 mM; Life Technologies) for 45 min in serum free DMEM. In this paper, elevation of CellROX Deep Red and MitoSOX Red fluorescence are used as the measure or indicator of increased nonmetabolic oxidation, which is consistent with oxidative stress. For mitochondrial membrane potential analyses, cells were incubated in DMEM with DiOC6 (318426, 10 nM; Sigma) for 30 min before analyses. For autophagic flux analyses, CWR22Rv1/GFP-LC3 cells were harvested after ADI-PEG20 treatment for different time periods and immediately analyzed by flow cytometry. Data were collected from three independent experiments and are presented in a histogram. The flow cytometry analyses were performed using FlowJo software (TreeStar).

Virus Production and Transduction.

Target gene DNA in a lentiviral backbone (pLKO.puro or pSin) (21 μg), pΔ8.7 (14 μg), and pVSV-G (7 μg) were transfected using Lipofectamine 2000 (11668-019, Life Technologies) into HEK293T/FT cells that had been seeded in a T-175 flask and had reached 60% confluence on the day of transfection. On the second day after transfection, cells were treated with sodium butyrate (10 mM) to stimulate virus production. Media containing viruses were harvested on the fifth day and filtered through a 0.45-μm filter. For viral transduction, cells were treated with media containing viruses overnight in the presence of polybrene (8.3 μg/mL) and this was followed by selection with puromycin (1 μg/mL).

Whole-Cell Extracts and Immunoblotting.

Cells were harvested and lysed on ice for 30 min in RIPA buffer (9806; Cell Signaling) containing complete protease inhibitor mixture (11836145001; Roche). The protein concentrations of whole-cell extracts were determined using a Bio-Rad Protein Assay Kit (500-0001; Bio-Rad). Approximately 40 μg of protein extract was mixed with an equal volume of 2×SDS loading buffer, boiled for 5 min, then separated by Tris-glycine SDS/PAGE and transferred to PVDF membranes. The membranes were blocked with 5% nonfat milk in PBST [PBS containing 0.05% (vol/vol) Tween 20] and incubated with primary antibodies at 4° C. overnight. The membranes were then washed with three times with PBST for 10 min, three times, and incubated with HRP-labeled secondary antibodies for 2 h at room temperature. Immunoblots were visualized using VersaDoc 5000 imaging system (Bio-Rad). All blots were performed with standard protocol.

Apoptosis and Mitotic Catastrophe Induction.

CWR22Rv1 cells were cultured in RPMI supplemented with 10% (vol/vol) FBS and 1% (vol/vol) penicillin/streptomycin. For UV-induced apoptosis, media was aspirated and cells were briefly washed with PBS. Cells were exposed to UV in UV Crosslinker box (Fisher Scientific) under optimal cross-link condition. Fresh RPMI-1640 was added, followed by 24 h incubation at 37° C. For mitotic catastrophe induction, cells were treated with paclitaxel (100 nmol/L; Sigma) for 24 h at 37° C., and cell samples were collected the next day.

Oxygen Consumption Rate.

Cellular mitochondrial function was measured using the Seahorse Bioscience XF24 Extracellular Flux Analyzer. The mitochondrial function was assayed by sequential injections of oligomycin (ATP synthase inhibitor), FCCP (carbonyl-cyanide p-trifluoromethoxy phenylhydrazone), mitochondrial oxidative phosphorylation protonophore and uncoupler, and rotenone (mitochondrial complex I inhibitor) to define basal oxygen consumption rate (OCR), ATP-linked OCR, proton leak, maximal respiratory capacity, reserve respiratory capacity, and nonmitochondrial oxygen consumption, all according to the manufacturer's instructions. Herein, basal OCR is used to represent the function of mitochondria. Briefly, $2 \times 10^4$ cells were seeded onto 24-well plates and incubated overnight before sequentially adding preoptimized concentrations of oligomycin, FCCP, and rotenone, in that order. After washing the cells with 1 mL seahorse buffer [DMEM without phenol red containing glucose (G7021, 4.5 g/L; Sigma), sodium pyruvate (Ser. No. 11/360,070, 1 mM; Gibco), and glutamine (25030081, 4 mM; Gibco)], 600 μL seahorse buffer plus 60 μL each of oligomycin (75351, 50 μg/mL; Sigma), FCCP (C2920, 10 μM; Sigma), and rotenone (R8875, 10 μM; Sigma) was automatically injected. At the end of recording period, cells were collected and the individual cell numbers were determined using a trypan blue exclusion assay. OCR values were calculated after normalizing with the cell number and plotted as the mean±SD.

8-OHdG ELISA.

DNAs were isolated using DNeasy blood and tissue kit (69504; Qiagen) according to the supplier's protocols. Extracted DNAs were dissolved in water to 1 mg/mL and the DNA sample was converted to single-stranded DNA by incubating the sample at 95° C. for 5 min and rapidly chilling on ice. DNA samples were digested to nucleosides by incubating the denatured DNA with 10 units of nuclease P1 (N8630; Sigma) for 2 h at 37° C. in 20 mM sodium acetate (S2889; Sigma), pH 5.2, and followed with treatment of 10 units of alkaline phosphatase (M0290S; New England Biolabs) for 1 h at 37° C. in 100 mM Tris (T5941; Sigma), pH 7.5. The reaction mixture was centrifuged for 5 min at 6,000×g and the supernatant was used for the 8-OHdG ELISA using Oxiselect oxidative DNA damage ELISAkit (STA-320; Cell Biolabs) according to supplier's protocols.

Results

ADI-PEG20 Targets Cancer Cells Via Atypical Death Pathway with Nuclear DNA Leakage.

Figure 14A:
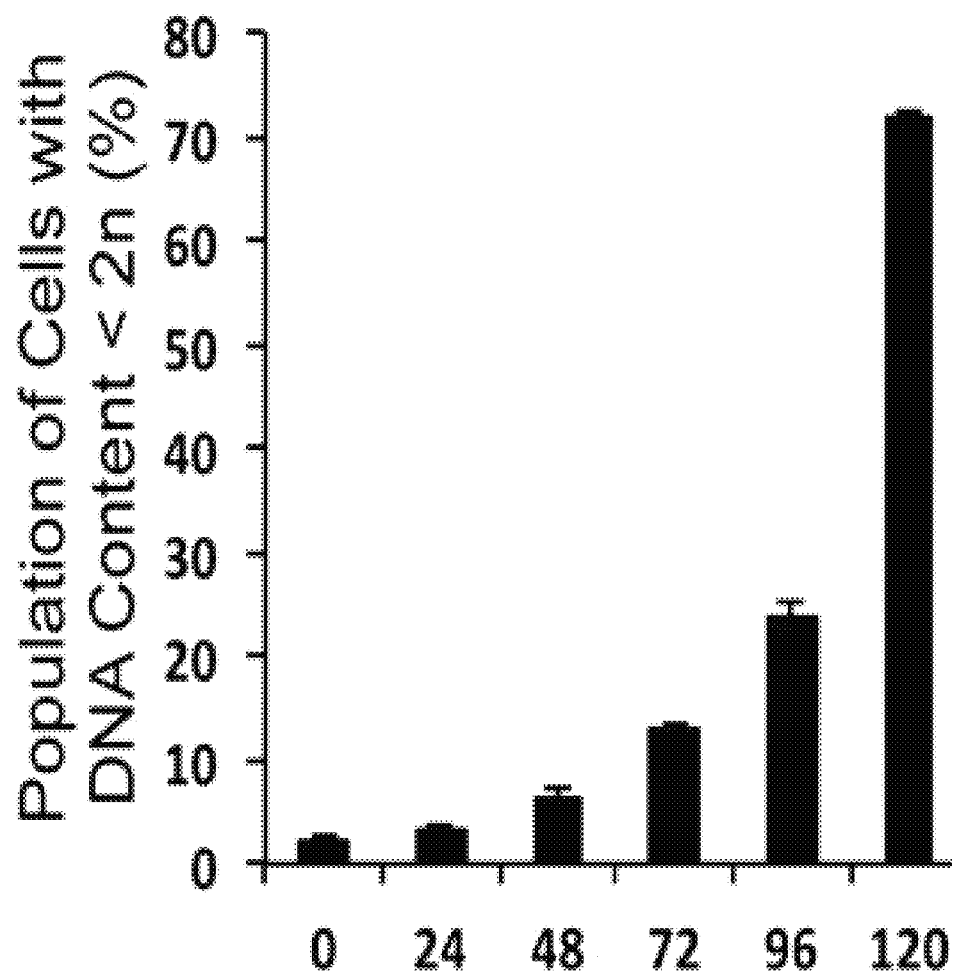
FIGS. 14A-F show that ADI-PEG20 induced both caspase-independent cell death and DNA leakage according to one embodiment.
Figure 14B:
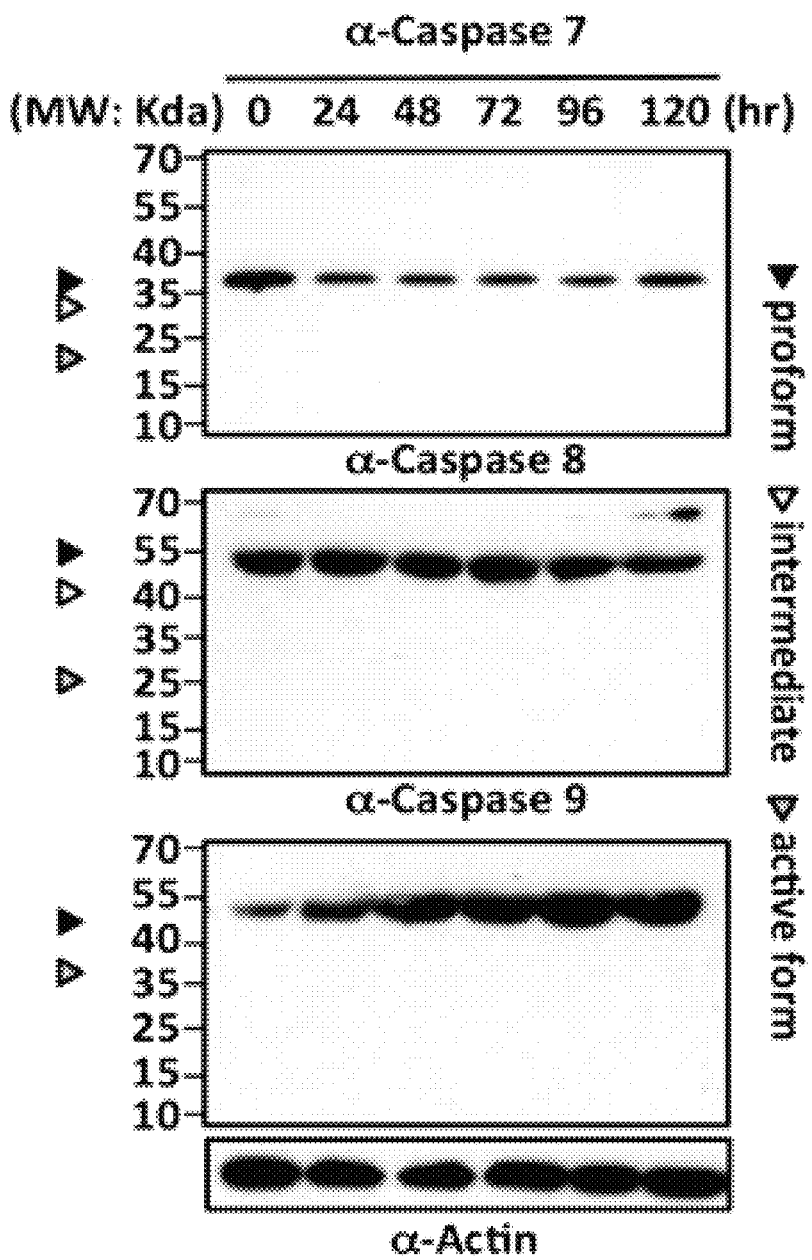

To explore the mechanism underlying ADI-PEG20- and arginine deprivation-mediated cytotoxic effect, prostate cancer CWR22Rv1 cells were treated with 0.3 μg/ml (IC50) of ADI-PEG20. This treatment resulted in cell death with two unusual features that distinguished it from conventional apoptosis. First, there was a long incubation period (48-h) before the emergence of hypodiploid cells (DNA content<2n) in flow-cytometric analysis (FIG. 14A). Second, the cell death is caspase-independent as caspase 7, 8 and 9 all remained in the respective pro-caspase form (FIG. 14B). This echoes earlier finding that treatment of cells with pan caspase inhibitor (vZAD) did not affect the extent of ADI-PEG20-induced cell death (Kim et al. 2009b). These data prompted us to study whether autophagy is involved in the late phase of cellular killing and to decipher the molecular mechanism underlying ADI-PEG20-induced cell killing.

Figure 14C:
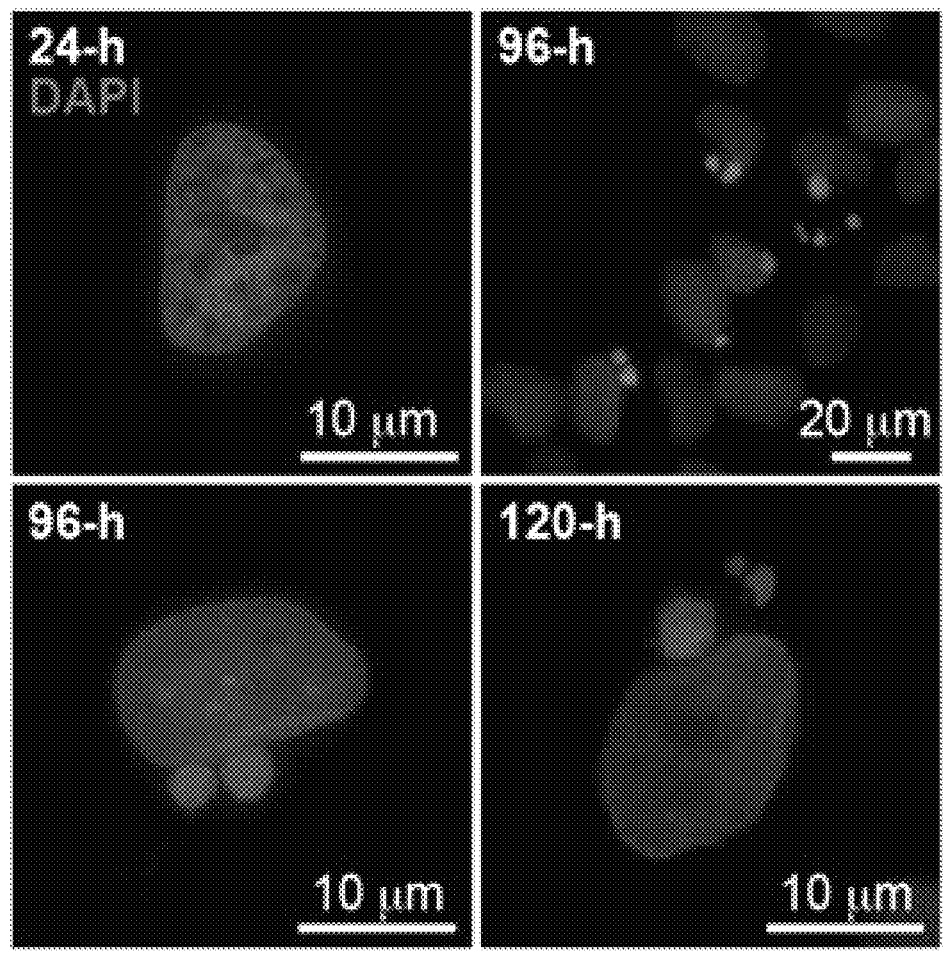
Figure 14D:
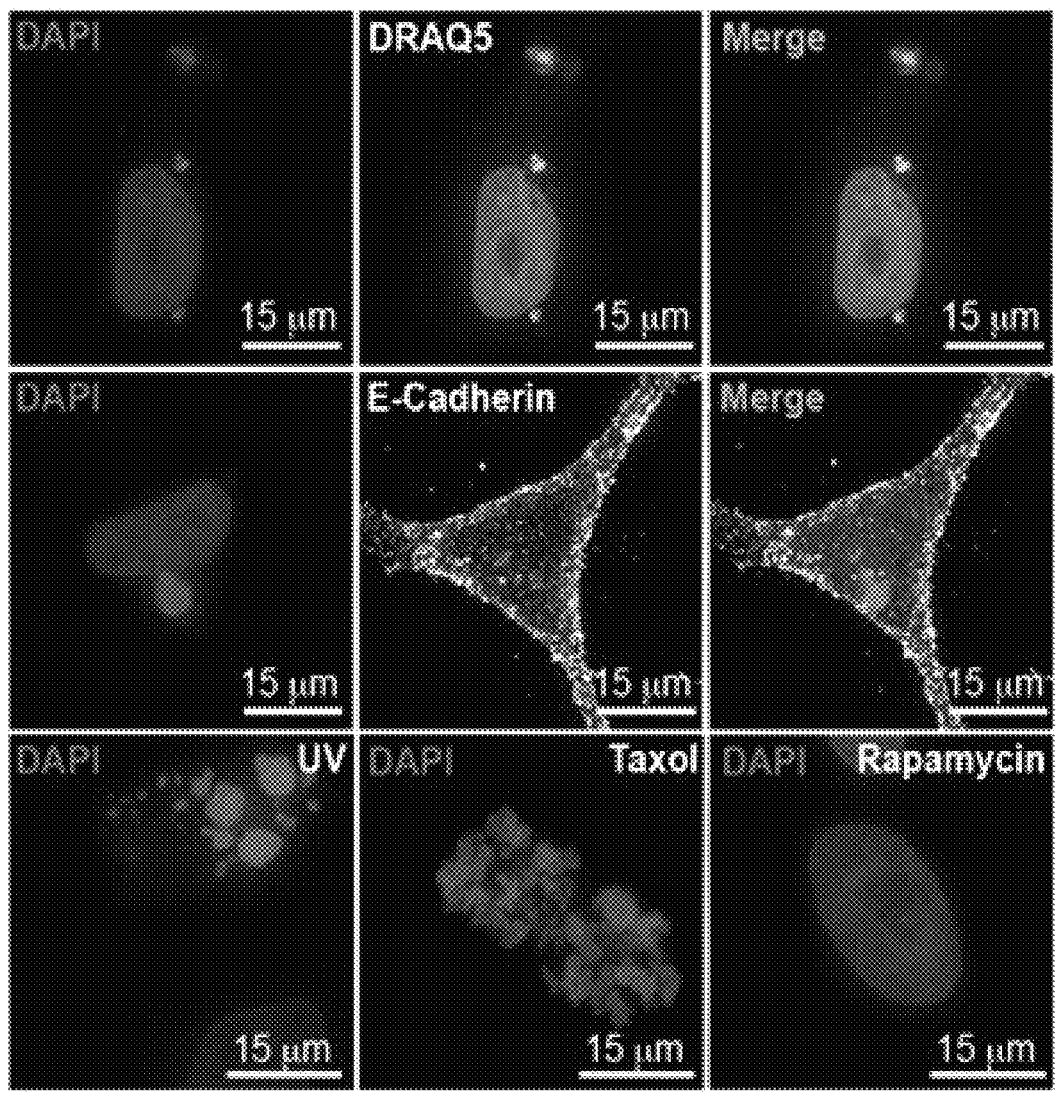

In order to investigate the mechanism underlying prostate cancer cell death by arginine deprivation, advanced 4-D fluorescence microscopy was used to examine the nuclear dynamics. As shown in FIG. 14C, one striking feature was that ADI-PEG20-treatment consistently induced nuclear DNA leakage at the onset of dying phase (48-h post-treatment) as identified by DAPI-positive particles outside the nucleus. DNA-leakage became more apparent after 72-h of treatment, and the size of leaked DNA puncta was notably larger than that of micronuclei and the number was more numerous (FIG. 14C). To ensure that these particles released from nucleus truly contain DNA (as opposed to RNA), DRAQ5 with higher specificity towards DNA was used. Merged images showed nearly perfect co-localization between DAPI and DRAQ5, confirming the DNA as the major cargo in these particles or puncta (FIG. 14D). It was also clear that the remaining nucleus became mis-shaped, often indented when adjacent to autophagosomes.

Figure 14E:
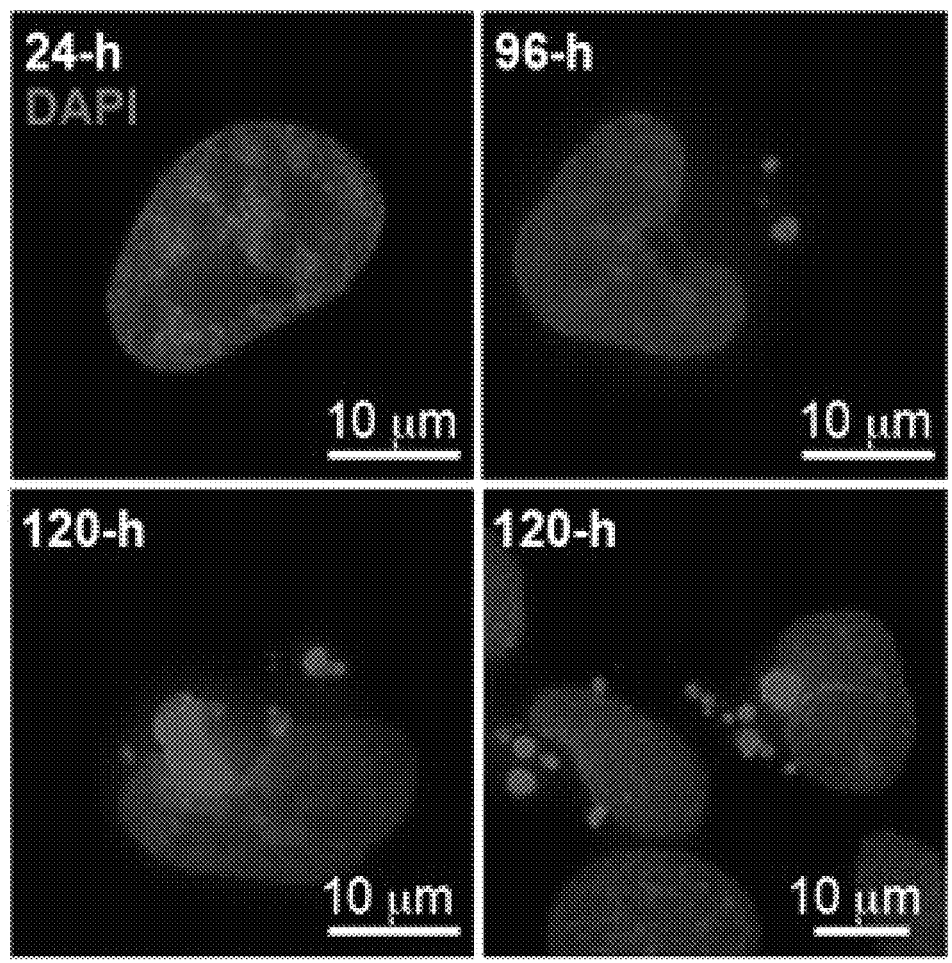
Figure 14F:
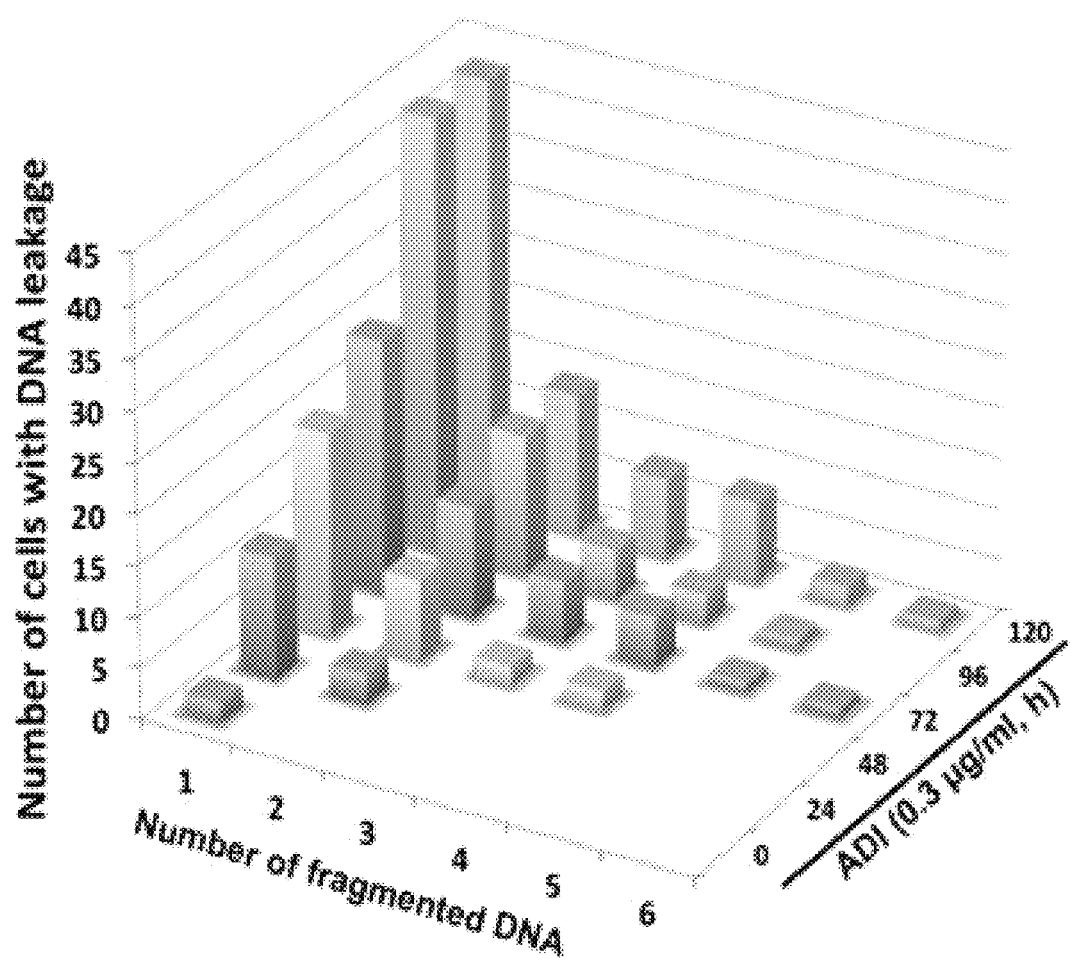
Figure 15A:
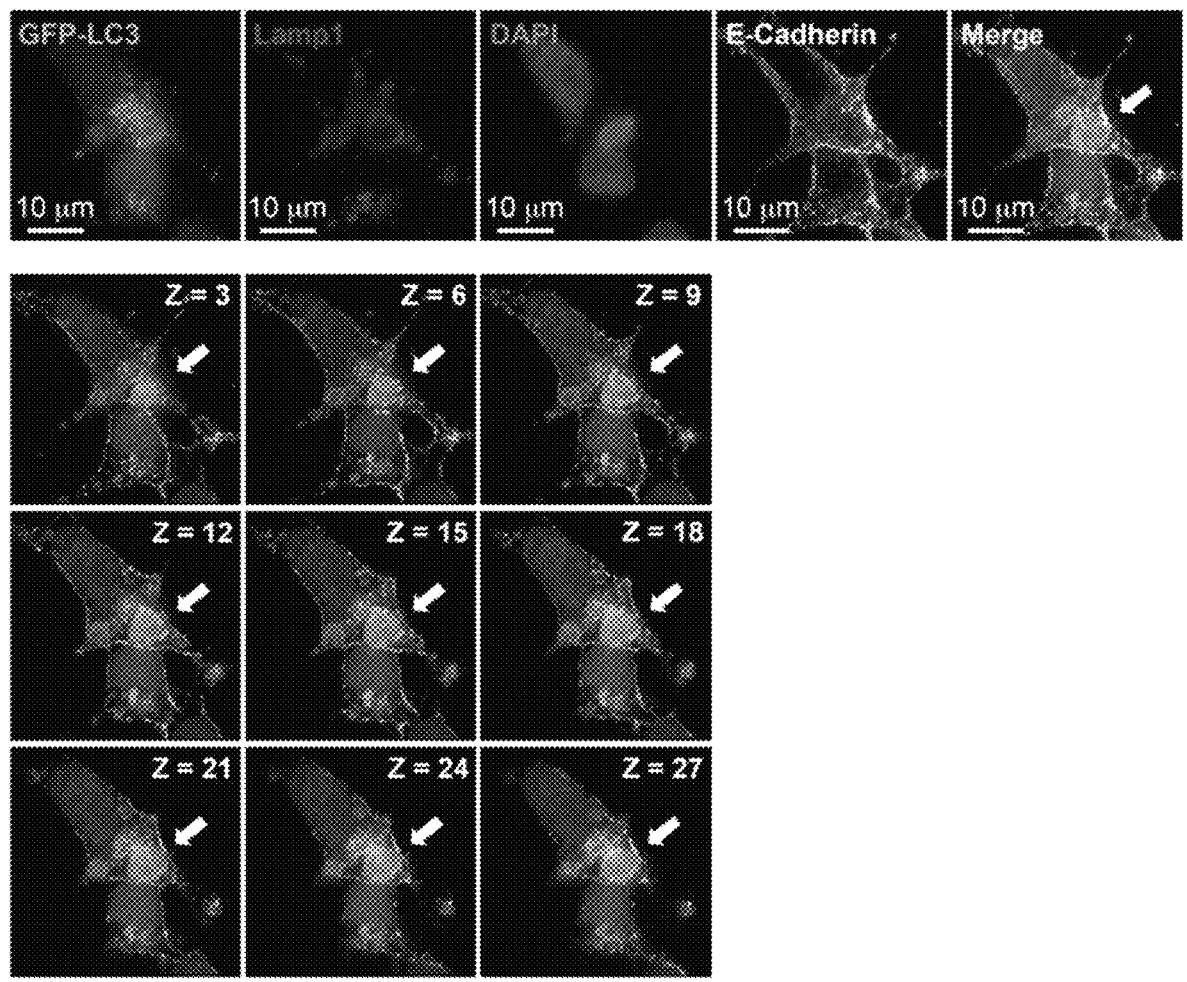
FIGS. 15A-B show that sustained arginine starvation induces DNA leakage according to one embodiment.
Figure 15B:
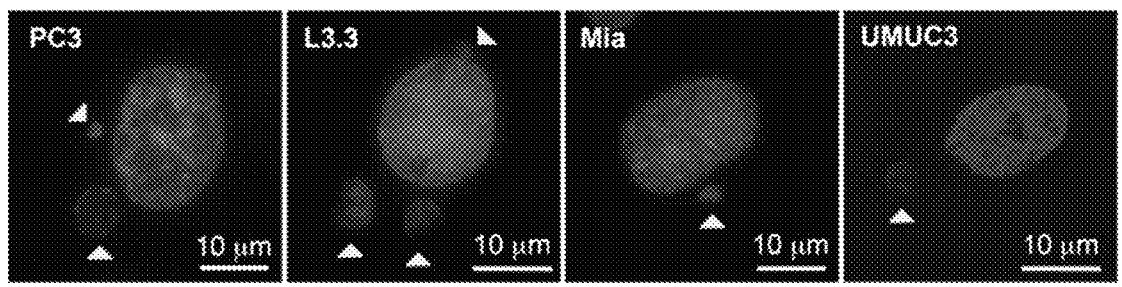

A notable feature of this phenotype, distinguishing it from apoptotic bodies, is that, the leaked DNA was not surrounded by plasma membrane and nucleus was not shattered either. In fact, the gross morphology of these cells containing leaked DNA, as indicated by cell membrane marker E-Cadherin staining, appeared to be intact (FIGS. 14D, 15A). Moreover, these cells were able to maintain cell adhesion in culture, suggesting that the DNA-leakage did not take place post cell death. The leaked DNA structures with largely intact nucleus (FIG. 14C) are distinct from the apoptotic bodies generated by UV- or mitotic catastrophe by taxol-treatment (FIG. 14D). To ascertain that these observations indeed resulted from arginine depletion, CWR22Rv1 cells were maintained in arginine-free media up to 120-h. DNA leakage was unequivocally observed (FIG. 14E). In addition, similar phenotype was identified in prostate cancer PC3 cells and pancreatic Mia and L3.3 cells (FIG. 15B), all are lacking ASS1 expression and sensitive to ADI-PEG20-induced cell killings. This phenotype is not restricted to CWR22Rv1 cells, and was found in ADI-PEG20-treated Mia and UMUC3 cells (FIG. 15B), which also exhibited caspase-dependent cell death (Bowles et al. 2008; Syed et al. 2013). Thus, DNA leakage is not exclusive to cells undergoing caspase-dependent death. By contrast, such a phenotype was not found in cells treated with rapamycin alone (FIG. 14D) or subjected to glutamine depletion (Lin et al. 2012). The number of puncta carrying DNA was at least 1, but up to more than 6, with an average of 1.92 per cell (n>300) (FIG. 15F). These data taken together suggest that prolonged arginine deprivation selectively induces DNA leakage.

ADI-PEG20 Induces Giant Autophagosome Formation.

Figure 16A:
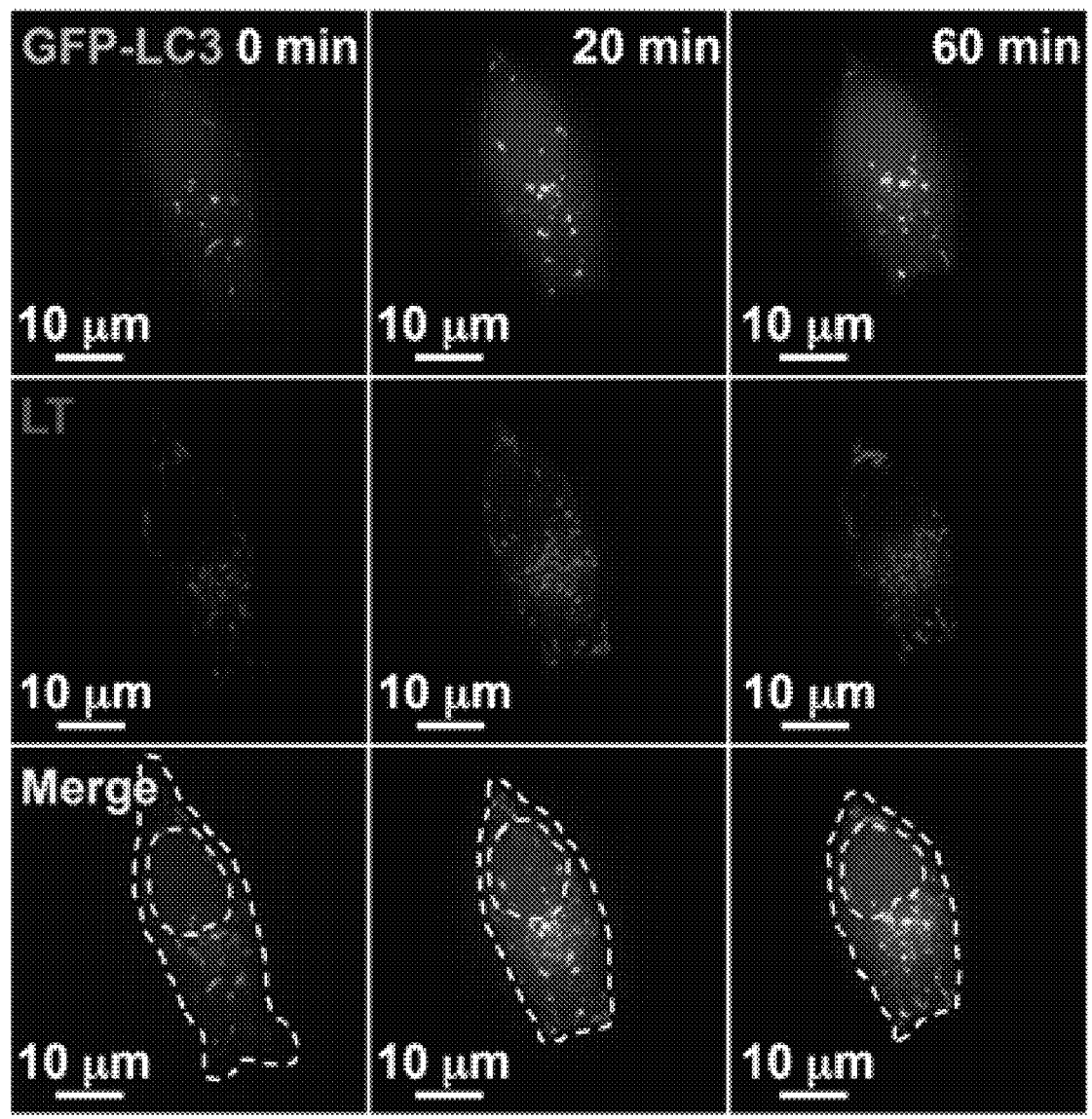
FIGS. 16A-C show that prolonged ADI-PEG20 treatment can induce giant-autophagosome formation and affect autophagic flux pattern according to one embodiment.
Figure 16B:
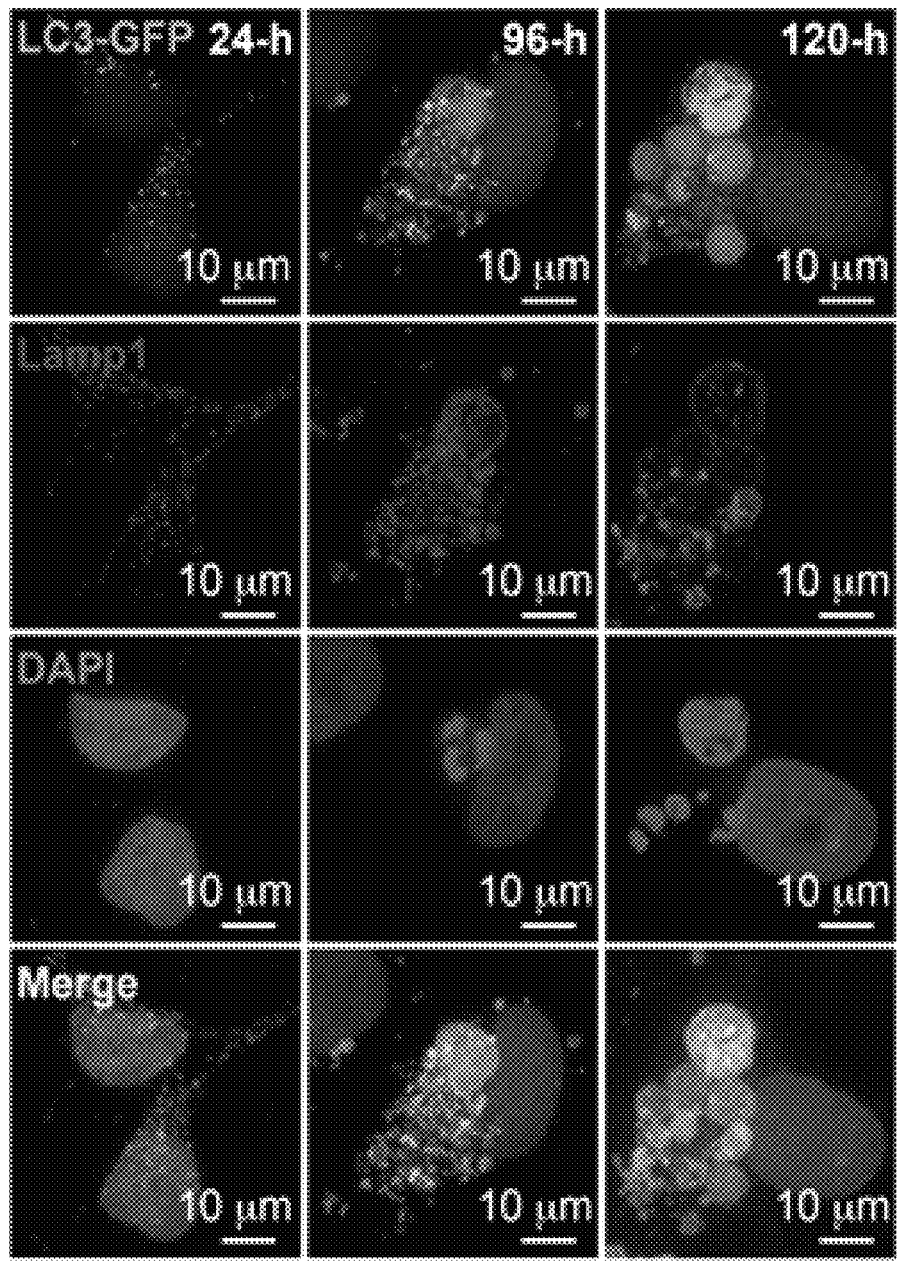
Figure 17A:
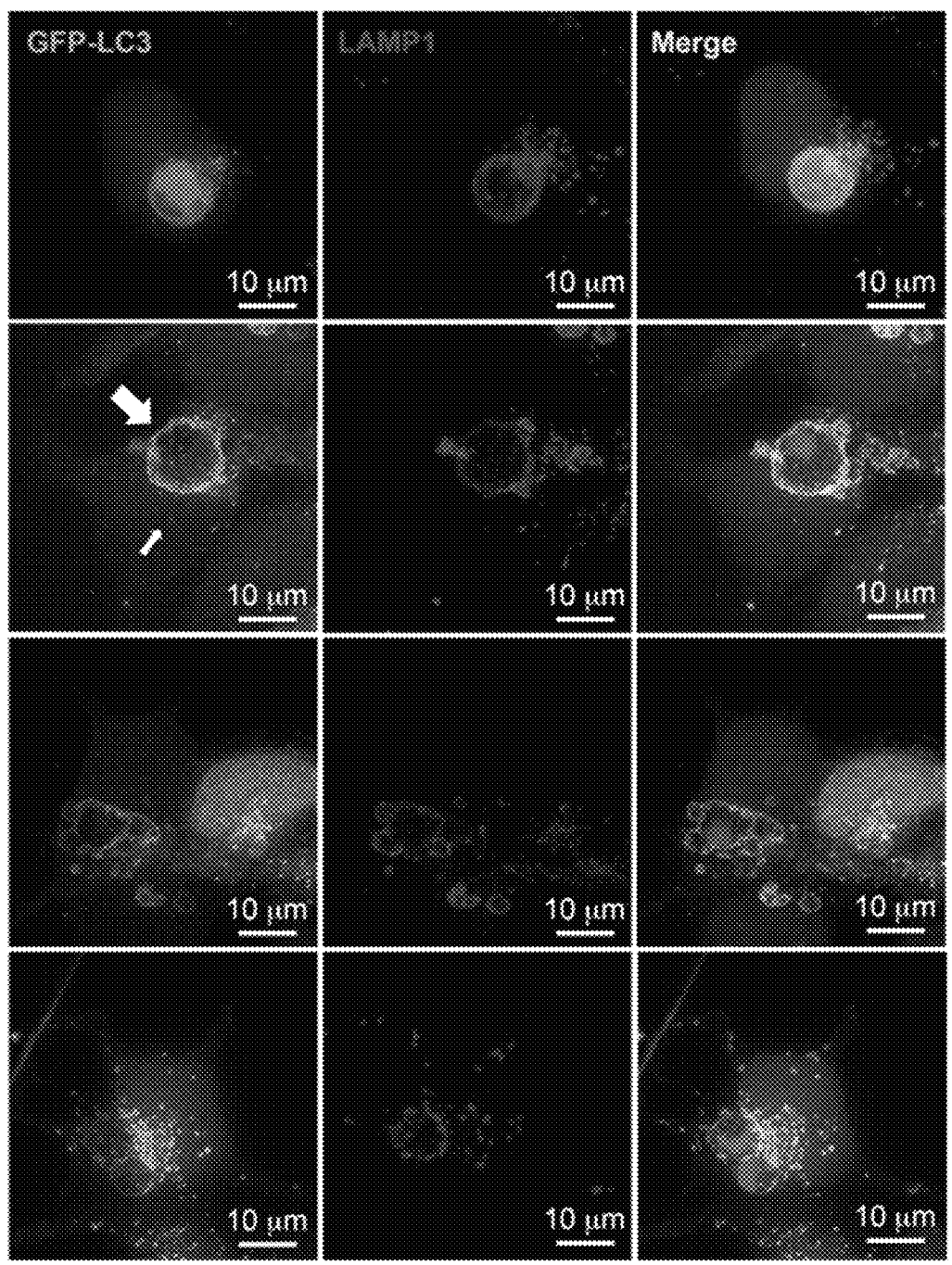
FIGS. 17A-B show that prolonged ADI-PEG20 treatment results in larger-than-normal autophagosome formation and colocalized with lysosome at 96 h post treatment according to one embodiment.
Figure 17B:
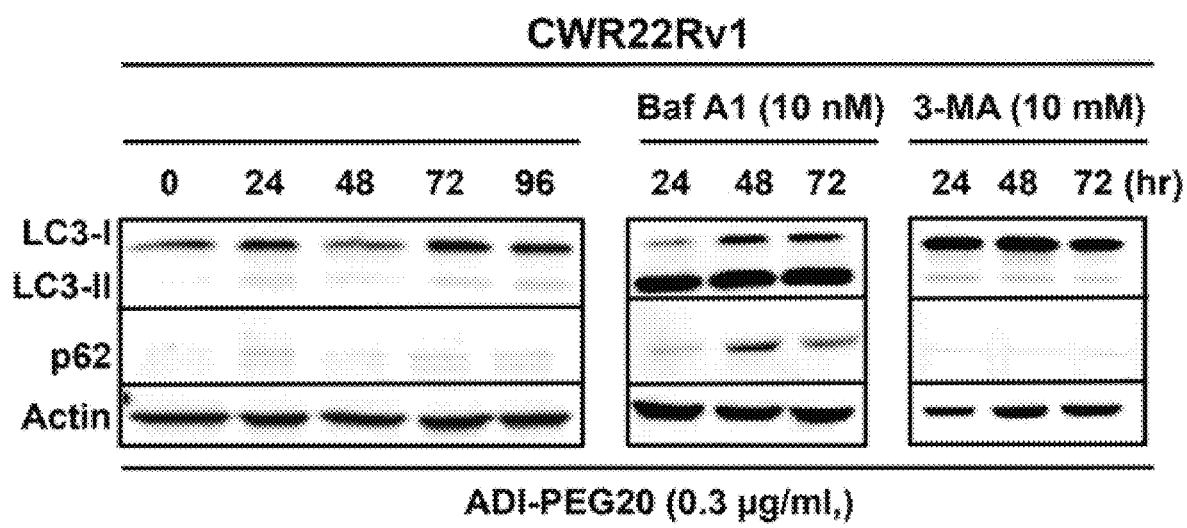

FIG. 16A shows that GFP-LC3, a marker for autophagy, was concentrated at the perinuclear region of the GFP-LC3 stably-transfected CWR22Rv1 cells within 20-min of ADI-PEG20-treatment. The number of autophagosome increased as autophagy proceeded. At the same time, lysosomes as marked by LysoTracker Red migrated toward the perinuclear region, where some of them began to fuse with autophagosome to form autolysosomes (FIG. 16A). This process persisted for at least 24-h in the presence of ADI-PEG20. In contrast to earlier stage of ADI-PEG20-treatment with conventional sized autophagosome puncta, subset of the puncta at later phase exhibited abnormally large autophagosomes and autolysosomes (as indicated by colocalization of GFP and LysoTracker (FIG. 16B) or LAMP1 (FIG. 17A). Some of the larger autophagosomes were greater than 20-fold of the size of conventional autophagosomes (FIG. 17A). Moreover, Western blot analysis demonstrated that the addition of bafilomycin A1, an inhibitor of vacuolar-type $H^+$-ATPase, caused accumulation of LC3-II and p62 in ADI-PEG20-treated cells (FIG. 17B), but not in cells treated with 3-MA alone, supporting the involvement of lysosomes in this atypical autophagy. Many of these abnormally-sized autophagosomes (GFP-C3, green) were colocalized with the LAMP1 (red) and leaked DNA (blue) described above (FIGS. 16B, 17A). Although some of the autophagosomes did not contain leaked DNA particles, all of the leaked DNA particles were contained within autophagosomes by analyzing more than 300 cells with leaked DNA at different time points post ADI-PEG20-treatment. Interestingly, strong DAPI signal could be found in these particles, suggesting dense DNA material were encapsulated within the autophagosomes.

Figure 16C:
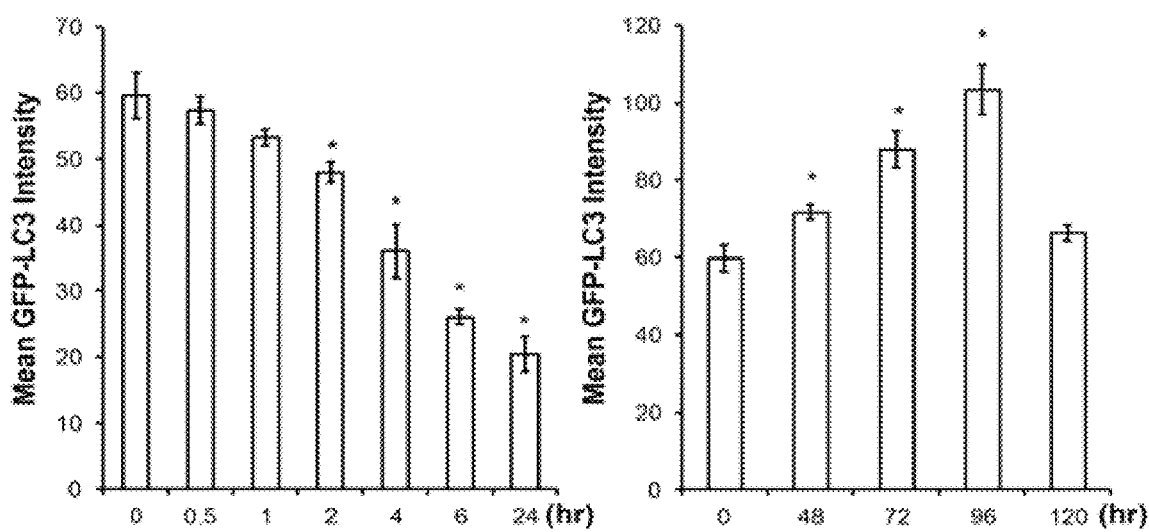

Lastly, autophagy flux was measured by using flow-cytometry. As shown in FIG. 16C (left panel), during the first 24-h, a decrease of GFP-LC3 level was noted, suggesting the progression of autophagic flux to overcome arginine-auxotrophy induced by ADI-PEG20 (Kim et al. 2009b). However, the level of GFP-LC3 increased at 48-h post-ADI-PEG20-treatment and then tapered off at 120-h (FIG. 16C, right panel). The second wave of increased GFP-LC3 coincided with appearance of giant autophagosomes (FIG. 16B). These results suggest that there are two phases of arginine starvation-mediated autophagy induction, with conventional autophagosome morphology at early phase and giant-autophagosomes at later dying phase.

Nuclear Membrane Remodels During ADI-PEG20-Induced Chromatophagy.

Figure 18A:
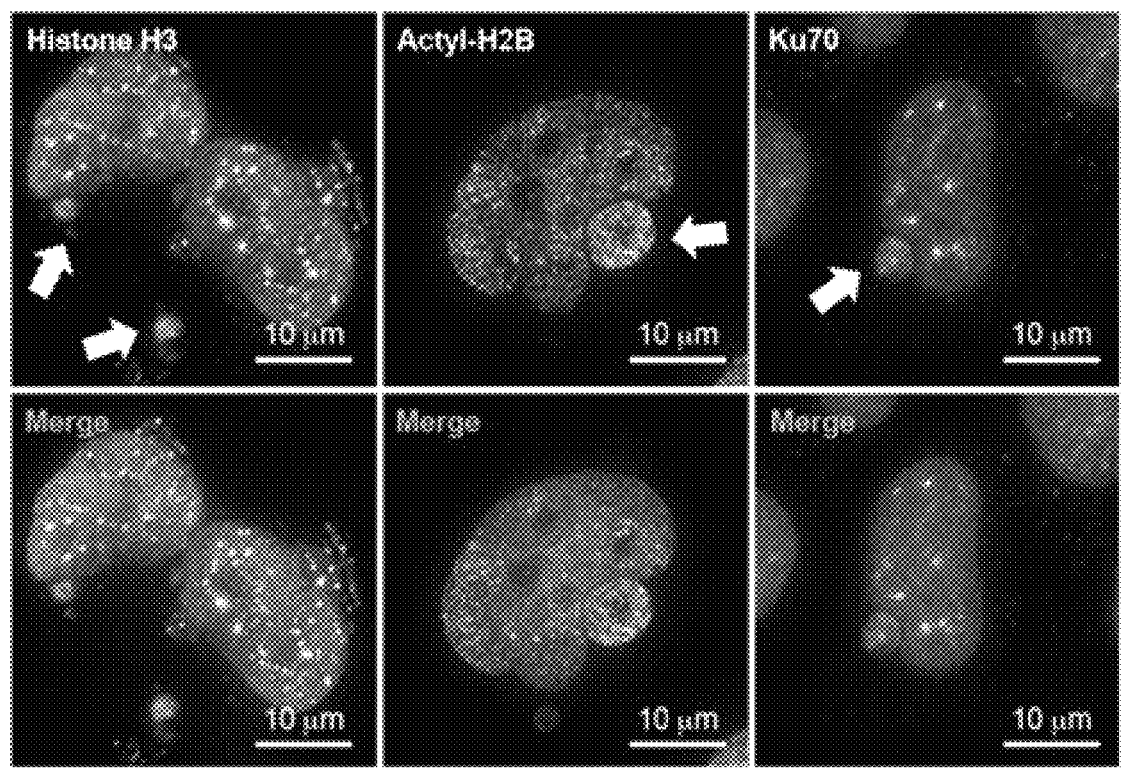
FIGS. 18A-F illustrate that prolonged arginine deprivation by ADI-PEG20 induces nuclear membrane remodeling according to one embodiment.
Figure 19A:
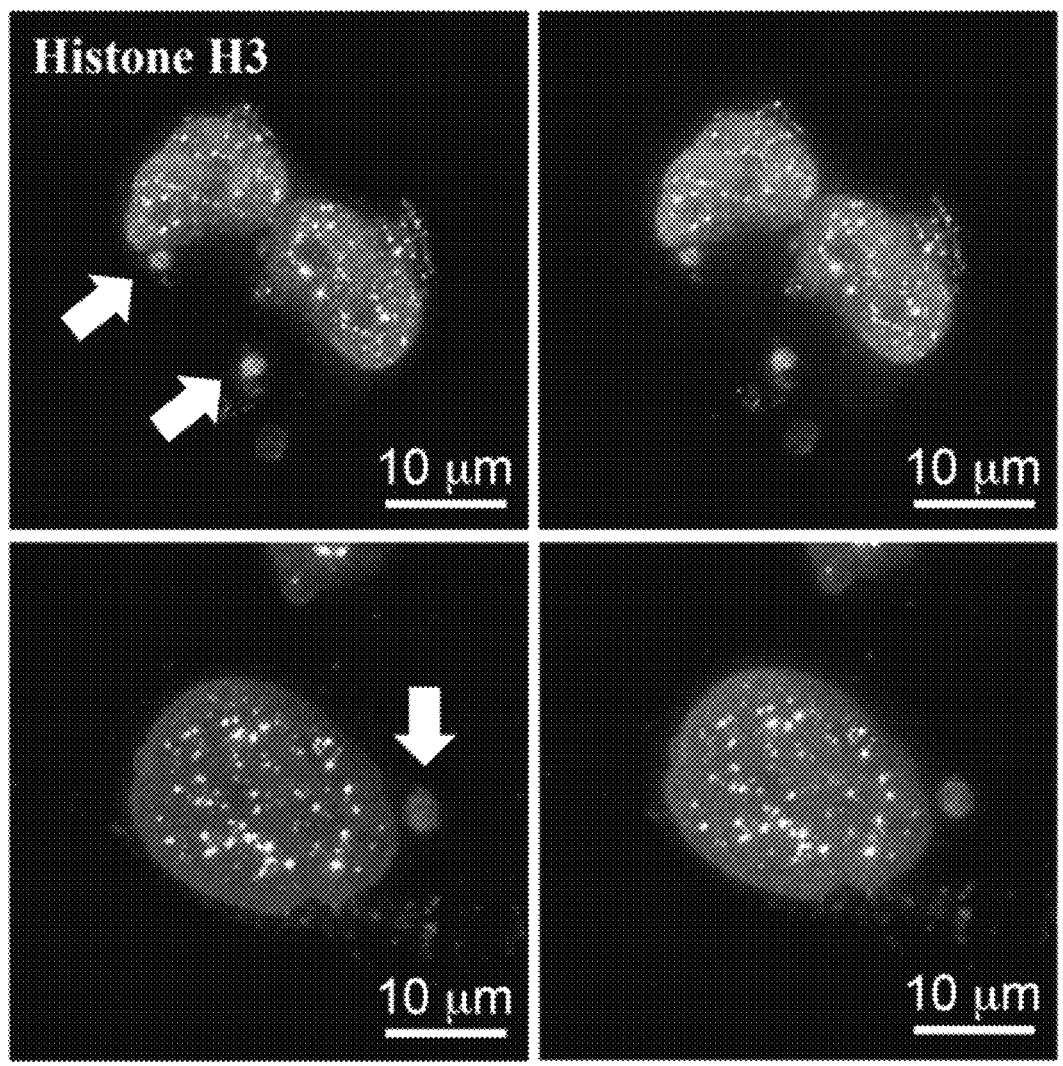
FIGS. 19A-C show that prolonged ADI-PEG20 treatment induces chromatophagy according to one embodiment. CWR22Rv1 cells stained with DAPI (blue) and anti-histone H3 (FIG. 19A) or anti-acetyl-H2B (FIG. 19B) to show that histone H3 colocalized with leaked DNA outside of nucleus (white arrows).
Figure 19B:
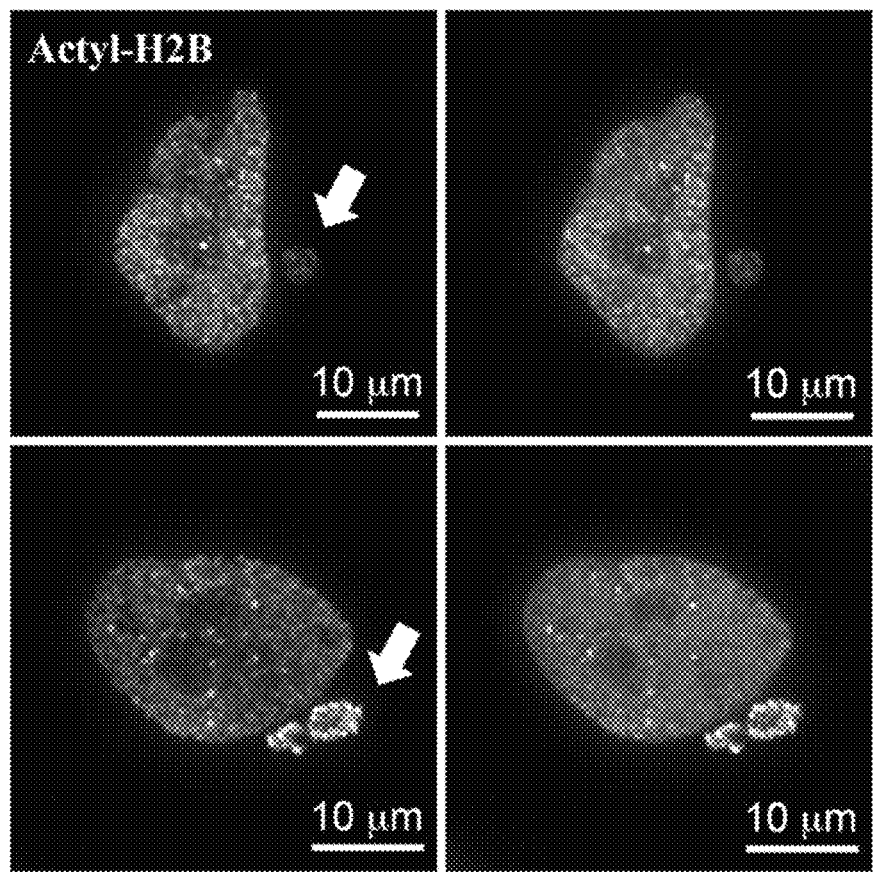
Figure 19C:
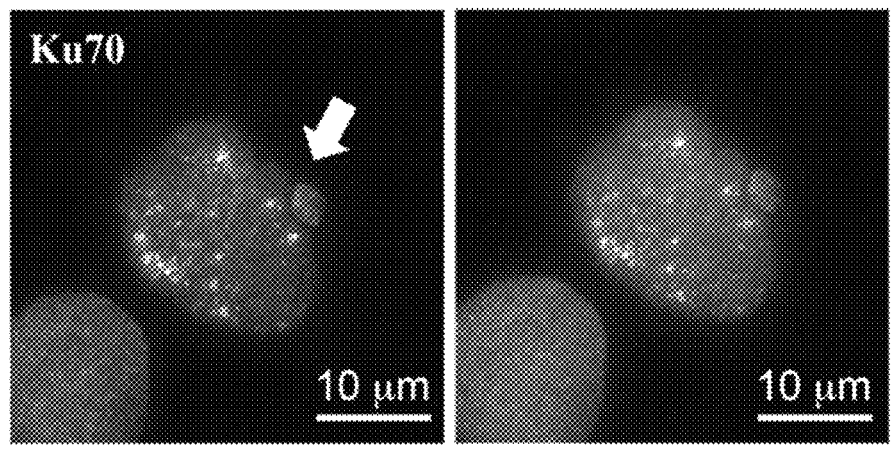

Next, it was determined whether the leaked DNAs were from nucleus. If so, it must be sheared from nuclear DNA and therefore, could be considered as damaged DNA. To investigate this, and to further characterize these DNA-containing autophagosome complexes, immunofluorescence was used to identify proteins known to be associated with chromatin and/or DNA repair. Nuclear DNA/chromatin-bound proteins, both H3 (FIG. 18A, 19A), and acetyl-H2B (Lys12) (FIG. 18A, 19B) were found within the DNA-containing autophagosomes. Acetylation of histone tail is believed to destabilize chromatin structure. Yet, acetylated histones can be found on the exo-nucleus DNA indicating destabilized chromatin existed in the autophagosome. Moreover, Ku70, known to be associated with DNA double-strand break (DSB) ends, was identified with leaked DNA (FIGS. 18A, 19C), suggesting that cells might attempt to repair the damaged DNA before it leaked into cytoplasm and engulfed by autophagosomes.

Figure 18B:
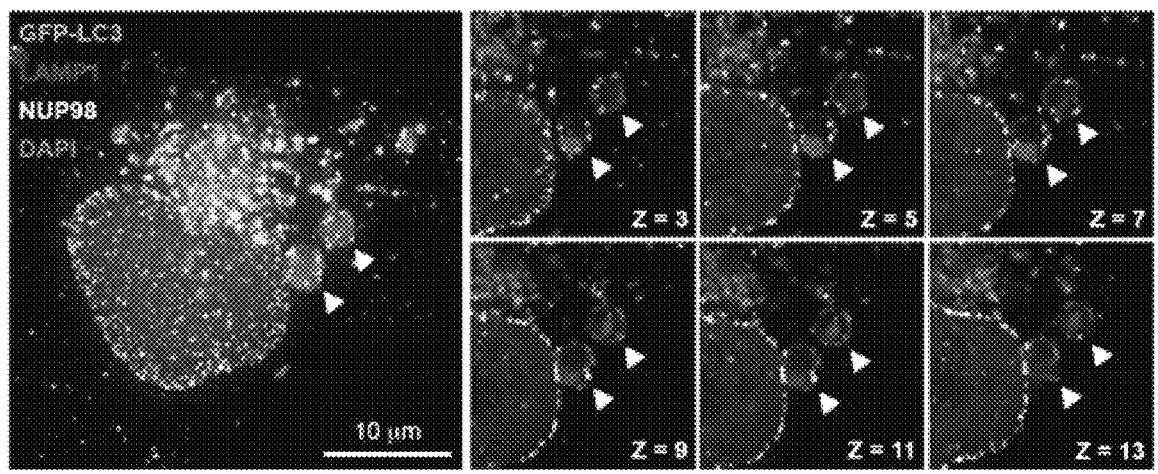
Figure 18C:
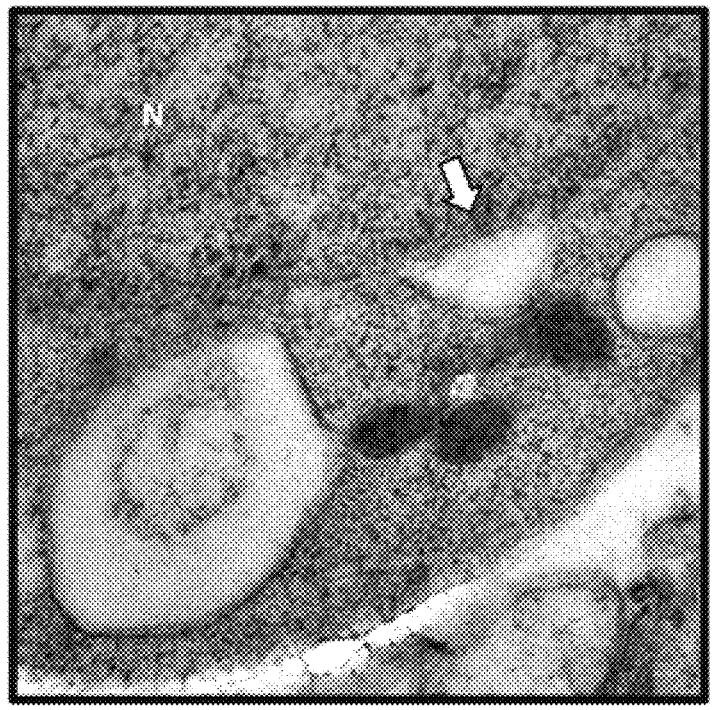
Figure 18D:
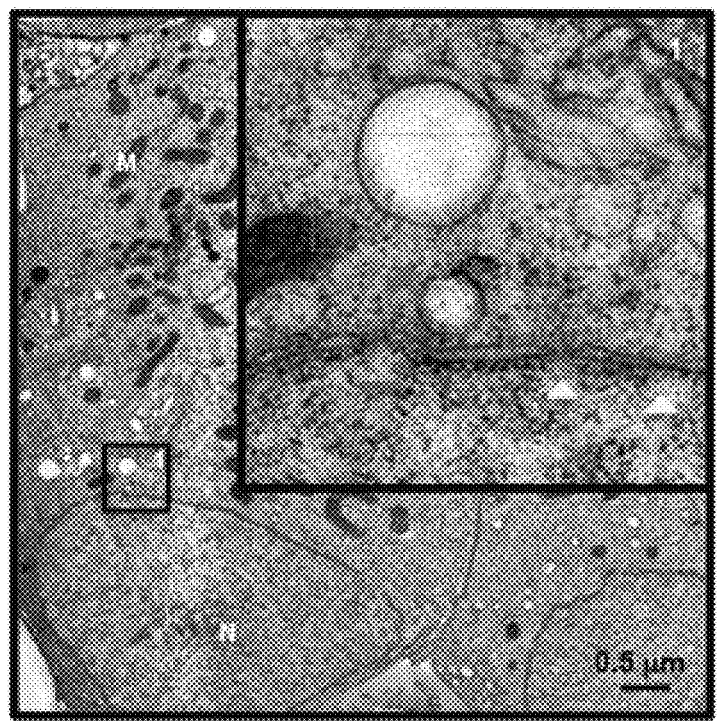

The nuclear membrane is composed of lipid bi-layer and its integrity is essential for cell survival. To examine whether the nuclear membrane integrity might have been compromised, resulting in DNA leakage, arginine-starved cells were stained with nuclear outer membrane marker nucleolin (NUP98). A series of Z-section fluorescence images revealed that portions of the outer membrane might have fused with autophagosome (FIG. 18B, white arrowheads), suggesting that (1) the generation of these complexes involve nuclear-autophagosome membrane fusion immediately adjacent to the nucleus, and (2) nuclear outer membrane protein nucleolin could provide a docking site for autophagosomes. Moreover, in order to achieve higher spatial resolution of nucleus and autophagosome junctures, ADI-PEG20-treated cells were subjected to transmission electron microscopy (TEM) analyses. Indeed, TEM image showed autophagosome seemingly fused with nuclear membrane (FIG. 18C, white arrow) and also showed partial nuclear membrane breakage (FIG. 18D, inset, red-line), which is different from a typical nuclear pore complex (FIG. 18D, inset, yellow arrowheads). Some autophagosomes were also found in close proximity to nucleus, and interestingly enough, the size of vesicle (FIG. 18D, inset, red arrowhead) is similar to the opening next to it (FIG. 18D, inset, red-line), suggesting there might be an increased activity of vesicle trafficking between the two. Together with results shown in FIG. 20, autophagosome formation might serve a previously overlooked function related to DSBs in the nucleus, and was capable to fuse with nuclear membranes; both of which were critical for DNA leakage.

Figure 18E:
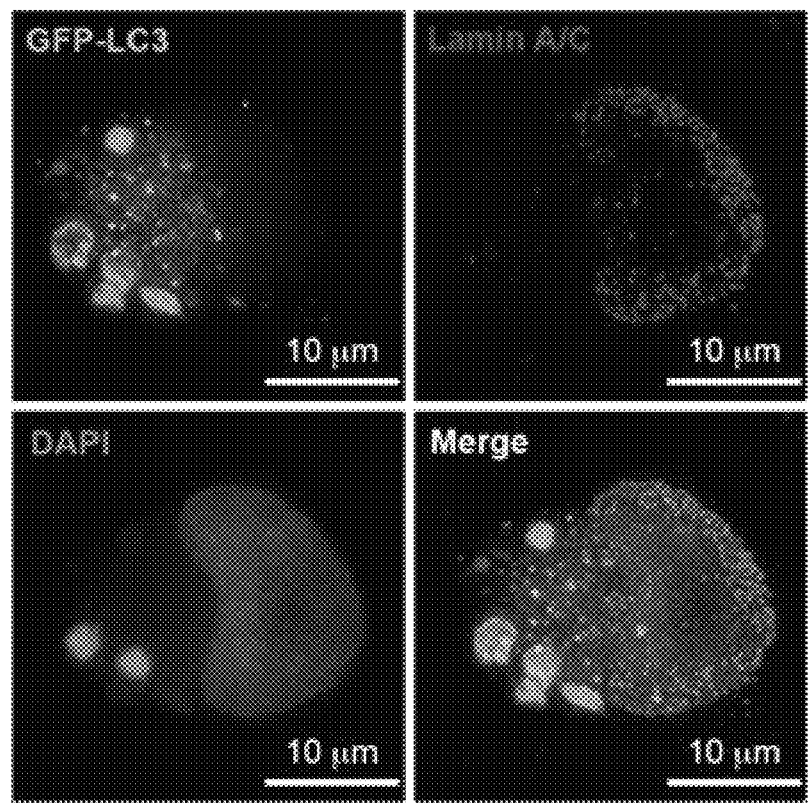
Figure 18F:
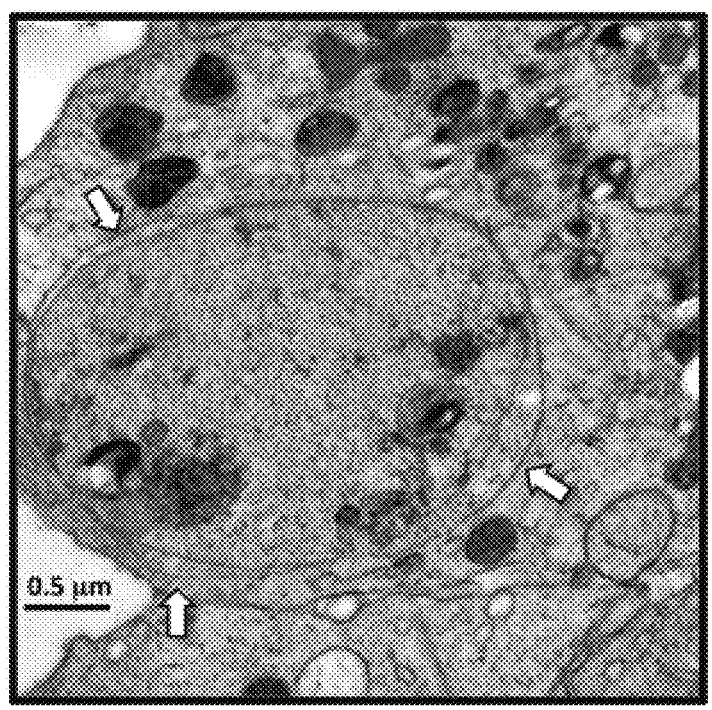

Next, the inner membrane structure of nucleus was examined using lamin A/C as markers. The detailed 3-D information shows (1) a discontinuity of lamin A/C signals peripherally surrounding the nucleus and (2) lamin A/C signals displaying a cave-in like shape at site of autophagy (FIG. 18E). Interestingly, stacked sections revealed that lamin A/C signals were markedly reduced at the interface between autophagosomes and nucleus showed discontinuity of lamins (FIG. 18E). Clearly, the lamin A/C signal was also severely reduced in many cells exhibiting chromatophagy phenotype, suggesting that compromised (or rearranged/remodeling of) nuclear envelope integrity might partake in DNA-leakage. In addition, parts of nuclear membrane also showed some defects and/or breakage (FIG. 18D, inset, red-line). Additional image also showed a separation between the inner and outer membranes (FIG. 18F, white arrows), indicating nuclear membrane integrity might have been compromised. The lack of lamin A/C structure in the area facing autophagosomes (FIG. 18E) implicated that autophagy likely engaged in capturing the damaged DNA at the interface.

ADI-PEG20 Impairs Mitochondrial Function and Induces ROS Generation.

Figure 20A:
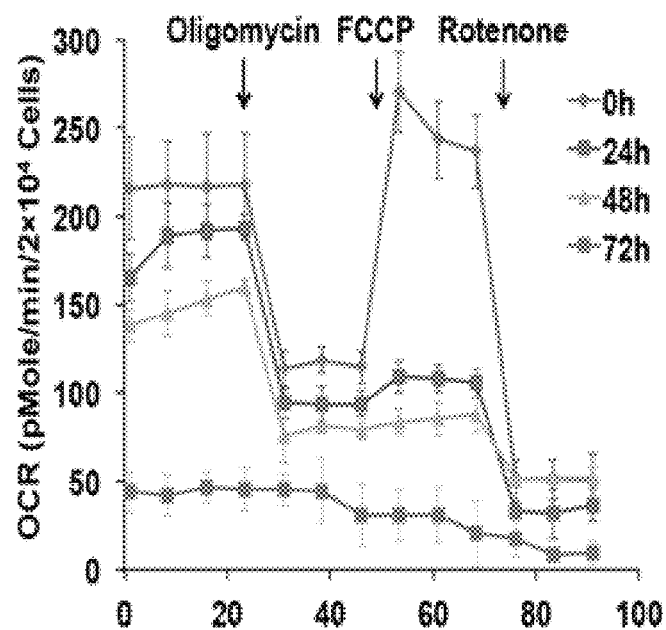
FIGS. 20A-F illustrate that ADI-PEG20-treatment impairs mitochondrial function and induces ROS production according to one embodiment.
Figure 20B:
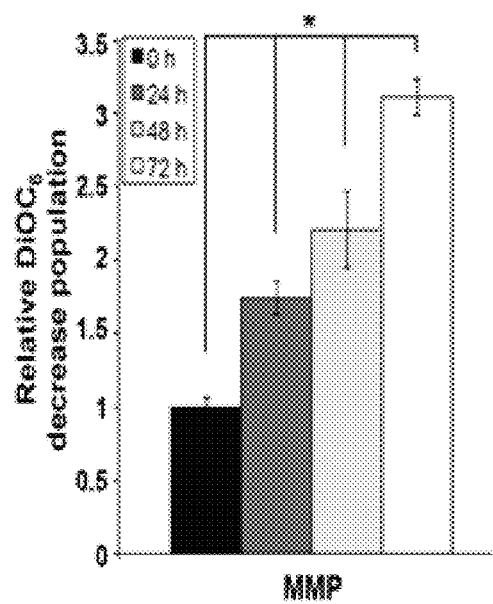
Figure 20C:
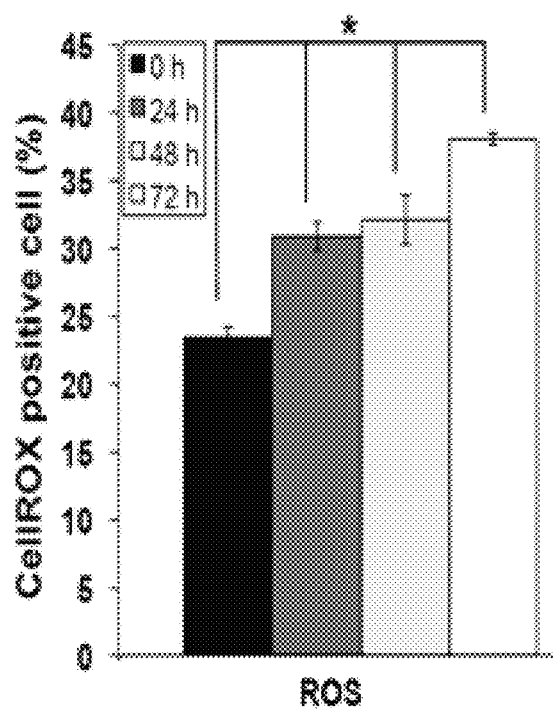
Figure 20D:
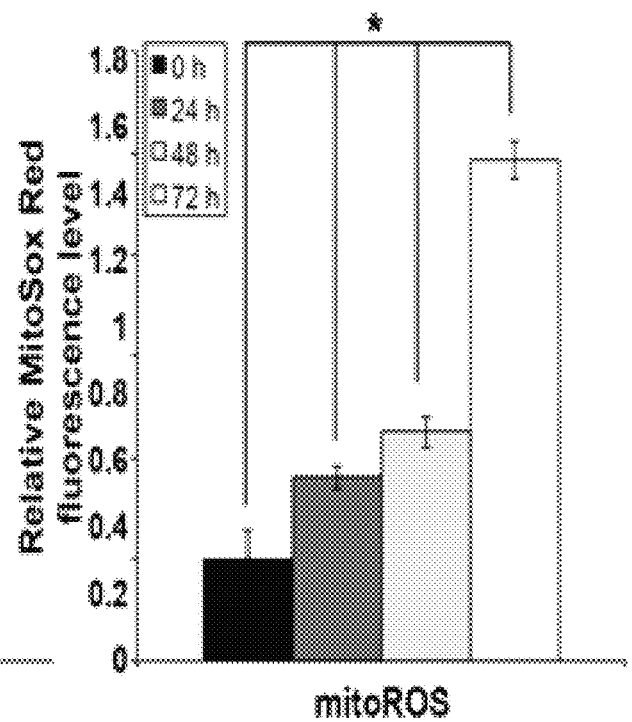
Figure 20E:
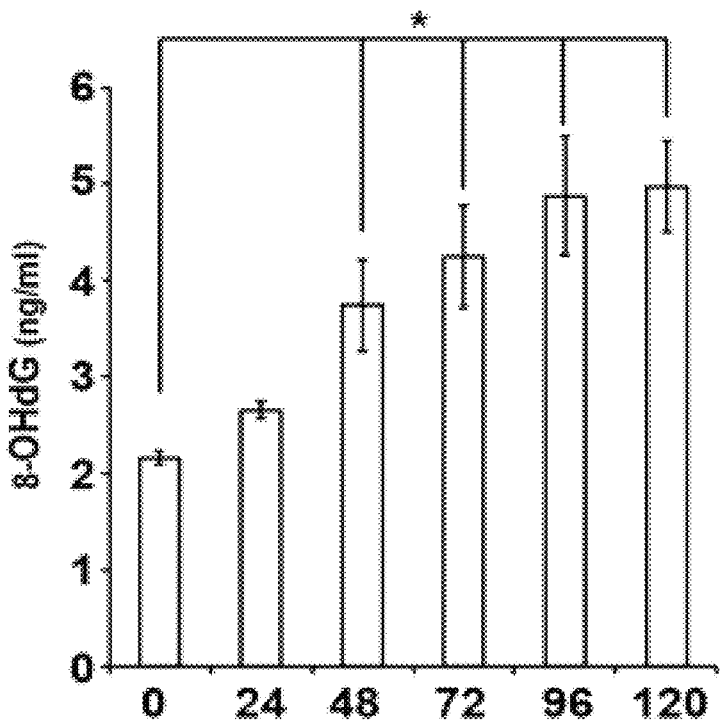
Figure 20F:
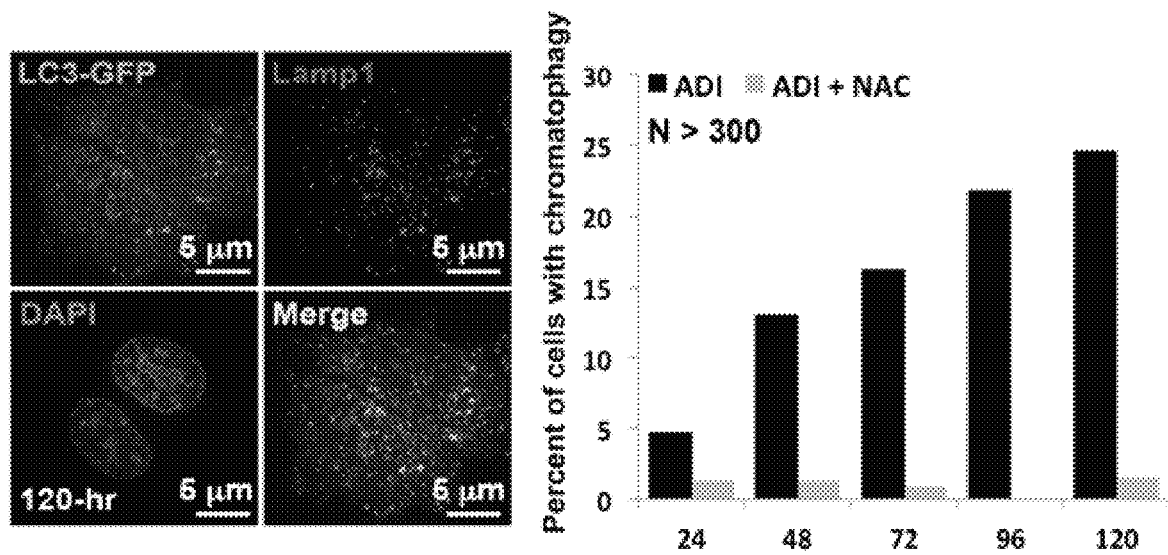

During the course of analyzing some of the TEM images, abnormal mitochondria were noted (FIG. 18D) in many cells. This led us to speculate that prolonged arginine deprivation has impaired mitochondrial function. To address this possibility, real-time oxygen consumption rate (OCR) was determined in ADI-PEG20-treated CWR22Rv1 cells at indicated time points post-treatment using Seahorse Extracellular Flux (XF-24) analyzer. FIG. 20A reveals that baseline OCR was suppressed by treatment with ADI-PEG20 in a time-dependent manner starting at 48-h post-treatment. At 72-h following ADI-PEG20-treatment, the basal OCR level showed an approximately 80% decrease and failed to respond to the inhibition of oligomycin, an H+-ATP-synthase inhibitor (Shchepina et al. 2002). Moreover, ADI-PEG20 impaired the reserve capacity for maximal oxygen consumption, evident by the lack of response to FCCP, an uncoupler of the proton gradient across the inner mitochondrial membrane (Brennan et al. 2006). Further, prolonged ADI treatment showed significant reduction of OCR level before addition of Rotenone, a mitochondrial complex I inhibitor. Consistent with OCR profile (FIG. 20A), mitochondrial membrane potential (MMP) level was reduced in a time-dependent manner and the $DiOC_6$-low population was approximately 2-fold more compared to vehicle-treated control (FIG. 20B). These results suggest that arginine deprivation leads to severe mitochondrial defects. Dysfunctional mitochondria are known to release reactive oxygen species (ROS). As shown in FIG. 20C, the CellROX positive population is elevated at 24-h post ADI-PEG20-treatment, suggesting an increase of ROS level. MitoSox staining verified an increase of mitochondrial ROS levels to approximate 5-fold higher than that in vehicle treated cells (FIG. 20D). One consequence of elevated ROS is the generation of base damages, 8-hydroxy-2'-deoxyguanosine (8-OHdG), ELISA analyses demonstrated that cellular 8-OHdG levels gradually increased after ADI-PEG20-treatment starting at 48-h post-treatment (FIG. 20E). To determine whether increased ROS contributes to chromatophagy, CWR22Rv1 cells were co-treated with N-Acetyl-Cysteine (NAC, a ROS scavenger, 10 µM) and ADI-PEG20 for 96-h. The addition of NAC essentially abolished the appearance of DNA-autophagosome structure after prolonged ADI-PEG20-treatment (FIG. 20F, left panel) and the percentage of cells containing leaked DNA was significantly reduced (FIG. 20F, right panel) confirming the involvement of ROS in DNA-leakage after prolonged ADI-PEG20-treatment.

Autophagy is Required for DNA Leakage.

Figure 21A:
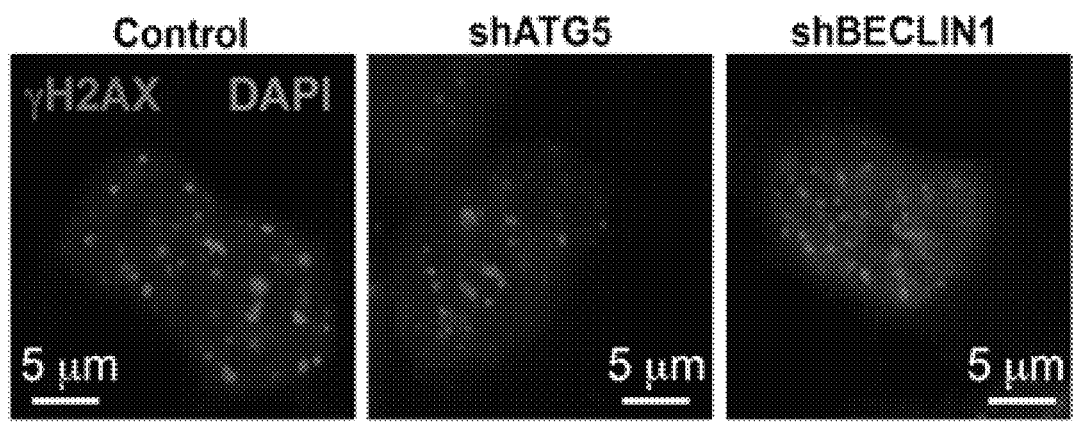
FIGS. 21A-B show that autophagy contributes to ADI-induced DNA leakage according to one embodiment. FIG.
Figure 21B:
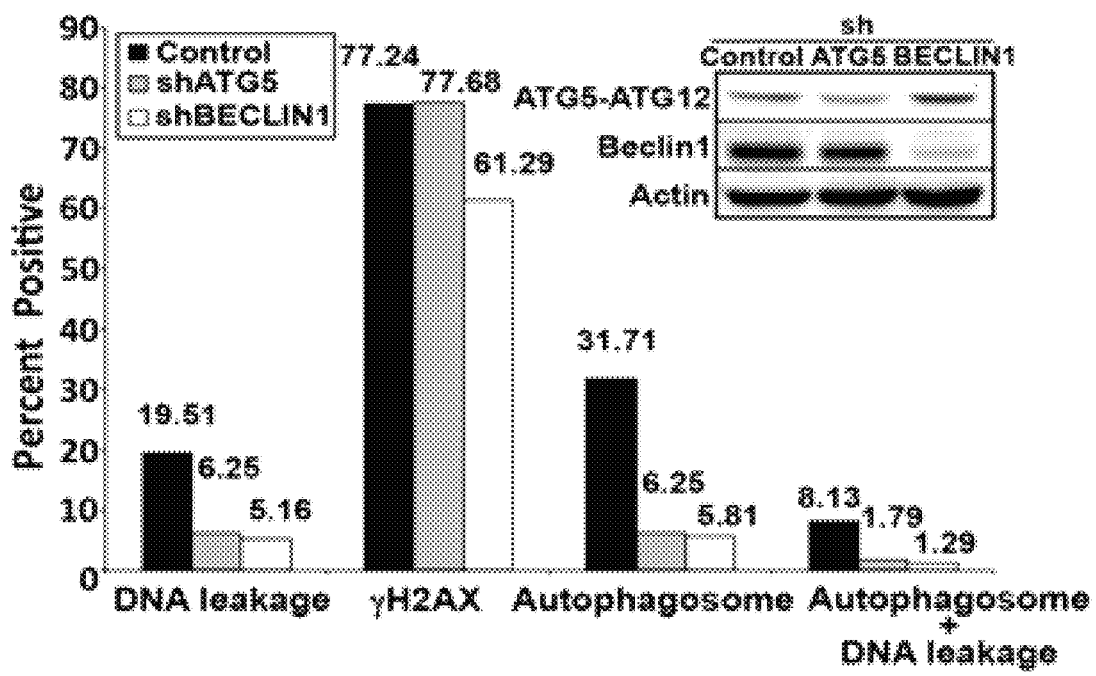
Figure 22A:
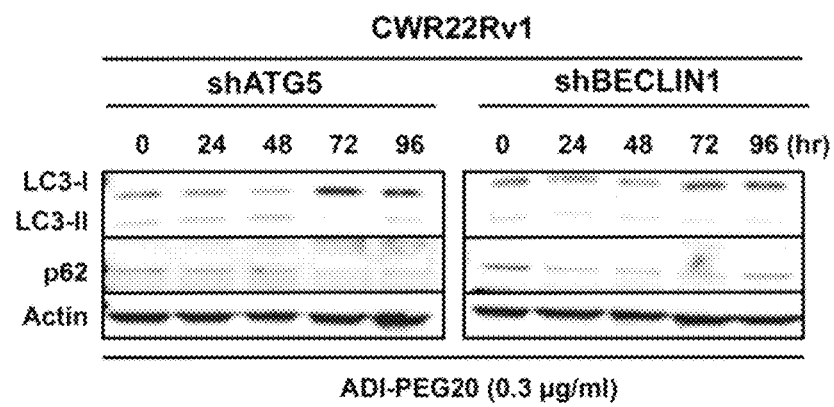
FIGS. 22A-C illustrate that inhibition of autophagosome formation can reduce the occurrence of chromatophagy according to one embodiment.
Figure 22B:
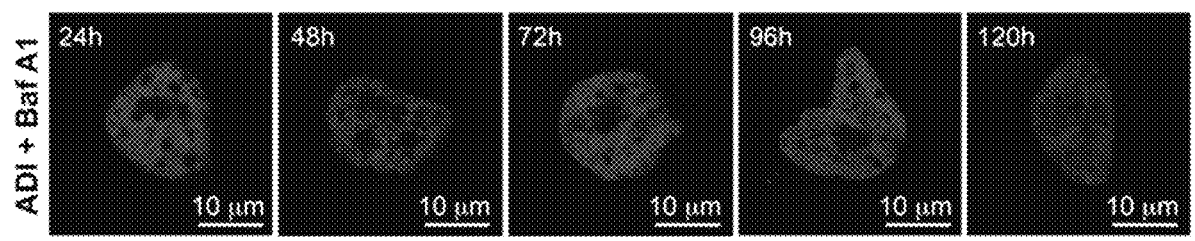
Figure 22C:
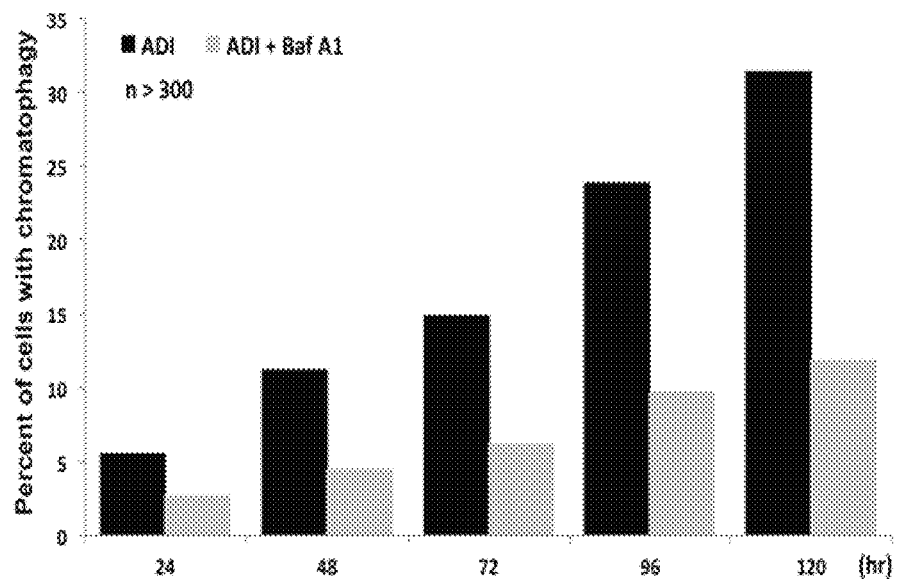

To investigate the potential contribution of autophagy to DNA leakage/DNA damage, shRNA was used to knockdown ATG5 or BECLIN1, essential proteins for autophagy initiation and autophagosome formation (Yue et al. 203; Pyo et al. 2005; Matsushita et al. 2007; Kang et al. 2011) in CWR22Rv1 cells over-expressing GFP-LC3. Western analyses of ATG5-ATG12 and BECLIN1 confirmed that the respective protein expression level was reduced to approximately 40 and 10% in the knockdown cells (FIG. 21B, inset) and that there was reduced autophagy induction in the knockdown cells (FIG. 22A). The reduced autophagy capacity due to ATG5 or BECLIN knockdown did not affect ADI-PEG20-induced appearance of γH2AX (FIGS. 21A, 21B), which presumably was a direct result of increased ROS. By contrast, the autophagosome formation was extensively inhibited in CWR22Rv1/shATG5 and/shBECLIN1 cells, dropping from 31.7 to 6.3, and 5.8%, respectively (FIG. 21B). The proportion of cells with DNA leakage showed approximately 66 and 75% decrease in shATG5 and shBECLIN1 cells (FIG. 21B). Furthermore, the percentage of hypodiploid cells was dramatically reduced in shATG5 and shBECLIN1 cells after 72-h of ADI-PEG20-treatment. As a complementary approach, pharmacological inhibitor 3-methyladenine (3-MA) was used to block autophagosome formation (Klionsky et al. 2012). As shown in FIG. 21D, such treatment diminished the DNA leakage phenotypes. In addition, bafilomycin A1 was added to prevent maturation of autophagic vacuoles by inhibiting fusion between autophagosomes and lysosomes. As shown in FIGS. 22B, 22C, the presence of bafilomycin A1 also reduced the DNA leakage phenotype. Together, the data suggest that autophagosome formation is at least in part involved in the DNA leakage process.

Discussion

Targeting "arginine-addiction" may be exploited therapeutically due to the preferential loss of ASS1 expression in tumor cells. The reduced ASS1 expression renders the cells unable to produce arginine intracellularly and become addictive to external arginine. In this study, it was found that ADI-PEG20 induces autophagy with two distinct phases. Conventional autophagy which protected cells from dying was seen in the first 48-h, and afterwards, atypical or excessive autophagy and formation of giant autophagosomes, leading to cell death were detected. This type of cell killing differs from the classical type I apoptosis, in that it can be caspase-independent, accompanied by DNA leakage from the nucleus, and autophagosome capturing of the leaked chromatin, referred to here as chromatophagy. The observation that both Ku70 and histones were also captured suggest that the leaked DNA is of nuclear, but not mitochondria origin.

One of the striking findings in these studies is the high level of "giant autophagosomes and autolysosomes" encapsulating the leaked DNA in the ADI-PEG20-treated dying cells. Nutritional starvation often leads to autophagosome induction and arginine deprivation is of no exception. However, the average volume of this chromatin-uptaken vesicle, with its diameter ranging from 2 μm to >10 μm, was several-fold greater than the conventional size (700 nm to 1 μm (Klonsky et al. 2012)) in the arginine-starved cell (FIG. 16B). These mega-vesicles appeared to be related to the autophagy pathway on the basis of three criteria: (i) as determined by 4-D fluorescence microscopy, almost all of them they were GFP-LC3 positive (FIG. 16B); (ii) TEM analyses indicated that many were enclosed by at least two lipid bilayers (FIGS. 18C, 18D) and (iii) they are ATG5- and BECLIN1-dependent (FIG. 21B). Importantly, 3-MA-treatment or ATG5- or BECLIN1-knockdown significantly reduced the number of DNA leakage structure (based on DAPI staining) and accumulation of hypodiploid cell populations (FIGS. 21B-21D), suggesting that autophagy contributes to the arginine starvation-induced DNA leakage phenotype and cell death. The accumulation of giant autophagosomes that were observed in arginine-starved cells may result from an increase in autophagosome formation and/or fusion, from a decrease in their degradation, or both. These giant autophagosomes could also be found in very close proximity next to the nucleus, sometimes seemingly pushing-into/budding-out the nucleus.

The correlation of the quantitative data on the time-dependent ROS production (FIGS. 20C, 20D), 8-OHdG accumulation (FIG. 20E) and the ability of NAC to reverse DNA-leakage (FIG. 20F) suggest the involvement of dysfunctional mitochondria-released ROS in chronic arginine starvation-induced genome instability. It is tempting to speculate that the intracellular arginine level might affect chromatin structure, thus retarding double-strand break repair. The leaked DNA could originate from heterochromatin and thus resistant to repair. However, the presence of acetyl-H2B may suggest otherwise. Given that the accumulation of hypodiploid cells was autophagy-dependent, it is likely that these leaked DNAs were irreversibly lost. While additional studies are warranted to elucidate the mechanisms underlying DNA loss, it is prudent to conclude that chromatinphagy is distinct from previously reported nucleophagy formation (Park et al. 2009; Rello-Varona et al. 2012) and Dnautophagy (Fujiwara et al. 2013).

Formation of perinuclear autophagic vacuoles and uptake of leaked DNA have been described in envelopathies LmnaH222P/H222P mouse embryonic fibroblasts (Park et al. 2009; Rello-Varona et al. 2012). These data illustrated an intimate relationship between the integrity of nuclear envelope, such as lamin, and DNA leakage. This suggests that autophagosome membrane formation/fusion with nuclear membrane might play a role in DNA leakage. Alternatively, as the inner membrane first disintegrated/dissolved, followed by the outer membrane fused with autophagosome, damaged DNA exited from the nucleus at the weakened site and was captured by autophagosomes. The common theme of these phenomena is that they are all in response to genome instability, whether caused by nuclear envelope defects, micronuclei formation (Park et al. 2009; Rello-Varona et al. 2012), or reactive oxygen species from damaged mitochondria (this paper). This highlights the role of chromatophagy in the loss of genome integrity and order. Another nucleophagy-related phenomenon has been described in yeast, named piecemeal microautophagy of the nucleus (PMN) (Kvam & Goldfarb 2007). The chromatophagy described here also differs from envelopathies- and micronuclei-associated nuclear-phagy: (i) a higher proportion of cells are affected, (ii) DNA is directly taken from nucleus instead of engulfing micronuclei—"free" micronuclei were never found in the cytosol, and (iii) The DNA-containing autophagosomes are usually significantly larger and contain more DNA than micronuclei. Furthermore, rapamycin treatment induced PMN in *Saccharomyces cerevisiae* (Roberts et al. 2003) but not chromatophagy in CWR22RV1 cells (this study). Further, a type of lysosome-dependent autophagy has been shown, namely RNautophagy, targeting RNA (Fujiwara et al. 2013a) and DNautophagy targeting DNA (Fujiwara et al. 2013b). In this type of autophagy, RNA or DNA may be able to bind to the cytosolic tail of LAMP2C on the surface of the lysosomal membrane and may be able bind to the cytosolic tail of LAMP2C. However, this cannot entirely explain the recruitment of leaked DNA into autophagosomes.

The results above strengthen and redefine the dynamic role of arginine-starvation-induced autophagy in ASS1-lacking cancer cells, which could be the mechanistic foundation of starvation therapy by FDA-approved ADI-PEG20. Application of ADI-PEG20, or arginine-starvation, seems to offer a specific therapeutic advantage of starving tumor cells to death without affecting the normal counterpart and utilizing a cell death mechanism distinct from apoptosis-based conventional therapy.

REFERENCES

The references, patents and published patent applications listed below, and all references cited in the specification above are hereby incorporated by reference in their entirety, as if fully set forth herein.

Ackrell, Progress in understanding structure-function relationships in respiratory chain complex II. FEBS letters 466, 1-5 (2000).

Ahn, H. S. Kim, S. Song, I. H. Lee, J. Liu, A. Vassilopoulos, C. X. Deng, T. Finkel, A role for the mitochondrial deacetylase Sirt3 in regulating energy homeostasis. Proceedings of the National Academy of Sciences of the United States of America 105, 14447-14452 (2008); published online EpubSep 23 (10.1073/pnas.0803790105).

Ascierto P A, Scala S, Castello G, Daponte A, Simeone E, Ottaiano A, Beneduce G, De Rosa V, et al. (2005) Pegylated arginine deiminase treatment of patients with metastatic melanoma: results from phase I and II studies. J Clin Oncol 23(30): 7660-7668.

Beloussow, L. Wang, J. Wu, D. Ann, W. C. Shen, Recombinant arginine deiminase as a potential anti-angiogenic agent. Cancer letters 183, 155-162 (2002).

Bianchi, M. L. Genova, G. Parenti Castelli, G. Lenaz, The mitochondrial respiratory chain is partially organized in a supercomplex assembly: kinetic evidence using flux control analysis. The Journal of biological chemistry 279, 36562-36569 (2004); published online EpubAug 27 (10.1074/jbc.M405135200).

Bianchi, R. Fato, M. L. Genova, G. Parenti Castelli, G. Lenaz, Structural and functional organization of Complex I in the mitochondrial respiratory chain. BioFactors 18, 3-9 (2003).

Birrell, J. Hirst, Investigation of NADH binding, hydride transfer, and NAD(+) dissociation during NADH oxidation by mitochondrial complex I using modified nicotinamide nucleotides. Biochemistry 52, 4048-4055 (2013); published online EpubJun 11 (10.1021/bi3016873).

Boren, K. M. Brindle, Apoptosis-induced mitochondrial dysfunction causes cytoplasmic lipid droplet formation. Cell Death Differ 19, 1561-1570 (2012); published online EpubSep (cdd201234 [pii]10.1038/cdd.2012.34).

Bowles T L, et al. (2008) Pancreatic cancer cell lines deficient in argininosuccinate synthetase are sensitive to arginine deprivation by arginine deiminase. Int J Cancer 123(8): 1950-1955.

Brennan J P, et al. (2006) Mitochondrial uncoupling, with low concentration FCCP, induces ROS-dependent cardioprotection independent of KATP channel activation. Cardiovascular Research 72(2): 313-321.

Bryant, N. Schultz, H. D. Thomas, K. M. Parker, D. Flower, E. Lopez, S. Kyle, M. Meuth, N. J. Curtin, T. Helleday, Specific killing of BRCA2-deficient tumours with inhibitors of poly(ADP-ribose) polymerase. Nature 434, 913-917 (2005); published online EpubApr 14 (10.1038/nature03443).

C. T. a. M. N. (Paramus, N J, 2005).

Cadenas, A. Boveris, Enhancement of hydrogen peroxide formation by protophores and ionophores in antimycin-supplemented mitochondria. The Biochemical journal 188, 31-37 (1980).

Cassidy-Stone, J. E. Chipuk, E. Ingerman, C. Song, C. Yoo, T. Kuwana, M. J. Kurth, J. T. Shaw, J. E. Hinshaw, D. R. Green, J. Nunnari, Chemical inhibition of the mitochondrial division dynamin reveals its role in Bax/Bak-dependent mitochondrial outer membrane permeabilization. Developmental cell 14, 193-204 (2008); published online EpubFeb (10.1016/j.devcel.2007.11.019).

Cecchini, Function and structure of complex II of the respiratory chain. Annual review of biochemistry 72, 77-109 (2003)10.1146/annurev.biochem.72.121801.161700).

Chan, Mitochondria: dynamic organelles in disease, aging, and development. Cell 125, 1241-1252 (2006); published online EpubJun 30 (10.1016/j.cell.2006.06.010).

Chang, D. S. Nuyten, J. B. Sneddon, T. Hastie, R. Tibshirani, T. Sorlie, H. Dai, Y. D. He, L. J. van't Veer, H. Bartelink, M. van de Rijn, P. O. Brown, M. J. van de Vijver, Robustness, scalability, and integration of a wound-response gene expression signature in predicting breast cancer survival. Proceedings of the National Academy of Sciences of the United States of America 102, 3738-3743 (2005); published online EpubMar 8 (10.1073/pnas.0409462102).

Cheng P N M, et al. (2007) Peglyated Recombinant Human Arginase (rhArg-peg5,000mw) inhibits the in vitro and in vivo proliferation of human hepatocellular carcinoma through arginine depletion. Cancer Research 67(1): 309-317.

Chou, P. Talalay, Quantitative analysis of dose-effect relationships: the combined effects of multiple drugs or enzyme inhibitors. Advances in enzyme regulation 22, 27-55 (1984).

Chou, Theoretical basis, experimental design, and computerized simulation of synergism and antagonism in drug combination studies. Pharmacological reviews 58, 621-681 (2006); published online EpubSep (10.1124/pr.58.3.10).

Dang C (2010) Rethinking the Warburg effect with Myc micromanaging glutamine metabolism. Cancer Res 70(3): 859-862.

DeBerardinis, C. B. Thompson, Cellular metabolism and disease: what do metabolic outliers teach us? Cell 148, 1132-1144 (2012); published online EpubMar 16 (10.1016/j.cell.2012.02.032).

Delage, P. Luong, L. Maharaj, C. O'Riain, N. Syed, T. Crook, E. Hatzimichael, A. Papoudou-Bai, T. J. Mitchell, S. J. Whittaker, R. Cerio, J. Gribben, N. Lemoine, J. Bomalaski, C. F. Li, S. Joel, J. Fitzgibbon, L. T. Chen, P. W. Szlosarek, Promoter methylation of argininosuccinate synthetase-1 sensitises lymphomas to arginine deiminase treatment, autophagy and caspase-dependent apoptosis. Cell death & disease 3, e342 (2012)10.1038/cddis.2012.83).

Denko, Hypoxia, HIF1 and glucose metabolism in the solid tumour. Nature reviews. Cancer 8, 705-713 (2008); published online EpubSep (10.1038/nrc2468).

Ding, F. Guo, H. M. Ni, A. Bockus, S. Manley, D. B. Stolz, E. L. Eskelinen, H. Jaeschke, X. M. Yin, Parkin and mitofusins reciprocally regulate mitophagy and mitochondrial spheroid formation. The Journal of biological chemistry, (2012); published online EpubOct 24 (10.1074/jbc.M112.413682).

Ensor C M, Holtsberg F W, Bomalaski J S, Clark M A (2002) Pegylated arginine deiminase (ADI-SS PEG20,000mw) inhibits human melanomas and hepatocellular carcinomas in vitro and in vivo. Cancer Res 62(19): 5443-5450.

Farmer, N. McCabe, C. J. Lord, A. N. Tutt, D. A. Johnson, T. B. Richardson, M. Santarosa, K. J. Dillon, I. Hickson, C. Knights, N. M. Martin, S. P. Jackson, G. C. Smith, A. Ashworth, Targeting the DNA repair defect in BRCA mutant cells as a therapeutic strategy. Nature 434, 917-921 (2005); published online EpubApr 14 (10.1038/nature03445).

Feun L, et al. (2008) Arginine deprivation as a targeted therapy for cancer. Curr Pharm Des 14(11): 1049-1057.

Forman, J. A. Kennedy, Role of superoxide radical in mitochondrial dehydrogenase reactions. Biochem Biophys Res Commun 60, 1044-1050 (1974); published online EpubOct 8 (0006-291X(74)90418-5 [pii]).

Frezza, E. Gottlieb, Mitochondria in cancer: not just innocent bystanders. Seminars in cancer biology 19, 4-11 (2009); published online EpubFeb (10.1016/j.semcancer.2008.11.008).

Fujiwara Y, et al. (2013a) Discovery of a novel type of autophagy targeting RNA. Autophagy 9(3):403-409.

Fujiwara Y, et al. (2013b) Direct uptake and degradation of DNA by lysosomes. Autophagy 9(8):1167-1171.

Gimenez-Xavier, R. Francisco, A. F. Santidrian, J. Gil, S. Ambrosio, Effects of dopamine on LC3-II activation as a marker of autophagy in a neuroblastoma cell model. Neurotoxicology 30, 658-665 (2009); published online EpubJul (10.1016/j.neuro.2009.04.007).

Glazer, M. Piccirillo, V. Albino, R. Di Giacomo, R. Palaia, A. A. Mastro, G. Beneduce, G. Castello, V. De Rosa, A. Petrillo, P. A. Ascierto, S. A. Curley, F. Izzo, Phase II study of pegylated arginine deiminase for nonresectable and metastatic hepatocellular carcinoma. Journal of clinical oncology: official journal of the American Society of Clinical Oncology 28, 2220-2226 (2010); published online EpubMay 1 (10.1200/JCO.2009.26.7765).

Gong H, Zolzer F, von Recklinghausen G, Havers W, Schweigerer L. (2000) Arginine deiminase inhibits proliferation of human leukemia cells more potently than asparaginase by inducing cell cycle arrest and apoptosis. Leukemia 14(5): 826-829.

Hatch E M, Fischer A H, Deerinck T J, Hetzer M W (2013) Catastrophic nuclear envelope collapse in cancer cell micronuclei. Cell 154(1):47-60.

Hirayama, K. Kami, M. Sugimoto, M. Sugawara, N. Toki, H. Onozuka, T. Kinoshita, N. Saito, A. Ochiai, M. Tomita, H. Esumi, T. Soga, Quantitative metabolome profiling of colon and stomach cancer microenvironment by capillary electrophoresis time-of-flight mass spectrometry. Cancer research 69, 4918-4925 (2009); published online EpubJun 1 (10.1158/0008-5472.CAN-08-4806).

Hsueh E C, et al. (2012) Deprivation of arginine by recombinant human arginase in prostate cancer cells. J Hematol Oncol 5: 17.

Huang C C, et al. (2012) Arginine deprivation as a new treatment strategy for head and neck cancer. Oral Oncol 48(12): 1227-1235.

Huang, W. R. Wu, Y. H. Wang, J. W. Wang, F. M. Fang, J. W. Tsai, S. H. Li, H. C. Hung, S. C. Yu, J. Lan, Y. L. Shiue, C. H. Hsing, L. T. Chen, C. F. Li, ASS1 as a novel tumor suppressor gene in myxofibrosarcomas: aberrant loss via epigenetic DNA methylation confers aggressive phenotypes, negative prognostic impact, and therapeutic relevance. Clinical cancer research: an official journal of the American Association for Cancer Research 19, 2861-2872 (2013); published online EpubJun 1 (10.1158/1078-0432.CCR-12-2641).

Husson, C. Brasse-Lagnel, A. Fairand, S. Renouf, A. Lavoinne, Argininosuccinate synthetase from the urea cycle to the citrulline-NO cycle. European journal of biochemistry/FEBS 270, 1887-1899 (2003).

Izzo, P. Marra, G. Beneduce, G. Castello, P. Vallone, V. De Rosa, F. Cremona, C. M. Ensor, F. W. Holtsberg, J. S. Bomalaski, M. A. Clark, C. Ng, S. A. Curley, Pegylated arginine deiminase treatment of patients with unresectable hepatocellular carcinoma: results from phase I/I studies. Journal of clinical oncology: official journal of the American Society of Clinical Oncology 22, 1815-1822 (2004); published online EpubMay 15 (10.1200/JCO.2004.11.120).

Jemal, F. Bray, M. M. Center, J. Ferlay, E. Ward, D. Forman, Global cancer statistics. CA: a cancer journal for clinicians 61, 69-90 (2011); published online Epub March-April (10.3322/caac.20107).

Kalyanaraman, V. Darley-Usmar, K. J. Davies, P. A. Dennery, H. J. Forman, M. B. Grisham, G. E. Mann, K. Moore, L. J. Roberts, 2nd, H. Ischiropoulos, Measuring reactive oxygen and nitrogen species with fluorescent probes: challenges and limitations. Free radical biology & medicine 52, 1-6 (2012); published online EpubJan 1 (10.1016/j.freeradbiomed.2011.09.030).

Kami, T. Fujimori, H. Sato, M. Sato, H. Yamamoto, Y. Ohashi, N. Sugiyama, Y. Ishihama, H. Onozuka, A. Ochiai, H. Esumi, T. Soga, M. Tomita, Metabolomic profiling of lung and prostate tumor tissues by capillary electrophoresis time-of-flight mass spectrometry. Metabolomics: Official journal of the Metabolomic Society 9, 444-453 (2013); published online EpubApr (10.1007/s11306-012-0452-2).

Kang R, Zeh H J, Lotze M T, Tang D (2011) The Beclin 1 network regulates autophagy and apoptosis. Cell Death Differ 18(4): 571-580.

Kelly M P, et al. (2012) Arginine deiminase PEG20 inhibits growth of small cell lung cancers lacking expression of argininosuccinate synthetase. Br J Cancer 106(2): 324-332.

Kim J W, Dang C (2006) Cancer's molecular sweeth tooth and the Warburg effect. Cancer Res 66(18): 8927-8930.

Kim R H, Bold R J, Kung H J (2009a) ADI, autophagy and apoptosis: metabolic stress as a therapeutic option for prostate cancer. Autophagy. 5(4): 567-568.

Kim R H, et al. (2009b) Arginine deiminase as a novel therapy for prostate cancer induces autophagy and caspase-independent apoptosis. Cancer Res 69(2): 700-708.

Klionsky D J et al (2012) Guidelines for the use and interpretation of assays for monitoring autophagy. Autophagy 8(4): 445-544.

Kobayashi E, et al. (2010) Reduced argininosuccinate synthetase is a predictive biomarker for the development of pulmonary metastasis in patients with osteosarcoma. Mol Cancer Ther 9(3): 535-544.

Kvam E, Goldfarb D S (2007) Nucleus-vacuole junctions and piecemeal microautophagy of the nucleus in S. cerevisiae. Autophagy 3(2):85-92.

Levine, G. Kroemer, Autophagy in the pathogenesis of disease. Cell 132, 27-42 (2008); published online EpubJan 11 (S0092-8674(07)01685-6 [pii]10.1016/j.cell.2007.12.018).

Lin T C, et al. (2012) Autophagy: resetting glutamine-dependent metabolism and oxygen consumption. Autophagy 8(10): 1477-1493.

Lind, Arginine and cancer. J Nutr 134, 2837S-2841S; discussion 2853S (2004); published online EpubOct (134/10/2837S [pii]).

Locasale, A. R. Grassian, T. Melman, C. A. Lyssiotis, K. R. Mattaini, A. J. Bass, G. Heffron, C. M. Metallo, T. Muranen, H. Sharfi, A. T. Sasaki, D. Anastasiou, E. Mullarky, N. I. Vokes, M. Sasaki, R. Beroukhim, G. Stephanopoulos, A. H. Ligon, M. Meyerson, A. L. Richardson, L. Chin, G. Wagner, J. M. Asara, J. S. Brugge, L. C. Cantley, M. G. Vander Heiden, Phosphoglycerate dehydrogenase diverts glycolytic flux and contributes to oncogenesis. Nature genetics 43, 869-874 (2011); published online EpubSep (10.1038/ng.890).

Matsushita M, et al. (2007) Structure of Atg5.Atg16, a complex essential for autophagy. J Biol Chem 282(9): 9763-9772.

Mitra, Mitochondrial fission-fusion as an emerging key regulator of cell proliferation and differentiation. BioEssays: news and reviews in molecular, cellular and developmental biology 35, 955-964 (2013); published online EpubNov (10.1002/bies.201300011).

Mizushima, M. Komatsu, Autophagy: renovation of cells and tissues. Cell 147, 728-741 (2011); published online EpubNov 11 (S0092-8674(11)01276-1 [pii]10.1016/j.cell.2011.10.026).

Morris, Jr., Arginine: beyond protein. The American journal of clinical nutrition 83, 508S-512S (2006).

Muller H J & Boos J (1998) Use of L-asparaginase in childhood ALL. Critical reviews in oncology/hematology. 28(2): 97-113.

Narendra, A. Tanaka, D. F. Suen, R. J. Youle, Parkin is recruited selectively to impaired mitochondria and promotes their autophagy. The Journal of cell biology 183, 795-803 (2008); published online EpubDec 1 (10.1083/jcb.200809125).

Narendra, S. M. Jin, A. Tanaka, D. F. Suen, C. A. Gautier, J. Shen, M. R. Cookson, R. J. Youle, PINK1 is selectively stabilized on impaired mitochondria to activate Parkin. PLoS biology 8, e1000298 (2010); published online EpubJan (10.1371/journal.pbio.1000298).

Ogawa-Goto K, et al. (2003) Microtubule network facilitates targeting of human cytomegalovirus capsid. J. Virol. 77(15): 84518547.

Park Y E, et al. (2009) Autophagic degradation of nuclear components in mammalian cells. Autophagy 5(6):795-804.

Perkins, E. Bossy-Wetzel, M. H. Ellisman, New insights into mitochondrial structure during cell death. Experimental neurology 218, 183-192 (2009); published online EpubAug (10.1016/j.expneurol.2009.05.021).

Perou, T. Sorlie, M. B. Eisen, M. van de Rijn, S. S. Jeffrey, C. A. Rees, J. R. Pollack, D. T. Ross, H. Johnsen, L. A. Akslen, O. Fluge, A. Pergamenschikov, C. Williams, S. X. Zhu, P. E. Lonning, A. L. Borresen-Dale, P. O. Brown, D. Botstein, Molecular portraits of human breast tumours. Nature 406, 747-752 (2000); published online EpubAug 17 (10.1038/35021093).

Possemato R, et al. (2011) Functional genomics reveal that the serine synthesis pathway is essential in breast cancer. Nature 476(7360): 346-350.

Pyo J O, et al. (2005) Essential roles of Atg5 and FADD in autophagic cell death: dissection of autophagic cell death into vacuole formation and cell death. J Biol Chem 280(21): 20722-20729.

Qiu F, et al. (2014) Arginine starvation impairs mitochondrial respiratory function in ASS1-deficient breast cancer cell. Sci Signal (319): ra31.

Rardin, J. C. Newman, J. M. Held, M. P. Cusack, D. J. Sorensen, B. Li, B. Schilling, S. D. Mooney, C. R. Kahn, E. Verdin, B. W. Gibson, Label-free quantitative proteomics of the lysine acetylome in mitochondria identifies substrates of SIRT3 in metabolic pathways. Proceedings of the National Academy of Sciences of the United States of America 110, 6601-6606 (2013); published online EpubApr 16 (10.1073/pnas.1302961110).

Rello-Varona S, et al. (2012) Autophagic removal of micronuclei. Cell Cycle 11(1): 170-176.

Roberts P, et al. (2003) Piecemeal microautophagy of nucleus in *Saccharomyces cerevisiae*. Mol Biol Cell 14(1):129-141.

Roth, W. Y. Chen, Sorting out functions of sirtuins in cancer. Oncogene, (2013); published online EpubApr 22 (10.1038/onc.2013.120).

Shacka, B. J. Klocke, K. A. Roth, Autophagy, bafilomycin and cell death: the "a-B-cs" of plecomacrolide-induced neuroprotection. Autophagy 2, 228-230 (2006).

Shchepina L A, et al. (2002) Oligomycin, inhibitor of the F0 part of H+-ATP-synthase suppresses the TNF-induced apoptosis. Oncogene. 21(53): 8149-8157.

Shvets E, Fass E, Elazar Z (2008) Utilizing flow cytometry to monitor autophagy in living mammalian cells. Autophagy 4(5): 621-628.

Society, Cancer Facts & Figures 2013. American Cancer Society, (2013).

Sorlie, C. M. Perou, R. Tibshirani, T. Aas, S. Geisler, H. Johnsen, T. Hastie, M. B. Eisen, M. van de Rijn, S. S. Jeffrey, T. Thorsen, H. Quist, J. C. Matese, P. O. Brown, D. Botstein, P. E. Lonning, A. L. Borresen-Dale, Gene expression patterns of breast carcinomas distinguish tumor subclasses with clinical implications. Proceedings of the National Academy of Sciences of the United States of America 98, 10869-10874 (2001); published online EpubSep 11 (10.1073/pnas.191367098).

Syed N, et al. (2013) Epigenetic status of argininosuccinate synthetase and argininosuccinate lyase modulates autophagy and cell death in glioblastoma. Cell Death Dis 4:e458.

Szlosarek, A. Klabatsa, A. Pallaska, M. Sheaff, P. Smith, T. Crook, M. J. Grimshaw, J. P. Steele, R. M. Rudd, F. R. Balkwill, D. A. Fennell, In vivo loss of expression of argininosuccinate synthetase in malignant pleural mesothelioma is a biomarker for susceptibility to arginine depletion. Clinical cancer research: an official journal of the American Association for Cancer Research 12, 7126-7131 (2006); published online EpubDec 1 (10.1158/1078-0432.CCR-06-1101).

Takaku, M. Takase, S. Abe, H. Hayashi, K. Miyazaki, In vivo anti-tumor activity of arginine deiminase purified from *Mycoplasma arginini*. International journal of cancer. Journal international du cancer 51, 244-249 (1992).

Tanida, T. Ueno, E. Kominami, LC3 and Autophagy. Methods in molecular biology 445, 77-88 (2008)10.1007/978-1-59745-157-4_4).

Tanida, T. Ueno, E. Kominami, LC3 conjugation system in mammalian autophagy. The international journal of biochemistry & cell biology 36, 2503-2518 (2004); published online EpubDec (10.1016/j.biocel.2004.05.009).

Tolkovsky, Mitophagy. Biochimica et biophysica acta 1793, 1508-1515 (2009); published online EpubSep (10.1016/j.bbamcr.2009.03.002).

Trachootham, J. Alexandre, P. Huang, Targeting cancer cells by ROS-mediated mechanisms: a radical therapeutic approach? Nature reviews. Drug discovery 8, 579-591 (2009); published online EpubJul (10.1038/nrd2803).

Tsai, I. Aiba, S. Y. Lee, L. Feun, N. Savaraj, M. T. Kuo, Resistance to arginine deiminase treatment in melanoma cells is associated with induced argininosuccinate synthetase expression involving c-Myc/HIF-1alpha/Sp4. Molecular cancer therapeutics 8, 3223-3233 (2009); published online EpubDec (10.1158/1535-7163. MCT-09-0794).

van de Vijver, Y. D. He, L. J. van't Veer, H. Dai, A. A. Hart, D. W. Voskuil, G. J. Schreiber, J. L. Peterse, C. Roberts, M. J. Marton, M. Parrish, D. Atsma, A. Witteveen, A. Glas, L. Delahaye, T. van der Velde, H. Bartelink, S. Rodenhuis, E. T. Rutgers, S. H. Friend, R. Bernards, A gene-expression signature as a predictor of survival in breast cancer. The New England journal of medicine 347, 1999-2009 (2002); published online EpubDec 19 (10.1056/NEJMoa021967).

Vander Heiden M G, Cantley L C, Thompson C G (2009) Understanding the Warburg effect: the metabolic requirements of cell proliferation. Science 324(5930): 1029.

Vargas J D, Hatch E M, Anderson D J, Hetzer M W (2012) Transient nuclear envelope rupturing during interphase in human cancer cells. Nucleus 3(1):88-100.

Vincow, G. Merrihew, R. E. Thomas, N. J. Shulman, R. P. Beyer, M. J. Maccoss, L. J. Pallanck, The PINK1-Parkin pathway promotes both mitophagy and selective respiratory chain turnover in vivo. Proceedings of the National Academy of Sciences of the United States of America 110, 6400-6405 (2013); published online EpubApr 16 (10.1073/pnas.1221132110).

Wang, X. Liu, A. Y. Li, L. Chen, L. Lai, H. H. Lin, S. Hu, L. Yao, J. Peng, S. Loera, L. Xue, B. Zhou, L. Zhou, S. Zheng, P. Chu, S. Zhang, D. K. Ann, Y. Yen, Overexpression of HMGA2 promotes metastasis and impacts survival of colorectal cancers. Clinical cancer research: an official journal of the American Association for Cancer Research 17, 2570-2580 (2011); published online EpubApr 15 (10.1158/1078-0432.CCR-10-2542).

Warburg, F. Wind, E. Negelein, The Metabolism of Tumors in the Body. The Journal of general physiology 8, 519-530 (1927).

Warburg, On respiratory impairment in cancer cells. Science (New York, N.Y 124, 269-270 (1956).

Westermann, Mitochondrial fusion and fission in cell life and death. Nature reviews. Molecular cell biology 11, 872-884 (2010); published online EpubDec (10.1038/nrm3013).

Wetzler M, et al. (2007) Effective asparagine depletion with pegylated asparaginase results in improved outcomes in adult acute lymphoblastic leukemia: Cancer and Leukemia Group Study 9511. Blood 109(10): 4164-4167.

Wheatley D N & Campbell E (2003) Arginine deprivation, growth inhibition and tumour cell death: 3. Deficient utilisation of citrulline by malignant cells. Br J Cancer 89(3): 573-576.

Wise D R & Thompson C B (2010) Glutamine addiction: a new therapeutic target in cancer. Trends in biochemical sciences 35(8): 427-433.

Wu, S. M. Morris, Jr., Arginine metabolism: nitric oxide and beyond. The Biochemical journal 336 (Pt 1), 1-17 (1998).

Wu, Y. F. Liang, Y. C. Chang, H. H. Yo, M. F. Wei, L. J. Shen, RNA interference of argininosuccinate synthetase restores sensitivity to recombinant arginine deiminase (rADI) in resistant cancer cells. Journal of biomedical science 18, 25 (2011)10.1186/1423-0127-18-25).

Yang, S. N. Lu, Y. Chao, I. S. Sheen, C. C. Lin, T. E. Wang, S. C. Chen, J. H. Wang, L. Y. Liao, J. A. Thomson, J. Wang-Peng, P. J. Chen, L. T. Chen, A randomised phase II study of pegylated arginine deiminase (ADI-PEG 20) in Asian advanced hepatocellular carcinoma patients. Br J Cancer 103, 954-960 (2010); published online EpubSep 28 (10.1038/sj.bjc.6605856).

Yoon, Y. J. Shim, E. H. Kim, J. H. Lee, N. H. Won, J. H. Kim, I. S. Park, D. K. Yoon, B. H. Min, Renal cell carcinoma does not express argininosuccinate synthetase and is highly sensitive to arginine deprivation via arginine deiminase. International journal of cancer. Journal international du cancer 120, 897-905 (2007); published online EpubFeb 15 (10.1002/ijc.22322).

Youle, A. M. van der Bliek, Mitochondrial fission, fusion, and stress. Science (New York, N.Y 337, 1062-1065 (2012); published online EpubAug 31 (10.1126/science.1219855).

Youle, D. P. Narendra, Mechanisms of mitophagy. Nature reviews. Molecular cell biology 12, 9-14 (2011); published online EpubJan (10.1038/nrm3028).

Yue Z, Jin S, Yang C, Levine A J, Heintz N (2003) Beclin1, an autophagy gene essential for early embryonic development, is a haploinsufficient tumor suppressor. Proc Natl Acad Sci U.S.A. 100(25): 15077-15082.

---

What is claimed is:

1. A method for killing one or more argininosuccinate synthetase 1 (ASS1)-deficient breast cancer cells comprising contacting the one or more ASS1-deficient breast cancer cells with an effective amount of ADI-PEG20 in combination with doxorubicin, wherein the effective amount is equivalent to a mouse dosage of 4 IU.

2. The method of claim 1, wherein the one or more ASS1-deficient breast cancer cells are part of a solid tumor.

3. The method of claim 2, wherein contacting the one or more ASS1-deficient breast cancer cells causes regression of the solid tumor.

4. The method of claim 1, wherein the arginine-depleting agent is part of a pharmaceutical composition.

5. A method for treating arginine-auxotrophic breast cancer comprising
administering a therapeutically effective amount of a pharmaceutical composition to a subject having arginine-auxotrophic breast cancer, wherein the pharmaceutical composition comprises an effective amount of ADI-PEG20 and a carrier, wherein the effective amount is equivalent to a mouse dosage of 4 IU, and
administering to the subject an additional pharmaceutical composition comprising doxorubicin.

6. The method of claim 5, wherein the subject is diagnosed with an arginine-auxotrophic breast cancer by detecting a low level of ASS1 expression in a breast tumor tissue obtained from the subject.

7. A method for optimizing treatment of breast cancer comprising
detecting an expression level of ASS1 in a breast tumor tissue sample from a subject having breast cancer;
identifying the subject as a responsive subject when the expression level of ASS1 is at or below a low level of ASS1;
administering a therapeutically effective amount of a pharmaceutical composition to the responsive subject, wherein the pharmaceutical composition comprises an effective amount of ADI-PEG20 and a carrier, wherein the effective amount is equivalent to a mouse dosage of 4 IU, and
administering to the subject an additional pharmaceutical composition comprising doxorubicin.

* * * * *

UNITED STATES PATENT AND TRADEMARK OFFICE
CERTIFICATE OF CORRECTION

| | | |
|---|---|---|
| PATENT NO. | : 11,311,608 B2 | Page 1 of 1 |
| APPLICATION NO. | : 15/089227 | |
| DATED | : April 26, 2022 | |
| INVENTOR(S) | : David K. Ann et al. | |

It is certified that error appears in the above-identified patent and that said Letters Patent is hereby corrected as shown below:

In the Specification

In the Government Interest section, Column 1, Lines 17-20, please delete:
"This invention was made with Government support under Grant Numbers R01DE10742 and R01DE14183, awarded by the National Institutes of Health. The Government has certain rights in the invention."
And replace with:
--"This invention was made with government support under R01 DE010742, and R01 DE014183 awarded by the National Institutes of Health. The government has certain rights in the invention.--

Signed and Sealed this
Fifth Day of September, 2023

Katherine Kelly Vidal
*Director of the United States Patent and Trademark Office*